(12) United States Patent
Hogrefe et al.

(10) Patent No.: US 7,932,070 B2
(45) Date of Patent: Apr. 26, 2011

(54) HIGH FIDELITY DNA POLYMERASE COMPOSITIONS AND USES THEREFOR

(75) Inventors: Holly Hogrefe, San Diego, CA (US); Michael Borns, Escondido, CA (US); Joseph A. Sorge, Wilson, WY (US)

(73) Assignee: Agilent Technologies, Inc., Santa Clara, CA (US)

( * ) Notice: Subject to any disclaimer, the term of this patent is extended or adjusted under 35 U.S.C. 154(b) by 629 days.

(21) Appl. No.: 10/227,110

(22) Filed: Aug. 23, 2002

(65) Prior Publication Data

US 2003/0143577 A1 Jul. 31, 2003

Related U.S. Application Data

(63) Continuation-in-part of application No. 10/208,508, filed on Jul. 30, 2002, which is a continuation-in-part of application No. 10/079,241, filed on Feb. 20, 2002, now abandoned, which is a continuation-in-part of application No. 10/035,091, filed on Dec. 21, 2001.

(51) Int. Cl.
*C12N 9/12* (2006.01)
*C07K 1/00* (2006.01)

(52) U.S. Cl. ........ 435/194; 435/183; 530/350; 424/94.5
(58) Field of Classification Search .............. 530/350; 435/194, 183
See application file for complete search history.

(56) References Cited

U.S. PATENT DOCUMENTS 5,436,149 A 7/1995 Barnes ........................ 435/194
6,881,559 B2 4/2005 Sobek et al.

FOREIGN PATENT DOCUMENTS

EP 1 088 891 A1 4/2001
WO WO 01/23583 A2 4/2001

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Evans, S.J. et al., (2000), "Improving dideoxynucleotide-triphosphate utilisation by the hyper-thermophilic DNA polymerase from the archaeon *Pyrococcus furiosus*", *Nucleic Acids Research*, 28(5): 1059-1066.
Komori, K. et al., (2000), "Functional interdependence of DNA polymerizing and 3'→5' exonucleolytic activities in *Pyrococcus furiosus* DNA polymerase I", *Protein Engineering*, 13(1): 41-47.
Kong, H. et al., (1993), "Characterization of a DNA Polymerase from the Hyperthermophile Archaea *Thennococcus litoralis*". *The Journal of Biological Chemistry*, 268(3): 1965-1975.
Lam, W. et al., (1998), "Effects of Mutations on the Partitioning of DNA Substrates between the Polymerase and 3'-5' Exonuclease Sites of DNA Polymerase I (Klenow Fragment)", *Biochemistry*, 37: 1513-1522.
Patel, P.H. et al., (2000), "DNA polymerase active site is highly mutable: Evolutionary consequences", *PNAS*, 97(10): 5095-5100.
Suzuki, M. et al., (1996), "Random mutagenesis of *Thermus aquaticus* DNA polymerase I: Concordance of immutable sites in vivo with the crystal structure", *Proc. Natl. Acad. Sci. USA*, 93: 9670-9675.
Zhu, W., et al., (1994), "Mutagenesis of highly conserved lysine 340 of the PRD1 DNA polymerase", *Bochim Biophys, Acta* , 1219:260-266.
Bohlke, et al.; PCR performance of the B-type DNA polymerase from the thermophilic euryarchaeon Thermococcus aggregans improved by mutations in the Y-GG/A motif:; 2000; *Nucleic Acids Research*; 28(20): 3910-3917.
Mattila, et al.; "Fidelity of DNA synthesis by the Thermococcus litoralis DNA polymerase-an extremely heat stable enzyme with proofreading activity"; 1991; *Nucleic Acids Research*; 19(18): 4967-4973.
Gardner, et al.; "Determinants of nucleotide sugar recognition in an archaeon DNA polymerase"; 1999; *Nucleic Acids Research*; 27(12): 2545-2553.
European Search Report dated May 23, 2005.
U.S. Appl. No. 10/208,508, filed Jul. 30, 2002, from which the present application claims priority.
U.S. Appl. No. 10/079,241, filed Feb. 20, 2002, from which the present application claims priority.
U.S. Appl. No. 10/035,091, filed Dec. 21, 2001, from which the present application claims priority.
Non-final office action mailed Jan. 28, 2008 in U.S. Appl. No. 10/208,508.
Non-final office action mailed Jan. 14, 2008 in U.S. Appl. No. 10/079,241.
Non-final office action mailed Feb. 19, 2008 in U.S. Appl. No. 10/035,091.
Edgell, et al., "Gene Duplications in Evolution of Archaeal Family B DNA Polymerases", J. Bacteriol. (1997) vol. 179, pp. 2632-2640.
Hopfner et al., "Crystal Structure od a Thermostable Type B DNA Polymerase from *Thermococcus gorgonarius*", Proc.Natl.Acad.Sci (1999) vol. 96, pp. 3600-3605.

\* cited by examiner

*Primary Examiner* — Richard G Hutson

(57) ABSTRACT

The subject invention relates to compositions comprising an enzyme mixture which comprises a first enzyme and a second enzyme, where the first enzyme comprises a DNA polymerization activity and the second enzyme comprises an 3'-5' exonuclease activity and a reduced DNA polymerization activity. The invention also relates to the above compositions in kit format and methods for high fidelity DNA synthesis using the subject compositions of the invention.

50 Claims, 57 Drawing Sheets

Figure 1. PCR Proofreading Activity Assay
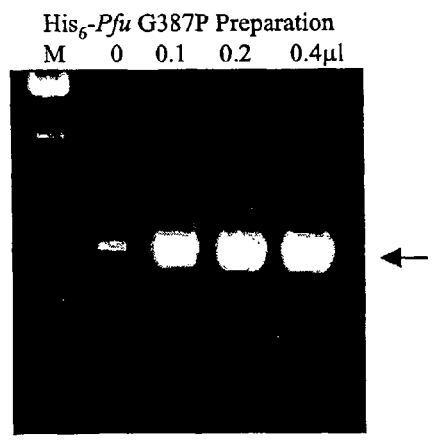
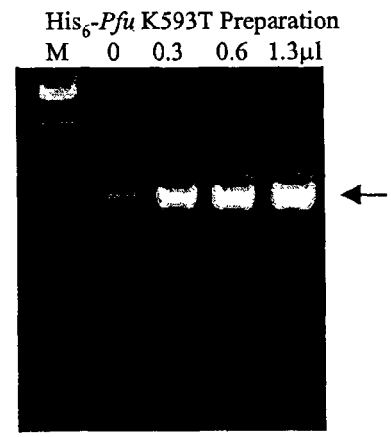

Figure 2. PCR Performance of *Pfu* plus *Pfu* G387P mutant blends
Long genomic targets:
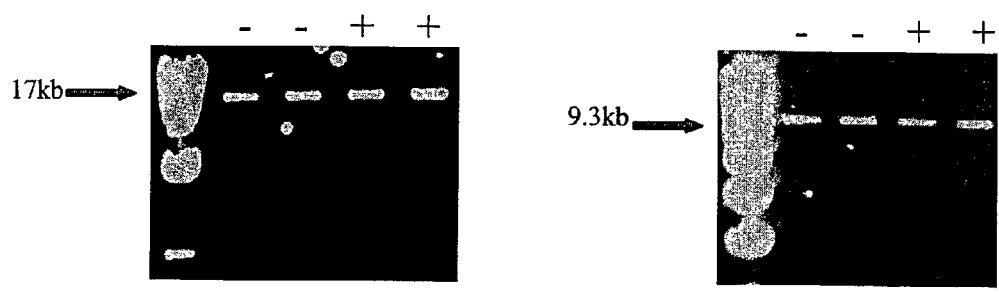
Short/medium genomic targets:
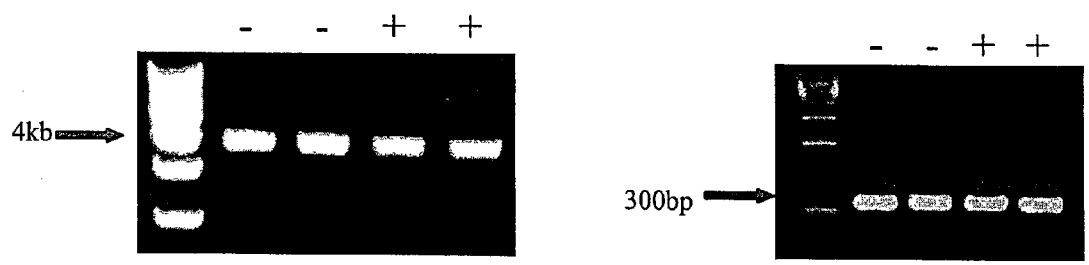

Figure 3. PCR Performance of *Taq* plus *Pfu* G387P mutant blends
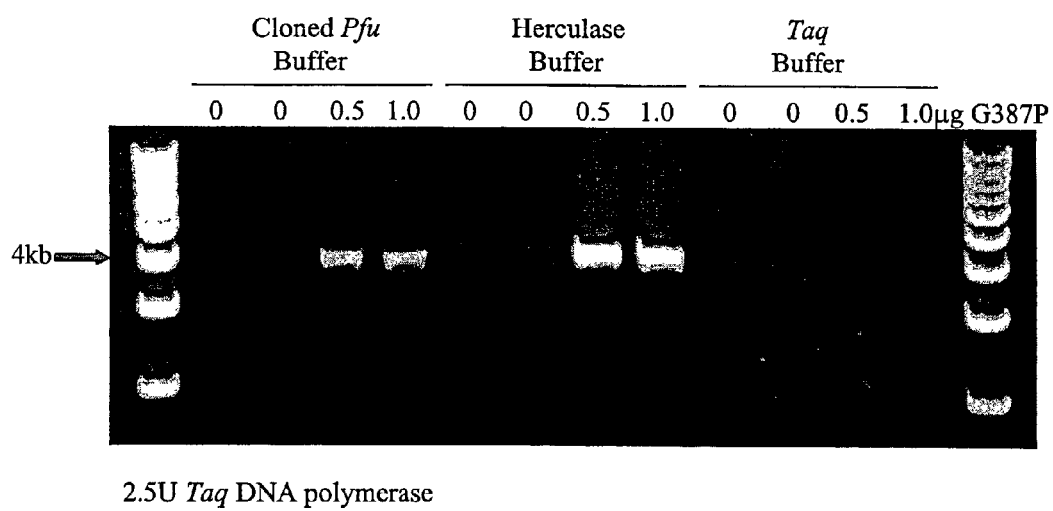
2.5U *Taq* DNA polymerase

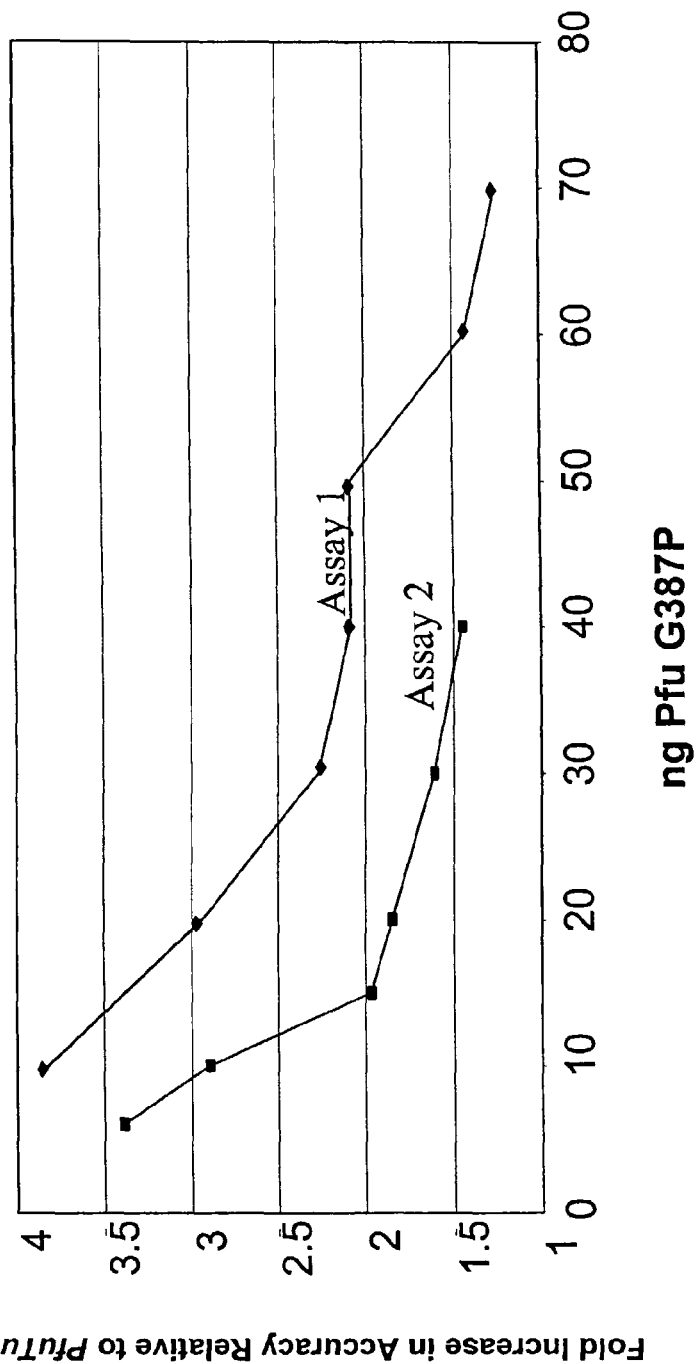
Figure 4. Variation in *PfuTurbo* Accuracy with Amount of *Pfu* G387P Mutant (Prep J)

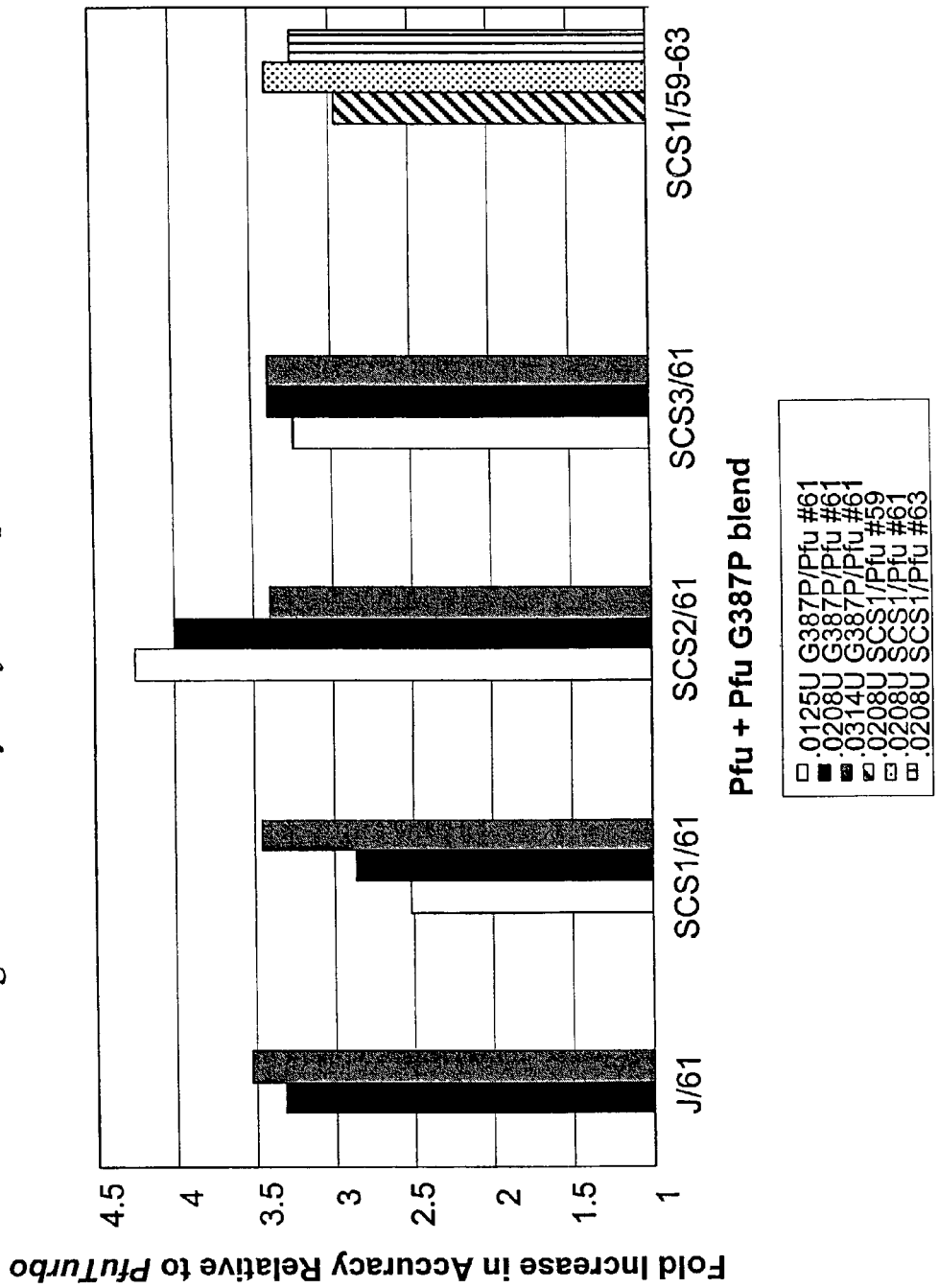
Figure 5. Accuracy of *PfuTurbo* plus *Pfu* G387P blends

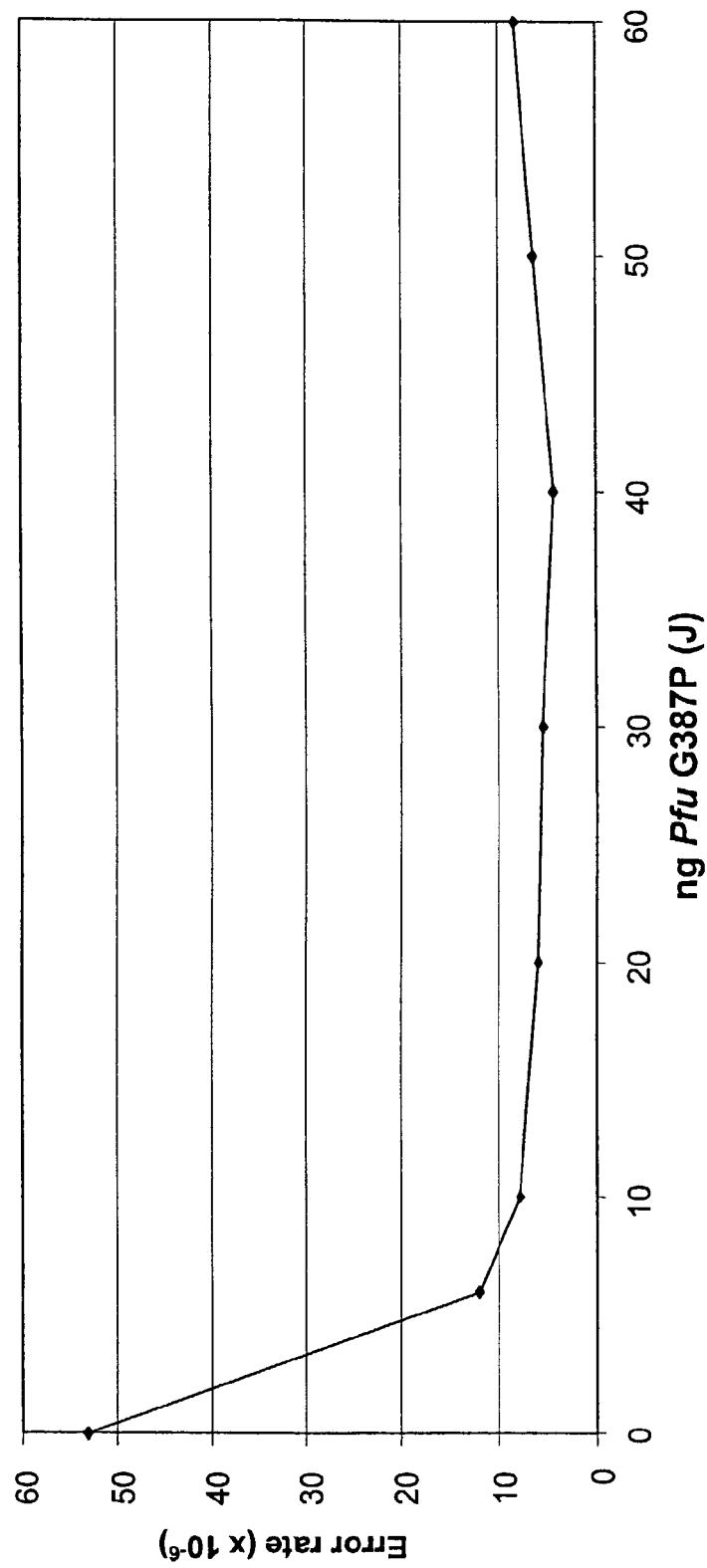

Figure 7

Figure 7 Polynucleotide and polypeptide sequences of various DNA polymerase mutants according to some embodiments of the invention Partitioning Domain Mutants >Pfu wild type
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tggfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks // [SEQ ID NO. 19]

>Pfu Y385N
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresn
tggfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks [SEQ ID NO. 20]

>Pfu Y385L
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresl
tggfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks [SEQ ID NO. 21]

>Pfu Y385H
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresh
tggfvkepekglwenivyldfralypsiiithnvspdtlnlegcknydiapqvghkfckdipgfipsllghlleerq

Figure 7 Continued

```
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks   [SEQ ID NO. 22]

>Pfu Y385Q
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresq
tggfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks   [SEQ ID NO. 23]

>Pfu Y385S
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlress
tggfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks   [SEQ ID NO. 24]

>Pfu G387S
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tsgfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks   [SEQ ID NO. 25]

>Pfu G387P
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tpgfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
```

2

Figure 7 Continued idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks [SEQ ID NO. 26]

>Pfu G388A
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tgafvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks [SEQ ID NO. 27]

>Pfu G388P
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tgpfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks [SEQ ID NO. 28]

>Tgo wild type
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
ggyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt [SEQ ID NO. 29]

>Tgo Y384N
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresna
ggyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws

Figure 7 Continued eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt   [SEQ ID NO. 30]

>Tgo Y384L
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresla
ggyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt   [SEQ ID NO. 31]

>Tgo Y384H
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresha
ggyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt   [SEQ ID NO. 32]

>Tgo Y384Q
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresqa
ggyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt   [SEQ ID NO. 33]

>Tgo Y384S
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrressa
ggyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki

Figure 7 Continued rpgtvisyivlkgsgrigdraipfdefdpakhkydaeyyienqvlpaverilrafgyrkedlryqktrqvglgawlk
pkt   [SEQ ID NO. 34]

>Tgo G386S
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
sgyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt   [SEQ ID NO. 35]

>Tgo G386P
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
pgyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt   [SEQ ID NO. 36]

>Tgo G387A
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
gayvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt   [SEQ ID NO. 37]

>Tgo G387P
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
gpyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki

5

Figure 7 Continued rpgtvisyivlkgsgrigdraipfdefdpakhkydaeyyienqvlpaverilrafgyrkedlryqktrqvglgawlk
pkt  [SEQ ID NO. 38]

>KOD wild type
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt  [SEQ ID NO. 39]

>KOD Y384N
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsne
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt  [SEQ ID NO. 40]

>KOD Y384L
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsle
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt  [SEQ ID NO. 41]

>KOD Y384H
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqshe
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki

Figure 7 Continued rpgtvisyivlkgsgrigdraipfderaptkhkydaeyyienqvlpaverilrafgyrkedlryqktrqvglsawlk
pkgt [SEQ ID NO. 42]

>KOD Y384Q
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsqe
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt [SEQ ID NO. 43]

>KOD Y384S
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsse
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt [SEQ ID NO. 44]

>KOD G386S
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
sgyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt [SEQ ID NO. 45]

>KOD G386P
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
pgyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki

Figure 7 Continued rpgtvisyivlkgsgrigdraipfdefdptkhkydaeyyienqvlpaverilrafgyrkedlryqktrqvglsawlk
pkgt    [SEQ ID NO. 46]

>KOD G387A
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
gayvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt    [SEQ ID NO. 47]

>KOD G387P
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
gpyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt    [SEQ ID NO. 48]

>Vent wild type
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tylggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr    [SEQ ID NO. 49]

>Vent Y387N
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tnlggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg

Figure 7 Continued ikvkpgtiisyivlkgsgkisdrvillteydprkhkydpdyyienqvlpavlrileafgyrkedlryqsskqtglda
wlkr    [SEQ ID NO. 50]

>Vent Y387L
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tllggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr    [SEQ ID NO. 51]

>Vent Y387H
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
thlggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr    [SEQ ID NO. 52]

>Vent Y387Q
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tqlggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr    [SEQ ID NO. 53]

>Vent Y387S
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tslggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg

Figure 7 Continued ikvkpgtiisyivlkgsgkisdrvillteydprkhkydpdyyienqvlpavlrileafgyrkedlryqsskqtglda
wlkr     [SEQ ID NO. 54]

>Vent G389S
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tylsgyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr     [SEQ ID NO. 55]

>Vent G389P
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tylpgyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr     [SEQ ID NO. 56]

>Vent G390A
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tylgayvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr     [SEQ ID NO. 57]

>Vent G390P
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tylgpyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg

Figure 7 Continued ikvkpgtiisyivlkgsgkisdrvillteydprkhkydpdyyienqvlpavlrileafgyrkedlryqsskqtglda
wlkr  [SEQ ID NO. 58]

>Deep Vent wild type
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 59]

>Deep Vent Y385N
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresn
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 60]

>Deep Vent Y385L
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresl
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 61]

>Deep Vent Y385H
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresh
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk

Figure 7 Continued

```
vrpgmvigyivlrgdgpiskrailaeefdlrkhkydaeyyienqvlpavlrileafgyrkedlrwqktkqtgltawl
nikkk  [SEQ ID NO. 62]

>Deep Vent Y385Q
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresq
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 63]

>Deep Vent Y385S
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlress
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 64]

>Deep Vent G387S
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
asgyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 65]

>Deep Vent G387P
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
apgyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk
```

Figure 7 Continued vrpgmvigyivlrgdgpiskrailaeefdlrkhkydaeyyienqvlpavlrileafgyrkedlrwqktkqtgltawl
nikkk  [SEQ ID NO. 66]

>Deep Vent G388A
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
agayvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkikvkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 67]

>Deep Vent G388P
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
agpyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkikvkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 68]

Polymerase Domain Mutants

>Pfu D405E
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tggfvkepekglwenivylefralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtdglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks  [SEQ ID NO. 69]

>Pfu T542P
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tggfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idpdglyatipggeseeikkkalefvkyinsklpglleleyegfykrgffvtkkryavideegkvitrgleivrrdw

Figure 7 Continued seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks   [SEQ ID NO. 70]

>Pfu D543G
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tggfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtgglyatipggeseeikkkalefvkyinsklpglleleyegfykrgffvtkkryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks   [SEQ ID NO. 71]

>Pfu K593T
mildvdyiteegkpvirlfkkengkfkiehdrtfrpyiyallrddskieevkkitgerhgkivrivdvekvekkflg
kpitvwklylehpqdvptirekvrehpavvdifeydipfakrylidkglipmegeeelkilafdietlyhegeefgk
gpiimisyadeneakvitwknidlpyvevvsseremikrflriirekdpdiivtyngdsfdfpylakraeklgiklt
igrdgsepkmqrigdmtavevkgrihfdlyhvitrtinlptytleavyeaifgkpkekvyadeiakawesgenlerv
akysmedakatyelgkeflpmeiqlsrlvgqplwdvsrsstgnlvewfllrkayernevapnkpseeeyqrrlresy
tggfvkepekglwenivyldfralypsiiithnvspdtlnlegcknydiapqvghkfckdipgfipsllghlleerq
kiktkmketqdpiekilldyrqkaikllansfygyygyakarwyckecaesvtawgrkyielvwkeleekfgfkvly
idtgglyatipggeseeikkkalefvkyinsklpglleleyegfykrgffvtktryavideegkvitrgleivrrdw
seiaketqarvletilkhgdveeavrivkeviqklanyeippeklaiyeqitrplheykaigphvavakklaakgvk
ikpgmvigyivlrgdgpisnrailaeeydpkkhkydaeyyienqvlpavlrilegfgyrkedlryqktrqvgltswl
nikks   [SEQ ID NO. 72]

>Tgo D404E
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
ggyvkeperglwenivylefrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dtdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaverilrafgyrkedlryqktrqvglgawlk
pkt   [SEQ ID NO. 73]

>Tgo T541P
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
ggyvkeperglwenivyldfrslypsiiithnvspdtlnregceeydvapqvghkfckdfpgfipsllgdlleerqk
vkkkmkatidpiekklldyrqraikilansfygyygyakarwyckecaesvtawgrqyiettireieekfgfkvlya
dpdgffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki

14

Figure 7 Continued rpgtvisyivlkgsgrigdraipfdefdpakhkydaeyyienqvlpaveril rafgyrkedlryqktrqvglgawlk
pkt   [SEQ ID NO. 74]

>Tgo D542G
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
ggyvkeperglwenivyldfrslypsiiithnvspdtlnregceeydvapqvghkfckdfpgfipsllgdlleerqk
vkkkmkatidpiekkllldyrqraikilansfygyygyakarwyckecaesvtawgrqyiettireieekfgfkvlya
dtggffatipgadaetvkkkakefldyinaklpglleleyegfykrgffvtkkkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaveril rafgyrkedlryqktrqvglgawlk
pkt   [SEQ ID NO. 75]

>Tgo K592T
mildtdyitedgkpvirifkkengefkidydrnfepyiyallkddsaiedvkkitaerhgttvrvvraekvkkkflg
rpievwklyfthpqdvpairdkikehpavvdiyeydipfakrylidkglipmegdeelkmlafdietlyhegeefae
gpilmisyadeegarvitwknidlpyvdvvstekemikrflkvvkekdpdvlityngdnfdfaylkkrseklgvkfi
lgregsepkiqrmgdrfavevkgrihfdlypvirrtinlptytleavyeaifgqpkekvyaeeiaqawetgeglerv
arysmedakvtyelgkeffpmeaqlsrlvgqslwdvsrsstgnlvewfllrkayernelapnkpderelarrresya
ggyvkeperglwenivyldfrslypsiiithnvspdtlnregceeydvapqvghkfckdfpgfipsllgdlleerqk
vkkkmkatidpiekkllldyrqraikilansfygyygyakarwyckecaesvtawgrqyiettireieekfgfkvlya
dtdgffatipgadaetvkkkakefldyinaklpglleleyegfykrgffvtktkyavideedkittrgleivrrdws
eiaketqarvleailkhgdveeavrivkevteklskyevppeklviyeqitrdlkdykatgphvavakrlaargiki
rpgtvisyivlkgsgrigdraipfdefdpakhkydaeyyienqvlpaveril rafgyrkedlryqktrqvglgawlk
pkt   [SEQ ID NO. 76]

>KOD D404E
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
ggyvkeperglwenivylefrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaveril rafgyrkedlryqktrqvglsawlk
pkgt   [SEQ ID NO. 77]

>KOD T541P
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dpdgffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki

Figure 7 Continued rpgtvisyivlkgsgrigdraipfdefdptkhkydaeyyienqvlpaverilrafgyrkedlryqktrqvglsawlk
pkgt [SEQ ID NO. 78]

>KOD D542G
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtggffatipgadaetvkkkameflnyinaklpgaleleyegfykrgffvtkkkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt [SEQ ID NO. 79]

>KOD K592T
mildtdyitedgkpvirifkkengefkieydrtfepyfyallkddsaieevkkitaerhgtvvtvkrvekvqkkflg
rpvevwklyfthpqdvpairdkirehgavidiyeydipfakrylidkglvpmegdeelkmlafdiqtlyhegeefae
gpilmisyadeegarvitwknvdlpyvdvvsteremikrflrvvkekdpdvlityngdnfdfaylkkrceklginfa
lgrdgsepkiqrmgdrfavevkgrihfdlypvirrtinlptytleavyeavfgqpkekvyaeeitpawetgenlerv
arysmedakvtyelgkeflpmeaqlsrligqslwdvsrsstgnlvewfllrkayernelapnkpdekelarrrqsye
ggyvkeperglwenivyldfrslypsiiithnvspdtlnregckeydvapqvghrfckdfpgfipsllgdlleerqk
ikkkmkatidpierklldyrqraikilansyygyygyararwyckecaesvtawgreyitmtikeieekygfkviys
dtdgffatipgadaetvkkkameflnyinaklpgaleleyegfykrgffvtktkyavideegkittrgleivrrdws
eiaketqarvleallkdgdvekavrivkevteklskyevppeklviheqitrdlkdykatgphvavakrlaargvki
rpgtvisyivlkgsgrigdraipfdefdptkhkydaeyyienqvlpaverilrafgyrkedlryqktrqvglsawlk
pkgt [SEQ ID NO. 80]

>Vent D407E
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tylggyvkepekglweniiylefrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr [SEQ ID NO. 81]

>Vent T544P
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktksklgaeeiaaiweteesmk
klaqysmedaratyelgkeffpmeaelakligqsvwdvsrsstgnlvewyllrvayarnelapnkpdeeeykrrlrt
tylggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadpdgfyatipgekpelikkkakeflnyinsklpglleleyegfylrgffvtkkryavideegrittrglevvrr
dwseiaketqakvleailkegsvekavevvrdvvekiakyrvpleklviheqitrdlkdykaigphvaiakrlaarg

Figure 7 Continued ikvkpgtiisyivlkgsgkisdrvillteydprkhkydpdyyienqvlpavlrileafgyrkedlryqsskqtglda
wlkr   [SEQ ID NO. 82]

>Vent D545G
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktkskl gaeeiaaiweteesmk
klaqysmedaratyelgkeffpmeaelakligqsvwdvsrsstgnlvewyllrvayarnelapnkpdeeeykrrlrt
tylggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtggfyatipgekpelikkkakeflnyinsklpgllelеyegfylrgffvtkkryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr   [SEQ ID NO. 83]

>Vent K595T
mildtdyitkdgkpiirifkkengefkieldphfqpyiyallkddsaieeikaikgerhgktvrvldavkvrkkflg
revevwklifehpqdvpamrgkirehpavvdiyeydipfakrylidkglipmegdeelkllafdietfyhegdefgk
geiimisyadeeearvitwknidlpyvdvvsneremikrfvqvvkekdpdviityngdnfdlpylikraeklgvrlv
lgrdkehpepkiqrmgdsfaveikgrihfdlfpvvrrtinlptytleavyeavlgktkskl gaeeiaaiweteesmk
klaqysmedaratyelgkeffpmeaelakligqsvwdvsrsstgnlvewyllrvayarnelapnkpdeeeykrrlrt
tylggyvkepekglweniiyldfrslypsiivthnvspdtlekegcknydvapivgyrfckdfpgfipsilgdliam
rqdikkkmkstidpiekkmldyrqraikllansyygymgypkarwyskecaesvtawgrhyiemtireieekfgfkv
lyadtdgfyatipgekpelikkkakeflnyinsklpgllelеyegfylrgffvtktryavideegrittrglevvrr
dwseiaketqakvleailkegsvekavevvrdvvekiakyrvpleklviheqitrdlkdykaigphvaiakrlaarg
ikvkpgtiisyivlkgsgkisdrvillteydprkhkydpdyyienqvlpavlrileafgyrkedlryqsskqtglda
wlkr   [SEQ ID NO. 84]

>Deep Vent D405E
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
aggyvkepekglweglvslefrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpgllelеyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk  [SEQ ID NO. 85]

>Deep Vent T542P
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idpdglyatipgakpeeikkkalefvdyinaklpgllelеyegfyvrgffvtkkkyalideegkiitrgleivrrdw
seiaketqakvleailkhgnveeavkivkevteklskyeippeklviyeqitrplheykaigphvavakrlaargvk

Figure 7 Continued vrpgmvigyivlrgdgpiskrailaeefdlrkhkydaeyyienqvlpavlrileafgyrkedlrwqktkqtgltawl
nikkk [SEQ ID NO. 86]

>Deep Vent D543G
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtgglyatipgakpeeikkkalefvdyinaklpgllleleyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk [SEQ ID NO. 87]

>Deep Vent K593T
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpgllleleyegfyvrgffvtktkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk [SEQ ID NO. 88]

Figure 7 Continued

Pfu DNA polymerase nucleotide sequence

```
atgattttag atgtggatta cataactgaa gaaggaaaac ctgttattag gctattcaaa   60
aaagagaacg gaaaatttaa gatagagcat gatagaactt ttagaccata catttacgct  120
cttctcaggg atgattcaaa gattgaagaa gttaagaaaa taacgggga aaggcatgga  180
aagattgtga gaattgttga tgtagagaag gttgagaaaa agtttctcgg caagcctatt  240
accgtgtgga aactttattt ggaacatccc caagatgttc ccactattag agaaaaagtt  300
agagaacatc cagcagttgt ggacatcttc gaatacgata ttccatttgc aaagagatac  360
ctcatcgaca aaggcctaat accaatggag ggggaagaag agctaaagat tcttgccttc  420
gatatagaaa ccctctatca cgaaggagaa gagtttggaa aggcccaat tataatgatt  480
agttatgcag atgaaaatga agcaaaggtg attacttgga aaaacataga tcttccatac  540
gttgaggttg tatcaagcga gagagatg ataaagagat ttctcaggat tatcagggag  600
aaggatcctg acattatagt tacttataat ggagactcat tcgcattccc atatttagcg  660
aaaaggcag aaaaacttgg gattaaatta accattggaa gagatggaag cgagcccaag  720
atgcagagaa taggcgatat gacggctgta gaagtcaagg gaagaataca tttcgacttg  780
tatcatgtaa taacaaggac aataaatctc ccaacataca cactagaggc tgtatatgaa  840
gcaatttttg gaaagccaaa ggagaaggta tacgccgacg agatagcaaa agcctgggaa  900
agtggagaga accttgagag agttgccaaa tactcgatgg aagatgcaaa ggcaacttat  960
gaactcggga agaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcagggaga gctacacagg tggattcgtt aaagagccag aaaaggggt gtgggaaaac 1200
atagtatacc tagatttag agccctatat ccctcgatta taattaccca caatgtttct 1260
cccgatactc taaatcttga gggatgcaag aactatgata tcgctcctca gtaggccac 1320
aagttctgca aggacatccc tggttttata ccaagtctct ggggacattt gttagaggaa 1380
agacaaaaga ttaagacaaa aatgaaggaa actcaagatc ctatagaaaa aatactcctt 1440
gactatagac aaaaagcgat aaaactctta gcaattcttt ctacggata ttatggctat 1500
gcaaaagcaa gatggtactg taaggagtgt gctgagagcg ttactgcctg gggaagaaag 1560
tacatcgagt tagtatggaa ggagctcgaa gaaagtttg gatttaaagt cctctacatt 1620
gacactgatg gtctctatgc aactatccca ggaggagaaa gtgaggaaat aaagaaaaag 1680
gctctagaat ttgtaaaata cataaattca aagctccctg gactgctaga gcttgaatat 1740
gaagggttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag.tacttagagg cgatggtcca attagcaata gggcaattct agctgaggaa 2160
tacgatccca aaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa atcctag    2328  [SEQ ID NO. 89]
```

Pfu Y385N NNN=AAT, AAC (All possible N codons)
Pfu Y385L NNN=TTA, TTG, CTT, CTC, CTA, CTG (All possible L codons)
Pfu Y385H NNN= CAT, CAC (All possible H codons)
Pfu Y385Q NNN= CAA, CAG (All possible Q codons)
Pfu Y385S NNN= TCT, TCC, TCA, TCG, AGT, AGC (All possible S codons)

```
atgattttag atgtggatta cataactgaa gaaggaaaac ctgttattag gctattcaaa   60
aaagagaacg gaaaatttaa gatagagcat gatagaactt ttagaccata catttacgct  120
cttctcaggg atgattcaaa gattgaagaa gttaagaaaa taacgggga aaggcatgga  180
aagattgtga gaattgttga tgtagagaag gttgagaaaa agtttctcgg caagcctatt  240
accgtgtgga aactttattt ggaacatccc caagatgttc ccactattag agaaaaagtt  300
agagaacatc cagcagttgt ggacatcttc gaatacgata ttccatttgc aaagagatac  360
```

Figure 7 Continued

```
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat tcgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaattttg gaaagccaaa ggagaaggta tacgccgacg atagcaaa agcctgggaa 900
agtggagaga accttgagag agttgccaaa tactcgatgg aagatgcaaa ggcaacttat 960
gaactcggga aagaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcaggGaga gcNNNacagg tggattcgtt aaagagccag aaaagggtt gtgggaaaac 1200
atagtatacc tagattttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg gggaagaaag 1560
tacatcgagt tagtatggaa ggagctcgaa gaaaagtttg gatttaaagt cctctacatt 1620
gacactgatg gtctctatgc aactatccca ggaggagaaa gtgaggaaat aagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328 [SEQ ID NO. 90]
```

Pfu G387S NNN= TCT, TCC, TCA, TCG, AGT, AGC (All possible S codons)
Pfu G387P NNN= CCT, CCA, CCG, CCC (All possible P codons)

```
atgattttag atgtggatta cataactgaa gaaggaaaac ctgttattag gctattcaaa 60
aaagagaacg gaaaatttaa gatagagcat gataagaactt ttagaccata catttacgct 120
cttctcaggg atgattcaaa gattgaagaa gttaagaaaa taacgggga aaggcatgga 180
aagattgtga gaattgttga tgtagagaag gttgagaaaa agtttctcgg caagcctatt 240
accgtgtgga aactttattt ggaacatccc caagatgttc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat tctcaggat tatcagggag 600
aaggatcctg acattatagt tacttataat ggagactcat tcgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaattttg gaaagccaaa ggagaaggta tacgccgacg atagcaaa agcctgggaa 900
agtggagaga accttgagag agttgccaaa tactcgatgg aagatgcaaa ggcaacttat 960
```

Figure 7 Continued

```
gaactcggga aagaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcagggaga gctacacaNN Nggattcgtt aaagagccag aaaaggggtt gtgggaaaac 1200
atagtatacc tagattttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg gggaagaaag 1560
tacatcgagt tagtatggaa ggagctcgaa gaaaagtttg gatttaaagt cctctacatt 1620
gacactgatg gtctctatgc aactatccca ggaggagaaa gtgaggaaat aaagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328    [SEQ ID NO. 91]
```

Pfu G388A NNN= GCA, GCT, GCC, GCG (All possible A codons)
Pfu G388P NNN= CCT, CCA, CCG, CCC (All possible P codons)

```
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacggggga aaggcatgga 180
aagattgtga gaattgttga tgtagagaag gttgagaaaa agtttctcgg caagcctatt 240
accgtgtgga aactttattt ggaacatccc caagatgttc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat cgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaattttg gaaagccaaa ggagaaggta tacgccgacg agatagcaaa agcctgggaa 900
agtggagaga accttgagag agttgccaaa tactcgatgg aagatgcaaa ggcaacttat 960
gaactcggga aagaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcagggaga gctacacagg tNNNttcgtt aaagagccag aaaaggggtt gtgggaaaac 1200
atagtatacc tagattttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
```

Figure 7 Continued

```
gcaaaagcaa gatggtactg taaggagtgt gctgagagcg ttactgcctg gggaagaaag 1560
tacatcgagt tagtatggaa ggagctcgaa gaaaagtttg gatttaaagt cctctacatt 1620
gacactgatg gtctctatgc aactatccca ggaggagaaa gtgaggaaat aagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag   2328   [SEQ ID NO. 92]

Pfu D405E NNN= GAA, GAG (All possible E codons)
atgattttag atgtggatta cataactgaa gaaggaaaac ctgttattag gctattcaaa 60
aaagagaacg gaaatttaa gatagagcat gatagaactt ttagaccata catttacgct 120
cttctcaggg atgattcaaa gattgaagaa gttaagaaaa taacggggga aaggcatgga 180
aagattgtga gaattgttga tgtagagaag gttgagaaaa agtttctcgg caagcctatt 240
accgtgtgga aacttttattt ggaacatccc caagatgttc ccactattag agaaaaagtt 300
agaacatc cagcagttgt ggacatcttc gaatacgata ttccatttgc aaagagatac 360
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat cgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaattttg gaaagccaaa ggagaaggta tacgccgacg agatagcaaa agcctgggaa 900
agtggagaga accttgagag agttgccaaa tactcgatgg aagatgcaaa ggcaacttat 960
gaactcggga agaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcagggaga gctacacagg tggattcgtt aaagagccag aaaaggggtt gtgggaaaac 1200
atagtatacc taNNNtttag agccctatat ccctcgatta taattaccca caatgtttct 1260
cccgatactc taaatcttga gggatgcaag aactatgata tcgctcctca gtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg gggaagaaag 1560
tacatcgagt tagtatggaa ggagctcgaa gaaaagtttg gatttaaagt cctctacatt 1620
gacactgatg gtctctatgc aactatccca ggaggagaaa gtgaggaaat aagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
```

Figure 7 Continued

```
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328  [SEQ ID NO. 93]

Pfu T542P NNN= CCT, CCA, CCG, CCC (All possible P codons)
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacggggga aaggcatgga 180
aagattgtga gaattgttga tgtagagaag gttgagaaaa agtttctcgg caagcctatt 240
accgtgtgga aactttattt ggaacatccc caagatgttc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat cgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaattttg gaaagccaaa ggagaaggta tacgccgacg agatagcaaa agcctgggaa 900
agtggagaga accttgagag agttgccaaa tactcgatgg aagatgcaaa ggcaacttat 960
gaactcggga agaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcagggaga gctacacagg tggattcgtt aaagagccag aaaaggggtt gtgggaaaac 1200
atagtatacc tagatttag agcccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg gggaagaaag 1560
tacatcgagt tagtatggaa ggagctcgaa gaaaagtttg gatttaaagt cctctacatt 1620
gacNNNgatg gtctctatgc aactatccca ggaggagaaa gtgaggaaat aaagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328  [SEQ ID NO. 94]

Pfu D543G NNN=GGT, GGC, GGA, GGG (All possible G codons)
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacggggga aaggcatgga 180
aagattgtga gaattgttga tgtagagaag gttgagaaaa agtttctcgg caagcctatt 240
accgtgtgga aactttattt ggaacatccc caagatgttc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
```

Figure 7 Continued

```
gatatagaaa ccctctatca cgaaggagaa gagtttggaa aaggcccaat tataatgatt  480
agttatgcag atgaaaatga agcaaaggtg attacttgga aaaacataga tcttccatac  540
gttgaggttg tatcaagcga gagagagatg ataaagagat ttctcaggat tatcagggag  600
aaggatcctg acattatagt tacttataat ggagactcat tcgcattccc atatttagcg  660
aaaagggcag aaaaacttgg gattaaatta accattggaa gagatggaag cgagcccaag  720
atgcagagaa taggcgatat gacggctgta gaagtcaagg gaagaataca tttcgacttg  780
tatcatgtaa taacaaggac aataaatctc ccaacataca cactagaggc tgtatatgaa  840
gcaattttg gaaagccaaa ggagaaggta tacgccgacg agatagcaaa agcctggaa   900
agtggagaga accttgagag agttgccaaa tactcgatgg aagatgcaaa ggcaacttat  960
gaactcggga aagaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcaggagga gctacacagg tggattcgtt aaagagccag aaaagggggtt gtgggaaaac 1200
atagtatacc tagatttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg gggaagaaag 1560
tacatcgagt tagtatggaa ggagctcgaa gaaaagtttg gatttaaagt cctctacatt 1620
gacactNNNg gtctctatgc aactatccca ggaggagaaa gtgaggaaat aaagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag   2328  [SEQ ID NO. 95]

Pfu K593T NNN=ACT, ACC, ACA, ACG (All possible T codons)
atgattttag atgtggatta cataactgaa gaaggaaaac tgttattag gctattcaaa   60
aaagagaacg gaaaattta gatagagcat gatagaactt ttagaccata catttacgct 120
cttctcaggg atgattcaaa gattgaagaa gttaagaaaa taacggggga aaggcatgga 180
aagattgtga gaattgttga tgtagagaag gttgagaaaa agtttctcgg caagcctatt 240
accgtgtgga aacttttatt ggaacatccc caagatgttc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat tcgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaattttg gaaagccaaa ggagaaggta tacgccgacg agatagcaaa agcctggaa  900
agtggagaga accttgagag agttgccaaa tactcgatgg aagatgcaaa ggcaacttat 960
gaactcggga aagaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
```

Figure 7 Continued

```
ctcagggaga gctacacagg tggattcgtt aaagagccag aaaagggtt  gtgggaaaac 1200
atagtatacc tagattttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg gggaagaaag 1560
tacatcgagt tagtatggaa ggagctcgaa gaaaagtttg gatttaaagt cctctacatt 1620
gacactgatg gtctctatgc aactatccca ggaggagaaa gtgaggaaat aaagaaaaag 1680
gctctagaat ttgtaaaata cataaattca aagctccctg gactgctaga gcttgaatat 1740
gaagggtttt ataagagggg attcttcgtt acgaagNNNa ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328    [SEQ ID NO. 96]
```

Figure 7 Continued

KOD DNA polymerase wild type
```
atgatcctcg acactgacta cataaccgag gatggaaagc ctgtcataag aatttcaag   60
aaggaaaacg gcgagtttaa gattgagtac gaccggactt ttgaacccta cttctacgcc  120
ctcctgaagg acgattctgc cattgaggaa gtcaagaaga taaccgccga gaggcacggg  180
acggttgtaa cggttaagcg ggttgaaaag gttcagaaga agttcctcgg agaccagtt  240
gaggtctgga aactctactt tactcatccg caggacgtcc cagcgataag ggacaagata  300
cgagagcatc cagcagttat tgacatctac gagtacgaca tacccttcgc caagcgctac  360
ctcatagaca agggattagt gccaatggaa ggcgacgagg agctgaaaat gctcgccttc  420
gacattgaaa ctctctacca tgagggcgag gagttcgccg aggggccaat ccttatgata  480
agctacgccg acgaggaagg ggccagggtg ataacttgga agaacgtgga tctcccctac  540
gttgacgtcg tctcgacgga gagggagatg ataaagcgct cctccgtgt tgtgaaggag  600
aaagacccgg acgttctcat aacctacaac ggcgacaact tcgacttcgc ctatctgaaa  660
aagcgctgtg aaaagctcgg aataaacttc gccctcggaa gggatggaag cgagccgaag  720
attcagagga tgggcgacag gtttgccgtc gaagtgaagg acggataca cttcgatctc  780
tatcctgtga taagacggac gataaacctg cccacataca cgcttgaggc cgtttatgaa  840
gccgtcttcg gtcagccgaa ggagaaggtt tacgctgagg aaataaccac agcctgggaa  900
accggcgaga accttgagag agtcgcccgc tactcgatgg aagatgcgaa ggtcacatac  960
gagcttggga aggagttcct tccgatggag gcccagcttt ctcgcttaat cggccagtcc 1020
ctctgggacg tctcccgctc cagcactggc aacctcgttg agtggttcct cctcaggaag 1080
gcctatgaga ggaatgagct ggccccgaac aagcccgatg aaaaggagct ggccagaaga 1140
cggcagagct atgaaggagg ctatgtaaaa gagcccgaga gagggttgtg ggagaacata 1200
gtgtacctag attttagatc cctgtacccc tcaatcatca tcacccacaa cgtctcgccg 1260
gatacgctca acagagaagg atgcaaggaa tatgacgttg ccccacaggt cggccaccgc 1320
ttctgcaagg acttcccagg atttatcccg agcctgcttg agacctcct agaggagagg 1380
cagaagataa agaagaagat gaaggccacg attgacccga tcgagaggaa gctcctcgat 1440
tacaggcaga gggccatcaa gatcctggca aacagctact acggttacta cggctatgca 1500
agggcgcgct ggtactgcaa ggagtgtgca gagagcgtaa cggcctgggg aagggagtac 1560
ataacgatga ccatcaagga gatagaggaa aagtacggct taaggtaat ctacagcgac 1620
accgacggat tttttgccac aataccctga gccgatgctg aaaccgtcaa aaagaaggct 1680
atggagttcc tcaagtatat caacgccaaa cttccgggcg cgcttgagct cgagtacgag 1740
ggcttctaca acgcggctt cttcgtcacg aagaagaagt atgcggtgat agacgaggaa 1800
ggcaagataa caacgcgcgg acttgagatt gtgaggcgtg actggagcga gatagcgaaa 1860
gagacgcagg cgagggttct tgaagctttg ctaaaggacg gtgacgtcga aaggccgtg 1920
aggatagtca agaagttac cgaaaagctg agcaagtacg aggttccgcc ggagaagctg 1980
gtgatccacg agcagataac gaggggattta aaggactaca aggcaaccgg tccccacgtt 2040
gccgttgcca agaggttggc cgcgagagga gtcaaaatac gccctggaac ggtgataagc 2100
tacatcgtgc tcaaggctc tgggaggata ggcgacaggg cgataccgtt cgacgagttc 2160
gacccgacga agcacaagta cgacgccgag tactacattg agaaccaggt tctcccagcc 2220
gttgagagaa ttctgagagc cttcggttac cgcaaggaag acctgcgcta ccagaagacg 2280
agacaggttg gtttgagtgc ttggctgaag ccgaagggaa cttga 2325 [SEQ ID NO. 97]
```

KOD Y384N NNN=AAT, AAC (All possible N codons)
KOD Y384L NNN=TTA, TTG, CTT, CTC, CTA, CTG (All possible L codons)
KOD Y384H NNN= CAT, CAC (All possible H codons)
KOD Y384Q NNN= CAA, CAG (All possible Q codons)
KOD Y384S NNN= TCT, TCC, TCA, TCG, AGT, AGC (All possible S codons)
```
atgatcctcg acactgacta cataaccgag gatggaaagc ctgtcataag aatttcaag   60
aaggaaaacg gcgagtttaa gattgagtac gaccggactt ttgaacccta cttctacgcc  120
ctcctgaagg acgattctgc cattgaggaa gtcaagaaga taaccgccga gaggcacggg  180
acggttgtaa cggttaagcg ggttgaaaag gttcagaaga agttcctcgg agaccagtt  240
gaggtctgga aactctactt tactcatccg caggacgtcc cagcgataag ggacaagata  300
cgagagcatc cagcagttat tgacatctac gagtacgaca tacccttcgc caagcgctac  360
```

Figure 7 Continued

```
ctcatagaca agggattagt gccaatggaa ggcgacgagg agctgaaaat gctcgccttc 420
gacattgaaa ctctctacca tgagggcgag gagttcgccg aggggccaat ccttatgata 480
agctacgccg acgaggaagg ggccaggqtg ataacttgga agaacgtgga tctcccctac 540
gttgacgtcg tctcgacgga gagggagatg ataaagcgct tcctccgtgt tgtgaaggag 600
aaagacccgg acgttctcat aacctacaac ggcgacaact tcgacttcgc ctatctgaaa 660
aagcgctgtg aaaagctcgg aataaacttc gccctcggaa gggatggaag cgagccgaag 720
attcagagga tgggcgacag gtttgccgtc gaagtgaagg gacggataca cttcgatctc 780
tatcctgtga taagacggac gataaacctg cccacataca cgcttgaggc cgtttatgaa 840
gccgtcttcg gtcagccgaa ggagaaggtt tacgctgagg aaataaccac agcctgggaa 900
accggcgaga accttgagag agtcgcccgc tactcgatgg aagatgcgaa ggtcacatac 960
gagcttggga aggagttcct tccgatggag gccagctttc tcgcttaat cggccagtcc 1020
ctctgggacg tctcccgctc cagcactggc aacctcgttg agtggttcct cctcaggaag 1080
gcctatgaga ggaatgagct ggccccgaac aagcccgatg aaaaggagct ggccagaaga 1140
cggcagagcN NNgaaggagg ctatgtaaaa gagcccgaga gagggttgtg ggagaacata 1200
gtgtacctag attttagatc cctgtacccc tcaatcatca tcacccacaa cgtctcgccg 1260
gatacgctca acagagaagg atgcaaggaa tatgacgttg ccccacaggt cggccaccgc 1320
ttctgcaagg acttccagg atttatcccg agcctgcttg gagacctcct agaggagagg 1380
cagaagataa agaagaagat gaaggccacg attgacccga tcgagaggaa gctcctcgat 1440
tacaggcaga gggccatcaa gatcctggca aacagctact acggttacta cggctatgca 1500
agggcgcgct ggtactgcaa ggagtgtgca gagagcgtaa cggcctgggg aagggagtac 1560
ataacgatga ccatcaagga gatagaggaa agtacggct ttaaggtaat ctacagcgac 1620
accgacggat ttttgccac aatacctgga gccgatgctg aaaccgtcaa aaagaaggct 1680
atggagttcc tcaagtatat caacgccaaa cttccgggcg cgcttgagct cgagtacgag 1740
ggcttctaca acgcggctt cttcgtcacg aagaagaagt atgcggtgat agacgaggaa 1800
ggcaagataa caacgcgcgg acttgagatt gtgaggcgtg actggagcga gatagcgaaa 1860
gagacgcagg cgagggttct tgaagctttg ctaaaggacg gtgacgtcga aaggccgtg 1920
aggatagtca aagaagttac cgaaaagctg agcaagtacg aggttccgcc ggagaagctg 1980
gtgatccacg agcagataac gagggattta aaggactaca aggcaaccgg tccccacgtt 2040
gccgttgcca agaggttggc cgcgagagga gtcaaaatac gccctggaac ggtgataagc 2100
tacatcgtgc tcaagggctc tgggaggata ggcgacaggg cgataccgtt cgacgagttc 2160
gacccgacga agcacaagta cgacgccgag tactacattg agaaccaggt tctcccagcc 2220
gttgagagaa ttctgagagc cttcggttac cgcaaggaag acctgcgcta ccagaagacg 2280
agacaggttg gtttgagtgc ttggctgaag ccgaagggaa cttga       2325  [SEQ ID NO. 98]
```

KOD G386S NNN= TCT, TCC, TCA, TCG, AGT, AGC (All possible S codons)
KOD G386P NNN= CCT, CCA, CCG, CCC (All possible P codons)

```
atgatcctcg acactgacta cataaccgag gatggaaagc ctgtcataag aattttcaag 60
aaggaaaacg gcgagtttaa gattgagtac gaccggactt ttgaaccta cttctacgcc 120
ctcctgaagg acgattctgc cattgaggaa gtcaagaaga taaccgccga gaggcacggg 180
acggttgtaa cggttaagcg ggttgaaaag gttcagaaga agttcctcgg agaccagtt 240
gaggtctgga aactctactt tactcatccg caggacgtcc cagcgataag ggacaagata 300
cgagagcatc cagcagttat tgacatctac gagtacgaca tacccttcgc caagcgctac 360
ctcatagaca agggattagt gccaatggaa ggcgacgagg agctgaaaat gctcgccttc 420
gacattgaaa ctctctacca tgagggcgag gagttcgccg aggggccaat ccttatgata 480
agctacgccg acgaggaagg ggccaggqtg ataacttgga agaacgtgga tctcccctac 540
gttgacgtcg tctcgacgga gagggagatg ataaagcgct tcctccgtgt tgtgaaggag 600
aaagacccgg acgttctcat aacctacaac ggcgacaact tcgacttcgc ctatctgaaa 660
aagcgctgtg aaaagctcgg aataaacttc gccctcggaa gggatggaag cgagccgaag 720
attcagagga tgggcgacag gtttgccgtc gaagtgaagg gacggataca cttcgatctc 780
tatcctgtga taagacggac gataaacctg cccacataca cgcttgaggc cgtttatgaa 840
gccgtcttcg gtcagccgaa ggagaaggtt tacgctgagg aaataaccac agcctgggaa 900
accggcgaga accttgagag agtcgcccgc tactcgatgg aagatgcgaa ggtcacatac 960
gagcttggga aggagttcct tccgatggag gccagctttc tcgcttaat cggccagtcc 1020
```

Figure 7 Continued

```
ctctgggacg tctcccgctc cagcactggc aacctcgttg agtggttcct cctcaggaag 1080
gcctatgaga ggaatgagct ggccccgaac aagcccgatg aaaaggagct ggccagaaga 1140
cggcagagct atgaaNNNgg ctatgtaaaa gagcccgaga gagggttgtg ggagaacata 1200
gtgtacctag attttagatc cctgtacccc tcaatcatca tcacccacaa cgtctcgccg 1260
gatacgctca acagagaagg atgcaaggaa tatgacgttg ccccacaggt cggccaccgc 1320
ttctgcaagg acttcccagg atttatcccg agcctgcttg agacctcct agaggagagg 1380
cagaagataa agaagaagat gaaggccacg attgacccga tcgagaggaa gctcctcgat 1440
tacaggcaga gggccatcaa gatcctggca aacagctact acggttacta cggctatgca 1500
agggcgcgct ggtactgcaa ggagtgtgca gagagcgtaa cggcctgggg aagggagtac 1560
ataacgatga ccatcaagga gatagaggaa aagtacggct ttaaggtaat ctacagcgac 1620
accgacggat tttttgccac aatacctgga gccgatgctg aaaccgtcaa aaagaaggct 1680
atggagttcc tcaagtatat caacgccaaa cttccgggcg cgcttgagct cgagtacgag 1740
ggcttctaca acgcggctt cttcgtcacg aagaagaagt atgcggtgat agacgaggaa 1800
ggcaagataa caacgcgcgg acttgagatt gtgaggcgtg actggagcga gatagcgaaa 1860
gagacgcagg cgagggttct tgaagctttg ctaaaggacg gtgacgtcga gaaggccgtg 1920
aggatagtca agaagttac cgaaaagctg agcaagtacg aggttccgcc ggagaagctg 1980
gtgatccacg agcagataac gagggattta aaggactaca aggcaaccgg tccccacgtt 2040
gccgttgcca agaggttggc cgcgagagga gtcaaaatac gccctggaac ggtgataagc 2100
tacatcgtgc tcaagggctc tgggaggata ggcgacaggg cgataccgtt cgacgagttc 2160
gacccgacga agcacaagta cgacgccgag tactacattg agaaccaggt tctcccagcc 2220
gttgagagaa ttctgagagc cttcggttac cgcaaggaag acctgcgcta ccagaagacg 2280
agacaggttg gtttgagtgc ttggctgaag ccgaagggaa cttga     2325  [SEQ ID NO. 99]

KOD G387A NNN= GCA, GCT, GCC, GCG (All possible A codons)
KOD G387P NNN= CCT, CCA, CCG, CCC (All possible P codons)
atgatcctcg acactgacta cataaccgag gatggaaagc ctgtcataag aattttcaag 60
aaggaaaacg gcgagtttaa gattgagtac gaccggactt tgaaccccta cttctacgcc 120
ctcctgaagg acgattctgc cattgaggaa gtcaagaaga taaccgccga gaggcacggg 180
acggttgtaa cggttaagcg ggttgaaaag gttcagaaga agttcctcgg agaccagtt 240
gaggtctgga aactctactt tactcatccg caggacgtcc cagcgataag ggacaagata 300
cgagagcatc cagcagttat tgacatctac gagtacgaca tacccttcgc caagcgctac 360
ctcatagaca agggattagt gccaatggaa ggcgacgagg agctgaaaat gctcgccttc 420
gacattgaaa ctctctacca tgagggcgag gagttcgccg aggggccaat ccttatgata 480
agctacgccg acgaggaagg ggccagggtg ataacttgga gaacgtgga tctcccctac 540
gttgacgtcg tctcgacgga gagggagatg ataaagcgct cctccgtgt tgtgaaggag 600
aaagacccgg acgttctcat aacctacaac ggcgacaact tcgacttcgc ctatctgaaa 660
aagcgctgtg aaaagctcgg aataaacttc gccctcggaa gggatggaag cgagccgaag 720
attcagagga tgggcgacag gtttgccgtc gaagtgaagg gacggataca cttcgatctc 780
tatcctgtga taagacggac gataaacctg cccacataca cgcttgaggc cgtttatgaa 840
gccgtcttcg gtcagccgaa ggagaaggtt tacgctgagg aaataaccac agcctgggaa 900
accggcgaga accttgagag agtcgcccgc tactcgatgg aagatgcgaa ggtcacatac 960
gagcttggga aggagttcct tccgatggag gcccagcttt ctcgcttaat cggccagtcc 1020
ctctgggacg tctcccgctc cagcactggc aacctcgttg agtggttcct cctcaggaag 1080
gcctatgaga ggaatgagct ggccccgaac aagcccgatg aaaaggagct ggccagaaga 1140
cggcagagct atgaaggaNN Ntatgtaaaa gagcccgaga gagggttgtg ggagaacata 1200
gtgtacctag attttagatc cctgtacccc tcaatcatca tcacccacaa cgtctcgccg 1260
gatacgctca acagagaagg atgcaaggaa tatgacgttg ccccacaggt cggccaccgc 1320
ttctgcaagg acttcccagg atttatcccg agcctgcttg agacctcct agaggagagg 1380
cagaagataa agaagaagat gaaggccacg attgacccga tcgagaggaa gctcctcgat 1440
tacaggcaga gggccatcaa gatcctggca aacagctact acggttacta cggctatgca 1500
agggcgcgct ggtactgcaa ggagtgtgca gagagcgtaa cggcctgggg aagggagtac 1560
ataacgatga ccatcaagga gatagaggaa aagtacggct ttaaggtaat ctacagcgac 1620
accgacggat tttttgccac aatacctgga gccgatgctg aaaccgtcaa aaagaaggct 1680
```

Figure 7 Continued

```
atggagttcc tcaagtatat caacgccaaa cttccgggcg cgcttgagct cgagtacgag 1740
ggcttctaca aacgcggctt cttcgtcacg aagaagaagt atgcggtgat agacgaggaa 1800
ggcaagataa caacgcgcgg acttgagatt gtgaggcgtg actggagcga gatagcgaaa 1860
gagacgcagg cgagggttct tgaagctttg ctaaaggacg gtgacgtcga aaggccgtg 1920
aggatagtca aagaagttac cgaaaagctg agcaagtacg aggttccgcc ggagaagctg 1980
gtgatccacg agcagataac gagggattta aaggactaca aggcaaccgg tccccacgtt 2040
gccgttgcca agaggttggc cgcgagagga gtcaaaatac gccctggaac ggtgataagc 2100
tacatcgtgc tcaagggctc tgggaggata ggcgacaggg cgataccgtt cgacgagttc 2160
gacccgacga agcacaagta cgacgccgag tactacattg agaaccaggt tctcccagcc 2220
gttgagagaa ttctgagagc cttcggttac cgcaaggaag acctgcgcta ccagaagacg 2280
agacaggttg gtttgagtgc ttggctgaag ccgaagggaa cttga 2325   [SEQ ID NO. 100]
```

KOD D404E NNN= GAA, GAG (All possible E codons)
```
atgatcctcg acactgacta cataaccgag gatggaaagc ctgtcataag aattttcaag 60
aaggaaaacg gcgagtttaa gattgagtac gaccggactt ttgaacccta cttctacgcc 120
ctcctgaagg acgattctgc cattgaggaa gtcaagaaga taaccgccga gaggcacggg 180
acggttgtaa cggttaagcg ggttgaaaag gttcagaaga agttcctcgg gagaccagtt 240
gaggtctgga aactctactt tactcatccg caggacgtcc cagcgataag ggacaagata 300
cgagagcatc cagcagttat tgacatctac gagtacgaca tacccttcgc caagcgctac 360
ctcatagaca agggattagt gccaatggaa ggcgacgagg agctgaaaat gctcgccttc 420
gacattgaaa ctctctacca tgagggcgag gagttcgccg aggggccaat ccttatgata 480
agctacgccg acgaggaagg ggccagggta taacttgga agaacgtgga tctcccctac 540
gttgacgtcg tctcgacgga gagggagatg ataaagcgct tcctccgtgt tgtgaaggag 600
aaagacccgg acgttctcat aacctacaac ggcgacaact cgacttcgc ctatctgaaa 660
aagcgctgtg aaaagctcgg aataaacttc gccctcggaa gggatggaag cgagccgaag 720
attcagagga tgggcgacag gtttgccgtc gaagtgaagg gacggataca cttcgatctc 780
tatcctgtga agacggac gataaacctg cccacataca cgcttgaggc cgtttatgaa 840
gccgtcttcg gtcagccgaa ggagaaggtt tacgctgagg aaataaccac agcctgggaa 900
accggcgaga accttgagag agtcgcccgc tactcgatgg aagatgcgaa ggtcacatac 960
gagcttggga aggagttcct tccgatggag gcccagcttt ctcgcttaat cggccagtcc 1020
ctctgggacg tctcccgctc cagcactggc aacctcgttg agtggttcct cctcaggaag 1080
gcctatgaga ggaatgagct ggccccgaac aagcccgatg aaaaggagct ggccagaaga 1140
cggcagagct atgaaggagg ctatgtaaaa gagcccgaga gagggttgtg ggagaacata 1200
gtgtacctaN NNtttagatc cctgtacccc tcaatcatca tcacccacaa cgtctcgccg 1260
gatacgctca acagagaagg atgcaaggaa tatgacgttg ccccacaggt cggccaccgc 1320
ttctgcaagg acttcccagg atttatcccg agcctgcttg agacctcct agaggagagg 1380
cagaagataa agaagaagat gaaggccacg attgacccga tcgagaggaa gctcctcgat 1440
tacaggcaga gggccatcaa gatcctggca aacagctact acggttacta cggctatgca 1500
agggcgcgct ggtactgcaa ggagtgtgca gagagcgtaa cggcctgggg aagggagtac 1560
ataacgatga ccatcaagga gatagaggaa aagtacggct taaggtaat ctacagcgac 1620
accgacggat ttttgccac aatacctgga gccgatgctg aaaccgtcaa aaagaaggct 1680
atggagttcc tcaagtatat caacgccaaa cttccgggcg cgcttgagct cgagtacgag 1740
ggcttctaca aacgcggctt cttcgtcacg aagaagaagt atgcggtgat agacgaggaa 1800
ggcaagataa caacgcgcgg acttgagatt gtgaggcgtg actggagcga gatagcgaaa 1860
gagacgcagg cgagggttct tgaagctttg ctaaaggacg gtgacgtcga aaggccgtg 1920
aggatagtca aagaagttac cgaaaagctg agcaagtacg aggttccgcc ggagaagctg 1980
gtgatccacg agcagataac gagggattta aaggactaca aggcaaccgg tccccacgtt 2040
gccgttgcca agaggttggc cgcgagagga gtcaaaatac gccctggaac ggtgataagc 2100
tacatcgtgc tcaagggctc tgggaggata ggcgacaggg cgataccgtt cgacgagttc 2160
gacccgacga agcacaagta cgacgccgag tactacattg agaaccaggt tctcccagcc 2220
gttgagagaa ttctgagagc cttcggttac cgcaaggaag acctgcgcta ccagaagacg 2280
agacaggttg gtttgagtgc ttggctgaag ccgaagggaa cttga 2325   [SEQ ID NO. 101]
```

Figure 7 Continued

KOD T541P NNN= CCT, CCA, CCG, CCC (All possible P codons)
```
atgatcctcg acactgacta cataaccgag gatggaaagc ctgtcataag aattttcaag    60
aaggaaaacg gcgagtttaa gattgagtac gaccggactt ttgaaccta cttctacgcc   120
ctcctgaagg acgattctgc cattgaggaa gtcaagaaga taaccgccga gaggcacggg   180
acggttgtaa cggttaagcg ggttgaaaag gttcagaaga agttcctcgg agaccagtt   240
gaggtctgga aactctactt tactcatccg caggacgtcc cagcgataag ggacaagata   300
cgagagcatc cagcagttat tgacatctac gagtacgaca tacccttcgc caagcgctac   360
ctcatagaca agggattagt gccaatggaa ggcgacgagg agctgaaaat gctcgccttc   420
gacattgaaa ctctctacca tgagggcgag gagttcgccg aggggccaat ccttatgata   480
agctacgccg acgaggaagg ggccagggtg ataacttgga gaacgtgga tctcccctac   540
gttgacgtcg tctcgacgga gagggagatg ataaagcgct cctccgtgt tgtgaaggag   600
aaagacccgg acgttctcat aacctacaac ggcgacaact tcgacttcgc ctatctgaaa   660
aagcgctgtg aaaagctcgg aataaacttc gccctcggaa gggatggaag cgagccgaag   720
attcagagga tgggcgacag gtttgccgtc gaagtgaagg gacggataca cttcgatctc   780
tatcctgtga taagacggac gataaacctg cccacataca cgcttgaggc cgttatgaa    840
gccgtcttcg gtcagccgaa ggagaaggtt tacgctgagg aaataaccac agcctgggaa   900
accggcgaga accttgagag agtcgcccgc tactcgatgg aagatgcgaa ggtcacatac   960
gagcttggga aggagttcct tccgatggag gcccagcttt ctcgcttaat cggccagtcc  1020
ctctgggacg tctcccgctc cagcactggc aacctcgttg agtggttcct cctcaggaag  1080
gcctatgaga ggaatgagct ggccccgaac aagcccgatg aaaaggagct ggccagaaga  1140
cggcagagct atgaaggagg ctatgtaaaa gagcccgaga gagggttgtg ggagaacata  1200
gtgtacctag attttagatc cctgtacccc tcaatcatca tcacccacaa cgtctcgccg  1260
gatacgctca acagagaagg atgcaaggaa tatgacgttg ccccacaggt cggccaccgc  1320
ttctgcaagg acttcccagg atttatcccg agcctgcttg agacctcct agaggagagg  1380
cagaagataa agaagaagat gaaggccacg attgacccga tcgagaggaa gctcctcgat  1440
tacaggcaga gggccatcaa gatcctggca aacagctact acggttacta cggctatgca  1500
agggcgcgct ggtactgcaa ggagtgtgca gagagcgtaa cggcctgggg aagggagtac  1560
ataacgatga ccatcaagga gatagaggaa aagtacggct taaggtaat ctacagcgac  1620
NNNgacggat ttttgccac aatacctgga gccgatgctg aaaccgtcaa aaagaaggct  1680
atggagttcc tcaagtatat caacgccaaa cttccgggcg cgcttgagct cgagtacgag  1740
ggcttctaca acgcggctt cttcgtcacg aagaagaagt atgcggtgat agacgaggaa  1800
ggcaagataa caacgcgcgg acttgagatt gtgaggcgtg actggagcga gatagcgaaa  1860
gagacgcagg cgagggttct tgaagctttg ctaaaggacg gtgacgtcga aaggccgtg   1920
aggatagtca aagaagttca cgaaaagctg agcaagtacg aggttccgcc ggagaagctg  1980
gtgatccacg agcagataac gagggattta aaggactaca aggcaaccgg tccccacgtt  2040
gccgttgcca agaggttggc cgcgagagga gtcaaaatac gccctggaac ggtgataagc  2100
tacatcgtgc tcaagggctc tgggaggata ggcgacaggg cgataccgtt cgacgagttc  2160
gacccgacga agcacaagta cgacgccgag tactacattg agaaccaggt tctcccagcc  2220
gttgagagaa ttctgagagc cttcggttac cgcaaggaag acctgcgcta ccagaagacg  2280
agacaggttg gtttgagtgc ttggctgaag ccgaagggaa cttga 2325    [SEQ ID NO. 102]
```

KOD D542G NNN=GGT, GGC, GGA, GGG (All possible G codons)
```
atgatcctcg acactgacta cataaccgag gatggaaagc ctgtcataag aattttcaag    60
aaggaaaacg gcgagtttaa gattgagtac gaccggactt ttgaaccta cttctacgcc   120
ctcctgaagg acgattctgc cattgaggaa gtcaagaaga taaccgccga gaggcacggg   180
acggttgtaa cggttaagcg ggttgaaaag gttcagaaga agttcctcgg agaccagtt   240
gaggtctgga aactctactt tactcatccg caggacgtcc cagcgataag ggacaagata   300
cgagagcatc cagcagttat tgacatctac gagtacgaca tacccttcgc caagcgctac   360
ctcatagaca agggattagt gccaatggaa ggcgacgagg agctgaaaat gctcgccttc   420
gacattgaaa ctctctacca tgagggcgag gagttcgccg aggggccaat ccttatgata   480
agctacgccg acgaggaagg ggccagggtg ataacttgga gaacgtgga tctcccctac   540
gttgacgtcg tctcgacgga gagggagatg ataaagcgct cctccgtgt tgtgaaggag   600
aaagacccgg acgttctcat aacctacaac ggcgacaact tcgacttcgc ctatctgaaa   660
```

Figure 7 Continued

```
aagcgctgtg aaaagctcgg aataaacttc gccctcggaa gggatggaag cgagccgaag 720
attcagagga tgggcgacag gtttgccgtc gaagtgaagg gacggataca cttcgatctc 780
tatcctgtga taagacggac gataaacctg cccacataca cgcttgaggc cgtttatgaa 840
gccgtcttcg gtcagccgaa ggagaaggtt tacgctgagg aaataaccac agcctgggaa 900
accggcgaga accttgagag agtcgcccgc tactcgatgg aagatgcgaa ggtcacatac 960
gagcttggga aggagttcct tccgatggag gcccagcttt ctcgcttaat cggccagtcc 1020
ctctgggacg tctcccgctc cagcactggc aacctcgttg agtggttcct cctcaggaag 1080
gcctatgaga ggaatgagct ggccccgaac aagcccgatg aaaaggagct ggccagaaga 1140
cggcagagct atgaaggagg ctatgtaaaa gagcccgaga gagggttgtg ggagaacata 1200
gtgtacctag attttagatc cctgtacccc tcaatcatca tcacccacaa cgtctcgccg 1260
gatacgctca acagagaagg atgcaaggaa tatgacgttg ccccacaggt cggccaccgc 1320
ttctgcaagg acttcccagg atttatcccg agcctgcttg agacctcct agaggagagg 1380
cagaagataa agaagaagat gaaggccacg attgacccga tcgagaggaa gctcctcgat 1440
tacaggcaga gggccatcaa gatcctggca aacagctact acggttacta cggctatgca 1500
agggcgcgct ggtactgcaa ggagtgtgca gagagcgtaa cggcctgggg aagggagtac 1560
ataacgatga ccatcaagga gatagaggaa aagtacggct ttaaggtaat ctacagcgac 1620
accNNNggat tttttgccac aatacctgga gccgatgctg aaaccgtcaa aaagaaggct 1680
atggagttcc tcaagtatat caacgccaaa cttccgggcg cgcttgagct cgagtacgag 1740
ggcttctaca acgcggctt cttcgtcacg aagaagaagt atgcggtgat agacgaggaa 1800
ggcaagataa caacgcgcgg acttgagatt gtgaggcgtg actggagcga gatagcgaaa 1860
gagacgcagg cgagggttct tgaagctttg ctaaaggacg gtgacgtcga gaaggccgtg 1920
aggatagtca aagaagttac cgaaaagctg agcaagtacg aggttccgcc ggagaagctg 1980
gtgatccacg agcagataac gagggattta aaggactaca aggcaaccgg tccccacgtt 2040
gccgttgcca agaggttggc cgcgagagga gtcaaaatac gccctggaac ggtgataagc 2100
tacatcgtgc tcaagggctc tgggaggata ggcgacaggg cgataccgtt cgacgagttc 2160
gacccgacga agcacaagta cgacgccgag tactacattg agaaccaggt tctcccagcc 2220
gttgagagaa ttctgagagc cttcggttac cgcaaggaag acctgcgcta ccagaagacg 2280
agacaggttg gtttgagtgc ttggctgaag ccgaagggaa cttga 2325   [SEQ ID NO. 103]
```

KOD K592T NNN=ACT, ACC, ACA, ACG (All possible T codons)
```
atgatcctcg acactgacta cataaccgag gatggaaagc ctgtcataag aattttcaag 60
aaggaaaacg gcgagtttaa gattgagtac gaccggactt tgaaccccta cttctacgcc 120
ctcctgaagg acgattctgc cattgaggaa gtcaagaaga taaccgccga gaggcacggg 180
acggttgtaa cggttaagcg ggttgaaaag gttcagaaga agttcctcgg agaccagtt 240
gaggtctgga aactctactt tactcatccg caggacgtcc cagcgataag ggacaagata 300
cgagagcatc cagcagttat tgacatctac gagtacgaca tacccttcgc caagcgctac 360
ctcatagaca agggattagt gccaatggaa ggcgacgagg agctgaaaat gctcgccttc 420
gacattgaaa ctctctacca tgagggcgag gagttcgccg aggggccaat cctttatgata 480
agctacgccg acgaggaagg ggccagggtg ataacttgga gaacgtgga tctcccctac 540
gttgacgtcg tctcgacgga gagggagatg ataaagcgct tcctccgtgt tgtgaaggag 600
aaagacccgg acgttctcat aacctacaac ggcgacaact tcgacttcgc ctatctgaaa 660
aagcgctgtg aaaagctcgg aataaacttc gccctcggaa gggatggaag cgagccgaag 720
attcagagga tgggcgacag gtttgccgtc gaagtgaagg gacggataca cttcgatctc 780
tatcctgtga taagacggac gataaacctg cccacataca cgcttgaggc cgtttatgaa 840
gccgtcttcg gtcagccgaa ggagaaggtt tacgctgagg aaataaccac agcctgggaa 900
accggcgaga accttgagag agtcgcccgc tactcgatgg aagatgcgaa ggtcacatac 960
gagcttggga aggagttcct tccgatggag gcccagcttt ctcgcttaat cggccagtcc 1020
ctctgggacg tctcccgctc cagcactggc aacctcgttg agtggttcct cctcaggaag 1080
gcctatgaga ggaatgagct ggccccgaac aagcccgatg aaaaggagct ggccagaaga 1140
cggcagagct atgaaggagg ctatgtaaaa gagcccgaga gagggttgtg ggagaacata 1200
gtgtacctag attttagatc cctgtacccc tcaatcatca tcacccacaa cgtctcgccg 1260
gatacgctca acagagaagg atgcaaggaa tatgacgttg ccccacaggt cggccaccgc 1320
ttctgcaagg acttcccagg atttatcccg agcctgcttg agacctcct agaggagagg 1380
```

Figure 7 Continued

```
cagaagataa agaagaagat gaaggccacg attgacccga tcgagaggaa gctcctcgat 1440
tacaggcaga gggccatcaa gatcctggca aacagctact acggttacta cggctatgca 1500
agggcgcgct ggtactgcaa ggagtgtgca gagagcgtaa cggcctgggg aagggagtac 1560
ataacgatga ccatcaagga gatagaggaa aagtacggct ttaaggtaat ctacagcgac 1620
accgacggat tttttgccac aatacctgga gccgatgctg aaaccgtcaa aaagaaggct 1680
atggagttcc tcaagtatat caacgccaaa cttccgggcg cgcttgagct cgagtacgag 1740
ggcttctaca aacgcggctt cttcgtcacg aagNNNaagt atgcggtgat agacgaggaa 1800
ggcaagataa caacgcgcgg acttgagatt gtgaggcgtg actggagcga gatagcgaaa 1860
gagacgcagg cgagggttct tgaagctttg ctaaaggacg gtgacgtcga aaggccgtg  1920
aggatagtca aagaagttac cgaaaagctg agcaagtacg aggttccgcc ggagaagctg 1980
gtgatccacg agcagataac gagggattta aaggactaca aggcaaccgg tccccacgtt 2040
gccgttgcca agaggttggc cgcgagagga gtcaaaatac gccctggaac ggtgataagc 2100
tacatcgtgc tcaagggctc tgggaggata ggcgacaggg cgataccgtt cgacgagttc 2160
gacccgacga agcacaagta cgacgccgag tactacattg agaaccaggt tctcccagcc 2220
gttgagagaa ttctgagagc cttcggttac cgcaaggaag acctgcgcta ccagaagacg 2280
agacaggttg gtttgagtgc ttggctgaag ccgaagggaa cttga      2325     [SEQ ID NO. 104]
```

Figure 7 Continued

Vent DNA polymerase wild type
```
atgatactgg acactgatta cataacaaaa gatggcaagc ctataatccg aattttttaag  60
aaagagaacg gggagtttaa aatagaactt gaccctcatt ttcagcccta tatatatgct 120
cttctcaaag atgactccgc tattgaggag ataaaggcaa taaagggcga gagacatgga 180
aaaactgtga gagtgctcga tgcagtgaaa gtcaggaaaa aattttttggg aagggaagtt 240
gaagtctgga agctcatttt cgagcatccc caagacgttc cagctatgcg gggcaaaata 300
agggaacatc cagctgtggt tgacatttac gaatatgaca tacccttttgc caagcgttat 360
ctcatagaca agggcttgat tcccatggag ggagacgagg agcttaagct ccttgccttt 420
gatattgaaa cgttttatca tgagggagat gaatttggaa agggcgagat aataatgatt 480
agttatgccg atgaagaaga ggccagagta atcacatgga aaaatatcga tttgccgtat 540
gtcgatgttg tgtccaatga aagagaaatg ataaagcgtt ttgttcaagt tgttaaagaa 600
aaagaccccg atgtgataat aacttacaat ggggacaatt ttgatttgcc gtatctcata 660
aaacgggcag aaaagctggg agttcggctt gtcttaggaa gggacaaaga acatcccgaa 720
cccaagattc agaggatggg tgatagtttt gctgtggaaa tcaagggtag aatccacttt 780
gatcttttcc cagttgtgcg aaggacgata aacctcccaa cgtatacgct tgaggcagtt 840
tatgaagcag tttttaggaaa aaccaaaagc aaattaggag cagaggaaat tgccgctata 900
tgggaaacag aagaaagcat gaaaaaacta gcccagtact caatggaaga tgctagggca 960
acgtatgagc tcgggaagga attcttcccc atggaagctg agctggcaaa gctgataggt 1020
caaagtgtat gggacgtctc gagatcaagc accggcaacc tcgtggagtg gtatctttta 1080
agggtggcat acgcgaggaa tgaacttgca ccgaacaaac ctgatgagga agagtataaa 1140
cggcgcttaa gaacaactta cctgggagga tatgtaaaag agccagaaaa aggtttgtgg 1200
gaaaatatca tttatttgga tttccgcagt ctgtacccct caataatagt tactcacaac 1260
gtatccccag ataccctctga aaaagagggc tgtaagaatt acgatgttgc tccgatagta 1320
ggatataggt tctgcaagga cttttccgggc tttattccct ccatactcgg ggacttaatt 1380
gcaatgagcc aagatataaa gaagaaaatg aaatccacaa ttgacccgat cgaaaagaaa 1440
atgctcgatt ataggcaaag ggctattaaa ttgcttgcaa acagctatta cggctatatg 1500
gggtatccta aggcaagatg gtactcgaag gaatgtgctg aaagcgttac cgcatggggg 1560
agacactaca tagagatgac gataagagaa atagaggaaa agttcggctt taaggttctt 1620
tatgcggaca ctgacggctt ttatgccaca atacccgggg aaaagcctga actcattaaa 1680
aagaaagcca aggaattcct aaactacata aactccaaac ttccaggtct gcttgagctt 1740
gagtatgagg gcttttactt gagaggattc tttgttacaa aaaagcgcta tgcagtcata 1800
gatgaagagg gcaggataac aacaaggggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaaatacag ggttccactt 1980
gaaaagcttg ttatccatga gcagattacc agggatttaa aggactacaa agccattggc 2040
cctcatgtcg cgatagcaaa aagacttgcc gcaagaggga taaagtgaa accgggcaca 2100
ataataagct atatcgttct caaagggagc ggaaagataa gcgatagggt aatttttactt 2160
acagaatacg atcctagaaa acacaagtac gatccggact actacataga aaaccaagtt 2220
ttgccggcag tacttaggat actcgaagcg tttggataca gaaaggagga tttaaggtat 2280
caaagctcaa aacaaaccgg cttagatgca tggctcaaga ggtag 2325   [SEQ ID NO. 105]
```
Vent Y387N NNN=AAT, AAC (All possible N codons)
Vent Y387L NNN=TTA, TTG, CTT, CTC, CTA, CTG (All possible L codons)
Vent Y387H NNN= CAT, CAC (All possible H codons)
Vent Y387Q NNN= CAA, CAG (All possible Q codons)
Vent Y387S NNN= TCT, TCC, TCA, TCG, AGT, AGC (All possible S codons)

```
atgatactgg acactgatta cataacaaaa gatggcaagc ctataatccg aattttttaag  60
aaagagaacg gggagtttaa aatagaactt gaccctcatt ttcagcccta tatatatgct 120
cttctcaaag atgactccgc tattgaggag ataaaggcaa taaagggcga gagacatgga 180
aaaactgtga gagtgctcga tgcagtgaaa gtcaggaaaa aattttttggg aagggaagtt 240
gaagtctgga agctcatttt cgagcatccc caagacgttc cagctatgcg gggcaaaata 300
agggaacatc cagctgtggt tgacatttac gaatatgaca tacccttttgc caagcgttat 360
```

Figure 7 Continued

```
ctcatagaca agggcttgat tcccatggag ggagacgagg agcttaagct ccttgccttt 420
gatattgaaa cgttttatca tgagggagat gaatttggaa agggcgagat aataatgatt 480
agttatgccg atgaagaaga ggccagagta atcacatgga aaaatatcga tttgccgtat 540
gtcgatgttg tgtccaatga agagaaatg ataaagcgtt ttgttcaagt tgttaaagaa 600
aaagaccccg atgtgataat aacttacaat ggggacaatt ttgatttgcc gtatctcata 660
aaacgggcag aaaagctggg agttcggctt gtcttaggaa gggacaaaga acatcccgaa 720
cccaagattc agaggatggg tgatagtttt gctgtggaaa tcaagggtag aatccacttt 780
gatcttttcc cagttgtgcg aaggacgata aacctcccaa cgtatacgct tgaggcagtt 840
tatgaagcag ttttaggaaa aaccaaaagc aaattaggag cagaggaaat tgccgctata 900
tgggaaacag aagaaagcat gaaaaaacta gcccagtact caatggaaga tgctagggca 960
acgtatgagc tcgggaagga attcttcccc atggaagctg agctggcaaa gctgataggt 1020
caaagtgtat gggacgtctc gagatcaagc accggcaacc tcgtggagtg gtatcttta 1080
agggtggcat acgcgaggaa tgaacttgca ccgaacaaac ctgatgagga agagtataaa 1140
cggcgcttaa gaacaactNN Nctgggagga tatgtaaaag agccagaaaa aggtttgtgg 1200
gaaaatatca tttatttgga tttccgcagt ctgtacccct caataatagt tactcacaac 1260
gtatccccag ataccttga aaaagagggc tgtaagaatt acgatgttgc tccgatagta 1320
ggatataggt tctgcaagga cttccgggc tttattcct ccatactcgg ggacttaatt 1380
gcaatgaggc aagatataaa gaagaaatg aaatccacaa ttgacccgat cgaaaagaaa 1440
atgctcgatt ataggcaaag ggctattaaa ttgcttgcaa acagctatta cggctatatg 1500
gggtatccta aggcaagatg gtactcgaag gaatgtgctg aaagcgttac cgcatggggg 1560
agacactaca tagagatgac gataagagaa atagaggaaa agttcggctt taaggttctt 1620
tatgcggaca ctgacggctt ttatgccaca ataccegggg aaaagcctga actcattaaa 1680
aagaaagcca aggaattcct aaactacata aactccaaac ttccaggtct gcttgagctt 1740
gagtatgagg gcttttactt gagaggattc tttgttacaa aaaagcgcta tgcagtcata 1800
gatgaagagg gcaggataac aacaaggggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaaatacag ggttccactt 1980
gaaaagcttg ttatccatga gcagattacc agggatttaa aggactacaa agccattggc 2040
cctcatgtcg cgatagcaaa aagacttgcc gcaagaggga taaaagtgaa accgggcaca 2100
ataataagct atatcgttct caagggagc ggaaagataa gcgataggg aattttactt 2160
acagaatacg atcctagaaa acacaagtac gatccggact actacataga aaaccaagtt 2220
ttgccggcag tacttaggat actcgaagcg tttggataca gaaggagga tttaaggtat 2280
caaagctcaa aacaaaccgg cttagatgca tggctcaaga ggtag 2325    [SEQ ID NO. 106]
```

Vent G389S NNN= TCT, TCC, TCA, TCG, AGT, AGC (All possible S codons)
Vent G389P NNN= CCT, CCA, CCG, CCC (All possible P codons)

```
atgatactgg acactgatta cataacaaaa gatggcaagc ctataatccg aattttttaag 60
aaagagaacg gggagtttaa aatagaactt gaccctcatt ttcagcccta tatatatgct 120
cttctcaaag atgactccgc tattgaggag ataaaggcaa taagggcga gagacatgga 180
aaaactgtga gagtgctcga tgcagtgaaa gtcaggaaaa aattttttggg aagggaagtt 240
gaagtctgga agctcatttt cgagcatccc caagacgttc cagctatgcg gggcaaaata 300
agggaacatc cagctgtggt tgacatttac gaatatgaca tacccttgc caagcgttat 360
ctcatagaca agggcttgat tcccatggag ggagacgagg agcttaagct ccttgccttt 420
gatattgaaa cgttttatca tgagggagat gaatttggaa agggcgagat aataatgatt 480
agttatgccg atgaagaaga ggccagagta atcacatgga aaaatatcga tttgccgtat 540
gtcgatgttg tgtccaatga agagaaatg ataaagcgtt ttgttcaagt tgttaaagaa 600
aaagaccccg atgtgataat aacttacaat ggggacaatt ttgatttgcc gtatctcata 660
aaacgggcag aaaagctggg agttcggctt gtcttaggaa gggacaaaga acatcccgaa 720
cccaagattc agaggatggg tgatagtttt gctgtggaaa tcaagggtag aatccactt 780
gatcttttcc cagttgtgcg aaggacgata aacctcccaa cgtatacgct tgaggcagtt 840
tatgaagcag ttttaggaaa aaccaaaagc aaattaggag cagaggaaat tgccgctata 900
tgggaaacag aagaaagcat gaaaaaacta gcccagtact caatggaaga tgctagggca 960
acgtatgagc tcgggaagga attcttcccc atggaagctg agctggcaaa gctgataggt 1020
```

Figure 7 Continued

```
caaagtgtat gggacgtctc gagatcaagc accggcaacc tcgtggagtg gtatctttta 1080
agggtggcat acgcgaggaa tgaacttgca ccgaacaaac ctgatgagga agagtataaa 1140
cggcgcttaa gaacaactta cctgNNNgga tatgtaaaag agccagaaaa aggtttgtgg 1200
gaaaatatca tttatttgga tttccgcagt ctgtacccct caataatagt tactcacaac 1260
gtatccccag atacccttga aaaagagggc tgtaagaatt acgatgttgc tccgatagta 1320
ggatataggt tctgcaagga ctttccgggc tttattccct ccatactcgg ggacttaatt 1380
gcaatgaggc aagatataaa gaagaaaatg aaatccacaa ttgacccgat cgaaaagaaa 1440
atgctcgatt ataggcaaag ggctattaaa ttgcttgcaa acagctatta cggctatatg 1500
gggtatccta aggcaagatg gtactcgaag gaatgtgctg aaagcgttac cgcatggggg 1560
agacactaca tagagatgac gataagagaa atagaggaaa agttcggctt taaggttctt 1620
tatgcggaca ctgacggctt ttatgccaca atacccgggg aaaagcctga actcattaaa 1680
aagaaagcca aggaattcct aaactacata aactccaaac ttccaggtct gcttgagctt 1740
gagtatgagg gcttttactt gagaggattc tttgttacaa aaaagcgcta tgcagtcata 1800
gatgaagagg gcaggataac aacaaggggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaaatacag ggttccactt 1980
gaaaagcttg ttatccatga gcagattacc agggatttaa aggactacaa agccattggc 2040
cctcatgtcg cgatagcaaa aagacttgcc gcaagaggga taaaagtgaa accgggcaca 2100
ataataagct atatcgttct caaagggagc ggaaagataa gcgataggt aattttactt 2160
acagaatacg atcctagaaa acacaagtac gatccggact actacataga aaaccaagtt 2220
ttgccggcag tacttaggat actcgaagcg tttggataca gaaaggagga tttaaggtat 2280
caaagctcaa aacaaaccgg cttagatgca tggctcaaga ggtag 2325 [SEQ ID NO. 107]
```

Vent G390A NNN= GCA, GCT, GCC, GCG (All possible A codons)
Vent G390P NNN= CCT, CCA, CCG, CCC (All possible P codons)

```
atgatactgg acactgatta cataacaaaa gatggcaagc ctataatccg aattttttaag 60
aaagagaacg gggagtttaa aatagaactt gaccctcatt ttcagcccta tatatatgct 120
cttctcaaag atgactccgc tattgaggag ataaaggcaa taaagggcga gagacatgga 180
aaaactgtga gagtgctcga tgcagtgaaa gtcaggaaaa aattttttggg aagggaagtt 240
gaagtctgga agctcatttt cgagcatccc caagacgttc agctatgcg gggcaaaata 300
agggaacatc cagctgtggt tgacatttac gaatatgaca tacccctttgc caagcgttat 360
ctcatagaca agggcttgat tcccatggag ggagacgagg agcttaagct ccttgccttt 420
gatattgaaa cgttttatca tgagggagat gaatttggaa agggcgagat aataatgatt 480
agttatgccg atgaagaaga ggccagagta atcacatgga aaaatatcga tttgccgtat 540
gtcgatgttg tgtccaatga aagagaaatg ataaagcgtt ttgttcaagt tgttaaagaa 600
aaagaccccg atgtgataat aacttacaat gggacaatt tgatttgcc gtatctcata 660
aaacgggcag aaaagctggg agttcggctt gtcttaggaa gggacaaaga acatcccgaa 720
cccaagattc agaggatggg tgatagtttt gctgtggaaa tcaagggtag aatccacttt 780
gatctttttcc cagttgtgcg aaggacgata aacctcccaa cgtatacgct tgaggcagtt 840
tatgaagcag ttttaggaaa aaccaaaagc aaattaggag cagaggaaat tgccgctata 900
tgggaaacag aagaaagcat gaaaaaacta gcccagtact caatggaaga tgctagggca 960
acgtatgagc tcgggaagga attcttcccc atggaagctg agctggcaaa gctgataggt 1020
caaagtgtat gggacgtctc gagatcaagc accggcaacc tcgtggagtg gtatctttta 1080
agggtggcat acgcgaggaa tgaacttgca ccgaacaaac ctgatgagga agagtataaa 1140
cggcgcttaa gaacaactta cctgggaNNN tatgtaaaag agccagaaaa aggtttgtgg 1200
gaaaatatca tttatttgga tttccgcagt ctgtacccct caataatagt tactcacaac 1260
gtatccccag atacccttga aaaagagggc tgtaagaatt acgatgttgc tccgatagta 1320
ggatataggt tctgcaagga ctttccgggc tttattccct ccatactcgg ggacttaatt 1380
gcaatgaggc aagatataaa gaagaaaatg aaatccacaa ttgacccgat cgaaaagaaa 1440
atgctcgatt ataggcaaag ggctattaaa ttgcttgcaa acagctatta cggctatatg 1500
gggtatccta aggcaagatg gtactcgaag gaatgtgctg aaagcgttac cgcatggggg 1560
agacactaca tagagatgac gataagagaa atagaggaaa agttcggctt taaggttctt 1620
tatgcggaca ctgacggctt ttatgccaca atacccgggg aaaagcctga actcattaaa 1680
```

Figure 7 Continued

```
aagaaagcca aggaattcct aaactacata aactccaaac ttccaggtct gcttgagctt 1740
gagtatgagg gcttttactt gagaggattc tttgttacaa aaaagcgcta tgcagtcata 1800
gatgaagagg gcaggataac aacaaggggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaaatacag ggttccactt 1980
gaaaagcttg ttatccatga gcagattacc agggatttaa aggactacaa agccattggc 2040
cctcatgtcg cgatagcaaa aagacttgcc gcaagaggga taaaagtgaa accgggcaca 2100
ataataagct atatcgttct caagggagc ggaaagataa gcgatagggt aattttactt 2160
acagaatacg atcctagaaa acacaagtac gatccggact actacataga aaaccaagtt 2220
ttgccggcag tacttaggat actcgaagcg tttggataca gaaggagga tttaaggtat 2280
caaagctcaa aacaaaccgg cttagatgca tggctcaaga ggtag 2325    [SEQ ID NO. 108]
```

Vent D407E NNN= GAA, GAG (All possible E codons)
```
atgatactgg acactgatta cataacaaaa gatggcaagc ctataatccg aattttttaag 60
aaagagaacg gggagtttaa aatagaactt gaccctcatt ttcagcccta tatatatgct 120
cttctcaaag atgactccgc tattgaggag ataaaggcaa taaagggcga gagacatgga 180
aaaactgtga gagtgctcga tgcagtgaaa gtcaggaaaa aattttttggg aagggaagtt 240
gaagtctgga agctcatttt cgagcatccc caagacgttc cagctatgcg gggcaaaata 300
agggaacatc cagctgtggt tgacatttac·gaatatgaca taccctttgc caagcgttat 360
ctcatagaca agggcttgat tcccatggag ggagacgagg agcttaagct ccttgccttt 420
gatattgaaa cgttttatca tgagggagat gaatttggaa agggcgagat aataatgatt 480
agttatgccg atgaagaaga ggccagagta atcacatgga aaaatatcga tttgccgtat 540
gtcgatgttg tgtccaatga aagagaaatg ataaagcgtt ttgttcaagt tgttaaagaa 600
aaagaccccg atgtgataat aacttacaat ggggacaatt ttgatttgcc gtatctcata 660
aaacgggcag aaaagctggg agttcggctt gtcttaggaa gggacaaaga acatcccgaa 720
cccaagattc agaggatggg tgatagtttt gctgtggaaa tcaagggtag aatccacttt 780
gatcttttcc cagttgtgcg aaggacgata aacctcccaa cgtatacgct tgaggcagtt 840
tatgaagcag ttttaggaaa aaccaaaagc aaattaggag cagaggaaat tgccgctata 900
tgggaaacag aagaaagcat gaaaaaacta gcccagtact caatggaaga tgctagggca 960
acgtatgagc tcgggaagga attcttcccc atggaagctg agctggcaaa gctgataggt 1020
caaagtgtat gggacgtctc gagatcaagc accggcaacc tcgtggagtg gtatcttttta 1080
agggtggcat acgcgaggaa tgaacttgca ccgaacaaac ctgatgagga agagtataaa 1140
cggcgcttaa gaacaactta cctgggagga tatgtaaaag agccagaaaa aggtttgtgg 1200
gaaaaatatca tttatttgNN Nttccgcagt ctgtacccct caataatagt tactcacaac 1260
gtatccccag ataccctttga aaaagagggg tgtaagaatt acgatgttgc tccgatagta 1320
ggatatggt tctgcaagga cttttccggggc tttattccct ccatactcgg ggacttaatt 1380
gcaatgaggc aagatataaa gaagaaaatg aaatccacaa ttgacccgat cgaaaagaaa 1440
atgctcgatt ataggcaaag ggctattaaa ttgcttgcaa acagctatta cggctatatg 1500
gggtatccta aggcaagatg gtactcgaag gaatgtgctg aaagcgttac cgcatggggg 1560
agacactaca tagagatgac gataagagaa atagaggaaa agttcggctt taaggttctt 1620
tatgcggaca ctgacggctt ttatgccaca atacccgggg aaaagcctga actcattaaa 1680
aagaaagcca aggaattcct aaactacata aactccaaac ttccaggtct gcttgagctt 1740
gagtatgagg gcttttactt gagaggattc tttgttacaa aaaagcgcta tgcagtcata 1800
gatgaagagg gcaggataac aacaaggggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaaatacag ggttccactt 1980
gaaaagcttg ttatccatga gcagattacc agggatttaa aggactacaa agccattggc 2040
cctcatgtcg cgatagcaaa aagacttgcc gcaagaggga taaaagtgaa accgggcaca 2100
ataataagct atatcgttct caagggagc ggaaagataa gcgatagggt aattttactt 2160
acagaatacg atcctagaaa acacaagtac gatccggact actacataga aaaccaagtt 2220
ttgccggcag tacttaggat actcgaagcg tttggataca gaaggagga tttaaggtat 2280
caaagctcaa aacaaaccgg cttagatgca tggctcaaga ggtag 2325    [SEQ ID NO. 109]
```

Figure 7 Continued

```
Vent T544P NNN= CCT, CCA, CCG, CCC (All possible P codons)
atgatactgg acactgatta cataacaaaa gatggcaagc ctataatccg aatttttaag  60
aaagagaacg gggagtttaa aatagaactt gaccctcatt ttcagcccta tatatatgct 120
cttctcaaag atgactccgc tattgaggag ataaaggcaa taaagggcga gagacatgga 180
aaaactgtga gagtgctcga tgcagtgaaa gtcaggaaaa aattttttggg aagggaagtt 240
gaagtctgga agctcatttt cgagcatccc caagacgttc cagctatgcg gggcaaaata 300
agggaacatc cagctgtggt tgacatttac gaatatgaca tacccttttgc caagcgttat 360
ctcatagaca agggcttgat tcccatggag ggagacgagg agcttaagct ccttgccttt 420
gatattgaaa cgttttatca tgagggagat gaatttggaa agggcgagat aataatgatt 480
agttatgccg atgaagaaga ggccagagta atcacatgga aaaatatcga tttgccgtat 540
gtcgatgttg tgtccaatga aagagaaatg ataaagcgtt ttgttcaagt tgttaaagaa 600
aaagaccccg atgtgataat aacttacaat ggggacaatt ttgatttgcc gtatctcata 660
aaacgggcag aaaagctggg agttcggctt gtcttaggaa gggacaaaga acatcccgaa 720
cccaagattc agaggatggg tgatagtttt gctgtggaaa tcaagggtag aatccacttt 780
gatcttttcc cagttgtgcg aaggacgata aacctcccaa cgtatacgct tgaggcagtt 840
tatgaagcag ttttaggaaa aaccaaaagc aaattaggag cagaggaaat tgccgctata 900
tgggaaacag aagaaagcat gaaaaaacta gcccagtact caatggaaga tgctagggca 960
acgtatgagc tcgggaagga attcttcccc atgaagctg agctggcaaa gctgataggt 1020
caaagtgtat gggacgtctc gagatcaagc accggcaacc tcgtggagtg gtatcttta 1080
agggtggcat acgcgaggaa tgaacttgca ccgaacaaac ctgatgagga agagtataaa 1140
cggcgcttaa gaacaactta cctgggagga tatgtaaaag agccagaaaa aggtttgtgg 1200
gaaaatatca tttatttgga tttccgcagt ctgtacccctt caataatagt tactcacaac 1260
gtatccccag atacccttga aaaagagggc tgtaagaatt acgatgttgc tccgatagta 1320
ggatataggt tctgcaagga cttccgggc tttattccct ccatactcgg ggacttaatt 1380
gcaatgaggc aagatataaa gaagaaaatg aaatccacaa ttgacccgat cgaaaagaaa 1440
atgctcgatt ataggcaaag ggctattaaa ttgcttgcaa acagctatta cggctatatg 1500
gggtatccta aggcaagatg gtactcgaag gaatgtgctg aaagcgttac cgcatggggg 1560
agacactaca tagagatgac gataagagaa atagaggaaa agttcggctt taaggttctt 1620
tatgcggacN NNgacggctt ttatgccaca atacccgggg aaaagcctga actcattaaa 1680
aagaaagcca aggaattcct aaactacata aactccaaac ttccaggtct gcttgagctt 1740
gagtatgagg gctttttactt gagaggattc tttgttacaa aaaagcgcta tgcagtcata 1800
gatgaagagg gcaggataac aacaaggggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaaatacag ggttccactt 1980
gaaaagcttg ttatccatga gcagattacc agggatttaa aggactacaa agccattggc 2040
cctcatgtcg cgatagcaaa aagacttgcc gcaagaggga taaaagtgaa accgggcaca 2100
ataataagct atatcgttct caaagggagc ggaaagataa gcgatagggt aatttttactt 2160
acagaatacg atcctagaaa acacaagtac gatccggact actacataga aaaccaagtt 2220
ttgccggcag tacttaggat actcgaagcg tttggataca gaaggagga tttaaggtat 2280
caaagctcaa aacaaaccgg cttagatgca tggctcaaga ggtag 2325   [SEQ ID NO. 110]

Vent D545G NNN=GGT, GGC, GGA, GGG (All possible G codons)
atgatactgg acactgatta cataacaaaa gatggcaagc ctataatccg aatttttaag  60
aaagagaacg gggagtttaa aatagaactt gaccctcatt ttcagcccta tatatatgct 120
cttctcaaag atgactccgc tattgaggag ataaaggcaa taaagggcga gagacatgga 180
aaaactgtga gagtgctcga tgcagtgaaa gtcaggaaaa aattttttggg aagggaagtt 240
gaagtctgga agctcatttt cgagcatccc caagacgttc cagctatgcg gggcaaaata 300
agggaacatc cagctgtggt tgacatttac gaatatgaca tacccttttgc caagcgttat 360
ctcatagaca agggcttgat tcccatggag ggagacgagg agcttaagct ccttgccttt 420
gatattgaaa cgttttatca tgagggagat gaatttggaa agggcgagat aataatgatt 480
agttatgccg atgaagaaga ggccagagta atcacatgga aaaatatcga tttgccgtat 540
gtcgatgttg tgtccaatga aagagaaatg ataaagcgtt ttgttcaagt tgttaaagaa 600
aaagaccccg atgtgataat aacttacaat ggggacaatt ttgatttgcc gtatctcata 660
```

Figure 7 Continued

```
aaacgggcag aaaagctggg agttcggctt gtcttaggaa gggacaaaga acatcccgaa 720
cccaagattc agaggatggg tgatagtttt gctgtggaaa tcaagggtag aatccacttt 780
gatctttttcc cagttgtgcg aaggacgata aacctcccaa cgtatacgct tgaggcagtt 840
tatgaagcag ttttaggaaa aaccaaaagc aaattaggag cagaggaaat tgccgctata 900
tgggaaacag aagaaagcat gaaaaaacta gcccagtact caatggaaga tgctagggca 960
acgtatgagc tcgggaagga attcttcccc atggaagctg agctggcaaa gctgataggt 1020
caaagtgtat gggacgtctc gagatcaagc accggcaacc tcgtggagtg gtatcttta 1080
agggtggcat acgcgaggaa tgaacttgca ccgaacaaac ctgatgagga agagtataaa 1140
cggcgcttaa gaacaactta cctgggagga tatgtaaaag agccagaaaa aggtttgtgg 1200
gaaaatatca tttatttgga tttccgcagt ctgtacccctt caataatagt tactcacaac 1260
gtatccccag ataccccttga aaaagagggc tgtaagaatt acgatgttgc tccgatagta 1320
ggatataggt tctgcaagga ctttccgggc tttattccct ccatactcgg ggacttaatt 1380
gcaatgaggc aagatataaa gaagaaaatg aaatccacaa ttgacccgat cgaaaagaaa 1440
atgctcgatt ataggcaaag ggctattaaa ttgcttgcaa acagctatta cggctatatg 1500
gggtatccta aggcaagatg gtactcgaag gaatgtgctg aaagcgttac cgcatggggg 1560
agacactaca tagagatgac gataagagaa atagaggaaa agttcggctt taaggttctt 1620
tatgcggaca ctNNNggctt ttatgccaca ataccggggg aaaagcctga actcattaaa 1680
aagaaagcca aggaattcct aaactacata aactccaaac ttccaggtct gcttgagctt 1740
gagtatgagg gcttttactt gagaggattc tttgttacaa aaaagcgcta tgcagtcata 1800
gatgaagagg gcaggataac aacaagggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaatacag ggttccactt 1980
gaaaagcttg ttatccatga gcagattacc agggatttaa aggactacaa agccattggc 2040
cctcatgtcg cgatagcaaa aagacttgcc gcaagaggga taaaagtgaa accgggcaca 2100
ataataagct atatcgttct caagggagc ggaaagataa gcgataggt aatttttactt 2160
acagaatacg atcctagaaa acacaagtac gatccggact actacataga aaaccaagtt 2220
ttgccggcag tacttaggat actcgaagcg tttggataca gaaaggagga tttaaggtat 2280
caaagctcaa aacaaaccgg cttagatgca tggctcaaga ggtag 2325  [SEQ ID NO. 111]
```

Vent K595T NNN=ACT, ACC, ACA, ACG (All possible T codons)
```
atgatactgg acactgatta cataacaaaa gatggcaagc ctataatccg aattttaag 60
aaagagaacg gggagtttaa aatagaactt gaccctcatt ttcagcccta tatatatgct 120
cttctcaaag atgactccgc tattgaggag ataaaggcaa taagggcga gagacatgga 180
aaaactgtga gagtgctcga tgcagtgaaa gtcaggaaaa aattttggg aagggaagtt 240
gaagtctgga agctcatttt cgagcatccc caagacgttc cagctatgcg gggcaaaata 300
agggaacatc cagctgtggt tgacatttac gaatatgaca tacccttgc caagcgttat 360
ctcatagaca agggcttgat tcccatggag ggagacgagg agcttaagct ccttgccttt 420
gatattgaaa cgttttatca tgagggagat gaattggaaa agggcgagat aataatgatt 480
agttatgccg atgaagaaga ggccagagta atcacatgga aaatatcga tttgccgtat 540
gtcgatgttg tgtccaatga aagagaaatg ataaagcgtt tgttcaagt tgttaaagaa 600
aaagaccccg atgtgataat aacttacaat ggggacaatt ttgatttgcc gtatctcata 660
aaacgggcag aaaagctggg agttcggctt gtcttaggaa gggacaaaga acatcccgaa 720
cccaagattc agaggatggg tgatagtttt gctgtggaaa tcaagggtag aatccacttt 780
gatctttttcc cagttgtgcg aaggacgata aacctcccaa cgtatacgct tgaggcagtt 840
tatgaagcag ttttaggaaa aaccaaaagc aaattaggag cagaggaaat tgccgctata 900
tgggaaacag aagaaagcat gaaaaaacta gcccagtact caatggaaga tgctagggca 960
acgtatgagc tcgggaagga attcttcccc atggaagctg agctggcaaa gctgataggt 1020
caaagtgtat gggacgtctc gagatcaagc accggcaacc tcgtggagtg gtatcttta 1080
agggtggcat acgcgaggaa tgaacttgca ccgaacaaac ctgatgagga agagtataaa 1140
cggcgcttaa gaacaactta cctgggagga tatgtaaaag agccagaaaa aggtttgtgg 1200
gaaaatatca tttatttgga tttccgcagt ctgtacccctt caataatagt tactcacaac 1260
gtatccccag ataccccttga aaaagagggc tgtaagaatt acgatgttgc tccgatagta 1320
ggatataggt tctgcaagga ctttccgggc tttattccct ccatactcgg ggacttaatt 1380
```

Figure 7 Continued

```
gcaatgaggc aagatataaa gaagaaaatg aaatccacaa ttgacccgat cgaaaagaaa 1440
atgctcgatt ataggcaaag ggctattaaa ttgcttgcaa acagctatta cggctatatg 1500
gggtatccta aggcaagatg gtactcgaag gaatgtgctg aaagcgttac cgcatggggg 1560
agacactaca tagagatgac gataagagaa atagaggaaa agttcggctt taaggttctt 1620
tatgcggaca ctgacggctt ttatgccaca atacccgggg aaaagcctga actcattaaa 1680
aagaaagcca aggaattcct aaactacata aactccaaac ttccaggtct gcttgagctt 1740
gagtatgagg gcttttactt gagaggattc tttgttacaa aaNNNcgcta tgcagtcata 1800
gatgaagagg gcaggataac aacaaggggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaaatacag ggttccactt 1980
gaaaagcttg ttatccatga gcagattacc agggatttaa aggactacaa agccattggc 2040
cctcatgtcg cgatagcaaa aagacttgcc gcaagaggga taaaagtgaa accgggcaca 2100
ataataagct atatcgttct caagggagc ggaaagataa gcgatagggt aattttactt 2160
acagaatacg atcctagaaa acacaagtac gatccggact actacataga aaaccaagtt 2220
ttgccggcag tacttaggat actcgaagcg tttggataca gaaggagga tttaaggtat 2280
caaagctcaa aacaaaccgg cttagatgca tggctcaaga ggtag 2325    [SEQ ID NO. 112]
```

Figure 7 Continued

Deep Vent
mildadyitedgkpiirifkkengefkveydrnfrpyiyallkddsqidevrkitaerhgkivriidaekvrkkflg
rpievwrlyfehpqdvpairdkirehsavidifeydipfakrylidkglipmegdeelkllafdietlyhegeefak
gpiimisyadeeeakvitwkkidlpyvevvsseremikrflkvirekdpdviityngdsfdlpylvkraeklgiklp
lgrdgsepkmqrlgdmtaveikgrihfdlyhvirrtinlptytleavyeaifgkpkekvyaheiaeawetgkglerv
akysmedakvtyelgreffpmeaqlsrlvgqplwdvsrsstgnlvewyllrkayernelapnkpdereyerrlresy
aggyvkepekglweglvsldfrslypsiiithnvspdtlnregcreydvapevghkfckdfpgfipsllkrllderq
eikrkmkaskdpiekkmldyrqraikilansyygyygyakarwyckecaesvtawgreyiefvrkeleekfgfkvly
idtdglyatipgakpeeikkkalefvdyinaklpglleleyegfyvrgffvtkkkyalideegkiitrgleivrrdw
seiaketqakvleailkhgnveeavkivkevteklskyeippeklviyeqitrplheykaigphvavakrlaargvk
vrpgmvigyivlrgdgpiskrailaeefdlrkhkydaeyyienqvlpavlrileafgyrkedlrwqktkqtgltawl
nikkk [SEQ ID NO. 113]

Deep Vent Y385N NNN= AAT, AAC (All possible N codons)
Deep Vent Y385L NNN= TTA, TTG, CTT, CTC, CTA, CTG (All possible L codons)
Deep Vent Y385H NNN= CAT, CAC (All possible H codons)
Deep Vent Y385Q NNN= CAA, CAG (All possible Q codons)
Deep Vent Y385S NNN= TCT, TCC, TCA, TCG, AGT, AGC (All possible S codons)

```
ATGATACTTG ACGCTGACTA CATCACCGAG GATGGGAAGC CGATTATAAG GATTTTCAAG      60
AAAGAAAACG GCGAGTTTAA GGTTGAGTAC GACAGAAACT TTAGACCTTA CATTTACGCT     120
CTCCTCAAAG ATGACTCGCA GATTGATGAG GTTAGGAAGA TAACCGCCGA GAGGCATGGG     180
AAGATAGTGA GAATTATAGA TGCCGAAAAG GTAAGGAAGA AGTTCCTGGG GAGGCCGATT     240
GAGGTATGGA GGCTGTACTT TGAACACCCT CAGGACGTTC CCGCAATAAG GGATAAGATA     300
AGAGAGCATT CCGCAGTTAT TGACATCTTT GAGTACGACA TTCCGTTCGC GAAGAGGTAC     360
CTAATAGACA AAGGCCTAAT TCCAATGGAA GGCGATGAAG AGCTCAAGTT GCTCGCATTT     420
GACATAGAAA CCCTCTATCA CGAAGGGGAG GAGTTCGCGA AGGGGCCCAT TATAATGATA     480
AGCTATGCTG ATGAGGAAGA AGCCAAAGTC ATAACGTGGA AAAAGATCGA TCTCCCGTAC     540
GTCGAGGTAG TTTCCAGCGA GAGGGAGATG ATAAAGCGGT TCCTCAAGGT GATAAGGGAG     600
AAAGATCCCG ATGTTATAAT TACCTACAAC GGCGATTCTT TCGACCTTCC CTATCTAGTT     660
AAGAGGGCCG AAAAGCTCGG GATAAAGCTA CCCCTGGGAA GGGACGGTAG TGAGCCAAAG     720
ATGCAGAGGC TTGGGGATAT GACAGCGGTG GAGATAAAGG GAAGGATACA CTTTGACCTC     780
TACCACGTGA TTAGGAGAAC GATAAACCTC CCAACATACA CCCTCGAGGC AGTTTATGAG     840
GCAATCTTCG GAAAGCCAAA GGAGAAAGTT TACGCTCACG AGATAGCTGA GGCCTGGGAG     900
ACTGGAAAGG GACTGGAGAG AGTTGCAAAG TATTCAATGG AGGATGCAAA GGTAACGTAC     960
GAGCTCGGTA GGGAGTTCTT CCCAATGGAG GCCCAGCTTT CAAGGTTAGT CGGCCAGCCC    1020
CTGTGGGATG TTTCTAGGTC TTCAACTGGC AACTTGGTGG AGTGGTACCT CCTCAGGAAG    1080
GCCTACGAGA GGAATGAATT GGCTCCAAAC AAGCCGGATG AGAGGGAGTA CGAGAGAAGG    1140
CTAAGGGAGA GCNNNGCTGG GGGATACGTT AAGGAGCCGG AGAAAGGGCT TGGGAGGGG    1200
TTAGTTTCCC TAGATTTCAG GAGCCTGTAC CCCTCGATAA TAATCACCCA TAACGTCTCA    1260
CCGGATACGC TGAACAGGGA AGGGTGTAGG GAATACGATG TCGCCCCAGA GGTTGGGCAC    1320
AAGTTCTGCA AGGACTTCCC GGGGTTTATC CCCAGCCTGC TCAAGAGGTT ATTGGATGAA    1380
AGGCAAGAAA TAAAAAGGAA GATGAAAGCT TCTAAAGACC CAATCGAGAA GAAGATGCTT    1440
GATTACAGGC AACGGGCAAT CAAAATCCTG GCAAACAGCT ATTATGGGTA TTATGGGTAC    1500
GCAAAAGCCC GTTGGTACTG TAAGGAGTGC GCAGAGAGCG TTACGGCCTG GGGGAGGGAA    1560
TATATAGAGT TCGTAAGGAA GGAACTGGAG GAAAAGTTCG GGTTCAAAGT CTTATACATA    1620
GACACAGATG GACTCTACGC CACAATTCCT GGGGCAAAAC CGGAGGAGAT AAAGAAGAAA    1680
GCCCTAGAGT TCGTAGATTA TATAAACGCC AAGCTCCCAG GCTGTTGGA GCTTGAGTAC    1740
GAGGGCTTCT ACGTGAGAGG GTTCTTCGTG ACGAAGAAGA AGTATGCGTT GATAGATGAG    1800
GAAGGGAAGA TAATCACTAG GGGGCTTGAA ATAGTCAGGA GGGACTGGAG CGAAATAGCC    1860
AAAGAAACCC AAGCAAAAGT CCTAGAGGCT ATCCTAAAGC ATGGCAACGT TGAGGAGGCA    1920
GTAAAGATAG TTAAGGAGGT AACTGAAAAG CTGAGCAAGT ACGAAATACC TCCAGAAAAG    1980
CTAGTTATTT ACGAGCAGAT CACGAGGCCC CTTCACGAGT ACAAGGCTAT AGGTCCGCAC    2040
GTTGCCGTGG CAAAAAGGTT AGCCGCTAGA GGAGTAAAGG TGAGGCCTGG CATGGTGATA    2100
```

```
GGGTACATAG TGCTGAGGGG AGACGGGCCA ATAAGCAAGA GGGCTATCCT TGCAGAGGAG    2160
TTCGATCTCA GGAAGCATAA GTATGACGCT GAGTATTACA TAGAAAATCA GGTTTTACCT    2220
GCCGTTCTTA GAATATTAGA GGCCTTTGGG TACAGGAAAG AAGACCTCAG GTGGCAGAAG    2280
ACTAAACAGA CAGGTCTTAC GGCATGGCTT AACATCAAGA AGAAGTAA                 2328
[SEQ ID NO. 114]
```

Deep Vent G387S NNN= TCT, TCC, TCA, TCG, AGT, AGC (All possible S codons)
Deep Vent G387P NNN= CCT, CCA, CCG, CCC (All possible P codons)

```
ATGATACTTG ACGCTGACTA CATCACCGAG GATGGGAAGC CGATTATAAG GATTTTCAAG      60
AAAGAAAACG GCGAGTTTAA GGTTGAGTAC GACAGAAACT TTAGACCTTA CATTTACGCT     120
CTCCTCAAAG ATGACTCGCA GATTGATGAG GTTAGGAAGA TAACCGCCGA GAGGCATGGG     180
AAGATAGTGA GAATTATAGA TGCCGAAAAG GTAAGGAAGA AGTTCCTGGG GAGGCCGATT     240
GAGGTATGGA GGCTGTACTT TGAACACCCT CAGGACGTTC CGCAATAAGG GATAAGATA      300
AGAGAGCATT CCGCAGTTAT TGACATCTTT GAGTACGACA TTCCGTTCGC GAAGAGGTAC     360
CTAATAGACA AAGGCCTAAT TCCAATGGAA GGCGATGAAG AGCTCAAGTT GCTCGCATTT     420
GACATAGAAA CCCTCTATCA CGAAGGGGAG GAGTTCGCGA AGGGGCCCAT TATAATGATA     480
AGCTATGCTG ATGAGGAAGA AGCCAAAGTC ATAACGTGGA AAAAGATCGA TCTCCCGTAC     540
GTCGAGGTAG TTTCCAGCGA GAGGGAGATG ATAAAGCGGT TCCTCAAGGT GATAAGGGAG     600
AAAGATCCCG ATGTTATAAT TACCTACAAC GGCGATTCTT TCGACCTTCC CTATCTAGTT     660
AAGAGGGCCG AAAAGCTCGG GATAAAGCTA CCCCTGGGAA GGGACGGTAG TGAGCCAAAG     720
ATGCAGAGGC TTGGGGATAT GACAGCGGTG GAGATAAAGG GAAGGATACA CTTTGACCTC     780
TACCACGTGA TTAGGAGAAC GATAAACCTC CCAACATACA CCCTCGAGGC AGTTTATGAG     840
GCAATCTTCG GAAAGCCAAA GGAGAAAGTT TACGCTCACG AGATAGCTGA GGCCTGGGAG     900
ACTGGAAAGG GACTGGAGAG AGTTGCAAAG TATTCAATGG AGGATGCAAA GGTAACGTAC     960
GAGCTCGGTA GGGAGTTCTT CCCAATGGAG GCCCAGCTTT CAAGGTTAGT CGGCCAGCCC    1020
CTGTGGGATG TTTCTAGGTC TTCAACTGGC AACTTGGTGG AGTGGTACCT CCTCAGGAAG    1080
GCCTACGAGA GGAATGAATT GGCTCCAAAC AAGCCGGATG AGAGGGAGTA CGAGAGAAGG    1140
CTAAGGGAGA GCTACGCTNN NGGATACGTT AAGGAGCCGG AGAAAGGGCT CTGGGAGGGG    1200
TTAGTTTCCC TAGATTTCAG GAGCCTGTAC CCCTCGATAA TAATCACCCA TAACGTCTCA    1260
CCGGATACGC TGAACAGGGA AGGGTGTAGG AATACGATG TCGCCCCAGA GGTTGGGCAC     1320
AAGTTCTGCA AGGACTTCCC GGGGTTTATC CCCAGCCTGC TCAAGAGGTT ATTGGATGAA    1380
AGGCAAGAAA TAAAAAGGAA GATGAAAGCT TCTAAAGACC CAATCGAGAA GAAGATGCTT    1440
GATTACAGGC AACGGGCAAT CAAAATCCTG GCAAACAGCT ATTATGGGTA TTATGGGTAC    1500
GCAAAAGCCC GTTGGTACTG TAAGGAGTGC GCAGAGAGCG TTACGGCCTG GGGGAGGGAA    1560
TATATAGAGT TCGTAAGGAA GGAACTGGAG GAAAAGTTCG GGTTCAAAGT CTTATACATA    1620
GACACAGATG GACTCTACGC CACAATTCCT GGGGCAAAAC CCGAGGAGAT AAAGAAGAAA    1680
GCCCTAGAGT TCGTAGATTA TATAAACGCC AAGCTCCCAG GGCTGTTGGA GCTTGAGTAC    1740
GAGGGCTTCT ACGTGAGAGG GTTCTTCGTG ACGAAGAAGA AGTATGCGTT GATAGATGAG    1800
GAAGGGAAGA TAATCACTAG GGGGCTTGAA ATAGTCAGGA GGGACTGGAG CGAAATAGCC    1860
AAAGAAACCC AAGCAAAAGT CCTAGAGGCT ATCCTAAAGC ATGGCAACGT TGAGGAGGCA    1920
GTAAAGATAG TTAAGGAGGT AACTGAAAAG CTGAGCAAGT ACGAAATACC TCCAGAAAAG    1980
CTAGTTATTT ACGAGCAGAT CACGAGGCCC CTTCACGAGT ACAAGGCTAT AGGTCCGCAC    2040
GTTGCCGTGG CAAAAAGGTT AGCCGCTAGA GGAGTAAAGG TGAGGCCTGG CATGGTGATA    2100
GGGTACATAG TGCTGAGGGG AGACGGGCCA ATAAGCAAGA GGGCTATCCT TGCAGAGGAG    2160
TTCGATCTCA GGAAGCATAA GTATGACGCT GAGTATTACA TAGAAAATCA GGTTTTACCT    2220
GCCGTTCTTA GAATATTAGA GGCCTTTGGG TACAGGAAAG AAGACCTCAG GTGGCAGAAG    2280
ACTAAACAGA CAGGTCTTAC GGCATGGCTT AACATCAAGA AGAAGTAA                 2328
[SEQ ID NO. 115]
```

Deep Vent G388A NNN= GCA, GCT, GCC, GCG (All possible A codons)
Deep Vent G388P NNN= CCT, CCA, CCG, CCC (All possible P codons)

```
ATGATACTTG ACGCTGACTA CATCACCGAG GATGGGAAGC CGATTATAAG GATTTTCAAG      60
AAAGAAAACG GCGAGTTTAA GGTTGAGTAC GACAGAAACT TTAGACCTTA CATTTACGCT     120
```

Figure 7 Continued

```
CTCCTCAAAG ATGACTCGCA GATTGATGAG GTTAGGAAGA TAACCGCCGA GAGGCATGGG      180
AAGATAGTGA GAATTATAGA TGCCGAAAAG GTAAGGAAGA AGTTCCTGGG GAGGCCGATT      240
GAGGTATGGA GGCTGTACTT TGAACACCCT CAGGACGTTC CCGCAATAAG GGATAAGATA      300
AGAGAGCATT CCGCAGTTAT TGACATCTTT GAGTACGACA TTCCGTTCGC GAAGAGGTAC      360
CTAATAGACA AAGGCCTAAT TCCAATGGAA GGCGATGAAG AGCTCAAGTT GCTCGCATTT      420
GACATAGAAA CCCTCTATCA CGAAGGGAG GAGTTCGCGA AGGGGCCCAT TATAATGATA       480
AGCTATGCTG ATGAGGAAGA AGCCAAAGTC ATAACGTGGA AAAGATCGA TCTCCCGTAC       540
GTCGAGGTAG TTTCCAGCGA GAGGGAGATG ATAAAGCGGT TCCTCAAGGT GATAAGGGAG      600
AAAGATCCCG ATGTTATAAT TACCTACAAC GGCGATTCTT TCGACCTTCC CTATCTAGTT      660
AAGAGGGCCG AAAAGCTCGG GATAAAGCTA CCCCTGGGAA GGGACGGTAG TGAGCCAAAG      720
ATGCAGAGGC TTGGGGATAT GACAGCGGTG GAGATAAAGG GAAGGATACA CTTTGACCTC      780
TACCACGTGA TTAGGAGAAC GATAAACCTC CCAACATACA CCCTCGAGGC AGTTTATGAG      840
GCAATCTTCG GAAAGCCAAA GGAGAAAGTT TACGCTCACG AGATAGCTGA GGCCTGGGAG      900
ACTGGAAAGG GACTGGAGAG AGTTGCAAAG TATTCAATGG AGGATGCAAA GGTAACGTAC      960
GAGCTCGGTA GGGAGTTCTT CCCAATGGAG GCCCAGCTTT CAAGGTTAGT CGGCCAGCCC     1020
CTGTGGGATG TTTCTAGGTC TTCAACTGGC AACTTGGTGG AGTGGTACCT CCTCAGGAAG     1080
GCCTACGAGA GGAATGAATT GGCTCCAAAC AAGCCGGATG AGAGGGAGTA CGAGAGAAGG     1140
CTAAGGGAGA GCTACGCTGG GNNNTACGTT AAGGAGCCGG AGAAAGGGCT CTGGGAGGGG     1200
TTAGTTTCCC TAGATTTCAG GAGCCTGTAC CCCTCGATAA TAATCACCCA TAACGTCTCA     1260
CCGGATACGC TGAACAGGGA AGGGTGTAGG GAATACGATG TCGCCCCAGA GGTTGGGCAC    .1320
AAGTTCTGCA AGGACTTCCC GGGGTTTATC CCCAGCCTGC TCAAGAGGTT ATTGGATGAA     1380
AGGCAAGAAA TAAAAAGGAA GATGAAAGCT TCTAAAGACC CAATCGAGAA GAAGATGCTT     1440
GATTACAGGC AACGGGCAAT CAAAATCCTG GCAAACAGCT ATTATGGGTA TTATGGGTAC     1500
GCAAAAGCCC GTTGGTACTG TAAGGAGTGC GCAGAGAGCG TTACGGCCTG GGGGAGGGAA     1560
TATATAGAGT TCGTAAGGAA GGAACTGGAG AAAAGTTCG GGTTCAAAGT CTTATACATA      1620
GACACAGATG GACTCTACGC CACAATTCCT GGGGCAAAAC CCGAGGAGAT AAAGAAGAAA     1680
GCCCTAGAGT TCGTAGATTA TATAAACGCC AAGCTCCCAG GCTGTTGGA GCTTGAGTAC      1740
GAGGGCTTCT ACGTGAGAGG GTTCTTCGTG ACGAAGAAGA AGTATGCGTT GATAGATGAG     1800
GAAGGGAAGA TAATCACTAG GGGGCTTGAA ATAGTCAGGA GGGACTGGAG CGAAATAGCC     1860
AAAGAAACCC AAGCAAAAGT CCTAGAGGCT ATCCTAAAGC ATGGCAACGT TGAGGAGGCA     1920
GTAAAGATAG TTAAGGAGGT AACTGAAAAG CTGAGCAAGT ACGAAATACC TCCAGAAAAG     1980
CTAGTTATTT ACGAGCAGAT CACGAGGCCC CTTCACGAGT ACAAGGCTAT AGGTCCGCAC     2040
GTTGCCGTGG CAAAAAGGTT AGCCGCTAGA GGAGTAAAGG TGAGGCCTGG CATGGTGATA     2100
GGGTACATAG TGCTGAGGGG AGACGGGCCA ATAAGCAAGA GGGCTATCCT TGCAGAGGAG     2160
TTCGATCTCA GGAAGCATAA GTATGACGCT GAGTATTACA TAGAAAATCA GGTTTTACCT     2220
GCCGTTCTTA GAATATTAGA GGCCTTTGGG TACAGGAAAG AAGACCTCAG GTGGCAGAAG     2280
ACTAAACAGA CAGGTCTTAC GGCATGGCTT AACATCAAGA AGAAGTAA                  2328
[SEQ ID NO. 116]

Deep Vent D405E NNN= GAA, GAG (All possible E codons)
ATGATACTTG ACGCTGACTA CATCACCGAG GATGGGAAGC CGATTATAAG GATTTTCAAG       60
AAAGAAAACG GCGAGTTTAA GGTTGAGTAC GACAGAAACT TTAGACCTTA CATTTACGCT      120
CTCCTCAAAG ATGACTCGCA GATTGATGAG GTTAGGAAGA TAACCGCCGA GAGGCATGGG      180
AAGATAGTGA GAATTATAGA TGCCGAAAAG GTAAGGAAGA AGTTCCTGGG GAGGCCGATT      240
GAGGTATGGA GGCTGTACTT TGAACACCCT CAGGACGTTC CCGCAATAAG GGATAAGATA      300
AGAGAGCATT CCGCAGTTAT TGACATCTTT GAGTACGACA TTCCGTTCGC GAAGAGGTAC      360
CTAATAGACA AAGGCCTAAT TCCAATGGAA GGCGATGAAG AGCTCAAGTT GCTCGCATTT      420
GACATAGAAA CCCTCTATCA CGAAGGGAG GAGTTCGCGA AGGGGCCCAT TATAATGATA       480
AGCTATGCTG ATGAGGAAGA AGCCAAAGTC ATAACGTGGA AAAGATCGA TCTCCCGTAC       540
GTCGAGGTAG TTTCCAGCGA GAGGGAGATG ATAAAGCGGT TCCTCAAGGT GATAAGGGAG      600
AAAGATCCCG ATGTTATAAT TACCTACAAC GGCGATTCTT TCGACCTTCC CTATCTAGTT      660
AAGAGGGCCG AAAAGCTCGG GATAAAGCTA CCCCTGGGAA GGGACGGTAG TGAGCCAAAG      720
ATGCAGAGGC TTGGGGATAT GACAGCGGTG GAGATAAAGG GAAGGATACA CTTTGACCTC      780
```

Figure 7 Continued

```
TACCACGTGA TTAGGAGAAC GATAAACCTC CCAACATACA CCCTCGAGGC AGTTTATGAG      840
GCAATCTTCG GAAAGCCAAA GGAGAAAGTT TACGCTCACG AGATAGCTGA GGCCTGGGAG      900
ACTGGAAAGG GACTGGAGAG AGTTGCAAAG TATTCAATGG AGGATGCAAA GGTAACGTAC      960
GAGCTCGGTA GGGAGTTCTT CCCAATGGAG GCCCAGCTTT CAAGGTTAGT CGGCCAGCCC     1020
CTGTGGGATG TTTCTAGGTC TTCAACTGGC AACTTGGTGG AGTGGTACCT CCTCAGGAAG     1080
GCCTACGAGA GGAATGAATT GGCTCCAAAC AAGCCGGATG AGAGGGAGTA CGAGAGAAGG     1140
CTAAGGGAGA GCTACGCTGG GGGATACGTT AAGGAGCCGG AGAAAGGGCT CTGGGAGGGG     1200
TTAGTTTCCC TANNNTTCAG GAGCCTGTAC CCCTCGATAA TAATCACCCA TAACGTCTCA     1260
CCGGATACGC TGAACAGGGA AGGGTGTAGG GAATACGATG TCGCCCCAGA GGTTGGGCAC     1320
AAGTTCTGCA AGGACTTCCC GGGGTTTATC CCCAGCCTGC TCAAGAGGTT ATTGGATGAA     1380
AGGCAAGAAA TAAAAAGGAA GATGAAAGCT TCTAAAGACC CAATCGAGAA GAAGATGCTT     1440
GATTACAGGC AACGGGCAAT CAAAATCCTG GCAAACAGCT ATTATGGGTA TTATGGGTAC     1500
GCAAAAGCCC GTTGGTACTG TAAGGAGTGC GCAGAGAGCG TTACGGCCTG GGGGAGGGAA     1560
TATATAGAGT TCGTAAGGAA GGAACTGGAG GAAAAGTTCG GGTTCAAAGT CTTATACATA     1620
GACACAGATG GACTCTACGC CACAATTCCT GGGGCAAAAC CCGAGGAGAT AAAGAAGAAA     1680
GCCCTAGAGT TCGTAGATTA TATAAACGCC AAGCTCCCAG GGCTGTTGGA GCTTGAGTAC     1740
GAGGGCTTCT ACGTGAGAGG GTTCTTCGTG ACGAAGAAGA AGTATGCGTT GATAGATGAG     1800
GAAGGGAAGA TAATCACTAG GGGGCTTGAA ATAGTCAGGA GGGACTGGAG CGAAATAGCC     1860
AAAGAAACCC AAGCAAAAGT CCTAGAGGCT ATCCTAAAGC ATGGCAACGT TGAGGAGGCA     1920
GTAAAGATAG TTAAGGAGGT AACTGAAAAG CTGAGCAAGT ACGAAATACC TCCAGAAAAG     1980
CTAGTTATTT ACGAGCAGAT CACGAGGCCC CTTCACGAGT ACAAGGCTAT AGGTCCGCAC     2040
GTTGCCGTGG CAAAAAGGTT AGCCGCTAGA GGAGTAAAGG TGAGGCCTGG CATGGTGATA     2100
GGGTACATAG TGCTGAGGGG AGACGGGCCA ATAAGCAAGA GGGCTATCCT TGCAGAGGAG     2160
TTCGATCTCA GGAAGCATAA GTATGACGCT GAGTATTACA TAGAAAATCA GGTTTTACCT     2220
GCCGTTCTTA GAATATTAGA GGCCTTTGGG TACAGGAAAG AAGACCTCAG GTGGCAGAAG     2280
ACTAAACAGA CAGGTCTTAC GGCATGGCTT AACATCAAGA AGAAGTAA                 2328
[SEQ ID NO. 117]
```

Deep Vent T542P NNN= CCT, CCA, CCG, CCC (All possible P codons)
```
ATGATACTTG ACGCTGACTA CATCACCGAG GATGGGAAGC CGATTATAAG GATTTTCAAG      60
AAAGAAAACG GCGAGTTTAA GGTTGAGTAC GACAGAAACT TTAGACCTTA CATTTACGCT     120
CTCCTCAAAG ATGACTCGCA GATTGATGAG GTTAGGAAGA TAACCGCCGA GAGGCATGGG     180
AAGATAGTGA GAATTATAGA TGCCGAAAAG GTAAGGAAGA AGTTCCTGGG GAGGCCGATT     240
GAGGTATGGA GGCTGTACTT TGAACACCCT CAGGACGTTC CCGCAATAAG GGATAAGATA     300
AGAGAGCATT CCGCAGTTAT TGACATCTTT GAGTACGACA TTCCGTTCGC GAAGAGGTAC     360
CTAATAGACA AAGGCCTAAT TCCAATGGAA GGCGATGAAG AGCTCAAGTT GCTCGCATTT     420
GACATAGAAA CCCTCTATCA CGAAGGGGAG GAGTTCGCGA AGGGGCCCAT TATAATGATA     480
AGCTATGCTG ATGAGGAAGA AGCCAAAGTC ATAACGTGGA AAAAGATCGA TCTCCCGTAC     540
GTCGAGGTAG TTTCCAGCGA GAGGGAGATG ATAAAGCGGT TCCTCAAGGT GATAAGGGAG     600
AAAGATCCCG ATGTTATAAT TACCTACAAC GGCGATTCTT TCGACCTTCC CTATCTAGTT     660
AAGAGGGCCG AAAAGCTCGG GATAAAGCTA CCCCTGGGAA GGGACGGTAG TGAGCCAAAG     720
ATGCAGAGGC TTGGGGATAT GACAGCGGTG GAGATAAAGG GAAGGATACA CTTTGACCTC     780
TACCACGTGA TTAGGAGAAC GATAAACCTC CCAACATACA CCCTCGAGGC AGTTTATGAG     840
GCAATCTTCG GAAAGCCAAA GGAGAAAGTT TACGCTCACG AGATAGCTGA GGCCTGGGAG     900
ACTGGAAAGG GACTGGAGAG AGTTGCAAAG TATTCAATGG AGGATGCAAA GGTAACGTAC     960
GAGCTCGGTA GGGAGTTCTT CCCAATGGAG GCCCAGCTTT CAAGGTTAGT CGGCCAGCCC    1020
CTGTGGGATG TTTCTAGGTC TTCAACTGGC AACTTGGTGG AGTGGTACCT CCTCAGGAAG    1080
GCCTACGAGA GGAATGAATT GGCTCCAAAC AAGCCGGATG AGAGGGAGTA CGAGAGAAGG    1140
CTAAGGGAGA GCTACGCTGG GGGATACGTT AAGGAGCCGG AGAAAGGGCT CTGGGAGGGG    1200
TTAGTTTCCC TAGATTTCAG GAGCCTGTAC CCCTCGATAA TAATCACCCA TAACGTCTCA    1260
CCGGATACGC TGAACAGGGA AGGGTGTAGG GAATACGATG TCGCCCCAGA GGTTGGGCAC    1320
AAGTTCTGCA AGGACTTCCC GGGGTTTATC CCCAGCCTGC TCAAGAGGTT ATTGGATGAA    1380
AGGCAAGAAA TAAAAAGGAA GATGAAAGCT TCTAAAGACC CAATCGAGAA GAAGATGCTT    1440
```

Figure 7 Continued

```
GATTACAGGC AACGGGCAAT CAAAATCCTG GCAAACAGCT ATTATGGGTA TTATGGGTAC   1500
GCAAAAGCCC GTTGGTACTG TAAGGAGTGC GCAGAGAGCG TTACGGCCTG GGGGAGGGAA   1560
TATATAGAGT TCGTAAGGAA GGAACTGGAG GAAAAGTTCG GGTTCAAAGT CTTATACATA   1620
GACNNNGATG GACTCTACGC CACAATTCCT GGGGCAAAAC CCGAGGAGAT AAAGAAGAAA   1680
GCCCTAGAGT TCGTAGATTA TATAAACGCC AAGCTCCCAG GGCTGTTGGA GCTTGAGTAC   1740
GAGGGCTTCT ACGTGAGAGG GTTCTTCGTG ACGAAGAAGA AGTATGCGTT GATAGATGAG   1800
GAAGGGAAGA TAATCACTAG GGGGCTTGAA ATAGTCAGGA GGGACTGGAG CGAAATAGCC   1860
AAAGAAACCC AAGCAAAAGT CCTAGAGGCT ATCCTAAAGC ATGGCAACGT TGAGGAGGCA   1920
GTAAAGATAG TTAAGGAGGT AACTGAAAAG CTGAGCAAGT ACGAAATACC TCCAGAAAAG   1980
CTAGTTATTT ACGAGCAGAT CACGAGGCCC CTTCACGAGT ACAAGGCTAT AGGTCCGCAC   2040
GTTGCCGTGG CAAAAAGGTT AGCCGCTAGA GGAGTAAAGG TGAGGCCTGG CATGGTGATA   2100
GGGTACATAG TGCTGAGGGG AGACGGGCCA ATAAGCAAGA GGGCTATCCT TGCAGAGGAG   2160
TTCGATCTCA GGAAGCATAA GTATGACGCT GAGTATTACA TAGAAAATCA GGTTTTACCT   2220
GCCGTTCTTA GAATATTAGA GGCCTTTGGG TACAGGAAAG AAGACCTCAG GTGGCAGAAG   2280
ACTAAACAGA CAGGTCTTAC GGCATGGCTT AACATCAAGA AGAAGTAA              2328
[SEQ ID NO. 118]
```

Deep Vent D543G NNN=GGT, GGC, GGA, GGG (All possible G codons)
```
ATGATACTTG ACGCTGACTA CATCACCGAG GATGGGAAGC CGATTATAAG GATTTTCAAG     60
AAAGAAAACG GCGAGTTTAA GGTTGAGTAC GACAGAAACT TTAGACCTTA CATTTACGCT    120
CTCCTCAAAG ATGACTCGCA GATTGATGAG GTTAGGAAGA TAACCGCCGA GAGGCATGGG    180
AAGATAGTGA GAATTATAGA TGCCGAAAAG GTAAGGAAGA AGTTCCTGGG GAGGCCGATT    240
GAGGTATGGA GGCTGTACTT TGAACACCCT CAGGACGTTC CGCAATAAG GGATAAGATA     300
AGAGAGCATT CCGCAGTTAT TGACATCTTT GAGTACGACA TTCCGTTCGC GAAGAGGTAC    360
CTAATAGACA AAGGCCTAAT TCCAATGGAA GGCGATGAAG AGCTCAAGTT GCTCGCATTT    420
GACATAGAAA CCCTCTATCA CGAAGGGGAG GAGTTCGCGA AGGGGCCCAT TATAATGATA    480
AGCTATGCTG ATGAGGAAGA AGCCAAAGTC ATAACGTGGA AAAAGATCGA TCTCCCGTAC    540
GTCGAGGTAG TTTCCAGCGA GAGGGAGATG ATAAAGCGGT TCCTCAAGGT GATAAGGGAG    600
AAAGATCCCG ATGTTATAAT TACCTACAAC GGCGATTCTT TCGACCTTCC CTATCTAGTT    660
AAGAGGGCCG AAAAGCTCGG GATAAAGCTA CCCCTGGGAA GGGACGGTAG TGAGCCAAAG    720
ATGCAGAGGC TTGGGGATAT GACAGCGGTG GAGATAAAGG GAAGGATACA CTTTGACCTC    780
TACCACGTGA TTAGGAGAAC GATAAACCTC CCAACATACA CCCTCGAGGC AGTTTATGAG    840
GCAATCTTCG GAAAGCCAAA GGAGAAAGTT TACGCTCACG AGATAGCTGA GGCCTGGGAG    900
ACTGGAAAGG GACTGGAGAG AGTTGCAAAG TATTCAATGG AGGATGCAAA GGTAACGTAC    960
GAGCTCGGTA GGGAGTTCTT CCCAATGGAG GCCCAGCTTT CAAGGTTAGT CGGCCAGCCC   1020
CTGTGGGATG TTTCTAGGTC TTCAACTGGC AACTTGGTGG AGTGGTACCT CCTCAGGAAG   1080
GCCTACGAGA GGAATGAATT GGCTCCAAAC AAGCCGGATG AGAGGGAGTA CGAGAGAAGG   1140
CTAAGGGAGA GCTACGCTGG GGGATACGTT AAGGAGCCGG AGAAAGGGCT CTGGGAGGGG   1200
TTAGTTTCCC TAGATTTCAG GAGCCTGTAC CCCTCGATAA TAATCACCCA TAACGTCTCA   1260
CCGGATACGC TGAACAGGGA AGGGTGTAGG AATACGATG TCGCCCCAGA GGTTGGGCAC    1320
AAGTTCTGCA AGGACTTCCC GGGGTTTATC CCCAGCCTGC TCAAGAGGTT ATTGGATGAA   1380
AGGCAAGAAA TAAAAGGAA GATGAAAGCT TCTAAAGACC CAATCGAGAA GAAGATGCTT   1440
GATTACAGGC AACGGGCAAT CAAAATCCTG GCAAACAGCT ATTATGGGTA TTATGGGTAC   1500
GCAAAAGCCC GTTGGTACTG TAAGGAGTGC GCAGAGAGCG TTACGGCCTG GGGGAGGGAA   1560
TATATAGAGT TCGTAAGGAA GGAACTGGAG GAAAAGTTCG GGTTCAAAGT CTTATACATA   1620
GACACANNNG GACTCTACGC CACAATTCCT GGGGCAAAAC CCGAGGAGAT AAAGAAGAAA   1680
GCCCTAGAGT TCGTAGATTA TATAAACGCC AAGCTCCCAG GGCTGTTGGA GCTTGAGTAC   1740
GAGGGCTTCT ACGTGAGAGG GTTCTTCGTG ACGAAGAAGA AGTATGCGTT GATAGATGAG   1800
GAAGGGAAGA TAATCACTAG GGGGCTTGAA ATAGTCAGGA GGGACTGGAG CGAAATAGCC   1860
AAAGAAACCC AAGCAAAAGT CCTAGAGGCT ATCCTAAAGC ATGGCAACGT TGAGGAGGCA   1920
GTAAAGATAG TTAAGGAGGT AACTGAAAAG CTGAGCAAGT ACGAAATACC TCCAGAAAAG   1980
CTAGTTATTT ACGAGCAGAT CACGAGGCCC CTTCACGAGT ACAAGGCTAT AGGTCCGCAC   2040
GTTGCCGTGG CAAAAAGGTT AGCCGCTAGA GGAGTAAAGG TGAGGCCTGG CATGGTGATA   2100
```

Figure 7 Continued

```
GGGTACATAG TGCTGAGGGG AGACGGGCCA ATAAGCAAGA GGGCTATCCT TGCAGAGGAG    2160
TTCGATCTCA GGAAGCATAA GTATGACGCT GAGTATTACA TAGAAAATCA GGTTTTACCT    2220
GCCGTTCTTA GAATATTAGA GGCCTTTGGG TACAGGAAAG AAGACCTCAG GTGGCAGAAG    2280
ACTAAACAGA CAGGTCTTAC GGCATGGCTT AACATCAAGA AGAAGTAA                 2328
[SEQ ID NO. 119]
```

Deep Vent K593T NNN=ACT, ACC, ACA, ACG (All possible T codons)
```
ATGATACTTG ACGCTGACTA CATCACCGAG GATGGGAAGC CGATTATAAG GATTTTCAAG      60
AAAGAAAACG GCGAGTTTAA GGTTGAGTAC GACAGAAACT TTAGACCTTA CATTTACGCT     120
CTCCTCAAAG ATGACTCGCA GATTGATGAG GTTAGGAAGA TAACCGCCGA GAGGCATGGG     180
AAGATAGTGA GAATTATAGA TGCCGAAAAG GTAAGGAAGA AGTTCCTGGG GAGGCCGATT     240
GAGGTATGGA GGCTGTACTT TGAACACCCT CAGGACGTTC CCGCAATAAG GATAAGATA     300
AGAGAGCATT CCGCAGTTAT TGACATCTTT GAGTACGACA TTCCGTTCGC GAAGAGGTAC     360
CTAATAGACA AAGGCCTAAT TCCAATGGAA GGCGATGAAG AGCTCAAGTT GCTCGCATTT     420
GACATAGAAA CCCTCTATCA CGAAGGGGAG GAGTTCGCGA AGGGGCCCAT TATAATGATA     480
AGCTATGCTG ATGAGGAAGA AGCCAAAGTC ATAACGTGGA AAAAGATCGA TCTCCCGTAC     540
GTCGAGGTAG TTTCCAGCGA GAGGGAGATG ATAAAGCGGT TCCTCAAGGT GATAAGGGAG     600
AAAGATCCCG ATGTTATAAT TACCTACAAC GGCGATTCTT TCGACCTTCC CTATCTAGTT     660
AAGAGGGCCG AAAAGCTCGG GATAAAGCTA CCCCTGGGAA GGGACGGTAG TGAGCCAAAG     720
ATGCAGAGGC TTGGGGATAT GACAGCGGTG GAGATAAAGG GAAGGATACA CTTTGACCTC     780
TACCACGTGA TTAGGAGAAC GATAAACCTC CCAACATACA CCCTCGAGGC AGTTTATGAG     840
GCAATCTTCG GAAAGCCAAA GGAGAAAGTT TACGCTCACG AGATAGCTGA GGCCTGGGAG     900
ACTGGAAAGG GACTGGAGAG AGTTGCAAAG TATTCAATGG AGGATGCAAA GGTAACGTAC     960
GAGCTCGGTA GGGAGTTCTT CCCAATGGAG GCCCAGCTTT CAAGGTTAGT CGGCCAGCCC    1020
CTGTGGGATG TTTCTAGGTC TTCAACTGGC AACTTGGTGG AGTGGTACCT CCTCAGGAAG    1080
GCCTACGAGA GGAATGAATT GGCTCCAAAC AAGCCGGATG AGAGGGAGTA CGAGAGAAGG    1140
CTAAGGGAGA GCTACGCTGG GGGATACGTT AAGGAGCCGG AGAAAGGGCT CTGGGAGGGG    1200
TTAGTTTCCC TAGATTTCAG GAGCCTGTAC CCCTCGATAA TAATCACCCA TAACGTCTCA    1260
CCGGATACGC TGAACAGGGA AGGGTGTAGG GAATACGATG TCGCCCCAGA GGTTGGGCAC    1320
AAGTTCTGCA AGGACTTCCC GGGGTTTATC CCCAGCCTGC TCAAGAGGTT ATTGGATGAA    1380
AGGCAAGAAA TAAAAAGGAA GATGAAAGCT TCTAAAGACC CAATCGAGAA AAGATGCTT    1440
GATTACAGGC AACGGGCAAT CAAAATCCTG GCAAACAGCT ATTATGGGTA TTATGGGTAC    1500
GCAAAAGCCC GTTGGTACTG TAAGGAGTGC GCAGAGAGCG TTACGGCCTG GGGGAGGGAA    1560
TATATAGAGT TCGTAAGGAA GGAACTGGAG GAAAAGTTCG GGTTCAAAGT CTTATACATA    1620
GACACAGATG GACTCTACGC CACAATTCCT GGGGCAAAAC CCGAGGAGAT AAAGAAGAAA    1680
GCCCTAGAGT TCGTAGATTA TATAAACGCC AAGCTCCCAG GCTGTTGGA GCTTGAGTAC    1740
GAGGGCTTCT ACGTGAGAGG GTTCTTCGTG ACGAAGNNNA AGTATGCGTT GATAGATGAG    1800
GAAGGGAAGA TAATCACTAG GGGGCTTGAA ATAGTCAGGA GGGACTGGAG CGAAATAGCC    1860
AAAGAAACCC AAGCAAAAGT CCTAGAGGCT ATCCTAAAGC ATGGCAACGT TGAGGAGGCA    1920
GTAAAGATAG TTAAGGAGGT AACTGAAAAG CTGAGCAAGT ACGAAATACC TCCAGAAAAG    1980
CTAGTTATTT ACGAGCAGAT CACGAGGCCC CTTCACGAGT ACAAGGCTAT AGGTCCGCAC    2040
GTTGCCGTGG CAAAAAGGTT AGCCGCTAGA GGAGTAAAGG TGAGGCCTGG CATGGTGATA    2100
GGGTACATAG TGCTGAGGGG AGACGGGCCA ATAAGCAAGA GGGCTATCCT TGCAGAGGAG    2160
TTCGATCTCA GGAAGCATAA GTATGACGCT GAGTATTACA TAGAAAATCA GGTTTTACCT    2220
GCCGTTCTTA GAATATTAGA GGCCTTTGGG TACAGGAAAG AAGACCTCAG GTGGCAGAAG    2280
ACTAAACAGA CAGGTCTTAC GGCATGGCTT AACATCAAGA AGAAGTAA                 2328
[SEQ ID NO. 120]
```

Tgo Y384N NNN=AAT, AAC
Tgo Y384L NNN=TTA, TTG, CTT, CTC, CTA, CTG
Tgo Y384H NNN=CAT, CAC
Tgo Y384Q NNN=CAA, CAG

Tgo Y384S NNN=TCT, TCC, TCA, TCG, AGT, AGC

```
atgatcctcg atacagacta cataactgag gatggaaagc ccgtcatcag gatcttcaag    60
aaggagaacg gcgagttcac catagactac gacagaaact ttgagccata catctacgcg   120
ctcttgaagg acgactctcc gattgaggac gtcaagaaga taactgccga gaggcacggc   180
actaccgtta gggttgtcag ggccgagaaa gtgaagaaga agttcctagg caggccgata   240
gaggtctgga agctctactt cactcacccc caggacgttc ccgcaatcag ggacaagata   300
aaggagcatc ctgccgttgt ggacatctac gagtacgaca tcccctccgc gaagcgctac   360
ctcatagaca aaggcttaat cccgatggag ggcgacgagg aacttaagat gctcgccttc   420
gacatcgaga cgctctatca cgagggcgag gagttcgccg aagggcctat cctgatgata   480
agctacgccg acgaggaagg ggcgcgcgtt attacctgga agaatatcga ccttccctat   540
gtcgacgtcg tttccaccga gaaggagatg ataaagcgct cctcaaggt cgtcaaggaa   600
aaggatcccg acgtcctcat aatctacaac ggcgacaact tcgacttcgc ctacctcaag   660
aagcgctccg agaagctcgg agtcaagttc atcctcggaa gggaagggag cgaaccgaaa   720
atccagcgca tgggcgatcg ctttgcggtg gaggtcaagg gaaggattca cttcgacctc   780
tacccgtca ttaggagaac gattaacctc cccacttaca cccttgaggc agtatatgaa   840
gccatctttg gacagccgaa ggagaaggtc tacgctgagg agatagcgca ggcctgggaa   900
acgggcgagg gattagaaag ggtggcccgc tactcgatgg aggacgcgaa ggtaacctat   960
gaactcggaa aagagttctt ccctatggaa gcccagctct cgcgcctcgt aggccagagc  1020
ctctgggatg tatctcgctc gagtaccgga aacctcgtcg agtggttttt gctgaggaag  1080
gcctacgaga ggaatgaact tgcaccaaac aagccggacg agagggagct ggcaagaaga  1140
agggagagcn nngcgggtgg atacgtcaag gagcccgaaa ggggactgtg ggagaacatc  1200
gtgtatctgg acttccgctc cctgtatcct tcgataataa tcacccataa cgtctcccct  1260
gatacactca acagggaggg ttgtgaggag tacgacgtgg ctcctcaggt aggccataag  1320
ttctgcaagg acttccccgg cttcatccca agcctcctcg agacctctt ggaggagaga  1380
cagaaggtaa agaagaagat gaaggccact atagacccaa tcgagaagaa actcctcgat  1440
tacaggcaac gagcaatcaa aatccttgct aatagcttct acggttacta cggctataca  1500
aaggcccgct ggtactacaa ggagtgcgcc gagagcgtta ccggttgggg cagggagtac  1560
atcgagacca cgataaggga aatagaggag aaatttggct ttaaagtcct ctacgcggac  1620
acagatggat ttttcgcaac aatacctgga gcggacgccg aaaccgtcaa aaagaaggca  1680
aaggagttcc tggactacat caacgccaaa ctgcccggcc tgctcgaact cgaatacgag  1740
ggcttctaca agcgcggctt cttcgtgacg aagaagaagt acgcggttat agacgaggag  1800
gacaagataa cgacgcgcgg gcttgaaata gttaggcgtg actggagcga gatagcgaag  1860
gagacgcagg cgagggttct tgaggcgata ctaaagcacg gtgacgttga agaagcggta  1920
aggattgtca aagaggttac ggagaagctg agcaagtacg aggttccacc ggagaagctg  1980
gtcatctacg agcagataac ccgcgacctg aaggactaca aggccaccgg ccgcatgtg  2040
gctgttgcaa acgcctcgc cgcaaggggg ataaaaatcc ggcccggaac ggtcataagc  2100
tacatcgtgc tcaaaggctc gggaaggatt ggggacaggg ctataccctt tgacgaattt  2160
gacccggcaa agcacaagta cgatgcagaa tactacatcg agaaccaggt tcttccagct  2220
gtggagagga ttctgagggc ctttggttac cgtaagaag atttaaggta tcagaaaacg  2280
cggcaggttg gcttgggggc gtggctaaaa cctaagacat ga                      2322
```
[SEQ ID NO. 121]

Tgo G386S NNN=TCT, TCC, TCA, TCG, AGT, AGC
Tgo G386P NNN=CCT, CCA, CCG, CCC

```
atgatcctcg atacagacta cataactgag gatggaaagc ccgtcatcag gatcttcaag    60
aaggagaacg gcgagttcac catagactac gacagaaact tgagccata catctacgcg   120
ctcttgaagg acgactctcc gattgaggac gtcaagaaga taactgccga gaggcacggc   180
actaccgtta gggttgtcag ggccgagaaa gtgaagaaga agttcctagg caggccgata   240
gaggtctgga agctctactt cactcacccc caggacgttc ccgcaatcag ggacaagata   300
aaggagcatc ctgccgttgt ggacatctac gagtacgaca tcccctccgc gaagcgctac   360
```

Figure 7 Continued

```
ctcatagaca aaggcttaat cccgatggag ggcgacgagg aacttaagat gctcgccttc    420
gacatcgaga cgctctatca cgagggcgag gagttcgccg aagggcctat cctgatgata    480
agctacgccg acgaggaagg ggcgcgcgtt attacctgga agaatatcga ccttccctat    540
gtcgacgtcg tttccaccga gaaggagatg ataaagcgct tcctcaaggt cgtcaaggaa    600
aaggatcccg acgtcctcat aatctacaac ggcgacaact tcgacttcgc ctacctcaag    660
aagcgctccg agaagctcgg agtcaagttc atcctcggaa gggaagggag cgaaccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcgaa ggtaacctat    960
gaactcggaa aagagttctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgnnngg atacgtcaag gagcccgaaa ggggactgtg ggagaacatc   1200
gtgtatctgg acttccgctc cctgtatcct tcgataataa tcacccataa cgtctcccct   1260
gatacactca acaggagggg ttgtgaggag tacgacgtgg ctcctcaggt aggccataag   1320
ttctgcaagg acttccccgg cttcatccca agcctcctcg agacctctt ggaggagaga   1380
cagaaggtaa agaagaagat gaaggccact atagacccaa tcgagaagaa actcctcgat   1440
tacaggcaac gagcaatcaa aatccttgct aatagcttct acggttacta cggctataca   1500
aaggcccgct ggtactacaa ggagtgcgcc gagagcgtta ccggttgggg cagggagtac   1560
atcgagacca cgataaggga aatagaggag aaatttggct ttaaagtcct ctacgcggac   1620
acagatggat ttttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacg aggttccacc ggagaagctg   1980
gtcatctacg agcagataac ccgcgacctg aaggactaca aggccaccgg ccgcatgtg    2040
gctgttgcaa aacgcctcgc cgcaaggggg ataaaaatcc ggcccggaac ggtcataagc   2100
tacatcgtgc tcaaaggctc gggaaggatt ggggacaggg ctatacccct tgacgaattt   2160
gacccggcaa agcacaagta cgatgcagaa tactacatcg agaaccaggt tcttccagct   2220
gtggagagga ttctgagggc cttggttac cgtaaagaag atttaaggta tcagaaaacg   2280
cggcaggttg cttgggggc gtggctaaaa cctaagacat ga                       2322
[SEQ ID NO. 122]

Tgo G387A NNN=GCA, GCT, GCC, GCG
Tgo G386P NNN=CCT, CCA, CCG, CCC atgatcctcg atacagacta cataactgag gatggaaagc ccgtcatcag gatcttcaag     60
aaggagaacg gcgagttcac catagactac gacagaaact ttgagccata catctacgcg    120
ctcttgaagg acgactctcc gattgaggac gtcaagaaga taactgccga gaggcacggc    180
actaccgtta gggttgtcag ggccgagaaa gtgaagaaga gttcctagg caggccgata    240
gaggtctgga agctctactt cactcacccc caggacgttc cgcaatcag gacaagata     300
aaggagcatc ctgccgttgt ggacatctac gagtacgaca tcccttcgc gaagcgctac    360
ctcatagaca aaggcttaat cccgatggag ggcgacgagg aacttaagat gctcgccttc    420
gacatcgaga cgctctatca cgagggcgag gagttcgccg aagggcctat cctgatgata    480
agctacgccg acgaggaagg ggcgcgcgtt attacctgga agaatatcga ccttccctat    540
gtcgacgtcg tttccaccga gaaggagatg ataaagcgct tcctcaaggt cgtcaaggaa    600
aaggatcccg acgtcctcat aatctacaac ggcgacaact tcgacttcgc ctacctcaag    660
aagcgctccg agaagctcgg agtcaagttc atcctcggaa gggaagggag cgaaccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
```

Figure 7 Continued

```
gccatctttg gacagccgaa ggagaaggtc tacgctgagg agatagcgca ggcctgggaa    900
acgggcgagg gattagaaag ggtggcccgc tactcgatgg aggacgcgaa ggtaacctat    960
gaactcggaa aagagttctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtnn ntacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg agacctcctt ggaggagaga   1380
cagaaggtaa agaagaagat gaaggccact atagacccaa tcgagaagaa actcctcgat   1440
tacaggcaac gagcaatcaa aatccttgct aatagcttct acggttacta cggctataca   1500
aaggcccgct ggtactacaa ggagtgcgcc gagagcgtta ccggttgggg cagggagtac   1560
atcgagacca cgataaggga aatagaggag aaatttggct ttaaagtcct ctacgcggac   1620
acagatggat ttttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacg aggttccacc ggagaagctg   1980
gtcatctacg agcagataac ccgcgacctg aaggactaca aggccaccgg gccgcatgtg   2040
gctgttgcaa aacgcctcgc cgcaaggggg ataaaaatcc ggcccggaac ggtcataagc   2100
tacatcgtgc tcaaaggctc gggaaggatt ggggacaggg ctatacccctt tgacgaattt   2160
gacccggcaa agcacaagta cgatgcagaa tactacatcg agaaccaggt tcttccagct   2220
gtggagagga ttctgagggc ctttggttac cgtaagaag atttaaggta tcagaaaacg   2280
cggcaggttg gcttggggc gtggctaaaa cctaagacat ga                       2322
[SEQ ID NO. 123]
```

Tgo D404E NNN=GAA, GAG

```
atgatcctcg atacagacta cataactgag gatggaaagc ccgtcatcag gatcttcaag    60
aaggagaacg gcgagttcac catagactac gacagaaact tgagccata catctacgcg    120
ctcttgaagg acgactctcc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggacgttc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gacatcgaga cgctctatca cgagggcgag gagttcgccg aagggcctat cctgatgata    480
agctacgccg acgaggaagg ggcgcgcgtt attacctgga agaatatcga ccttccctat    540
gtcgacgtcg tttccaccga gaaggagatg ataaagcgct tcctcaaggt cgtcaaggaa    600
aaggatcccg acgtcctcat aatctacaac ggcgacaact cgacttcgc ctacctcaag    660
aagcgctccg agaagctcgg agtcaagttc atcctcggaa gggaagggag cgaaccgaaa    720
atccagcgca tgggcgatcg ctttgcggtg gaggtcaagg gaaggattca cttcgacctc    780
taccccgtca ttaggagaac gattaacctc ccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcgaa ggtaacctat    960
gaactcggaa aagagttctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgn nnttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg agacctcctt ggaggagaga   1380
```

Figure 7 Continued

```
cagaaggtaa agaagaagat gaaggccact atagacccaa tcgagaagaa actcctcgat    1440
tacaggcaac gagcaatcaa aatccttgct aatagcttct acggttacta cggctataca    1500
aaggcccgct ggtactacaa ggagtgcgcc gagagcgtta ccggttgggg cagggagtac    1560
atcgagacca cgataaggga aatagaggag aaatttggct ttaaagtcct ctacgcggac    1620
acagatggat ttttcgcaac aatacctgga gcggacgccg aaaccgtcaa aaagaaggca    1680
aaggagttcc tggactacat caacgccaaa ctgcccggcc tgctcgaact cgaatacgag    1740
ggcttctaca agcgcggctt cttcgtgacg aagaagaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga agaagcggta    1920
aggattgtca aagaggttac ggagaagctg agcaagtacg aggttccacc ggagaagctg    1980
gtcatctacg agcagataac ccgcgacctg aaggactaca aggccaccgg gccgcatgtg    2040
gctgttgcaa aacgcctcgc cgcaaggggg ataaaaatcc ggcccggaac ggtcataagc    2100
tacatcgtgc tcaaaggctc gggaaggatt ggggacaggg ctataccctt tgacgaattt    2160
gacccggcaa agcacaagta cgatgcagaa tactacatcg agaaccaggt tcttccagct    2220
gtggagagga ttctgagggc cttttggttac cgtaaagaag atttaaggta tcagaaaacg    2280
cggcaggttg gcttgggggc gtggctaaaa cctaagacat ga                       2322
[SEQ ID NO. 124]
```

Tgo T541P NNN=CCT, CCA, CCG, CCC

```
atgatcctcg atacagacta cataactgag gatgaaagc ccgtcatcag gatcttcaag      60
aaggagaacg gcgagttcac catagactac gacagaaact ttgagccata catctacgcg    120
ctcttgaagg acgactctcc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggacgttc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gacatcgaga cgctctatca cgagggcgag gagttcgccg aagggcctat cctgatgata    480
agctacgccg acgaggaagg ggcgcgcgtt attacctgga gaaatatcga ccttccctat    540
gtcgacgtcg tttccaccga gaaggagatg ataaagcgct cctcaaggt cgtcaaggaa    600
aaggatcccg acgtcctcat aatctacaac ggcgacaact cgacttcgc ctacctcaag    660
aagcgctccg agaagctcgg agtcaagttc atcctcggaa gggaagggag cgaaccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcgaa ggtaacctat    960
gaactcggaa aagagttctt ccctatggaa gccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agggagct ggcaagaaga    1140
aggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca caggaggg ttgtgaggag tacgacgtgg ctcctcaggt aggccataag    1320
ttctgcaagg acttccccgg cttcatccca agcctcctcg gagacctctt ggaggagaga   1380
cagaaggtaa agaagaagat gaaggccact atagacccaa tcgagaagaa actcctcgat   1440
tacaggcaac gagcaatcaa aatccttgct aatagcttct acggttacta cggctataca   1500
aaggcccgct ggtactacaa ggagtgcgcc gagagcgtta ccggttgggg cagggagtac   1560
atcgagacca cgataaggga aatagaggag aaatttggct ttaaagtcct ctacgcggac   1620
nnngatggat ttttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
```

Figure 7 Continued

```
aggattgtca aagaggttac ggagaagctg agcaagtacg aggttccacc ggagaagctg    1980
gtcatctacg agcagataac ccgcgacctg aaggactaca aggccaccgg gccgcatgtg    2040
gctgttgcaa aacgcctcgc cgcaaggggg ataaaaatcc ggcccggaac ggtcataagc    2100
tacatcgtgc tcaaaggctc gggaaggatt ggggacaggg ctatacccctt tgacgaattt   2160
gacccggcaa agcacaagta cgatgcagaa tactacatcg agaaccaggt tcttccagct    2220
gtggagagga ttctgagggc ctttggttac cgtaaagaag atttaaggta tcagaaaacg    2280
cggcaggttg gcttgggggc gtggctaaaa cctaagacat ga                      2322
[SEQ ID NO. 125]
```

Tgo D542G NNN=GGT, GGA, GGG, GGC

```
atgatcctcg atacagacta cataactgag gatggaaagc ccgtcatcag gatcttcaag    60
aaggagaacg gcgagttcac catagactac gacagaaact ttgagccata catctacgcg    120
ctcttgaagg acgactctcc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggacgttc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gacatcgaga cgctctatca cgagggcgag gagttcgccg aagggcctat cctgatgata    480
agctacgccg acgaggaagg ggcgcgcgtt attacctgga agaatatcga ccttccctat    540
gtcgacgtcg tttccaccga aaggagatg ataaagcgct tcctcaaggt cgtcaaggaa    600
aaggatcccg acgtcctcat aatctacaac ggcgacaact tcgacttcgc ctacctcaag    660
aagcgctccg agaagctcgg agtcaagttc atcctcggaa gggaagggag cgaaccgaaa    720
atccagcgca tgggcgatcg ctttgcggtg gaggtcaagg gaaggattca cttcgacctc    780
taccccgtca ttaggagaac gattaaccct cccactttaca cccttgaggc agtatatgaa    840
gccatctttg acagccgaa ggagaaggtc tacgctgagg agatagcgca ggcctgggaa    900
acgggcgagg gattagaaag ggtggcccgc tactcgatgg aggacgcgaa ggtaacctat    960
gaactcggaa aagagttctt ccctatggaa gcccagctct cgcgcctcgt aggccagagc    1020
ctctgggatg tatctcgctc gagtaccgga aacctcgtcg agtggttttt gctgaggaag    1080
gcctacgaga ggaatgaact tgcaccaaac aagccggacg agagggagct ggcaagaaga    1140
agggagagct acgcgggtgg atacgtcaag gagcccgaaa ggggactgtg ggagaacatc    1200
gtgtatctgg acttccgctc cctgtatcct tcgataataa tcacccataa cgtctcccct    1260
gatacactca acagggaggg ttgtgaggag tacgacgtgg ctcctcaggt aggccataag    1320
ttctgcaagg acttccccgg cttcatccca agcctcctcg agacctctt ggaggagaga    1380
cagaaggtaa agaagaagat gaaggccact atagacccaa tcgagaagaa actcctcgat    1440
tacaggcaac gagcaatcaa aatccttgct aatagcttct acggttacta cggctataca    1500
aaggcccgct ggtactacaa ggagtgcgcc gagagcgtta ccggttgggg cagggagtac    1560
atcgagacca cgataaggga aatagaggag aaatttggct ttaaagtcct ctacgcggac    1620
acannnggat ttttcgcaac aatacctgga gcggacgccg aaaccgtcaa aagaaggca    1680
aaggagttcc tggactacat caacgccaaa ctgccccggcc tgctcgaact cgaatacgag    1740
ggcttctaca agcgcggctt cttcgtgacg aagaagaagt acgcggttat agacgaggag    1800
gacaagataa cgacgcgcgg gcttgaaata gttaggcgtg actggagcga atagcgaag    1860
gagacgcagg cgagggttct tgaggcgata ctaaagcacg gtgacgttga agaagcggta    1920
aggattgtca aagaggttac ggagaagctg agcaagtacg aggttccacc ggagaagctg    1980
gtcatctacg agcagataac ccgcgacctg aaggactaca aggccaccgg gccgcatgtg    2040
gctgttgcaa aacgcctcgc cgcaaggggg ataaaaatcc ggcccggaac ggtcataagc    2100
tacatcgtgc tcaaaggctc gggaaggatt ggggacaggg ctatacccctt tgacgaattt   2160
gacccggcaa agcacaagta cgatgcagaa tactacatcg agaaccaggt tcttccagct    2220
gtggagagga ttctgagggc ctttggttac cgtaaagaag atttaaggta tcagaaaacg    2280
cggcaggttg gcttgggggc gtggctaaaa cctaagacat ga                      2322
[SEQ ID NO. 126]
```

Figure 7 Continued

Tgo K592T NNN=ACT, ACC, ACA, ACG

```
atgatcctcg atacagacta cataactgag gatggaaagc ccgtcatcag gatcttcaag      60
aaggagaacg gcgagttcac catagactac gacagaaact ttgagccata catctacgcg     120
ctcttgaagg acgactctcc gattgaggac gtcaagaaga taactgccga gaggcacggc     180
actaccgtta gggttgtcag ggccgagaaa gtgaagaaga agttcctagg caggccgata     240
gaggtctgga agctctactt cactcacccc caggacgttc ccgcaatcag ggacaagata     300
aaggagcatc ctgccgttgt ggacatctac gagtacgaca tccccttcgc gaagcgctac     360
ctcatagaca aaggcttaat cccgatggag ggcgacgagg aacttaagat gctcgccttc     420
gacatcgaga cgctctatca cgagggcgag gagttcgccg aagggcctat cctgatgata     480
agctacgccg acgaggaagg ggcgcgcgtt attacctgga agaatatcga ccttccctat     540
gtcgacgtcg tttccaccga gaaggagatg ataaagcgct tcctcaaggt cgtcaaggaa     600
aaggatcccg acgtcctcat aatctacaac ggcgacaact tcgacttcgc ctacctcaag     660
aagcgctccg agaagctcgg agtcaagttc atcctcggaa gggaagggag cgaaccgaaa     720
atccagcgca tgggcgatcg ctttgcggtg gaggtcaagg gaaggattca cttcgacctc     780
tacccgtca ttaggagaac gattaacctc cccacttaca cccttgaggc agtatatgaa     840
gccatctttg gacagccgaa ggagaaggtc tacgctgagg agatagcgca ggcctgggaa     900
acgggcgagg gattagaaag ggtggcccgc tactcgatgg aggacgcgaa ggtaacctat     960
gaactcggaa aagagttctt ccctatggaa gcccagctct cgcgcctcgt aggccagagc    1020
ctctgggatg tatctcgctc gagtaccgga aacctcgtcg agtggttttt gctgaggaag    1080
gcctacgaga ggaatgaact tgcaccaaac aagccggacg agagggagct ggcaagaaga    1140
agggagagct acgcgggtgg atacgtcaag gagcccgaaa ggggactgtg ggagaacatc    1200
gtgtatctgg acttccgctc cctgtatcct tcgataataa tcacccataa cgtctcccct    1260
gatacactca acaggaggg ttgtgaggag tacgacgtgg ctcctcaggt aggccataag    1320
ttctgcaagg acttccccgg cttcatccca agcctcctcg agacctctt ggaggagaga    1380
cagaaggtaa agaagaagat gaaggccact atagacccaa tcgagaagaa actcctcgat    1440
tacaggcaac gagcaatcaa aatccttgct aatagcttct acggttacta cggctataca    1500
aaggcccgct ggtactacaa ggagtgcgcc gagagcgtta ccggttgggg cagggagtac    1560
atcgagacca cgataaggga aatagaggag aaatttggct ttaaagtcct ctacgcggac    1620
acagatggat ttttcgcaac aataccggaa gcggacgccg aaaccgtcaa aaagaaggca    1680
aaggagttcc tggactacat caacgccaaa ctgcccggcc tgctcgaact cgaatacgag    1740
ggcttctaca gcgcggctt cttcgtgacg aagnnnaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga agaagcggta    1920
aggattgtca agagggttac ggagaagctg agcaagtacg aggttccacc ggagaagctg    1980
gtcatctacg agcagataac ccgcgacctg aaggactaca aggccaccgg ccgcatgtg    2040
gctgttgcaa acgcctcgc cgcaaggggg ataaaaatcc ggcccggaac ggtcataagc    2100
tacatcgtgc tcaaaggctc ggggaaggatt ggggacaggg ctataccctt tgacgaattt    2160
gacccggcaa agcacaagta cgatgcagaa tactacatcg agaaccaggt tcttccagct    2220
gtggagagga ttctgagggc ctttggttac cgtaaagaag atttaaggta tcagaaaacg    2280
cggcaggttg gcttgggggc gtggctaaaa cctaagacat ga                       2322
[SEQ ID NO. 127]
```

```
                         SEQUENCE LISTING

<160> NUMBER OF SEQ ID NOS: 128

<210> SEQ ID NO 1
<211> LENGTH: 7
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(3)
<223> OTHER INFORMATION: X at position 2 or 3 is any amino acid.

<400> SEQUENCE: 1

Asp Xaa Xaa Ser Leu Tyr Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(7)
<223> OTHER INFORMATION: X at position 2, 3, 4, or 7 is any amino acid.

<400> SEQUENCE: 2

Lys Xaa Xaa Xaa Asn Ser Xaa Tyr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(3)
<223> OTHER INFORMATION: X at position 2 or 3 is any amino acid.

<400> SEQUENCE: 3

Thr Xaa Xaa Gly Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X at position 2 is any amino acid.

<400> SEQUENCE: 4
```

```
Tyr Xaa Asp Thr Asp Ser
1               5

<210> SEQ ID NO 5
<211> LENGTH: 3
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: X at position 2 is any amino acid.

<400> SEQUENCE: 5

Lys Xaa Tyr
1

<210> SEQ ID NO 6
<211> LENGTH: 4
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X at position 2 is any amino acid.

<400> SEQUENCE: 6

Tyr Xaa Gly Gly
1

<210> SEQ ID NO 7
<211> LENGTH: 6
<212> TYPE: PRT
<213> ORGANISM: Artificial Sequence
<220> FEATURE:
<223> OTHER INFORMATION: Consensus sequence

<400> SEQUENCE: 7

Ser Tyr Thr Gly Gly Phe
1               5

<210> SEQ ID NO 8
<211> LENGTH: 23
<212> TYPE: DNA
<213> ORGANISM: Artificial Sequence
<220> FEATURE:
<223> OTHER INFORMATION: Consensus sequence

<400> SEQUENCE: 8
gaggagagca ggaaaggtgg aag                                     23

<210> SEQ ID NO 9
<211> LENGTH: 23
<212> TYPE: DNA
<213> ORGANISM: Artificial Sequence
<220> FEATURE:
<223> OTHER INFORMATION: Consensus sequence

<400> SEQUENCE: 9
gaggtacagg gttgaggcta ctg                                     23

<210> SEQ ID NO 10
<211> LENGTH: 6
<212> TYPE: PRT
<213> ORGANISM: Artificial Sequence
```

```
<220> FEATURE:
<223> OTHER INFORMATION: Consensus sequence
<220> FEATURE:
<221> NAME/KEY: DOMAIN
<222> LOCATION: (1)..(6)
<223> OTHER INFORMATION: Consensus sequence

<400> SEQUENCE: 10

Ser Tyr Ala Gly Gly Tyr
1               5

<210> SEQ ID NO 11
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(6)
<223> OTHER INFORMATION: Consensus sequence

<400> SEQUENCE: 11

Ser Tyr Glu Gly Gly Tyr
1               5

<210> SEQ ID NO 12
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(6)
<223> OTHER INFORMATION: Consensus sequence

<400> SEQUENCE: 12

Thr Tyr Leu Gly Gly Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(7)
<223> OTHER INFORMATION: Consensus sequence

<400> SEQUENCE: 13

Asp Phe Arg Ala Leu Tyr Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(6)
<223> OTHER INFORMATION: Consensus sequence

<400> SEQUENCE: 14

Asp Phe Arg Ser Leu Tyr Pro
1               5
```

```
<210> SEQ ID NO 15
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(3)
<223> OTHER INFORMATION: Consensus sequence

<400> SEQUENCE: 15

Tyr Ile Asp Thr Asp Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(6)
<223> OTHER INFORMATION: Consensus sequence

<400> SEQUENCE: 16

Tyr Ala Asp Thr Asp Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(3)
<223> OTHER INFORMATION: Consensus sequence

<400> SEQUENCE: 17

Tyr Ser Asp Thr Asp Gly
1               5

<210> SEQ ID NO 18
<211> LENGTH: 3
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(3)
<223> OTHER INFORMATION: Consensus sequence

<400> SEQUENCE: 18

Lys Arg Tyr
1

<210> SEQ ID NO 19
<211> LENGTH: 775
<212> TYPE: PRT
<213> ORGANISM: Pyrococcus furiosus

<400> SEQUENCE: 19

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
```

-continued

```
                20                  25                  30
Thr Phe Arg Pro Tyr Ile Tyr Ala Leu Leu Arg Asp Asp Ser Lys Ile
            35                  40                  45
Glu Glu Val Lys Lys Ile Thr Gly Glu Arg His Gly Lys Ile Val Arg
        50                  55                  60
Ile Val Asp Val Glu Lys Val Glu Lys Lys Phe Leu Gly Lys Pro Ile
65                  70                  75                  80
Thr Val Trp Lys Leu Tyr Leu Glu His Pro Gln Asp Val Pro Thr Ile
                85                  90                  95
Arg Glu Lys Val Arg Glu His Pro Ala Val Val Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Glu Glu Leu Lys Ile Leu Ala Phe Asp Ile Glu Thr
        130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Ser Ser Glu Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
        210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
        290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Tyr Gln Arg Arg Leu Arg Glu Ser
        370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
```

```
Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
770                 775

<210> SEQ ID NO 20
<211> LENGTH: 775
<212> TYPE: PRT
<213> ORGANISM: Pyrococcus furiosus

<400> SEQUENCE: 20

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45
```

```
Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Glu Glu Leu Lys Ile Leu Ala Phe Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
                180                 185                 190

Arg Phe Leu Arg Ile Ile Arg Glu Lys Asp Pro Asp Ile Ile Val Thr
                195                 200                 205

Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Lys Ala Trp Glu Ser Gly Glu Asn
                290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
            370                 375                 380

Asn Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Lys Ile Leu Leu
465                 470                 475                 480
```

```
Asp Tyr Arg Gln Lys Ala Ile Lys Leu Leu Ala Asn Ser Phe Tyr Gly
            485                 490                 495
Tyr Tyr Gly Tyr Ala Lys Ala Arg Trp Tyr Cys Lys Glu Cys Ala Glu
        500                 505                 510
Ser Val Thr Ala Trp Gly Arg Lys Tyr Ile Glu Leu Val Trp Lys Glu
            515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
    595                 600                 605
Leu Glu Ile Val Arg Arg Asp Trp Ser Glu Ile Ala Lys Glu Thr Gln
610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
    675                 680                 685
Ala Lys Gly Val Lys Ile Lys Pro Gly Met Val Ile Gly Tyr Ile Val
690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
    755                 760                 765
Trp Leu Asn Ile Lys Lys Ser
    770                 775

<210> SEQ ID NO 21
<211> LENGTH: 775
<212> TYPE: PRT
<213> ORGANISM: Pyrococcus furiosus

<400> SEQUENCE: 21

Met Ile Leu Asp Val Asp Tyr Ile Thr Glu Glu Gly Lys Pro Val Ile
1               5                   10                  15
Arg Leu Phe Lys Lys Glu Asn Gly Lys Phe Lys Ile Glu His Asp Arg
            20                  25                  30
Thr Phe Arg Pro Tyr Ile Tyr Ala Leu Leu Arg Asp Asp Ser Lys Ile
        35                  40                  45
Glu Glu Val Lys Lys Ile Thr Gly Glu Arg His Gly Lys Ile Val Arg
    50                  55                  60
Ile Val Asp Val Glu Lys Val Glu Lys Lys Phe Leu Gly Lys Pro Ile
65                  70                  75                  80
```

-continued

```
Thr Val Trp Lys Leu Tyr Leu Glu His Pro Gln Asp Val Pro Thr Ile
             85                  90                  95
Arg Glu Lys Val Arg Glu His Pro Ala Val Val Asp Ile Phe Glu Tyr
            100                 105                 110
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Asp Ile Glu Thr
130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Arg Glu Met Ile Lys
            180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
            210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
            355                 360                 365
Pro Asn Lys Pro Ser Glu Glu Glu Tyr Gln Arg Arg Leu Arg Glu Ser
            370                 375                 380
Leu Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
            450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
```

```
                    500             505             510
Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Ile Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 22
<211> LENGTH: 775
<212> TYPE: PRT
<213> ORGANISM: Pyrococcus furiosus

<400> SEQUENCE: 22

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
```

-continued

```
            100                 105                 110
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Asp Ile Glu Thr
130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Glu Arg Glu Met Ile Lys
            180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
            210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
            355                 360                 365
Pro Asn Lys Pro Ser Glu Glu Tyr Gln Arg Arg Leu Arg Glu Ser
            370                 375                 380
His Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
            450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
            515                 520                 525
```

```
Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
770                 775

<210> SEQ ID NO 23
<211> LENGTH: 775
<212> TYPE: PRT
<213> ORGANISM: Pyrococcus furiosus

<400> SEQUENCE: 23

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125
```

```
Met Glu Gly Glu Glu Glu Leu Lys Ile Leu Ala Phe Asp Ile Glu Thr
130                 135                 140

Leu Tyr His Glu Gly Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Gln Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560
```

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Val Thr Lys
            580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
            770                 775

<210> SEQ ID NO 24
<211> LENGTH: 775
<212> TYPE: PRT
<213> ORGANISM: Pyrococcus furiosus

<400> SEQUENCE: 24

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

```
Ser Tyr Ala Asp Glu Asn Glu Ala Lys Val Ile Thr Trp Lys Asn Ile
            165                 170                 175
Asp Leu Pro Tyr Val Glu Val Ser Ser Glu Arg Glu Met Ile Lys
        180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
            245                 250                 255
His Phe Asp Leu Tyr His Val Ile Thr Arg Thr Ile Asn Leu Pro Thr
        260                 265                 270
Tyr Thr Leu Glu Ala Val Tyr Glu Ala Ile Phe Gly Lys Pro Lys Glu
    275                 280                 285
Lys Val Tyr Ala Asp Glu Ile Ala Lys Ala Trp Glu Ser Gly Glu Asn
290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
            325                 330                 335
Val Gly Gln Pro Leu Trp Asp Val Ser Arg Ser Ser Thr Gly Asn Leu
        340                 345                 350
Val Glu Trp Phe Leu Leu Arg Lys Ala Tyr Glu Arg Asn Glu Val Ala
    355                 360                 365
Pro Asn Lys Pro Ser Glu Glu Tyr Gln Arg Arg Leu Arg Glu Ser
370                 375                 380
Ser Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
            405                 410                 415
His Asn Val Ser Pro Asp Thr Leu Asn Leu Glu Gly Cys Lys Asn Tyr
        420                 425                 430
Asp Ile Ala Pro Gln Val Gly His Lys Phe Cys Lys Asp Ile Pro Gly
    435                 440                 445
Phe Ile Pro Ser Leu Leu Gly His Leu Leu Glu Glu Arg Gln Lys Ile
450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
            485                 490                 495
Tyr Tyr Gly Tyr Ala Lys Ala Arg Trp Tyr Cys Lys Glu Cys Ala Glu
        500                 505                 510
Ser Val Thr Ala Trp Gly Arg Lys Tyr Ile Glu Leu Val Trp Lys Glu
    515                 520                 525
Leu Glu Glu Lys Phe Gly Phe Lys Val Leu Tyr Ile Asp Thr Asp Gly
530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
            565                 570                 575
Glu Leu Glu Tyr Glu Gly Phe Tyr Lys Arg Gly Phe Phe Val Thr Lys
```

```
                    580             585             590
Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
        770                 775

<210> SEQ ID NO 25
<211> LENGTH: 775
<212> TYPE: PRT
<213> ORGANISM: Pyrococcus furiosus

<400> SEQUENCE: 25

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
```

```
                180                 185                 190
Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
        210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
370                 375                 380

Tyr Thr Ser Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605
```

```
Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
                755                 760                 765

Trp Leu Asn Ile Lys Lys Ser
    770                 775

<210> SEQ ID NO 26
<211> LENGTH: 775
<212> TYPE: PRT
<213> ORGANISM: Pyrococcus furiosus

<400> SEQUENCE: 26

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Asp Ile Glu Thr
        130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
            195                 200                 205
```

-continued

```
Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Pro Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640
```

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
        770                 775

<210> SEQ ID NO 27
<211> LENGTH: 775
<212> TYPE: PRT
<213> ORGANISM: Pyrococcus furiosus

<400> SEQUENCE: 27

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

```
Met Gln Arg Ile Gly Asp Met Thr Ala Val Glu Val Lys Gly Arg Ile
                    245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Lys Ala Trp Glu Ser Gly Glu Asn
            290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                    325                 330                 335

Val Gly Gln Pro Leu Trp Asp Val Ser Arg Ser Thr Gly Asn Leu
                340                 345                 350

Val Glu Trp Phe Leu Leu Arg Lys Ala Tyr Glu Arg Asn Glu Val Ala
                355                 360                 365

Pro Asn Lys Pro Ser Glu Glu Tyr Gln Arg Arg Leu Arg Glu Ser
            370                 375                 380

Tyr Thr Gly Ala Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                    405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
                435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                    485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
                515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                    565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                    645                 650                 655

Pro Pro Glu Lys Leu Ala Ile Tyr Glu Gln Ile Thr Arg Pro Leu His
```

```
                    660                 665                 670
Glu Tyr Lys Ala Ile Gly Pro His Val Ala Val Ala Lys Lys Leu Ala
                675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
                755                 760                 765

Trp Leu Asn Ile Lys Lys Ser
        770                 775

<210> SEQ ID NO 28
<211> LENGTH: 775
<212> TYPE: PRT
<213> ORGANISM: Pyrococcus furiosus

<400> SEQUENCE: 28

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
```

```
                    260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
                340                 345                 350
Val Glu Trp Phe Leu Leu Arg Lys Ala Tyr Glu Arg Asn Glu Val Ala
                355                 360                 365
Pro Asn Lys Pro Ser Glu Glu Glu Tyr Gln Arg Arg Leu Arg Glu Ser
            370                 375                 380
Tyr Thr Gly Pro Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
                420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
            450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Lys Tyr Ile Glu Leu Val Trp Lys Glu
            515                 520                 525
Leu Glu Glu Lys Phe Gly Phe Lys Val Leu Tyr Ile Asp Thr Asp Gly
            530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
            595                 600                 605
Leu Glu Ile Val Arg Arg Asp Trp Ser Glu Ile Ala Lys Glu Thr Gln
            610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
            675                 680                 685
```

```
Ala Lys Gly Val Lys Ile Lys Pro Gly Met Val Ile Gly Tyr Ile Val
        690             695             700

Leu Arg Gly Asp Gly Pro Ile Ser Asn Arg Ala Ile Leu Ala Glu Glu
705             710             715             720

Tyr Asp Pro Lys Lys His Lys Tyr Asp Ala Glu Tyr Tyr Ile Glu Asn
                725             730             735

Gln Val Leu Pro Ala Val Leu Arg Ile Leu Glu Gly Phe Gly Tyr Arg
                740             745             750

Lys Glu Asp Leu Arg Tyr Gln Lys Thr Arg Gln Val Gly Leu Thr Ser
                755             760             765

Trp Leu Asn Ile Lys Lys Ser
                770             775

<210> SEQ ID NO 29
<211> LENGTH: 773
<212> TYPE: PRT
<213> ORGANISM: Thermococcus gorgonarius

<400> SEQUENCE: 29

Met Ile Leu Asp Thr Asp Tyr Ile Thr Glu Asp Gly Lys Pro Val Ile
1               5               10              15

Arg Ile Phe Lys Lys Glu Asn Gly Glu Phe Lys Ile Asp Tyr Asp Arg
                20              25              30

Asn Phe Glu Pro Tyr Ile Tyr Ala Leu Leu Lys Asp Asp Ser Ala Ile
            35              40              45

Glu Asp Val Lys Lys Ile Thr Ala Glu Arg His Gly Thr Thr Val Arg
        50              55              60

Val Val Arg Ala Glu Lys Val Lys Lys Phe Leu Gly Arg Pro Ile
65              70              75              80

Glu Val Trp Lys Leu Tyr Phe Thr His Pro Gln Asp Val Pro Ala Ile
                85              90              95

Arg Asp Lys Ile Lys Glu His Pro Ala Val Val Asp Ile Tyr Glu Tyr
                100             105             110

Asp Ile Pro Phe Ala Lys Arg Tyr Leu Ile Asp Lys Gly Leu Ile Pro
            115             120             125

Met Glu Gly Asp Glu Glu Leu Lys Met Leu Ala Phe Asp Ile Glu Thr
130             135             140

Leu Tyr His Glu Gly Glu Glu Phe Ala Glu Gly Pro Ile Leu Met Ile
145             150             155             160

Ser Tyr Ala Asp Glu Glu Gly Ala Arg Val Ile Thr Trp Lys Asn Ile
                165             170             175

Asp Leu Pro Tyr Val Asp Val Val Ser Thr Glu Lys Glu Met Ile Lys
            180             185             190

Arg Phe Leu Lys Val Val Lys Glu Lys Asp Pro Asp Val Leu Ile Thr
        195             200             205

Tyr Asn Gly Asp Asn Phe Asp Phe Ala Tyr Leu Lys Lys Arg Ser Glu
        210             215             220

Lys Leu Gly Val Lys Phe Ile Leu Gly Arg Glu Gly Ser Glu Pro Lys
225             230             235             240

Ile Gln Arg Met Gly Asp Arg Phe Ala Val Glu Val Lys Gly Arg Ile
                245             250             255

His Phe Asp Leu Tyr Pro Val Ile Arg Arg Thr Ile Asn Leu Pro Thr
            260             265             270

Tyr Thr Leu Glu Ala Val Tyr Glu Ala Ile Phe Gly Gln Pro Lys Glu
        275             280             285
```

```
Lys Val Tyr Ala Glu Glu Ile Ala Gln Ala Trp Glu Thr Gly Gly
    290                 295                 300
Leu Glu Arg Val Ala Arg Tyr Ser Met Glu Asp Ala Lys Val Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Leu Ala Arg Arg Glu Ser Tyr
    370                 375                 380
Ala Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Glu Glu Tyr Asp
            420                 425                 430
Val Ala Pro Gln Val Gly His Lys Phe Cys Lys Asp Phe Pro Gly Phe
        435                 440                 445
Ile Pro Ser Leu Leu Gly Asp Leu Leu Glu Glu Arg Gln Lys Val Lys
    450                 455                 460
Lys Lys Met Lys Ala Thr Ile Asp Pro Ile Glu Lys Lys Leu Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Gln Tyr Ile Glu Thr Thr Ile Arg Glu Ile
        515                 520                 525
Glu Glu Lys Phe Gly Phe Lys Val Leu Tyr Ala Asp Thr Asp Gly Phe
    530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Asp Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile Tyr Glu Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Ile Lys Ile Arg Pro Gly Thr Val Ile Ser Tyr Ile Val Leu
    690                 695                 700
Lys Gly Ser Gly Arg Ile Gly Asp Arg Ala Ile Pro Phe Asp Glu Phe
705                 710                 715                 720
```

```
Asp Pro Ala Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
            755                 760                 765

Leu Lys Pro Lys Thr
        770

<210> SEQ ID NO 30
<211> LENGTH: 773
<212> TYPE: PRT
<213> ORGANISM: Thermococcus gorgonarius

<400> SEQUENCE: 30

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320
```

```
Glu Leu Gly Lys Glu Phe Phe Pro Met Glu Ala Gln Leu Ser Arg Leu
                325                 330                 335

Val Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Glu Ser Asn
370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
        450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
            515                 520                 525

Glu Glu Lys Phe Gly Phe Lys Val Leu Tyr Ala Asp Thr Asp Gly Phe
        530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
```

```
                        740                 745                 750
Glu Asp Leu Arg Tyr Gln Lys Thr Arg Gln Val Gly Leu Gly Ala Trp
            755                 760                 765

Leu Lys Pro Lys Thr
        770

<210> SEQ ID NO 31
<211> LENGTH: 773
<212> TYPE: PRT
<213> ORGANISM: Thermococcus gorgonarius

<400> SEQUENCE: 31

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
```

```
                340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Leu Ala Arg Arg Arg Glu Ser Leu
        370                 375                 380
Ala Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Glu Glu Tyr Asp
                420                 425                 430
Val Ala Pro Gln Val Gly His Lys Phe Cys Lys Asp Phe Pro Gly Phe
                435                 440                 445
Ile Pro Ser Leu Leu Gly Asp Leu Leu Glu Glu Arg Gln Lys Val Lys
        450                 455                 460
Lys Lys Met Lys Ala Thr Ile Asp Pro Ile Glu Lys Lys Leu Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
                500                 505                 510
Val Thr Ala Trp Gly Arg Gln Tyr Ile Glu Thr Ile Arg Glu Ile
        515                 520                 525
Glu Glu Lys Phe Gly Phe Lys Val Leu Tyr Ala Asp Thr Asp Gly Phe
        530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                565                 570                 575
Leu Glu Tyr Glu Gly Phe Tyr Lys Arg Gly Phe Phe Val Thr Lys Lys
                580                 585                 590
Lys Tyr Ala Val Ile Asp Glu Glu Asp Lys Ile Thr Thr Arg Gly Leu
                595                 600                 605
Glu Ile Val Arg Arg Asp Trp Ser Glu Ile Ala Lys Glu Thr Gln Ala
        610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile Tyr Glu Gln Ile Thr Arg Asp Leu Lys Asp
                660                 665                 670
Tyr Lys Ala Thr Gly Pro His Val Ala Val Ala Lys Arg Leu Ala Ala
                675                 680                 685
Arg Gly Ile Lys Ile Arg Pro Gly Thr Val Ile Ser Tyr Ile Val Leu
        690                 695                 700
Lys Gly Ser Gly Arg Ile Gly Asp Arg Ala Ile Pro Phe Asp Glu Phe
705                 710                 715                 720
Asp Pro Ala Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
                740                 745                 750
Glu Asp Leu Arg Tyr Gln Lys Thr Arg Gln Val Gly Leu Gly Ala Trp
        755                 760                 765
```

```
Leu Lys Pro Lys Thr
    770

<210> SEQ ID NO 32
<211> LENGTH: 773
<212> TYPE: PRT
<213> ORGANISM: Thermococcus gorgonarius

<400> SEQUENCE: 32

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365
```

```
Pro Asn Lys Pro Asp Glu Arg Glu Leu Ala Arg Arg Glu Ser His
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
                420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
    515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
    595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
    675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
    755                 760                 765

Leu Lys Pro Lys Thr
    770

<210> SEQ ID NO 33
```

```
<211> LENGTH: 773
<212> TYPE: PRT
<213> ORGANISM: Thermococcus gorgonarius

<400> SEQUENCE: 33

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Gln
    370                 375                 380

Ala Gly Gly Tyr Val Lys Glu Pro Glu Arg Gly Leu Trp Glu Asn Ile
385                 390                 395                 400
```

```
Val Tyr Leu Asp Phe Arg Ser Leu Tyr Pro Ser Ile Ile Thr His
            405                 410                 415
Asn Val Ser Pro Asp Thr Leu Asn Arg Glu Gly Cys Glu Tyr Asp
            420                 425                 430
Val Ala Pro Gln Val Gly His Lys Phe Cys Lys Asp Phe Pro Gly Phe
            435                 440                 445
Ile Pro Ser Leu Leu Gly Asp Leu Leu Glu Glu Arg Gln Lys Val Lys
        450                 455                 460
Lys Lys Met Lys Ala Thr Ile Asp Pro Ile Glu Lys Leu Leu Asp
465                 470                 475                 480
Tyr Arg Gln Arg Ala Ile Lys Ile Leu Ala Asn Ser Phe Tyr Gly Tyr
                    485                 490                 495
Tyr Gly Tyr Ala Lys Ala Arg Trp Tyr Cys Lys Glu Cys Ala Glu Ser
            500                 505                 510
Val Thr Ala Trp Gly Arg Gln Tyr Ile Glu Thr Thr Ile Arg Glu Ile
            515                 520                 525
Glu Glu Lys Phe Gly Phe Lys Val Leu Tyr Ala Asp Thr Asp Gly Phe
        530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                    565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Asp Lys Ile Thr Thr Arg Gly Leu
            595                 600                 605
Glu Ile Val Arg Arg Asp Trp Ser Glu Ile Ala Lys Glu Thr Gln Ala
        610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                    645                 650                 655
Pro Glu Lys Leu Val Ile Tyr Glu Gln Ile Thr Arg Asp Leu Lys Asp
            660                 665                 670
Tyr Lys Ala Thr Gly Pro His Val Ala Val Ala Lys Arg Leu Ala Ala
            675                 680                 685
Arg Gly Ile Lys Ile Arg Pro Gly Thr Val Ile Ser Tyr Ile Val Leu
        690                 695                 700
Lys Gly Ser Gly Arg Ile Gly Asp Arg Ala Ile Pro Phe Asp Glu Phe
705                 710                 715                 720
Asp Pro Ala Lys His Lys Tyr Asp Ala Glu Tyr Tyr Ile Glu Asn Gln
                    725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Gly Ala Trp
            755                 760                 765
Leu Lys Pro Lys Thr
    770

<210> SEQ ID NO 34
<211> LENGTH: 773
<212> TYPE: PRT
<213> ORGANISM: Thermococcus gorgonarius

<400> SEQUENCE: 34
```

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Ser Ala Ile
        35                  40                  45

Glu Asp Val Lys Lys Ile Thr Ala Glu Arg His Gly Thr Thr Val Arg
50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
            85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
        130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
            165                 170                 175

Asp Leu Pro Tyr Val Asp Val Ser Thr Glu Lys Glu Met Ile Lys
        180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
        210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
            325                 330                 335

Val Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Ser
        370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415

Asn Val Ser Pro Asp Thr Leu Asn Arg Glu Gly Cys Glu Glu Tyr Asp

```
                      420              425                430
Val Ala Pro Gln Val Gly His Lys Phe Cys Lys Asp Phe Pro Gly Phe
            435                  440                445

Ile Pro Ser Leu Leu Gly Asp Leu Leu Glu Glu Arg Gln Lys Val Lys
        450                  455                460

Lys Lys Met Lys Ala Thr Ile Asp Pro Ile Glu Lys Lys Leu Leu Asp
465                  470                  475                480

Tyr Arg Gln Arg Ala Ile Lys Ile Leu Ala Asn Ser Phe Tyr Gly Tyr
                485                  490                495

Tyr Gly Tyr Ala Lys Ala Arg Trp Tyr Cys Lys Glu Cys Ala Glu Ser
            500                  505                510

Val Thr Ala Trp Gly Arg Gln Tyr Ile Glu Thr Thr Ile Arg Glu Ile
        515                  520                525

Glu Glu Lys Phe Gly Phe Lys Val Leu Tyr Ala Asp Thr Asp Gly Phe
    530                  535                540

Phe Ala Thr Ile Pro Gly Ala Asp Ala Glu Thr Val Lys Lys Lys Ala
545                  550                  555                560

Lys Glu Phe Leu Asp Tyr Ile Asn Ala Lys Leu Pro Gly Leu Leu Glu
                565                  570                575

Leu Glu Tyr Glu Gly Phe Tyr Lys Arg Gly Phe Phe Val Thr Lys Lys
            580                  585                590

Lys Tyr Ala Val Ile Asp Glu Asp Lys Ile Thr Thr Arg Gly Leu
        595                  600                605

Glu Ile Val Arg Arg Asp Trp Ser Glu Ile Ala Lys Glu Thr Gln Ala
    610                  615                620

Arg Val Leu Glu Ala Ile Leu Lys His Gly Asp Val Glu Glu Ala Val
625                  630                  635                640

Arg Ile Val Lys Glu Val Thr Glu Lys Leu Ser Lys Tyr Glu Val Pro
                645                  650                655

Pro Glu Lys Leu Val Ile Tyr Glu Gln Ile Thr Arg Asp Leu Lys Asp
            660                  665                670

Tyr Lys Ala Thr Gly Pro His Val Ala Val Ala Lys Arg Leu Ala Ala
        675                  680                685

Arg Gly Ile Lys Ile Arg Pro Gly Thr Val Ile Ser Tyr Ile Val Leu
    690                  695                700

Lys Gly Ser Gly Arg Ile Gly Asp Arg Ala Ile Pro Phe Asp Glu Phe
705                  710                  715                720

Asp Pro Ala Lys His Lys Tyr Asp Ala Glu Tyr Tyr Ile Glu Asn Gln
                725                  730                735

Val Leu Pro Ala Val Glu Arg Ile Leu Arg Ala Phe Gly Tyr Arg Lys
            740                  745                750

Glu Asp Leu Arg Tyr Gln Lys Thr Arg Gln Val Gly Leu Gly Ala Trp
        755                  760                765

Leu Lys Pro Lys Thr
    770

<210> SEQ ID NO 35
<211> LENGTH: 773
<212> TYPE: PRT
<213> ORGANISM: Thermococcus gorgonarius

<400> SEQUENCE: 35

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
```

```
                   20                  25                  30
Asn Phe Glu Pro Tyr Ile Tyr Ala Leu Leu Lys Asp Asp Ser Ala Ile
                35                  40                  45
Glu Asp Val Lys Lys Ile Thr Ala Glu Arg His Gly Thr Thr Val Arg
 50                  55                  60
Val Val Arg Ala Glu Lys Val Lys Lys Phe Leu Gly Arg Pro Ile
 65                  70                  75                  80
Glu Val Trp Lys Leu Tyr Phe Thr His Pro Gln Asp Val Pro Ala Ile
                85                  90                  95
Arg Asp Lys Ile Lys Glu His Pro Ala Val Val Asp Ile Tyr Glu Tyr
                100                 105                 110
Asp Ile Pro Phe Ala Lys Arg Tyr Leu Ile Asp Lys Gly Leu Ile Pro
                115                 120                 125
Met Glu Gly Asp Glu Glu Leu Lys Met Leu Ala Phe Asp Ile Glu Thr
                130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Ile
                165                 170                 175
Asp Leu Pro Tyr Val Asp Val Val Ser Thr Glu Lys Glu Met Ile Lys
                180                 185                 190
Arg Phe Leu Lys Val Val Lys Glu Lys Asp Pro Asp Val Leu Ile Thr
                195                 200                 205
Tyr Asn Gly Asp Asn Phe Asp Phe Ala Tyr Leu Lys Lys Arg Ser Glu
                210                 215                 220
Lys Leu Gly Val Lys Phe Ile Leu Gly Arg Glu Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Ile Phe Gly Gln Pro Lys Glu
                275                 280                 285
Lys Val Tyr Ala Glu Glu Ile Ala Gln Ala Trp Glu Thr Gly Glu Gly
                290                 295                 300
Leu Glu Arg Val Ala Arg Tyr Ser Met Glu Asp Ala Lys Val Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Arg Glu Leu Ala Arg Arg Arg Glu Ser Tyr
                370                 375                 380
Ala Ser Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Glu Glu Tyr Asp
                420                 425                 430
Val Ala Pro Gln Val Gly His Lys Phe Cys Lys Asp Phe Pro Gly Phe
                435                 440                 445
```

```
Ile Pro Ser Leu Leu Gly Asp Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770

<210> SEQ ID NO 36
<211> LENGTH: 773
<212> TYPE: PRT
<213> ORGANISM: Thermococcus gorgonarius

<400> SEQUENCE: 36

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
                20                  25                  30

Asn Phe Glu Pro Tyr Ile Tyr Ala Leu Leu Lys Asp Asp Ser Ala Ile
            35                  40                  45
```

```
Glu Asp Val Lys Lys Ile Thr Ala Glu Arg His Gly Thr Thr Val Arg
 50                  55                  60

Val Val Arg Ala Glu Lys Val Lys Lys Phe Leu Gly Arg Pro Ile
 65                  70                  75                  80

Glu Val Trp Lys Leu Tyr Phe Thr His Pro Gln Asp Val Pro Ala Ile
                     85                  90                  95

Arg Asp Lys Ile Lys Glu His Pro Ala Val Val Asp Ile Tyr Glu Tyr
                    100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
                180                 185                 190

Arg Phe Leu Lys Val Val Lys Glu Lys Asp Pro Asp Val Leu Ile Thr
                195                 200                 205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Gln Pro Lys Glu
                275                 280                 285

Lys Val Tyr Ala Glu Glu Ile Ala Gln Ala Trp Glu Thr Gly Glu Gly
                290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Leu Ala Arg Arg Glu Ser Tyr
370                 375                 380

Ala Pro Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
                420                 425                 430

Val Ala Pro Gln Val Gly His Lys Phe Cys Lys Asp Phe Pro Gly Phe
                435                 440                 445

Ile Pro Ser Leu Leu Gly Asp Leu Leu Glu Glu Arg Gln Lys Val Lys
                450                 455                 460

Lys Lys Met Lys Ala Thr Ile Asp Pro Ile Glu Lys Lys Leu Leu Asp
465                 470                 475                 480
```

```
Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770

<210> SEQ ID NO 37
<211> LENGTH: 773
<212> TYPE: PRT
<213> ORGANISM: Thermococcus gorgonarius

<400> SEQUENCE: 37

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80
```

```
Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Ala Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
```

```
                500             505             510
Val Thr Ala Trp Gly Arg Gln Tyr Ile Glu Thr Thr Ile Arg Glu Ile
            515                 520                 525

Glu Glu Lys Phe Gly Phe Lys Val Leu Tyr Ala Asp Thr Asp Gly Phe
        530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
                580                 585                 590

Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
                660                 665                 670

Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
770

<210> SEQ ID NO 38
<211> LENGTH: 773
<212> TYPE: PRT
<213> ORGANISM: Thermococcus gorgonarius

<400> SEQUENCE: 38

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
```

```
                100                 105                 110
Asp Ile Pro Phe Ala Lys Arg Tyr Leu Ile Asp Lys Gly Leu Ile Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
            165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
            195                 200                 205

Tyr Asn Gly Asp Asn Phe Asp Phe Ala Tyr Leu Lys Lys Arg Ser Glu
            210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Gln Pro Lys Glu
            275                 280                 285

Lys Val Tyr Ala Glu Glu Ile Ala Gln Ala Trp Glu Thr Gly Glu Gly
            290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Arg Glu Ser Tyr
370                 375                 380

Ala Gly Pro Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
            450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
            515                 520                 525
```

-continued

```
Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770

<210> SEQ ID NO 39
<211> LENGTH: 774
<212> TYPE: PRT
<213> ORGANISM: Pyrococcus sp.

<400> SEQUENCE: 39

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125
```

```
Met Glu Gly Asp Glu Glu Leu Lys Met Leu Ala Phe Asp Ile Gln Thr
130                 135                 140

Leu Tyr His Glu Gly Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560
```

```
Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Val Thr Lys Lys
            580                 585                 590

Lys Tyr Ala Val Ile Asp Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Ser Ala Trp
            755                 760                 765

Leu Lys Pro Lys Gly Thr
    770

<210> SEQ ID NO 40
<211> LENGTH: 774
<212> TYPE: PRT
<213> ORGANISM: Pyrococcus sp.

<400> SEQUENCE: 40

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
        50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Gln Thr
        130                 135                 140

Leu Tyr His Glu Gly Glu Glu Phe Ala Glu Gly Pro Ile Leu Met Ile
145                 150                 155                 160
```

```
Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Asn
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
```

```
                            580                 585                 590
Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
                755                 760                 765

Leu Lys Pro Lys Gly Thr
    770

<210> SEQ ID NO 41
<211> LENGTH: 774
<212> TYPE: PRT
<213> ORGANISM: Pyrococcus sp.

<400> SEQUENCE: 41

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
```

```
                    180                 185                 190
Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
        210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Pro Ala Trp Glu Thr Gly Glu Asn
        290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
            325                 330                 335

Ile Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Leu
        370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Lys Glu Tyr Asp
        420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
            485                 490                 495

Tyr Gly Tyr Ala Arg Ala Arg Trp Tyr Cys Lys Glu Cys Ala Glu Ser
        500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605
```

-continued

```
Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 42
<211> LENGTH: 774
<212> TYPE: PRT
<213> ORGANISM: Pyrococcus sp.

<400> SEQUENCE: 42

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205
```

-continued

```
Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Pro Ala Trp Glu Thr Gly Glu Asn
            290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser His
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640
```

```
Arg Ile Val Lys Glu Val Thr Glu Lys Leu Ser Lys Tyr Glu Val Pro
            645                 650                 655
Pro Glu Lys Leu Val Ile His Glu Gln Ile Thr Arg Asp Leu Lys Asp
        660                 665                 670
Tyr Lys Ala Thr Gly Pro His Val Ala Val Ala Lys Arg Leu Ala Ala
            675                 680                 685
Arg Gly Val Lys Ile Arg Pro Gly Thr Val Ile Ser Tyr Ile Val Leu
    690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
            725                 730                 735
Val Leu Pro Ala Val Glu Arg Ile Leu Arg Ala Phe Gly Tyr Arg Lys
        740                 745                 750
Glu Asp Leu Arg Tyr Gln Lys Thr Arg Gln Val Gly Leu Ser Ala Trp
            755                 760                 765
Leu Lys Pro Lys Gly Thr
        770

<210> SEQ ID NO 43
<211> LENGTH: 774
<212> TYPE: PRT
<213> ORGANISM: Pyrococcus sp.

<400> SEQUENCE: 43

Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
            20                  25                  30
Thr Phe Glu Pro Tyr Phe Tyr Ala Leu Leu Lys Asp Asp Ser Ala Ile
        35                  40                  45
Glu Glu Val Lys Lys Ile Thr Ala Glu Arg His Gly Thr Val Val Thr
    50                  55                  60
Val Lys Arg Val Glu Lys Val Gln Lys Phe Leu Gly Arg Pro Val
65                  70                  75                  80
Glu Val Trp Lys Leu Tyr Phe Thr His Pro Gln Asp Val Pro Ala Ile
            85                  90                  95
Arg Asp Lys Ile Arg Glu His Gly Ala Val Ile Asp Ile Tyr Glu Tyr
            100                 105                 110
Asp Ile Pro Phe Ala Lys Arg Tyr Leu Ile Asp Lys Gly Leu Val Pro
        115                 120                 125
Met Glu Gly Asp Glu Glu Leu Lys Met Leu Ala Phe Asp Ile Gln Thr
    130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
            165                 170                 175
Asp Leu Pro Tyr Val Asp Val Val Ser Thr Glu Arg Glu Met Ile Lys
        180                 185                 190
Arg Phe Leu Arg Val Val Lys Glu Lys Asp Pro Asp Val Leu Ile Thr
    195                 200                 205
Tyr Asn Gly Asp Asn Phe Asp Phe Ala Tyr Leu Lys Lys Arg Cys Glu
    210                 215                 220
Lys Leu Gly Ile Asn Phe Ala Leu Gly Arg Asp Gly Ser Glu Pro Lys
225                 230                 235                 240
```

```
Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Pro Ala Trp Glu Thr Gly Glu Asn
290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Gln Ser Gln
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
```

```
                     660                 665                 670
Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                    725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 44
<211> LENGTH: 774
<212> TYPE: PRT
<213> ORGANISM: Pyrococcus sp.

<400> SEQUENCE: 44

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
```

```
                260                 265                 270
Tyr Thr Leu Glu Ala Val Tyr Glu Ala Val Phe Gly Gln Pro Lys Glu
            275                 280                 285
Lys Val Tyr Ala Glu Glu Ile Thr Pro Ala Trp Glu Thr Gly Glu Asn
            290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Lys Glu Leu Ala Arg Arg Gln Ser Ser
            370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Arg Phe Cys Lys Asp Phe Pro Gly Phe
                435                 440                 445
Ile Pro Ser Leu Leu Gly Asp Leu Leu Glu Glu Arg Gln Lys Ile Lys
                450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
                500                 505                 510
Val Thr Ala Trp Gly Arg Glu Tyr Ile Thr Met Thr Ile Lys Glu Ile
                515                 520                 525
Glu Glu Lys Tyr Gly Phe Lys Val Ile Tyr Ser Asp Thr Asp Gly Phe
                530                 535                 540
Phe Ala Thr Ile Pro Gly Ala Asp Ala Glu Thr Val Lys Lys Lys Ala
545                 550                 555                 560
Met Glu Phe Leu Asn Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
                580                 585                 590
Lys Tyr Ala Val Ile Asp Glu Glu Gly Lys Ile Thr Thr Arg Gly Leu
                595                 600                 605
Glu Ile Val Arg Arg Asp Trp Ser Glu Ile Ala Lys Glu Thr Gln Ala
            610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
            660                 665                 670
Tyr Lys Ala Thr Gly Pro His Val Ala Val Ala Lys Arg Leu Ala Ala
                675                 680                 685
```

```
Arg Gly Val Lys Ile Arg Pro Gly Thr Val Ile Ser Tyr Ile Val Leu
        690             695                 700

Lys Gly Ser Gly Arg Ile Gly Asp Arg Ala Ile Pro Phe Asp Glu Phe
705             710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
    770

<210> SEQ ID NO 45
<211> LENGTH: 774
<212> TYPE: PRT
<213> ORGANISM: Pyrococcus sp.

<400> SEQUENCE: 45

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285
```

```
Lys Val Tyr Ala Glu Glu Ile Thr Pro Ala Trp Glu Thr Gly Glu Asn
        290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
370                 375                 380

Glu Ser Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
                580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720
```

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
        770

<210> SEQ ID NO 46
<211> LENGTH: 774
<212> TYPE: PRT
<213> ORGANISM: Pyrococcus sp.

<400> SEQUENCE: 46

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

```
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Lys Glu Leu Ala Arg Arg Gln Ser Tyr
370                 375                 380
Glu Pro Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Arg Phe Cys Lys Asp Phe Pro Gly Phe
                435                 440                 445
Ile Pro Ser Leu Leu Gly Asp Leu Leu Glu Glu Arg Gln Lys Ile Lys
                450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
                500                 505                 510
Val Thr Ala Trp Gly Arg Glu Tyr Ile Thr Met Thr Ile Lys Glu Ile
                515                 520                 525
Glu Glu Lys Tyr Gly Phe Lys Val Ile Tyr Ser Asp Thr Asp Gly Phe
                530                 535                 540
Phe Ala Thr Ile Pro Gly Ala Asp Ala Glu Thr Val Lys Lys Lys Ala
545                 550                 555                 560
Met Glu Phe Leu Asn Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
                580                 585                 590
Lys Tyr Ala Val Ile Asp Glu Glu Gly Lys Ile Thr Thr Arg Gly Leu
                595                 600                 605
Glu Ile Val Arg Arg Asp Trp Ser Glu Ile Ala Lys Glu Thr Gln Ala
610                 615                 620
Arg Val Leu Glu Ala Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
                660                 665                 670
Tyr Lys Ala Thr Gly Pro His Val Ala Val Ala Lys Arg Leu Ala Ala
                675                 680                 685
Arg Gly Val Lys Ile Arg Pro Gly Thr Val Ile Ser Tyr Ile Val Leu
                690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
```

```
                        740                 745                 750
Glu Asp Leu Arg Tyr Gln Lys Thr Arg Gln Val Gly Leu Ser Ala Trp
                    755                 760                 765

Leu Lys Pro Lys Gly Thr
        770

<210> SEQ ID NO 47
<211> LENGTH: 774
<212> TYPE: PRT
<213> ORGANISM: Pyrococcus sp.

<400> SEQUENCE: 47

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
```

-continued

```
                340                 345                 350
Val Glu Trp Phe Leu Leu Arg Lys Ala Tyr Glu Arg Asn Glu Leu Ala
            355                 360                 365
Pro Asn Lys Pro Asp Glu Lys Glu Leu Ala Arg Arg Gln Ser Tyr
        370                 375                 380
Glu Gly Ala Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
        450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
        515                 520                 525
Glu Glu Lys Tyr Gly Phe Lys Val Ile Tyr Ser Asp Thr Asp Gly Phe
        530                 535                 540
Phe Ala Thr Ile Pro Gly Ala Asp Ala Glu Thr Val Lys Lys Lys Ala
545                 550                 555                 560
Met Glu Phe Leu Asn Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
        610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
        690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Ser Ala Trp
        755                 760                 765
```

Leu Lys Pro Lys Gly Thr
    770

<210> SEQ ID NO 48
<211> LENGTH: 774
<212> TYPE: PRT
<213> ORGANISM: Pyrococcus sp.

<400> SEQUENCE: 48

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
370                 375                 380

Glu Gly Pro Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
770

<210> SEQ ID NO 49

<211> LENGTH: 774
<212> TYPE: PRT
<213> ORGANISM: Thermococcus litoralis

<400> SEQUENCE: 49

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
370                 375                 380

Thr Thr Tyr Leu Gly Gly Tyr Val Lys Glu Pro Glu Lys Gly Leu Trp
385                 390                 395                 400
```

```
Glu Asn Ile Ile Tyr Leu Asp Phe Arg Ser Leu Tyr Pro Ser Ile Ile
                405                 410                 415
Val Thr His Asn Val Ser Pro Asp Thr Leu Glu Lys Glu Gly Cys Lys
            420                 425                 430
Asn Tyr Asp Val Ala Pro Ile Val Gly Tyr Arg Phe Cys Lys Asp Phe
        435                 440                 445
Pro Gly Phe Ile Pro Ser Ile Leu Gly Asp Leu Ile Ala Met Arg Gln
    450                 455                 460
Asp Ile Lys Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
            500                 505                 510
Ala Glu Ser Val Thr Ala Trp Gly Arg His Tyr Ile Glu Met Thr Ile
        515                 520                 525
Arg Glu Ile Glu Glu Lys Phe Gly Phe Lys Val Leu Tyr Ala Asp Thr
    530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
            580                 585                 590
Thr Lys Lys Arg Tyr Ala Val Ile Asp Glu Glu Gly Arg Ile Thr Thr
        595                 600                 605
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Val Glu Lys Ile Ala Lys Tyr
                645                 650                 655
Arg Val Pro Leu Glu Lys Leu Val Ile His Glu Gln Ile Thr Arg Asp
            660                 665                 670
Leu Lys Asp Tyr Lys Ala Ile Gly Pro His Val Ala Ile Ala Lys Arg
        675                 680                 685
Leu Ala Ala Arg Gly Ile Lys Val Lys Pro Gly Thr Ile Ile Ser Tyr
    690                 695                 700
Ile Val Leu Lys Gly Ser Gly Lys Ile Ser Asp Arg Val Ile Leu Leu
705                 710                 715                 720
Thr Glu Tyr Asp Pro Arg Lys His Lys Tyr Asp Pro Asp Tyr Tyr Ile
                725                 730                 735
Glu Asn Gln Val Leu Pro Ala Val Leu Arg Ile Leu Glu Ala Phe Gly
            740                 745                 750
Tyr Arg Lys Glu Asp Leu Arg Tyr Gln Ser Ser Lys Gln Thr Gly Leu
        755                 760                 765
Asp Ala Trp Leu Lys Arg
    770

<210> SEQ ID NO 50
<211> LENGTH: 774
<212> TYPE: PRT
<213> ORGANISM: Thermococcus litoralis

<400> SEQUENCE: 50
```

-continued

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Ser Ala Ile
        35                  40                  45

Glu Glu Ile Lys Ala Ile Lys Gly Glu Arg His Gly Lys Thr Val Arg
50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
        130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Tyr Lys Arg Arg Leu Arg
370                 375                 380

Thr Thr Asn Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
```

```
                420             425             430
Asn Tyr Asp Val Ala Pro Ile Val Gly Tyr Arg Phe Cys Lys Asp Phe
            435             440             445

Pro Gly Phe Ile Pro Ser Ile Leu Gly Asp Leu Ile Ala Met Arg Gln
    450             455             460

Asp Ile Lys Lys Met Lys Ser Thr Ile Asp Pro Ile Glu Lys Lys
465             470             475             480

Met Leu Asp Tyr Arg Gln Arg Ala Ile Lys Leu Leu Ala Asn Ser Tyr
                485             490             495

Tyr Gly Tyr Met Gly Tyr Pro Lys Ala Arg Trp Tyr Ser Lys Glu Cys
            500             505             510

Ala Glu Ser Val Thr Ala Trp Gly Arg His Tyr Ile Glu Met Thr Ile
        515             520             525

Arg Glu Ile Glu Glu Lys Phe Gly Phe Lys Val Leu Tyr Ala Asp Thr
    530             535             540

Asp Gly Phe Tyr Ala Thr Ile Pro Gly Glu Lys Pro Glu Leu Ile Lys
545             550             555             560

Lys Lys Ala Lys Glu Phe Leu Asn Tyr Ile Asn Ser Lys Leu Pro Gly
                565             570             575

Leu Leu Glu Leu Glu Tyr Glu Gly Phe Tyr Leu Arg Gly Phe Phe Val
            580             585             590

Thr Lys Lys Arg Tyr Ala Val Ile Asp Glu Gly Arg Ile Thr Thr
    595             600             605

Arg Gly Leu Glu Val Val Arg Arg Asp Trp Ser Glu Ile Ala Lys Glu
    610             615             620

Thr Gln Ala Lys Val Leu Glu Ala Ile Leu Lys Glu Gly Ser Val Glu
625             630             635             640

Lys Ala Val Glu Val Val Arg Asp Val Val Glu Lys Ile Ala Lys Tyr
                645             650             655

Arg Val Pro Leu Glu Lys Leu Val Ile His Glu Gln Ile Thr Arg Asp
            660             665             670

Leu Lys Asp Tyr Lys Ala Ile Gly Pro His Val Ala Ile Ala Lys Arg
    675             680             685

Leu Ala Ala Arg Gly Ile Lys Val Lys Pro Gly Thr Ile Ile Ser Tyr
    690             695             700

Ile Val Leu Lys Gly Ser Gly Lys Ile Ser Asp Arg Val Ile Leu Leu
705             710             715             720

Thr Glu Tyr Asp Pro Arg Lys His Lys Tyr Asp Pro Asp Tyr Tyr Ile
                725             730             735

Glu Asn Gln Val Leu Pro Ala Val Leu Arg Ile Leu Glu Ala Phe Gly
            740             745             750

Tyr Arg Lys Glu Asp Leu Arg Tyr Gln Ser Ser Lys Gln Thr Gly Leu
    755             760             765

Asp Ala Trp Leu Lys Arg
    770

<210> SEQ ID NO 51
<211> LENGTH: 774
<212> TYPE: PRT
<213> ORGANISM: Thermococcus litoralis

<400> SEQUENCE: 51

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
```

```
                    20                  25                  30
His Phe Gln Pro Tyr Ile Tyr Ala Leu Leu Lys Asp Asp Ser Ala Ile
                35                  40                  45

Glu Glu Ile Lys Ala Ile Lys Gly Glu Arg His Gly Lys Thr Val Arg
 50                  55                  60

Val Leu Asp Ala Val Lys Val Arg Lys Lys Phe Leu Gly Arg Glu Val
 65                  70                  75                  80

Glu Val Trp Lys Leu Ile Phe Glu His Pro Gln Asp Val Pro Ala Met
                 85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Leu Ala Phe Asp Ile Glu Thr
                130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
                180                 185                 190

Arg Phe Val Gln Val Val Lys Glu Lys Asp Pro Asp Val Ile Ile Thr
                195                 200                 205

Tyr Asn Gly Asp Asn Phe Asp Leu Pro Tyr Leu Ile Lys Arg Ala Glu
                210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
                260                 265                 270

Pro Thr Tyr Thr Leu Glu Ala Val Tyr Glu Ala Val Leu Gly Lys Thr
                275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
                340                 345                 350

Asn Leu Val Glu Trp Tyr Leu Leu Arg Val Ala Tyr Ala Arg Asn Glu
                355                 360                 365

Leu Ala Pro Asn Lys Pro Asp Glu Glu Tyr Lys Arg Arg Leu Arg
                370                 375                 380

Thr Thr Leu Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
                420                 425                 430

Asn Tyr Asp Val Ala Pro Ile Val Gly Tyr Arg Phe Cys Lys Asp Phe
                435                 440                 445
```

```
Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 52
<211> LENGTH: 774
<212> TYPE: PRT
<213> ORGANISM: Thermococcus litoralis

<400> SEQUENCE: 52

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45
```

```
Glu Glu Ile Lys Ala Ile Lys Gly Glu Arg His Gly Lys Thr Val Arg
     50                  55                  60

Val Leu Asp Ala Val Lys Val Arg Lys Lys Phe Leu Gly Arg Glu Val
 65                  70                  75                  80

Glu Val Trp Lys Leu Ile Phe Glu His Pro Gln Asp Val Pro Ala Met
                 85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
        130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
            245                 250                 255

Arg Ile His Phe Asp Leu Phe Pro Val Val Arg Arg Thr Ile Asn Leu
                260                 265                 270

Pro Thr Tyr Thr Leu Glu Ala Val Tyr Glu Ala Val Leu Gly Lys Thr
            275                 280                 285

Lys Ser Lys Leu Gly Ala Glu Glu Ile Ala Ala Ile Trp Glu Thr Glu
        290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
                355                 360                 365

Leu Ala Pro Asn Lys Pro Asp Glu Glu Glu Tyr Lys Arg Arg Leu Arg
        370                 375                 380

Thr Thr His Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
                435                 440                 445

Pro Gly Phe Ile Pro Ser Ile Leu Gly Asp Leu Ile Ala Met Arg Gln
        450                 455                 460

Asp Ile Lys Lys Lys Met Lys Ser Thr Ile Asp Pro Ile Glu Lys Lys
465                 470                 475                 480
```

```
Met Leu Asp Tyr Arg Gln Arg Ala Ile Lys Leu Leu Ala Asn Ser Tyr
            485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
        530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
770

<210> SEQ ID NO 53
<211> LENGTH: 774
<212> TYPE: PRT
<213> ORGANISM: Thermococcus litoralis

<400> SEQUENCE: 53

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80
```

```
Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
                165                 170                 175

Asp Leu Pro Tyr Val Asp Val Ser Asn Glu Arg Glu Met Ile Lys
                180                 185                 190

Arg Phe Val Gln Val Val Lys Glu Lys Asp Pro Asp Val Ile Ile Thr
            195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
            245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
            325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380

Thr Thr Gln Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
    435                 440                 445

Pro Gly Phe Ile Pro Ser Ile Leu Gly Asp Leu Ile Ala Met Arg Gln
    450                 455                 460

Asp Ile Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
```

```
                500             505             510
Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
        530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
        770

<210> SEQ ID NO 54
<211> LENGTH: 774
<212> TYPE: PRT
<213> ORGANISM: Thermococcus litoralis

<400> SEQUENCE: 54

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
```

```
                    100                 105                 110
Asp Ile Pro Phe Ala Lys Arg Tyr Leu Ile Asp Lys Gly Leu Ile Pro
                115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
                165                 170                 175

Asp Leu Pro Tyr Val Asp Val Val Ser Asn Glu Arg Glu Met Ile Lys
                180                 185                 190

Arg Phe Val Gln Val Val Lys Glu Lys Asp Pro Asp Val Ile Ile Thr
                195                 200                 205

Tyr Asn Gly Asp Asn Phe Asp Leu Pro Tyr Leu Ile Lys Arg Ala Glu
                210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
                260                 265                 270

Pro Thr Tyr Thr Leu Glu Ala Val Tyr Glu Ala Val Leu Gly Lys Thr
                275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
                340                 345                 350

Asn Leu Val Glu Trp Tyr Leu Leu Arg Val Ala Tyr Ala Arg Asn Glu
                355                 360                 365

Leu Ala Pro Asn Lys Pro Asp Glu Glu Glu Tyr Lys Arg Arg Leu Arg
                370                 375                 380

Thr Thr Ser Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
                420                 425                 430

Asn Tyr Asp Val Ala Pro Ile Val Gly Tyr Arg Phe Cys Lys Asp Phe
                435                 440                 445

Pro Gly Phe Ile Pro Ser Ile Leu Gly Asp Leu Ile Ala Met Arg Gln
                450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
                500                 505                 510

Ala Glu Ser Val Thr Ala Trp Gly Arg His Tyr Ile Glu Met Thr Ile
                515                 520                 525
```

```
Arg Glu Ile Glu Glu Lys Phe Gly Phe Lys Val Leu Tyr Ala Asp Thr
            530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
            610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 55
<211> LENGTH: 774
<212> TYPE: PRT
<213> ORGANISM: Thermococcus litoralis

<400> SEQUENCE: 55

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
        50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125
```

```
Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
                165                 170                 175

Asp Leu Pro Tyr Val Asp Val Val Ser Asn Glu Arg Glu Met Ile Lys
                180                 185                 190

Arg Phe Val Gln Val Val Lys Glu Lys Asp Pro Asp Val Ile Ile Thr
                195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
                260                 265                 270

Pro Thr Tyr Thr Leu Glu Ala Val Tyr Glu Ala Val Leu Gly Lys Thr
                275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
                340                 345                 350

Asn Leu Val Glu Trp Tyr Leu Arg Val Ala Tyr Ala Arg Asn Glu
                355                 360                 365

Leu Ala Pro Asn Lys Pro Asp Glu Glu Tyr Lys Arg Arg Leu Arg
                370                 375                 380

Thr Thr Tyr Leu Ser Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
                420                 425                 430

Asn Tyr Asp Val Ala Pro Ile Val Gly Tyr Arg Phe Cys Lys Asp Phe
                435                 440                 445

Pro Gly Phe Ile Pro Ser Ile Leu Gly Asp Leu Ile Ala Met Arg Gln
450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
                500                 505                 510

Ala Glu Ser Val Thr Ala Trp Gly Arg His Tyr Ile Glu Met Thr Ile
                515                 520                 525

Arg Glu Ile Glu Glu Lys Phe Gly Phe Lys Val Leu Tyr Ala Asp Thr
                530                 535                 540

Asp Gly Phe Tyr Ala Thr Ile Pro Gly Glu Lys Pro Glu Leu Ile Lys
545                 550                 555                 560
```

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Gly Arg Ile Thr Thr
        595                 600                 605

Arg Gly Leu Glu Val Val Arg Arg Asp Trp Ser Glu Ile Ala Lys Glu
        610                 615                 620

Thr Gln Ala Lys Val Leu Glu Ala Ile Leu Lys Glu Gly Ser Val Glu
625                 630                 635                 640

Lys Ala Val Glu Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
        690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
        770

<210> SEQ ID NO 56
<211> LENGTH: 774
<212> TYPE: PRT
<213> ORGANISM: Thermococcus litoralis

<400> SEQUENCE: 56

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

```
Ser Tyr Ala Asp Glu Glu Ala Arg Val Ile Thr Trp Lys Asn Ile
            165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
            195                 200                 205

Tyr Asn Gly Asp Asn Phe Asp Leu Pro Tyr Leu Ile Lys Arg Ala Glu
            210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
            245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
            275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
            325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
            355                 360                 365

Leu Ala Pro Asn Lys Pro Asp Glu Glu Tyr Lys Arg Arg Leu Arg
370                 375                 380

Thr Thr Tyr Leu Pro Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
            405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
            435                 440                 445

Pro Gly Phe Ile Pro Ser Ile Leu Gly Asp Leu Ile Ala Met Arg Gln
            450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
            485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
            530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
            565                 570                 575

Leu Leu Glu Leu Glu Tyr Glu Gly Phe Tyr Leu Arg Gly Phe Phe Val
```

-continued

```
                580                 585                 590
Thr Lys Lys Arg Tyr Ala Val Ile Asp Glu Glu Gly Arg Ile Thr Thr
            595                 600                 605

Arg Gly Leu Glu Val Val Arg Arg Asp Trp Ser Glu Ile Ala Lys Glu
        610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
        690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
        770

<210> SEQ ID NO 57
<211> LENGTH: 774
<212> TYPE: PRT
<213> ORGANISM: Thermococcus litoralis

<400> SEQUENCE: 57

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
        50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
```

-continued

```
                180                 185                 190
Arg Phe Val Gln Val Val Lys Glu Lys Asp Pro Asp Val Ile Ile Thr
            195                 200                 205
Tyr Asn Gly Asp Asn Phe Asp Leu Pro Tyr Leu Ile Lys Arg Ala Glu
        210                 215                 220
Lys Leu Gly Val Arg Leu Val Leu Gly Arg Asp Lys Glu His Pro Glu
225                 230                 235                 240
Pro Lys Ile Gln Arg Met Gly Asp Ser Phe Ala Val Glu Ile Lys Gly
                245                 250                 255
Arg Ile His Phe Asp Leu Phe Pro Val Val Arg Arg Thr Ile Asn Leu
            260                 265                 270
Pro Thr Tyr Thr Leu Glu Ala Val Tyr Glu Ala Val Leu Gly Lys Thr
        275                 280                 285
Lys Ser Lys Leu Gly Ala Glu Glu Ile Ala Ala Ile Trp Glu Thr Glu
290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
                325                 330                 335
Lys Leu Ile Gly Gln Ser Val Trp Asp Val Ser Arg Ser Thr Gly
            340                 345                 350
Asn Leu Val Glu Trp Tyr Leu Arg Val Ala Tyr Ala Arg Asn Glu
        355                 360                 365
Leu Ala Pro Asn Lys Pro Asp Glu Glu Tyr Lys Arg Arg Leu Arg
        370                 375                 380
Thr Thr Tyr Leu Gly Ala Tyr Val Lys Glu Pro Glu Lys Gly Leu Trp
385                 390                 395                 400
Glu Asn Ile Ile Tyr Leu Asp Phe Arg Ser Leu Tyr Pro Ser Ile Ile
                405                 410                 415
Val Thr His Asn Val Ser Pro Asp Thr Leu Glu Lys Glu Gly Cys Lys
            420                 425                 430
Asn Tyr Asp Val Ala Pro Ile Val Gly Tyr Arg Phe Cys Lys Asp Phe
        435                 440                 445
Pro Gly Phe Ile Pro Ser Ile Leu Gly Asp Leu Ile Ala Met Arg Gln
        450                 455                 460
Asp Ile Lys Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
            500                 505                 510
Ala Glu Ser Val Thr Ala Trp Gly Arg His Tyr Ile Glu Met Thr Ile
        515                 520                 525
Arg Glu Ile Glu Glu Lys Phe Gly Phe Lys Val Leu Tyr Ala Asp Thr
        530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
            580                 585                 590
Thr Lys Lys Arg Tyr Ala Val Ile Asp Glu Glu Gly Arg Ile Thr Thr
        595                 600                 605
```

```
Arg Gly Leu Glu Val Val Arg Arg Asp Trp Ser Glu Ile Ala Lys Glu
            610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 58
<211> LENGTH: 774
<212> TYPE: PRT
<213> ORGANISM: Thermococcus litoralis

<400> SEQUENCE: 58

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205
```

```
Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
370                 375                 380

Thr Thr Tyr Leu Gly Pro Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
610                 615                 620

Thr Gln Ala Lys Val Leu Glu Ala Ile Leu Lys Glu Gly Ser Val Glu
625                 630                 635                 640
```

```
Lys Ala Val Glu Val Val Arg Asp Val Glu Lys Ile Ala Lys Tyr
                645                 650                 655

Arg Val Pro Leu Glu Lys Leu Val Ile His Glu Gln Ile Thr Arg Asp
                660                 665                 670

Leu Lys Asp Tyr Lys Ala Ile Gly Pro His Val Ala Ile Ala Lys Arg
                675                 680                 685

Leu Ala Ala Arg Gly Ile Lys Val Lys Pro Gly Thr Ile Ile Ser Tyr
                690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
                740                 745                 750

Tyr Arg Lys Glu Asp Leu Arg Tyr Gln Ser Ser Lys Gln Thr Gly Leu
                755                 760                 765

Asp Ala Trp Leu Lys Arg
                770

<210> SEQ ID NO 59
<211> LENGTH: 775
<212> TYPE: PRT
<213> ORGANISM: Pyrococcus sp.

<400> SEQUENCE: 59

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
                35                  40                  45

Asp Glu Val Arg Lys Ile Thr Ala Glu Arg His Gly Lys Ile Val Arg
            50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Leu Ala Phe Asp Ile Glu Thr
130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Val Ile Arg Glu Lys Asp Pro Asp Val Ile Ile Thr
                195                 200                 205

Tyr Asn Gly Asp Ser Phe Asp Leu Pro Tyr Leu Val Lys Arg Ala Glu
                210                 215                 220

Lys Leu Gly Ile Lys Leu Pro Leu Gly Arg Asp Gly Ser Glu Pro Lys
225                 230                 235                 240
```

```
Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala His Glu Ile Ala Glu Ala Trp Glu Thr Gly Lys Gly
                290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Tyr Leu Leu Arg Lys Ala Tyr Glu Arg Asn Glu Leu Ala
                355                 360                 365

Pro Asn Lys Pro Asp Glu Arg Glu Tyr Glu Arg Arg Leu Arg Glu Ser
                370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
                420                 425                 430

Asp Val Ala Pro Glu Val Gly His Lys Phe Cys Lys Asp Phe Pro Gly
                435                 440                 445

Phe Ile Pro Ser Leu Leu Lys Arg Leu Leu Asp Glu Arg Gln Glu Ile
                450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Phe Val Arg Lys Glu
                515                 520                 525

Leu Glu Glu Lys Phe Gly Phe Lys Val Leu Tyr Ile Asp Thr Asp Gly
                530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Lys Tyr Ala Leu Ile Asp Glu Glu Gly Lys Ile Ile Thr Arg Gly
                595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
```

```
                    660                 665                 670
Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
        690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys
        770                 775

<210> SEQ ID NO 60
<211> LENGTH: 775
<212> TYPE: PRT
<213> ORGANISM: Pyrococcus sp.

<400> SEQUENCE: 60

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
```

-continued

```
                260                 265                 270
Tyr Thr Leu Glu Ala Val Tyr Glu Ala Ile Phe Gly Lys Pro Lys Glu
            275                 280                 285
Lys Val Tyr Ala His Glu Ile Ala Glu Ala Trp Glu Thr Gly Lys Gly
            290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Tyr Leu Leu Arg Lys Ala Tyr Glu Arg Asn Glu Leu Ala
            355                 360                 365
Pro Asn Lys Pro Asp Glu Arg Glu Tyr Glu Arg Arg Leu Arg Glu Ser
            370                 375                 380
Asn Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
            435                 440                 445
Phe Ile Pro Ser Leu Leu Lys Arg Leu Leu Asp Glu Arg Gln Glu Ile
            450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Arg Lys Glu
            515                 520                 525
Leu Glu Glu Lys Phe Gly Phe Lys Val Leu Tyr Ile Asp Thr Asp Gly
            530                 535                 540
Leu Tyr Ala Thr Ile Pro Gly Ala Lys Pro Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Val Arg Gly Phe Phe Val Thr Lys
            580                 585                 590
Lys Lys Tyr Ala Leu Ile Asp Glu Glu Gly Lys Ile Ile Thr Arg Gly
            595                 600                 605
Leu Glu Ile Val Arg Arg Asp Trp Ser Glu Ile Ala Lys Glu Thr Gln
            610                 615                 620
Ala Lys Val Leu Glu Ala Ile Leu Lys His Gly Asn Val Glu Glu Ala
625                 630                 635                 640
Val Lys Ile Val Lys Glu Val Thr Glu Lys Leu Ser Lys Tyr Glu Ile
                645                 650                 655
Pro Pro Glu Lys Leu Val Ile Tyr Glu Gln Ile Thr Arg Pro Leu His
            660                 665                 670
Glu Tyr Lys Ala Ile Gly Pro His Val Ala Val Ala Lys Arg Leu Ala
            675                 680                 685
```

```
Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
                740                 745                 750

Lys Glu Asp Leu Arg Trp Gln Lys Thr Lys Gln Thr Gly Leu Thr Ala
                755                 760                 765

Trp Leu Asn Ile Lys Lys Lys
770                 775

<210> SEQ ID NO 61
<211> LENGTH: 775
<212> TYPE: PRT
<213> ORGANISM: Pyrococcus sp.

<400> SEQUENCE: 61

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
                35                  40                  45

Asp Glu Val Arg Lys Ile Thr Ala Glu Arg His Gly Lys Ile Val Arg
            50                  55                  60

Ile Ile Asp Ala Glu Lys Val Arg Lys Lys Phe Leu Gly Arg Pro Ile
65              70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Leu Ala Phe Asp Ile Glu Thr
            130                 135                 140

Leu Tyr His Glu Gly Glu Glu Phe Ala Lys Gly Pro Ile Ile Met Ile
145             150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Val Ile Arg Glu Lys Asp Pro Asp Val Ile Ile Thr
                195                 200                 205

Tyr Asn Gly Asp Ser Phe Asp Leu Pro Tyr Leu Val Lys Arg Ala Glu
            210                 215                 220

Lys Leu Gly Ile Lys Leu Pro Leu Gly Arg Asp Gly Ser Glu Pro Lys
225             230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
                275                 280                 285
```

-continued

```
Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Leu Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720
```

```
Phe Asp Leu Arg Lys His Lys Tyr Asp Ala Glu Tyr Tyr Ile Glu Asn
            725                 730                 735

Gln Val Leu Pro Ala Val Leu Arg Ile Leu Glu Ala Phe Gly Tyr Arg
        740                 745                 750

Lys Glu Asp Leu Arg Trp Gln Lys Thr Lys Gln Thr Gly Leu Thr Ala
    755                 760                 765

Trp Leu Asn Ile Lys Lys Lys
    770             775

<210> SEQ ID NO 62
<211> LENGTH: 775
<212> TYPE: PRT
<213> ORGANISM: Pyrococcus sp.

<400> SEQUENCE: 62

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320
```

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Thr Gly Asn Leu
            340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375                 380

His Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
        450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
        690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg

```
                    740                 745                 750
Lys Glu Asp Leu Arg Trp Gln Lys Thr Lys Gln Thr Gly Leu Thr Ala
            755                 760                 765

Trp Leu Asn Ile Lys Lys Lys
        770                 775

<210> SEQ ID NO 63
<211> LENGTH: 775
<212> TYPE: PRT
<213> ORGANISM: Pyrococcus sp.

<400> SEQUENCE: 63

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
```

```
                340             345             350
Val Glu Trp Tyr Leu Leu Arg Lys Ala Tyr Glu Arg Asn Glu Leu Ala
            355             360             365
Pro Asn Lys Pro Asp Glu Arg Glu Tyr Glu Arg Arg Leu Arg Glu Ser
        370             375             380
Gln Ala Gly Gly Tyr Val Lys Glu Pro Glu Lys Gly Leu Trp Glu Gly
385             390             395             400
Leu Val Ser Leu Asp Phe Arg Ser Leu Tyr Pro Ser Ile Ile Ile Thr
                405             410             415
His Asn Val Ser Pro Asp Thr Leu Asn Arg Glu Gly Cys Arg Glu Tyr
                420             425             430
Asp Val Ala Pro Glu Val Gly His Lys Phe Cys Lys Asp Phe Pro Gly
            435             440             445
Phe Ile Pro Ser Leu Leu Lys Arg Leu Leu Asp Glu Arg Gln Glu Ile
        450             455             460
Lys Arg Lys Met Lys Ala Ser Lys Asp Pro Ile Glu Lys Lys Met Leu
465             470             475             480
Asp Tyr Arg Gln Arg Ala Ile Lys Ile Leu Ala Asn Ser Tyr Tyr Gly
                485             490             495
Tyr Tyr Gly Tyr Ala Lys Ala Arg Trp Tyr Cys Lys Glu Cys Ala Glu
            500             505             510
Ser Val Thr Ala Trp Gly Arg Glu Tyr Ile Glu Phe Val Arg Lys Glu
        515             520             525
Leu Glu Glu Lys Phe Gly Phe Lys Val Leu Tyr Ile Asp Thr Asp Gly
        530             535             540
Leu Tyr Ala Thr Ile Pro Gly Ala Lys Pro Glu Glu Ile Lys Lys Lys
545             550             555             560
Ala Leu Glu Phe Val Asp Tyr Ile Asn Ala Lys Leu Pro Gly Leu Leu
                565             570             575
Glu Leu Glu Tyr Glu Gly Phe Tyr Val Arg Gly Phe Phe Val Thr Lys
            580             585             590
Lys Lys Tyr Ala Leu Ile Asp Glu Glu Gly Lys Ile Ile Thr Arg Gly
            595             600             605
Leu Glu Ile Val Arg Arg Asp Trp Ser Glu Ile Ala Lys Glu Thr Gln
        610             615             620
Ala Lys Val Leu Glu Ala Ile Leu Lys His Gly Asn Val Glu Glu Ala
625             630             635             640
Val Lys Ile Val Lys Glu Val Thr Glu Lys Leu Ser Lys Tyr Glu Ile
                645             650             655
Pro Pro Glu Lys Leu Val Ile Tyr Glu Gln Ile Thr Arg Pro Leu His
            660             665             670
Glu Tyr Lys Ala Ile Gly Pro His Val Ala Val Ala Lys Arg Leu Ala
        675             680             685
Ala Arg Gly Val Lys Val Arg Pro Gly Met Val Ile Gly Tyr Ile Val
            690             695             700
Leu Arg Gly Asp Gly Pro Ile Ser Lys Arg Ala Ile Leu Ala Glu Glu
705             710             715             720
Phe Asp Leu Arg Lys His Lys Tyr Asp Ala Glu Tyr Tyr Ile Glu Asn
                725             730             735
Gln Val Leu Pro Ala Val Leu Arg Ile Leu Glu Ala Phe Gly Tyr Arg
            740             745             750
Lys Glu Asp Leu Arg Trp Gln Lys Thr Lys Gln Thr Gly Leu Thr Ala
            755             760             765
```

```
Trp Leu Asn Ile Lys Lys Lys
770                 775

<210> SEQ ID NO 64
<211> LENGTH: 775
<212> TYPE: PRT
<213> ORGANISM: Pyrococcus sp.

<400> SEQUENCE: 64

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365
```

```
Pro Asn Lys Pro Asp Glu Arg Glu Tyr Glu Arg Arg Leu Arg Glu Ser
    370                 375                 380

Ser Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775

<210> SEQ ID NO 65
```

-continued

```
<211> LENGTH: 775
<212> TYPE: PRT
<213> ORGANISM: Pyrococcus sp.

<400> SEQUENCE: 65

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Ser Gly Tyr Val Lys Glu Pro Glu Lys Gly Leu Trp Glu Gly
385                 390                 395                 400
```

```
Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775

<210> SEQ ID NO 66
<211> LENGTH: 775
<212> TYPE: PRT
<213> ORGANISM: Pyrococcus sp.

<400> SEQUENCE: 66
```

```
Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Ser Gln Ile
        35                  40                  45

Asp Glu Val Arg Lys Ile Thr Ala Glu Arg His Gly Lys Ile Val Arg
50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Pro Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
```

```
                    420             425             430
Asp Val Ala Pro Glu Val Gly His Lys Phe Cys Lys Asp Phe Pro Gly
            435                 440                 445
Phe Ile Pro Ser Leu Leu Lys Arg Leu Leu Asp Glu Arg Gln Glu Ile
            450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
            485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Arg Lys Glu
            515                 520                 525
Leu Glu Glu Lys Phe Gly Phe Lys Val Leu Tyr Ile Asp Thr Asp Gly
            530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
            565                 570                 575
Glu Leu Glu Tyr Glu Gly Phe Tyr Val Arg Gly Phe Phe Val Thr Lys
            580                 585                 590
Lys Lys Tyr Ala Leu Ile Asp Glu Glu Gly Lys Ile Ile Thr Arg Gly
            595                 600                 605
Leu Glu Ile Val Arg Arg Asp Trp Ser Glu Ile Ala Lys Glu Thr Gln
            610                 615                 620
Ala Lys Val Leu Glu Ala Ile Leu Lys His Gly Asn Val Glu Glu Ala
625                 630                 635                 640
Val Lys Ile Val Lys Glu Val Thr Glu Lys Leu Ser Lys Tyr Glu Ile
            645                 650                 655
Pro Pro Glu Lys Leu Val Ile Tyr Glu Gln Ile Thr Arg Pro Leu His
            660                 665                 670
Glu Tyr Lys Ala Ile Gly Pro His Val Ala Val Ala Lys Arg Leu Ala
            675                 680                 685
Ala Arg Gly Val Lys Val Arg Pro Gly Met Val Ile Gly Tyr Ile Val
            690                 695                 700
Leu Arg Gly Asp Gly Pro Ile Ser Lys Arg Ala Ile Leu Ala Glu Glu
705                 710                 715                 720
Phe Asp Leu Arg Lys His Lys Tyr Asp Ala Glu Tyr Tyr Ile Glu Asn
            725                 730                 735
Gln Val Leu Pro Ala Val Leu Arg Ile Leu Glu Ala Phe Gly Tyr Arg
            740                 745                 750
Lys Glu Asp Leu Arg Trp Gln Lys Thr Lys Gln Thr Gly Leu Thr Ala
            755                 760                 765
Trp Leu Asn Ile Lys Lys Lys
            770                 775

<210> SEQ ID NO 67
<211> LENGTH: 775
<212> TYPE: PRT
<213> ORGANISM: Pyrococcus sp.

<400> SEQUENCE: 67

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
```

```
            20                  25                  30
Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
            50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                    85                  90                  95

Arg Asp Lys Ile Arg Glu His Ser Ala Val Ile Asp Ile Phe Glu Tyr
                    100                 105                 110

Asp Ile Pro Phe Ala Lys Arg Tyr Leu Ile Asp Lys Gly Leu Ile Pro
                    115                 120                 125

Met Glu Gly Asp Glu Glu Leu Lys Leu Leu Ala Phe Asp Ile Glu Thr
                    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                    165                 170                 175

Asp Leu Pro Tyr Val Glu Val Ser Ser Glu Arg Glu Met Ile Lys
                    180                 185                 190

Arg Phe Leu Lys Val Ile Arg Glu Lys Asp Pro Asp Val Ile Ile Thr
                    195                 200                 205

Tyr Asn Gly Asp Ser Phe Asp Leu Pro Tyr Leu Val Lys Arg Ala Glu
                    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                    245                 250                 255

His Phe Asp Leu Tyr His Val Ile Arg Arg Thr Ile Asn Leu Pro Thr
                    260                 265                 270

Tyr Thr Leu Glu Ala Val Tyr Glu Ala Ile Phe Gly Lys Pro Lys Glu
                    275                 280                 285

Lys Val Tyr Ala His Glu Ile Ala Glu Ala Trp Glu Thr Gly Lys Gly
                    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                    325                 330                 335

Val Gly Gln Pro Leu Trp Asp Val Ser Arg Ser Ser Thr Gly Asn Leu
                    340                 345                 350

Val Glu Trp Tyr Leu Leu Arg Lys Ala Tyr Glu Arg Asn Glu Leu Ala
                    355                 360                 365

Pro Asn Lys Pro Asp Glu Arg Glu Tyr Glu Arg Arg Leu Arg Glu Ser
                    370                 375                 380

Tyr Ala Gly Ala Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                    405                 410                 415

His Asn Val Ser Pro Asp Thr Leu Asn Arg Glu Gly Cys Arg Glu Tyr
                    420                 425                 430

Asp Val Ala Pro Glu Val Gly His Lys Phe Cys Lys Asp Phe Pro Gly
                    435                 440                 445
```

```
Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775

<210> SEQ ID NO 68
<211> LENGTH: 775
<212> TYPE: PRT
<213> ORGANISM: Pyrococcus sp.

<400> SEQUENCE: 68

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45
```

```
Asp Glu Val Arg Lys Ile Thr Ala Glu Arg His Gly Lys Ile Val Arg
     50                  55                  60

Ile Ile Asp Ala Glu Lys Val Arg Lys Lys Phe Leu Gly Arg Pro Ile
 65                  70                  75                  80

Glu Val Trp Arg Leu Tyr Phe Glu His Pro Gln Asp Val Pro Ala Ile
                 85                  90                  95

Arg Asp Lys Ile Arg Glu His Ser Ala Val Ile Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
        130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Arg Glu Met Ile Lys
                180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
            245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
            275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Pro Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480
```

```
Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775

<210> SEQ ID NO 69
<211> LENGTH: 775
<212> TYPE: PRT
<213> ORGANISM: Pyrococcus sp.

<400> SEQUENCE: 69

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80
```

-continued

```
Thr Val Trp Lys Leu Tyr Leu Glu His Pro Gln Asp Val Pro Thr Ile
                85                  90                  95
Arg Glu Lys Val Arg Glu His Pro Ala Val Val Asp Ile Phe Glu Tyr
            100                 105                 110
Asp Ile Pro Phe Ala Lys Arg Tyr Leu Ile Asp Lys Gly Leu Ile Pro
        115                 120                 125
Met Glu Gly Glu Glu Leu Lys Ile Leu Ala Phe Asp Ile Glu Thr
130                 135                 140
Leu Tyr His Glu Gly Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Ser Ser Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Glu Tyr Gln Arg Arg Leu Arg Glu Ser
370                 375                 380
Tyr Thr Gly Gly Phe Val Lys Glu Pro Glu Lys Gly Leu Trp Glu Asn
385                 390                 395                 400
Ile Val Tyr Leu Glu Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
```

```
                500             505             510
Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Ile Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
            610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
770                 775

<210> SEQ ID NO 70
<211> LENGTH: 775
<212> TYPE: PRT
<213> ORGANISM: Pyrococcus furiosus

<400> SEQUENCE: 70

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
```

```
                100              105              110
Asp Ile Pro Phe Ala Lys Arg Tyr Leu Ile Asp Lys Gly Leu Ile Pro
            115                 120                 125
Met Glu Gly Glu Glu Leu Lys Ile Leu Ala Phe Asp Ile Glu Thr
    130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Glu Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Tyr Gln Arg Arg Leu Arg Glu Ser
    370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
```

```
Leu Glu Glu Lys Phe Gly Phe Lys Val Leu Tyr Ile Asp Pro Asp Gly
            530                 535                 540

Leu Tyr Ala Thr Ile Pro Gly Gly Glu Ser Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
770                 775

<210> SEQ ID NO 71
<211> LENGTH: 775
<212> TYPE: PRT
<213> ORGANISM: Pyrococcus furiosus

<400> SEQUENCE: 71

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125
```

```
Met Glu Gly Glu Glu Glu Leu Lys Ile Leu Ala Phe Asp Ile Glu Thr
    130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                    165                 170                 175
Asp Leu Pro Tyr Val Glu Val Val Ser Ser Glu Arg Glu Met Ile Lys
                180                 185                 190
Arg Phe Leu Arg Ile Ile Arg Glu Lys Asp Pro Asp Ile Ile Val Thr
                195                 200                 205
Tyr Asn Gly Asp Ser Phe Asp Phe Pro Tyr Leu Ala Lys Arg Ala Glu
                210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                    245                 250                 255
His Phe Asp Leu Tyr His Val Ile Thr Arg Thr Ile Asn Leu Pro Thr
                260                 265                 270
Tyr Thr Leu Glu Ala Val Tyr Glu Ala Ile Phe Gly Lys Pro Lys Glu
                275                 280                 285
Lys Val Tyr Ala Asp Glu Ile Ala Lys Ala Trp Glu Ser Gly Glu Asn
                290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                    325                 330                 335
Val Gly Gln Pro Leu Trp Asp Val Ser Arg Ser Ser Thr Gly Asn Leu
                340                 345                 350
Val Glu Trp Phe Leu Leu Arg Lys Ala Tyr Glu Arg Asn Glu Val Ala
                355                 360                 365
Pro Asn Lys Pro Ser Glu Glu Glu Tyr Gln Arg Arg Leu Arg Glu Ser
                370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                    405                 410                 415
His Asn Val Ser Pro Asp Thr Leu Asn Leu Glu Gly Cys Lys Asn Tyr
                420                 425                 430
Asp Ile Ala Pro Gln Val Gly His Lys Phe Cys Lys Asp Ile Pro Gly
                435                 440                 445
Phe Ile Pro Ser Leu Leu Gly His Leu Leu Glu Glu Arg Gln Lys Ile
                450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                    485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Lys Tyr Ile Glu Leu Val Trp Lys Glu
                515                 520                 525
Leu Glu Glu Lys Phe Gly Phe Lys Val Leu Tyr Ile Asp Thr Gly Gly
                530                 535                 540
Leu Tyr Ala Thr Ile Pro Gly Gly Glu Ser Glu Glu Ile Lys Lys Lys
545                 550                 555                 560
```

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Val Thr Lys
            580                 585                 590        Lys

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
        770                 775

<210> SEQ ID NO 72
<211> LENGTH: 775
<212> TYPE: PRT
<213> ORGANISM: Pyrococcus furiosus

<400> SEQUENCE: 72

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

```
Ser Tyr Ala Asp Glu Asn Glu Ala Lys Val Ile Thr Trp Lys Asn Ile
                165                 170                 175

Asp Leu Pro Tyr Val Glu Val Ser Ser Arg Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
        210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
```

```
                580                 585                 590
Thr Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
        770                 775

<210> SEQ ID NO 73
<211> LENGTH: 773
<212> TYPE: PRT
<213> ORGANISM: Thermococcus gorgonarius

<400> SEQUENCE: 73

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
```

```
                180             185             190
Arg Phe Leu Lys Val Val Lys Glu Lys Asp Pro Asp Val Leu Ile Thr
            195                 200             205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Gln Pro Lys Glu
            275                 280                 285

Lys Val Tyr Ala Glu Glu Ile Ala Gln Ala Trp Glu Thr Gly Glu Gly
            290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Glu Ser Tyr
            370                 375                 380

Ala Gly Gly Tyr Val Lys Glu Pro Glu Arg Gly Leu Trp Glu Asn Ile
385                 390                 395                 400

Val Tyr Leu Glu Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
            450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
            515                 520                 525

Glu Glu Lys Phe Gly Phe Lys Val Leu Tyr Ala Asp Thr Asp Gly Phe
            530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
            595                 600                 605
```

```
Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                    645                 650                 655

Pro Glu Lys Leu Val Ile Tyr Glu Gln Ile Thr Arg Asp Leu Lys Asp
                660                 665                 670

Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                    725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
            755                 760                 765

Leu Lys Pro Lys Thr
    770

<210> SEQ ID NO 74
<211> LENGTH: 773
<212> TYPE: PRT
<213> ORGANISM: Thermococcus gorgonarius

<400> SEQUENCE: 74

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
                20                  25                  30

Asn Phe Glu Pro Tyr Ile Tyr Ala Leu Leu Lys Asp Asp Ser Ala Ile
            35                  40                  45

Glu Asp Val Lys Lys Ile Thr Ala Glu Arg His Gly Thr Thr Val Arg
50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205
```

-continued

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Ile Phe Gly Gln Pro Lys Glu
    275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
            325                 330                 335

Val Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Arg Glu Leu Ala Arg Arg Arg Glu Ser Tyr
370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415

Asn Val Ser Pro Asp Thr Leu Asn Arg Glu Gly Cys Glu Glu Tyr Asp
        420                 425                 430

Val Ala Pro Gln Val Gly His Lys Phe Cys Lys Asp Phe Pro Gly Phe
    435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
        500                 505                 510

Val Thr Ala Trp Gly Arg Gln Tyr Ile Glu Thr Thr Ile Arg Glu Ile
    515                 520                 525

Glu Glu Lys Phe Gly Phe Lys Val Leu Tyr Ala Asp Pro Asp Gly Phe
530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
            565                 570                 575

Leu Glu Tyr Glu Gly Phe Tyr Lys Arg Gly Phe Phe Val Thr Lys Lys
        580                 585                 590

Lys Tyr Ala Val Ile Asp Glu Glu Asp Lys Ile Thr Thr Arg Gly Leu
    595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

```
Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
        770

<210> SEQ ID NO 75
<211> LENGTH: 773
<212> TYPE: PRT
<213> ORGANISM: Thermococcus gorgonarius

<400> SEQUENCE: 75

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240
```

```
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Ile Phe Gly Gln Pro Lys Glu
        275                 280                 285
Lys Val Tyr Ala Glu Glu Ile Ala Gln Ala Trp Glu Thr Gly Glu Gly
    290                 295                 300
Leu Glu Arg Val Ala Arg Tyr Ser Met Glu Asp Ala Lys Val Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Arg Glu Leu Ala Arg Arg Arg Glu Ser Tyr
    370                 375                 380
Ala Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Glu Glu Tyr Asp
            420                 425                 430
Val Ala Pro Gln Val Gly His Lys Phe Cys Lys Asp Phe Pro Gly Phe
        435                 440                 445
Ile Pro Ser Leu Leu Gly Asp Leu Leu Glu Glu Arg Gln Lys Val Lys
    450                 455                 460
Lys Lys Met Lys Ala Thr Ile Asp Pro Ile Glu Lys Lys Leu Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Gln Tyr Ile Glu Thr Thr Ile Arg Glu Ile
        515                 520                 525
Glu Glu Lys Phe Gly Phe Lys Val Leu Tyr Ala Asp Thr Gly Gly Phe
    530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Asp Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile Tyr Glu Gln Ile Thr Arg Asp Leu Lys Asp
```

```
                      660                 665                 670
Tyr Lys Ala Thr Gly Pro His Val Ala Val Ala Lys Arg Leu Ala Ala
                675                 680                 685

Arg Gly Ile Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
                755                 760                 765

Leu Lys Pro Lys Thr
        770

<210> SEQ ID NO 76
<211> LENGTH: 773
<212> TYPE: PRT
<213> ORGANISM: Thermococcus gorgonarius

<400> SEQUENCE: 76

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
```

```
                260                 265                 270
Tyr Thr Leu Glu Ala Val Tyr Glu Ala Ile Phe Gly Gln Pro Lys Glu
            275                 280                 285
Lys Val Tyr Ala Glu Glu Ile Ala Gln Ala Trp Glu Thr Gly Glu Gly
            290                 295                 300
Leu Glu Arg Val Ala Arg Tyr Ser Met Glu Asp Ala Lys Val Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Arg Glu Leu Ala Arg Arg Glu Ser Tyr
            370                 375                 380
Ala Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Thr His
                    405                 410                 415
Asn Val Ser Pro Asp Thr Leu Asn Arg Glu Gly Cys Glu Glu Tyr Asp
                420                 425                 430
Val Ala Pro Gln Val Gly His Lys Phe Cys Lys Asp Phe Pro Gly Phe
                435                 440                 445
Ile Pro Ser Leu Leu Gly Asp Leu Leu Glu Glu Arg Gln Lys Val Lys
            450                 455                 460
Lys Lys Met Lys Ala Thr Ile Asp Pro Ile Glu Lys Lys Leu Leu Asp
465                 470                 475                 480
Tyr Arg Gln Arg Ala Ile Lys Ile Leu Ala Asn Ser Phe Tyr Gly Tyr
                    485                 490                 495
Tyr Gly Tyr Ala Lys Ala Arg Trp Tyr Cys Lys Glu Cys Ala Glu Ser
                500                 505                 510
Val Thr Ala Trp Gly Arg Gln Tyr Ile Glu Thr Thr Ile Arg Glu Ile
            515                 520                 525
Glu Glu Lys Phe Gly Phe Lys Val Leu Tyr Ala Asp Thr Asp Gly Phe
            530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                565                 570                 575
Leu Glu Tyr Glu Gly Phe Tyr Lys Arg Gly Phe Phe Val Thr Lys Thr
                580                 585                 590
Lys Tyr Ala Val Ile Asp Glu Glu Asp Lys Ile Thr Thr Arg Gly Leu
            595                 600                 605
Glu Ile Val Arg Arg Asp Trp Ser Glu Ile Ala Lys Glu Thr Gln Ala
            610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                    645                 650                 655
Pro Glu Lys Leu Val Ile Tyr Glu Gln Ile Thr Arg Asp Leu Lys Asp
                660                 665                 670
Tyr Lys Ala Thr Gly Pro His Val Ala Val Ala Lys Arg Leu Ala Ala
                675                 680                 685
```

```
Arg Gly Ile Lys Ile Arg Pro Gly Thr Val Ile Ser Tyr Ile Val Leu
            690                 695                 700
Lys Gly Ser Gly Arg Ile Gly Asp Arg Ala Ile Pro Phe Asp Glu Phe
705                 710                 715                 720
Asp Pro Ala Lys His Lys Tyr Asp Ala Glu Tyr Tyr Ile Glu Asn Gln
                    725                 730                 735
Val Leu Pro Ala Val Glu Arg Ile Leu Arg Ala Phe Gly Tyr Arg Lys
                740                 745                 750
Glu Asp Leu Arg Tyr Gln Lys Thr Arg Gln Val Gly Leu Gly Ala Trp
                755                 760                 765
Leu Lys Pro Lys Thr
    770

<210> SEQ ID NO 77
<211> LENGTH: 773
<212> TYPE: PRT
<213> ORGANISM: Pyrococcus sp.

<400> SEQUENCE: 77

Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
                20                  25                  30
Thr Phe Glu Pro Tyr Phe Tyr Ala Leu Leu Lys Asp Asp Ser Ala Ile
            35                  40                  45
Glu Glu Val Lys Lys Ile Thr Ala Glu Arg His Gly Thr Val Val Thr
        50                  55                  60
Val Lys Arg Val Glu Lys Val Gln Lys Lys Phe Leu Gly Arg Pro Val
65                  70                  75                  80
Glu Val Trp Lys Leu Tyr Phe Thr His Pro Gln Asp Val Pro Ala Ile
                85                  90                  95
Arg Asp Lys Ile Arg Glu His Gly Ala Val Ile Asp Ile Tyr Glu Tyr
                100                 105                 110
Asp Ile Pro Phe Ala Lys Arg Tyr Leu Ile Asp Lys Gly Leu Val Pro
            115                 120                 125
Met Glu Gly Asp Glu Glu Leu Lys Met Leu Ala Phe Asp Ile Gln Thr
        130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Val Ser Thr Glu Arg Glu Met Ile Lys
            180                 185                 190
Arg Phe Leu Arg Val Val Lys Glu Lys Asp Pro Asp Val Leu Ile Thr
        195                 200                 205
Tyr Asn Gly Asp Asn Phe Asp Phe Ala Tyr Leu Lys Lys Arg Cys Glu
    210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
```

```
Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
        370                 375                 380

Glu Gly Gly Tyr Val Lys Glu Pro Glu Arg Gly Leu Trp Glu Asn Ile
385                 390                 395                 400

Val Tyr Leu Glu Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720
```

```
Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly
    770

<210> SEQ ID NO 78
<211> LENGTH: 774
<212> TYPE: PRT
<213> ORGANISM: Pyrococcus sp.

<400> SEQUENCE: 78

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
            85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Gln Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
            165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Pro Ala Trp Glu Thr Gly Glu Asn
            290                 295                 300

Leu Glu Arg Val Ala Arg Tyr Ser Met Glu Asp Ala Lys Val Thr Tyr
305                 310                 315                 320
```

```
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Thr Gly Asn Leu
            340                 345                 350
Val Glu Trp Phe Leu Leu Arg Lys Ala Tyr Glu Arg Asn Glu Leu Ala
            355                 360                 365
Pro Asn Lys Pro Asp Glu Lys Glu Leu Ala Arg Arg Gln Ser Tyr
370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Arg Phe Cys Lys Asp Phe Pro Gly Phe
            435                 440                 445
Ile Pro Ser Leu Leu Gly Asp Leu Leu Glu Glu Arg Gln Lys Ile Lys
            450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
            515                 520                 525
Glu Glu Lys Tyr Gly Phe Lys Val Ile Tyr Ser Asp Pro Asp Gly Phe
            530                 535                 540
Phe Ala Thr Ile Pro Gly Ala Asp Ala Glu Thr Val Lys Lys Lys Ala
545                 550                 555                 560
Met Glu Phe Leu Asn Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
                660                 665                 670
Tyr Lys Ala Thr Gly Pro His Val Ala Val Ala Lys Arg Leu Ala Ala
            675                 680                 685
Arg Gly Val Lys Ile Arg Pro Gly Thr Val Ile Ser Tyr Ile Val Leu
            690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
```

```
                740                 745                 750
Glu Asp Leu Arg Tyr Gln Lys Thr Arg Gln Val Gly Leu Ser Ala Trp
                755                 760                 765

Leu Lys Pro Lys Gly Thr
    770

<210> SEQ ID NO 79
<211> LENGTH: 774
<212> TYPE: PRT
<213> ORGANISM: Pyrococcus sp.

<400> SEQUENCE: 79

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
```

```
                340             345             350
Val Glu Trp Phe Leu Leu Arg Lys Ala Tyr Glu Arg Asn Glu Leu Ala
            355                 360                 365
Pro Asn Lys Pro Asp Glu Lys Glu Leu Ala Arg Arg Gln Ser Tyr
        370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Arg Phe Cys Lys Asp Phe Pro Gly Phe
                435                 440                 445
Ile Pro Ser Leu Leu Gly Asp Leu Leu Glu Glu Arg Gln Lys Ile Lys
            450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
            515                 520                 525
Glu Glu Lys Tyr Gly Phe Lys Val Ile Tyr Ser Asp Thr Gly Gly Phe
            530                 535                 540
Phe Ala Thr Ile Pro Gly Ala Asp Ala Glu Thr Val Lys Lys Lys Ala
545                 550                 555                 560
Met Glu Phe Leu Asn Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
        610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
                660                 665                 670
Tyr Lys Ala Thr Gly Pro His Val Ala Val Ala Lys Arg Leu Ala Ala
            675                 680                 685
Arg Gly Val Lys Ile Arg Pro Gly Thr Val Ile Ser Tyr Ile Val Leu
        690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
                740                 745                 750
Glu Asp Leu Arg Tyr Gln Lys Thr Arg Gln Val Gly Leu Ser Ala Trp
            755                 760                 765
```

Leu Lys Pro Lys Gly Thr
    770

<210> SEQ ID NO 80
<211> LENGTH: 774
<212> TYPE: PRT
<213> ORGANISM: Pyrococcus sp.

<400> SEQUENCE: 80

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

```
Pro Asn Lys Pro Asp Glu Lys Glu Leu Ala Arg Arg Gln Ser Tyr
        370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                    405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Thr
            580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
        610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
                755                 760                 765

Leu Lys Pro Lys Gly Thr
770
```

<210> SEQ ID NO 81

<211> LENGTH: 774
<212> TYPE: PRT
<213> ORGANISM: Thermococcus litoralis

<400> SEQUENCE: 81

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
370                 375                 380

Thr Thr Tyr Leu Gly Gly Tyr Val Lys Glu Pro Glu Lys Gly Leu Trp
385                 390                 395                 400
```

```
Glu Asn Ile Ile Tyr Leu Glu Phe Arg Ser Leu Tyr Pro Ser Ile Ile
                405                 410                 415
Val Thr His Asn Val Ser Pro Asp Thr Leu Glu Lys Glu Gly Cys Lys
            420                 425                 430
Asn Tyr Asp Val Ala Pro Ile Val Gly Tyr Arg Phe Cys Lys Asp Phe
        435                 440                 445
Pro Gly Phe Ile Pro Ser Ile Leu Gly Asp Leu Ile Ala Met Arg Gln
    450                 455                 460
Asp Ile Lys Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
            500                 505                 510
Ala Glu Ser Val Thr Ala Trp Gly Arg His Tyr Ile Glu Met Thr Ile
        515                 520                 525
Arg Glu Ile Glu Glu Lys Phe Gly Phe Lys Val Leu Tyr Ala Asp Thr
    530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
            580                 585                 590
Thr Lys Lys Arg Tyr Ala Val Ile Asp Glu Glu Gly Arg Ile Thr Thr
        595                 600                 605
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Val Glu Lys Ile Ala Lys Tyr
                645                 650                 655
Arg Val Pro Leu Glu Lys Leu Val Ile His Glu Gln Ile Thr Arg Asp
            660                 665                 670
Leu Lys Asp Tyr Lys Ala Ile Gly Pro His Val Ala Ile Ala Lys Arg
        675                 680                 685
Leu Ala Ala Arg Gly Ile Lys Val Lys Pro Gly Thr Ile Ile Ser Tyr
    690                 695                 700
Ile Val Leu Lys Gly Ser Gly Lys Ile Ser Asp Arg Val Ile Leu Leu
705                 710                 715                 720
Thr Glu Tyr Asp Pro Arg Lys His Lys Tyr Asp Pro Asp Tyr Tyr Ile
                725                 730                 735
Glu Asn Gln Val Leu Pro Ala Val Leu Arg Ile Leu Glu Ala Phe Gly
            740                 745                 750
Tyr Arg Lys Glu Asp Leu Arg Tyr Gln Ser Ser Lys Gln Thr Gly Leu
        755                 760                 765
Asp Ala Trp Leu Lys Arg
    770

<210> SEQ ID NO 82
<211> LENGTH: 774
<212> TYPE: PRT
<213> ORGANISM: Thermococcus litoralis

<400> SEQUENCE: 82
```

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
        50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
        130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
                260                 265                 270

Pro Thr Tyr Thr Leu Glu Ala Val Tyr Glu Ala Val Leu Gly Lys Thr
            275                 280                 285

Lys Ser Lys Leu Gly Ala Glu Glu Ile Ala Ala Ile Trp Glu Thr Glu
        290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
                340                 345                 350

Asn Leu Val Glu Trp Tyr Leu Leu Arg Val Ala Tyr Ala Arg Asn Glu
            355                 360                 365

Leu Ala Pro Asn Lys Pro Asp Glu Glu Tyr Lys Arg Arg Leu Arg
        370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
```

```
                420              425              430
Asn Tyr Asp Val Ala Pro Ile Val Gly Tyr Arg Phe Cys Lys Asp Phe
            435              440              445

Pro Gly Phe Ile Pro Ser Ile Leu Gly Asp Leu Ile Ala Met Arg Gln
    450              455              460

Asp Ile Lys Lys Met Lys Ser Thr Ile Asp Pro Ile Glu Lys Lys
465              470              475              480

Met Leu Asp Tyr Arg Gln Arg Ala Ile Lys Leu Leu Ala Asn Ser Tyr
                485              490              495

Tyr Gly Tyr Met Gly Tyr Pro Lys Ala Arg Trp Tyr Ser Lys Glu Cys
            500              505              510

Ala Glu Ser Val Thr Ala Trp Gly Arg His Tyr Ile Glu Met Thr Ile
        515              520              525

Arg Glu Ile Glu Glu Lys Phe Gly Phe Lys Val Leu Tyr Ala Asp Pro
    530              535              540

Asp Gly Phe Tyr Ala Thr Ile Pro Gly Glu Lys Pro Glu Leu Ile Lys
545              550              555              560

Lys Lys Ala Lys Glu Phe Leu Asn Tyr Ile Asn Ser Lys Leu Pro Gly
                565              570              575

Leu Leu Glu Leu Glu Tyr Glu Gly Phe Tyr Leu Arg Gly Phe Phe Val
            580              585              590

Thr Lys Lys Arg Tyr Ala Val Ile Asp Glu Gly Arg Ile Thr Thr
        595              600              605

Arg Gly Leu Glu Val Val Arg Arg Asp Trp Ser Glu Ile Ala Lys Glu
    610              615              620

Thr Gln Ala Lys Val Leu Glu Ala Ile Leu Lys Glu Gly Ser Val Glu
625              630              635              640

Lys Ala Val Glu Val Val Arg Asp Val Val Glu Lys Ile Ala Lys Tyr
                645              650              655

Arg Val Pro Leu Glu Lys Leu Val Ile His Glu Gln Ile Thr Arg Asp
            660              665              670

Leu Lys Asp Tyr Lys Ala Ile Gly Pro His Val Ala Ile Ala Lys Arg
        675              680              685

Leu Ala Ala Arg Gly Ile Lys Val Lys Pro Gly Thr Ile Ile Ser Tyr
    690              695              700

Ile Val Leu Lys Gly Ser Gly Lys Ile Ser Asp Arg Val Ile Leu Leu
705              710              715              720

Thr Glu Tyr Asp Pro Arg Lys His Lys Tyr Asp Pro Asp Tyr Tyr Ile
                725              730              735

Glu Asn Gln Val Leu Pro Ala Val Leu Arg Ile Leu Glu Ala Phe Gly
            740              745              750

Tyr Arg Lys Glu Asp Leu Arg Tyr Gln Ser Ser Lys Gln Thr Gly Leu
        755              760              765

Asp Ala Trp Leu Lys Arg
    770

<210> SEQ ID NO 83
<211> LENGTH: 774
<212> TYPE: PRT
<213> ORGANISM: Thermococcus litoralis

<400> SEQUENCE: 83

Met Ile Leu Asp Thr Asp Tyr Ile Thr Lys Asp Gly Lys Pro Ile Ile
1               5                  10                  15

Arg Ile Phe Lys Lys Glu Asn Gly Glu Phe Lys Ile Glu Leu Asp Pro
```

-continued

```
                    20                  25                  30
His Phe Gln Pro Tyr Ile Tyr Ala Leu Leu Lys Asp Asp Ser Ala Ile
                35                  40                  45
Glu Glu Ile Lys Ala Ile Lys Gly Glu Arg His Gly Lys Thr Val Arg
50                  55                  60
Val Leu Asp Ala Val Lys Val Arg Lys Lys Phe Leu Gly Arg Glu Val
65                  70                  75                  80
Glu Val Trp Lys Leu Ile Phe Glu His Pro Gln Asp Val Pro Ala Met
                85                  90                  95
Arg Gly Lys Ile Arg Glu His Pro Ala Val Val Asp Ile Tyr Glu Tyr
                100                 105                 110
Asp Ile Pro Phe Ala Lys Arg Tyr Leu Ile Asp Lys Gly Leu Ile Pro
                115                 120                 125
Met Glu Gly Asp Glu Glu Leu Lys Leu Leu Ala Phe Asp Ile Glu Thr
                130                 135                 140
Phe Tyr His Glu Gly Asp Glu Phe Gly Lys Gly Glu Ile Ile Met Ile
145                 150                 155                 160
Ser Tyr Ala Asp Glu Glu Ala Arg Val Ile Thr Trp Lys Asn Ile
                165                 170                 175
Asp Leu Pro Tyr Val Asp Val Ser Asn Glu Arg Glu Met Ile Lys
                180                 185                 190
Arg Phe Val Gln Val Val Lys Glu Lys Asp Pro Asp Val Ile Ile Thr
                195                 200                 205
Tyr Asn Gly Asp Asn Phe Asp Leu Pro Tyr Leu Ile Lys Arg Ala Glu
                210                 215                 220
Lys Leu Gly Val Arg Leu Val Leu Gly Arg Asp Lys Glu His Pro Glu
225                 230                 235                 240
Pro Lys Ile Gln Arg Met Gly Asp Ser Phe Ala Val Glu Ile Lys Gly
                245                 250                 255
Arg Ile His Phe Asp Leu Phe Pro Val Val Arg Arg Thr Ile Asn Leu
                260                 265                 270
Pro Thr Tyr Thr Leu Glu Ala Val Tyr Glu Ala Val Leu Gly Lys Thr
                275                 280                 285
Lys Ser Lys Leu Gly Ala Glu Glu Ile Ala Ala Ile Trp Glu Thr Glu
290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
                325                 330                 335
Lys Leu Ile Gly Gln Ser Val Trp Asp Val Ser Arg Ser Ser Thr Gly
                340                 345                 350
Asn Leu Val Glu Trp Tyr Leu Leu Arg Val Ala Tyr Ala Arg Asn Glu
                355                 360                 365
Leu Ala Pro Asn Lys Pro Asp Glu Glu Tyr Lys Arg Arg Leu Arg
                370                 375                 380
Thr Thr Tyr Leu Gly Gly Tyr Val Lys Glu Pro Glu Lys Gly Leu Trp
385                 390                 395                 400
Glu Asn Ile Ile Tyr Leu Asp Phe Arg Ser Leu Tyr Pro Ser Ile Ile
                405                 410                 415
Val Thr His Asn Val Ser Pro Asp Thr Leu Glu Lys Glu Gly Cys Lys
                420                 425                 430
Asn Tyr Asp Val Ala Pro Ile Val Gly Tyr Arg Phe Cys Lys Asp Phe
                435                 440                 445
```

```
Pro Gly Phe Ile Pro Ser Ile Leu Gly Asp Leu Ile Ala Met Arg Gln
        450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Gly Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 84
<211> LENGTH: 774
<212> TYPE: PRT
<213> ORGANISM: Thermococcus litoralis

<400> SEQUENCE: 84

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45
```

```
Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
 65                  70                  75                  80

Glu Val Trp Lys Leu Ile Phe Glu His Pro Gln Asp Val Pro Ala Met
                 85                  90                  95

Arg Gly Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
    195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
            245                 250                 255

Arg Ile His Phe Asp Leu Phe Pro Val Val Arg Arg Thr Ile Asn Leu
    260                 265                 270

Pro Thr Tyr Thr Leu Glu Ala Val Tyr Glu Ala Val Leu Gly Lys Thr
    275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
    355                 360                 365

Leu Ala Pro Asn Lys Pro Asp Glu Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
            435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480
```

```
Met Leu Asp Tyr Arg Gln Arg Ala Ile Lys Leu Leu Ala Asn Ser Tyr
            485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
        530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Thr Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 85
<211> LENGTH: 775
<212> TYPE: PRT
<213> ORGANISM: Pyrococcus sp.

<400> SEQUENCE: 85

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80
```

```
Glu Val Trp Arg Leu Tyr Phe Glu His Pro Gln Asp Val Pro Ala Ile
                85                  90                  95
Arg Asp Lys Ile Arg Glu His Ser Ala Val Ile Asp Ile Phe Glu Tyr
            100                 105                 110
Asp Ile Pro Phe Ala Lys Arg Tyr Leu Ile Asp Lys Gly Leu Ile Pro
            115                 120                 125
Met Glu Gly Asp Glu Glu Leu Lys Leu Leu Ala Phe Asp Ile Glu Thr
130                 135                 140
Leu Tyr His Glu Gly Glu Glu Phe Ala Lys Gly Pro Ile Ile Met Ile
145                 150                 155                 160
Ser Tyr Ala Asp Glu Glu Glu Ala Lys Val Ile Thr Trp Lys Lys Ile
                165                 170                 175
Asp Leu Pro Tyr Val Glu Val Val Ser Ser Glu Arg Glu Met Ile Lys
            180                 185                 190
Arg Phe Leu Lys Val Ile Arg Glu Lys Asp Pro Asp Val Ile Ile Thr
            195                 200                 205
Tyr Asn Gly Asp Ser Phe Asp Leu Pro Tyr Leu Val Lys Arg Ala Glu
210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala His Glu Ile Ala Glu Ala Trp Glu Thr Gly Lys Gly
            290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Tyr Leu Leu Arg Lys Ala Tyr Glu Arg Asn Glu Leu Ala
            355                 360                 365
Pro Asn Lys Pro Asp Glu Arg Glu Tyr Glu Arg Arg Leu Arg Glu Ser
370                 375                 380
Tyr Ala Gly Gly Tyr Val Lys Glu Pro Glu Lys Gly Leu Trp Glu Gly
385                 390                 395                 400
Leu Val Ser Leu Glu Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
            435                 440                 445
Phe Ile Pro Ser Leu Leu Lys Arg Leu Leu Asp Glu Arg Gln Glu Ile
450                 455                 460
Lys Arg Lys Met Lys Ala Ser Lys Asp Pro Ile Glu Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
```

```
                500             505             510
Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
            530                 535             540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
            565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
            610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
            645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
            690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
            725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys
770                 775

<210> SEQ ID NO 86
<211> LENGTH: 775
<212> TYPE: PRT
<213> ORGANISM: Pyrococcus sp.

<400> SEQUENCE: 86

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
            85                  90                  95

Arg Asp Lys Ile Arg Glu His Ser Ala Val Ile Asp Ile Phe Glu Tyr
```

```
                       100                 105                 110
Asp Ile Pro Phe Ala Lys Arg Tyr Leu Ile Asp Lys Gly Leu Ile Pro
            115                 120                 125
Met Glu Gly Asp Glu Glu Leu Lys Leu Leu Ala Phe Asp Ile Glu Thr
        130                 135                 140
Leu Tyr His Glu Gly Glu Glu Phe Ala Lys Gly Pro Ile Ile Met Ile
145                 150                 155                 160
Ser Tyr Ala Asp Glu Glu Ala Lys Val Ile Thr Trp Lys Lys Ile
            165                 170                 175
Asp Leu Pro Tyr Val Glu Val Ser Ser Glu Arg Glu Met Ile Lys
        180                 185                 190
Arg Phe Leu Lys Val Ile Arg Glu Lys Asp Pro Asp Val Ile Ile Thr
        195                 200                 205
Tyr Asn Gly Asp Ser Phe Asp Leu Pro Tyr Leu Val Lys Arg Ala Glu
    210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
            245                 250                 255
His Phe Asp Leu Tyr His Val Ile Arg Arg Thr Ile Asn Leu Pro Thr
        260                 265                 270
Tyr Thr Leu Glu Ala Val Tyr Glu Ala Ile Phe Gly Lys Pro Lys Glu
    275                 280                 285
Lys Val Tyr Ala His Glu Ile Ala Glu Ala Trp Glu Thr Gly Lys Gly
        290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
            325                 330                 335
Val Gly Gln Pro Leu Trp Asp Val Ser Arg Ser Ser Thr Gly Asn Leu
        340                 345                 350
Val Glu Trp Tyr Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
            405                 410                 415
His Asn Val Ser Pro Asp Thr Leu Asn Arg Glu Gly Cys Arg Glu Tyr
        420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Glu Ile
    450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
            485                 490                 495
Tyr Tyr Gly Tyr Ala Lys Ala Arg Trp Tyr Cys Lys Glu Cys Ala Glu
        500                 505                 510
Ser Val Thr Ala Trp Gly Arg Glu Tyr Ile Glu Phe Val Arg Lys Glu
        515                 520                 525
```

-continued

Leu Glu Glu Lys Phe Gly Phe Lys Val Leu Tyr Ile Asp Pro Asp Gly
530                 535                 540

Leu Tyr Ala Thr Ile Pro Gly Ala Lys Pro Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
                740                 745                 750

Lys Glu Asp Leu Arg Trp Gln Lys Thr Lys Gln Thr Gly Leu Thr Ala
            755                 760                 765

Trp Leu Asn Ile Lys Lys Lys
    770                 775

<210> SEQ ID NO 87
<211> LENGTH: 775
<212> TYPE: PRT
<213> ORGANISM: Pyrococcus sp.

<400> SEQUENCE: 87

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
        50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

```
Met Glu Gly Asp Glu Glu Leu Lys Leu Leu Ala Phe Asp Ile Glu Thr
    130                 135                 140

Leu Tyr His Glu Gly Glu Phe Ala Lys Gly Pro Ile Ile Met Ile
145                 150                 155                 160

Ser Tyr Ala Asp Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Val Ile Arg Glu Lys Asp Pro Asp Val Ile Thr
        195                 200                 205

Tyr Asn Gly Asp Ser Phe Asp Leu Pro Tyr Leu Val Lys Arg Ala Glu
210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Gly Gly
    530                 535                 540

Leu Tyr Ala Thr Ile Pro Gly Ala Lys Pro Glu Glu Ile Lys Lys Lys
545                 550                 555                 560
```

Ala Leu Glu Phe Val Asp Tyr Ile Asn Ala Lys Leu Pro Gly Leu Leu
                    565                 570                 575

Glu Leu Glu Tyr Glu Gly Phe Tyr Val Arg Gly Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                    645                 650                 655

Pro Pro Glu Lys Leu Val Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
            690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                    725                 730                 735

Gln Val Leu Pro Ala Val Leu Arg Ile Leu Glu Ala Phe Gly Tyr Arg
                740                 745                 750

Lys Glu Asp Leu Arg Trp Gln Lys Thr Lys Gln Thr Gly Leu Thr Ala
            755                 760                 765

Trp Leu Asn Ile Lys Lys Lys
770                 775

<210> SEQ ID NO 88
<211> LENGTH: 775
<212> TYPE: PRT
<213> ORGANISM: Pyrococcus sp.

<400> SEQUENCE: 88

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
        50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

```
Ser Tyr Ala Asp Glu Glu Ala Lys Val Ile Thr Trp Lys Lys Ile
                165                 170                 175
Asp Leu Pro Tyr Val Glu Val Ser Ser Glu Arg Glu Met Ile Lys
                180                 185                 190
Arg Phe Leu Lys Val Ile Arg Glu Lys Asp Pro Asp Val Ile Ile Thr
                195                 200                 205
Tyr Asn Gly Asp Ser Phe Asp Leu Pro Tyr Leu Val Lys Arg Ala Glu
                210                 215                 220
Lys Leu Gly Ile Lys Leu Pro Leu Gly Arg Asp Gly Ser Glu Pro Lys
225                 230                 235                 240
Met Gln Arg Leu Gly Asp Met Thr Ala Val Glu Ile Lys Gly Arg Ile
                245                 250                 255
His Phe Asp Leu Tyr His Val Ile Arg Arg Thr Ile Asn Leu Pro Thr
                260                 265                 270
Tyr Thr Leu Glu Ala Val Tyr Glu Ala Ile Phe Gly Lys Pro Lys Glu
                275                 280                 285
Lys Val Tyr Ala His Glu Ile Ala Glu Ala Trp Glu Thr Gly Lys Gly
                290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Val Gly Gln Pro Leu Trp Asp Val Ser Arg Ser Ser Thr Gly Asn Leu
                340                 345                 350
Val Glu Trp Tyr Leu Leu Arg Lys Ala Tyr Glu Arg Asn Glu Leu Ala
                355                 360                 365
Pro Asn Lys Pro Asp Glu Arg Glu Tyr Glu Arg Arg Leu Arg Glu Ser
370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
                420                 425                 430
Asp Val Ala Pro Glu Val Gly His Lys Phe Cys Lys Asp Phe Pro Gly
                435                 440                 445
Phe Ile Pro Ser Leu Leu Lys Arg Leu Leu Asp Glu Arg Gln Glu Ile
450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Glu Tyr Ile Glu Phe Val Arg Lys Glu
                515                 520                 525
Leu Glu Glu Lys Phe Gly Phe Lys Val Leu Tyr Ile Asp Thr Asp Gly
                530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Val Arg Gly Phe Phe Val Thr Lys
```

|   |   |   |   |   | 580 |   |   |   |   | 585 |   |   |   |   | 590 |   |   |
|---|---|---|---|---|---|---|---|---|---|---|---|---|---|---|---|---|---|
| Thr | Lys | Tyr | Ala | Leu | Ile | Asp | Glu | Glu | Gly | Lys | Ile | Ile | Thr | Arg | Gly | | |
|   |   |   | 595 |   |   |   |   | 600 |   |   |   |   | 605 |   |   |   |   |
| Leu | Glu | Ile | Val | Arg | Arg | Asp | Trp | Ser | Glu | Ile | Ala | Lys | Glu | Thr | Gln | | |
|   | 610 |   |   |   |   | 615 |   |   |   |   | 620 |   |   |   |   | | |
| Ala | Lys | Val | Leu | Glu | Ala | Ile | Leu | Lys | His | Gly | Asn | Val | Glu | Glu | Ala | | |
| 625 |   |   |   |   | 630 |   |   |   |   | 635 |   |   |   |   | 640 | | |
| Val | Lys | Ile | Val | Lys | Glu | Val | Thr | Glu | Lys | Leu | Ser | Lys | Tyr | Glu | Ile | | |
|   |   |   |   | 645 |   |   |   |   | 650 |   |   |   |   | 655 |   | | |
| Pro | Pro | Glu | Lys | Leu | Val | Ile | Tyr | Glu | Gln | Ile | Thr | Arg | Pro | Leu | His | | |
|   |   |   | 660 |   |   |   |   | 665 |   |   |   |   | 670 |   |   | | |
| Glu | Tyr | Lys | Ala | Ile | Gly | Pro | His | Val | Ala | Val | Ala | Lys | Arg | Leu | Ala | | |
|   | 675 |   |   |   |   | 680 |   |   |   |   | 685 |   |   |   |   | | |
| Ala | Arg | Gly | Val | Lys | Val | Arg | Pro | Gly | Met | Val | Ile | Gly | Tyr | Ile | Val | | |
| 690 |   |   |   |   | 695 |   |   |   |   | 700 |   |   |   |   |   | | |
| Leu | Arg | Gly | Asp | Gly | Pro | Ile | Ser | Lys | Arg | Ala | Ile | Leu | Ala | Glu | Glu | | |
| 705 |   |   |   |   | 710 |   |   |   |   | 715 |   |   |   |   | 720 | | |
| Phe | Asp | Leu | Arg | Lys | His | Lys | Tyr | Asp | Ala | Glu | Tyr | Tyr | Ile | Glu | Asn | | |
|   |   |   |   | 725 |   |   |   |   | 730 |   |   |   |   | 735 |   | | |
| Gln | Val | Leu | Pro | Ala | Val | Leu | Arg | Ile | Leu | Glu | Ala | Phe | Gly | Tyr | Arg | | |
|   |   |   | 740 |   |   |   |   | 745 |   |   |   |   | 750 |   |   | | |
| Lys | Glu | Asp | Leu | Arg | Trp | Gln | Lys | Thr | Lys | Gln | Thr | Gly | Leu | Thr | Ala | | |
|   |   |   | 755 |   |   |   |   | 760 |   |   |   |   | 765 |   |   | | |
| Trp | Leu | Asn | Ile | Lys | Lys | Lys |   |   |   |   |   |   |   |   |   | | |
|   | 770 |   |   |   | 775 |   |   |   |   |   |   |   |   |   |   | | |

<210> SEQ ID NO 89
<211> LENGTH: 2328
<212> TYPE: DNA
<213> ORGANISM: Pyrococcus furiosus

<400> SEQUENCE: 89

```
atgattttag atgtggatta cataactgaa gaaggaaaac ctgttattag gctattcaaa      60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga aattgttga tgtagagaag gttgagaaaa gtttctcgg caagcctat     240
accgtgtgga aactttattt ggaacatccc caagatgttc ccactattag agaaaaagtt    300
agagaacatc cagcagttgt ggacatcttc aatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgcattccc atatttagcg    660
aaaaggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaattttg gaaagccaaa ggagaaggta tacgccgacg atagcaaa agcctgggaa      900
agtggagaga acttgagag agttgccaaa tactcgatgg aagatgcaaa ggcaacttat    960
gaactcggga agaattcct tccaatggaa attcagcttt caagattagt tggacaacct   1020
```

```
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaaccca ggttcttcca   2220 gcggtactta ggatattgga gggatttgga tacagaaagg aagacctcag ataccaaaag   2280
acaagacaag tcggcctaac ttcctggctt aacattaaaa aatcctag             2328
```

<210> SEQ ID NO 90
<211> LENGTH: 2328
<212> TYPE: DNA
<213> ORGANISM: Pyrococcus furiosus
<220> FEATURE:
<221> NAME/KEY: misc_feature
<222> LOCATION: (1153)..(1155)
<223> OTHER INFORMATION: Ns at position 1153 to 1155 may be any nucleotides so that the codon at 1153-1155 encodes for Asn, Leu, His, Gln, or Ser.

<400> SEQUENCE: 90

```
atgattttag atgtggatta cataactgaa gaaggaaaac ctgttattag gctattcaaa    60
aaagagaacg gaaatttaa gatagagcat gatagaactt ttagaccata catttacgct   120
cttctcaggg atgattcaaa gattgaagaa gttaagaaaa taacggggga aaggcatgga   180
aagattgtga gaattgttga tgtagagaag gttgagaaaa gtttctcgg caagcctatt   240 accgtgtgga aactttattt ggaacatccc caagatgttc ccactattag agaaaaagtt   300
agagaacatc cagcagttgt ggacatcttc gaatacgata ttccatttgc aaagagatac   360
ctcatcgaca aaggcctaat accaatggag ggggaagaag agctaaagat tcttgccttc   420
gatatagaaa ccctctatca cgaaggagaa gagtttggaa aaggcccaat tataatgatt   480
agttatgcag atgaaaatga agcaaaggtg attacttgga aaaacataga tcttccatac   540
gttgaggttg tatcaagcga gagagagatg ataaagagat ttctcaggat tatcagggag   600
aaggatcctg acattatagt tacttataat ggagactcat tcgcattccc atatttagcg   660
```

```
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg gaaagccaaa ggagaaggta tacgccgacg agatagcaaa agcctgggaa     900
agtggagaga accttgagag agttgccaaa tactcgatgg aagatgcaaa ggcaacttat    960
gaactcggga agaattcct tccaatgaaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gcnnnacagg tggattcgtt aaagagccag aaaaggggtt gtgggaaaac    1200
atagtatacc tagattttag agccctatat ccctcgatta taattaccca caatgttct     1260 cccgatactc taaatcttga gggatgcaag aactatgata tcgctcctca agtaggccac    1320
aagttctgca aggacatccc tggttttata ccaagtctct tgggacattt gttagaggaa    1380
agacaaaaga ttaagacaaa aatgaaggaa actcaagatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gtctctatgc aactatccca ggaggagaaa gtgaggaaat aaagaaaaag    1680
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca tggagaacca ggttcttcca    2220
gcggtactta ggatattgga gggatttgga tacagaaagg aagacctcag ataccaaaag    2280
acaagacaag tcggcctaac ttcctggctt aacattaaaa aatcctag               2328
```

<210> SEQ ID NO 91
<211> LENGTH: 2328
<212> TYPE: DNA
<213> ORGANISM: Pyrococcus furiosus
<220> FEATURE:
<221> NAME/KEY: misc_feature
<222> LOCATION: (1159)..(1161)
<223> OTHER INFORMATION: Ns at position 1159-1161 may ne any nucleotide
      so that the codon at 1159-1161 encodes Ser or Pro.

<400> SEQUENCE: 91

```
atgattttag atgtggatta cataactgaa gaaggaaaac ctgttattag gctattcaaa     60
aaagagaacg gaaaatttaa gatagagcat gatagaactt ttagaccata catttacgct    120
cttctcaggg atgattcaaa gattgaagaa gttaagaaaa taacgggga aaggcatgga     180 aagattgtga gaattgttga tgtagagaag gttgagaaaa agtttctcgg caagcctatt    240
accgtgtgga aactttatt ggaacatccc caagatgttc ccactattag agaaaaagtt    300
agagaacatc cagcagttgt ggacatcttc gaatacgata ttccatttgc aaagagatac    360
```

```
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgcattccc atatttagcg    660
aaaagggcag aaaacttggg attaaaatta accattggaa gagatggaag cgagcccaag    720
atgcagagaa taggcgatat gacggctgta aagtcaagg gaagaataca tttcgacttg    780
tatcatgtaa taacaaggac aataaatctc ccaacataca cactagaggc tgtatatgaa    840
gcaatttttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacann nggattcgtt aagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaacca ggttcttcca   2220
gcggtactta ggatattgga gggatttgga tacagaaagg aagacctcag ataccaaaag   2280
acaagacaag tcggcctaac ttcctggctt aacattaaaa aatcctag               2328
```

<210> SEQ ID NO 92
<211> LENGTH: 2328
<212> TYPE: DNA
<213> ORGANISM: Pyrococcus furiosus
<220> FEATURE:
<221> NAME/KEY: misc_feature
<222> LOCATION: (1162)..(1164)
<223> OTHER INFORMATION: Ns at position 1162-1164 may be any nucleotides
      so that the codon at 1162-1164 encodes for Ala or Pro.

<400> SEQUENCE: 92

```
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa agtttctcgg caagcctatt     240
accgtgtgga aactttattt ggaacatccc caagatgttc ccactattag agaaaagtt      300 agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat ttctcaggat tatcagggag     600
aaggatcctg acattatagt tacttataat ggagactcat tcgcattccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840 gcaattttg gaaagccaaa ggagaaggta tacgccgacg atagcaaa agcctgggaa       900 agtggagaga accttgagag agttgccaaa tactcgatgg aagatgcaaa ggcaacttat     960
gaactcggga agaattcct tccaatggaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tnnnttcgtt aaagagccag aaaaggggtt gtgggaaaac    1200
atagtatacc tagattttag agccctatat ccctcgatta taattaccca caatgtttct    1260
cccgatactc taaatcttga gggatgcaag aactatgata tcgctcctca agtaggccac    1320
aagttctgca aggacatccc tggttttata ccaagtctct tgggacattt gttagaggaa    1380
agacaaaaga ttaagacaaa aatgaaggaa actcaagatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gtctctatgc aactatccca ggaggagaaa gtgaggaaat aaagaaaaag    1680
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca tggagaacca ggttcttcca    2220
gcggtactta ggatattgga gggatttgga tacagaaagg aagacctcag ataccaaaag    2280
acaagacaag tcggcctaac ttcctggctt aacattaaaa aatcctag               2328
```

<210> SEQ ID NO 93

```
<211> LENGTH: 2328
<212> TYPE: DNA
<213> ORGANISM: Pyrococcus furiosus
<220> FEATURE:
<221> NAME/KEY: misc_feature
<222> LOCATION: (1213)..(1215)
<223> OTHER INFORMATION: Ns at position 1213-1215 may be any nucleotides
      so that the codon at 1213-1215 encodes for Glu.

<400> SEQUENCE: 93
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga aattgttgaa tgtagagaag gttgagaaaa gtttctcgg caagcctatt      240
accgtgtgga aactttattt ggaacatccc caagatgttc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggcccaat tataatgatt     480
agttatgcag atgaaaatga agcaaggtg attacttgga aaaacataga tcttccatac      540
gttgaggttg tatcaagcga gagagagatg ataaagagat tctcaggat tatcagggag      600
aaggatcctg acattatagt tacttataat ggagactcat tcgcattccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840
gcaattttg gaaagccaaa ggagaaggta tacgccgacg agatagcaaa agcctgggaa      900
agtggagaga accttgagag agttgccaaa tactcgatgg aagatgcaaa ggcaacttat     960
gaactcggga agaattcct tccaatggaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaaggggtt gtgggaaaac    1200
atagtatacc tannntttag agccctatat ccctcgatta taattaccca caatgtttct    1260
cccgatactc taaatcttga gggatgcaag aactatgata tcgctcctca gtaggccac    1320
aagttctgca aggacatccc tggttttata ccaagtctct tgggacatt gttagaggaa      1380
agacaaaaga ttaagacaaa aatgaaggaa actcaagatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gtctctatgc aactatccca ggaggagaaa gtgaggaaat aaagaaaaag    1680
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
```

```
ggatacatag tacttagagg cgatggtcca attagcaata gggcaattct agctgaggaa    2160
tacgatccca aaaagcacaa gtatgacgca gaatattaca tggagaacca ggttcttcca    2220
gcggtactta ggatattgga gggatttgga tacagaaagg aagacctcag ataccaaaag    2280
acaagacaag tcggcctaac ttcctggctt aacattaaaa aatcctag                 2328

<210> SEQ ID NO 94
<211> LENGTH: 2328
<212> TYPE: DNA
<213> ORGANISM: Pyrococcus furiosus
<220> FEATURE:
<221> NAME/KEY: misc_feature
<222> LOCATION: (1624)..(1626)
<223> OTHER INFORMATION: Ns at position 1624-1626 may be any nucleotides
      so that the codon at 1624-1626 encodes Pro.

<400> SEQUENCE: 94
atgattttag atgtggatta cataactgaa gaaggaaaac ctgttattag gctattcaaa      60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga gaattgttga tgtagagaag gttgagaaaa agtttctcgg caagcctatt    240
accgtgtgga aactttattt ggaacatccc caagatgttc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgcattccc atatttagcg    660
aaaagggcag aaaacttggg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactgagggc tgtatatgaa    840 gcaattttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct gggacattt gttagaggaa   1380 agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg ggaagaaag   1560 tacatcgagt tagtatggaa ggagctcgaa gaaaagtttg gatttaaagt cctctacatt   1620
gacnnngatg gtctctatgc aactatccca ggaggagaaa gtgaggaaat aaagaaaaag   1680
gctctagaat ttgtaaaata cataaaattca aagctccctg gactgctaga gcttgaatat   1740
```

-continued

```
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag     1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca tggagaacca ggttcttcca    2220
gcggtactta ggatattgga gggatttgga tacagaaagg aagacctcag ataccaaaag    2280
acaagacaag tcggcctaac ttcctggctt aacattaaaa aatcctag                 2328
```

<210> SEQ ID NO 95
<211> LENGTH: 2328
<212> TYPE: DNA
<213> ORGANISM: Pyrococcus furiosus
<220> FEATURE:
<221> NAME/KEY: misc_feature
<222> LOCATION: (1627)..(1629)
<223> OTHER INFORMATION: Ns at position 1627-1629 may be any nucleotides
      so that the codon at 1627-1629 encodes for Gly.

<400> SEQUENCE: 95

```
atgattttag atgtggatta cataactgaa gaaggaaaac ctgttattag gctattcaaa     60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga aattgttga tgtagagaag gttgagaaaa agtttctcgg caagcctatt     240
accgtgtgga aactttattt ggaacatccc caagatgttc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgcattccc atatttagcg    660
aaaagggcag aaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaatttttg gaaagccaaa ggagaaggta tacgccgacg atagcaaa agcctgggaa     900 agtggagaga acccttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaagggggtt gtgggaaaac   1200 atagtatacc tagatttttag agccctatat ccctcgatta taattaccca caatgttttct   1260 cccgatactc taaatcttga gggatgcaag aactatgata tcgctcctca agtaggccac   1320
aagttctgca aggacatccc tggttttata ccaagtctct tgggcatttt gttagaggaa   1380
agacaaaaga ttaagacaaa aatgaaggaa actcaagatc ctatagaaaa aatactcctt   1440
```

```
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactnnng gtctctatgc aactatccca ggaggagaaa gtgaggaaat aaagaaaaag    1680
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca tggagaacca ggttcttcca    2220
gcggtactta ggatattgga gggatttgga tacagaaagg aagacctcag ataccaaaag    2280
acaagacaag tcggcctaac ttcctggctt aacattaaaa aatcctag               2328
```

<210> SEQ ID NO 96
<211> LENGTH: 2328
<212> TYPE: DNA
<213> ORGANISM: Pyrococcus furiosus
<220> FEATURE:
<221> NAME/KEY: misc_feature
<222> LOCATION: (1777)..(1779)
<223> OTHER INFORMATION: Ns at position 1777-1779 may be any nucleotides
      so that the codon at 1777-1779 encodes for Thr.

<400> SEQUENCE: 96

```
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240 accgtgtgga aactttattt ggaacatccc caagatgttc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat tctcaggat tatcagggag     600 aaggatcctg acattatagt tacttataat ggagactcat tcgcattccc atatttagcg     660
aaaagggcag aaaaacttgg gattaaatta accattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactagaggc tgtatatgaa     840 gcaattttg gaaagccaaa ggagaaggta tacgccgacg agatagcaaa agcctgggaa     900
agtggagaga accttgagag agttgccaaa tactcgatgg aagatgcaaa ggcaacttat     960
gaactcggga agaattcct tccaatgaaa attcagcttt caagattagt tggacaacct    1020
ttatgggatg tttcaaggtc aagcacaggg aaccttgtag agtggttctt acttaggaaa    1080
```

|  |  |  |  |  |
|---|---|---|---|---|
| gcctacgaaa | gaaacgaagt | agctccaaac | aagccaagtg | aagaggagta tcaaagaagg | 1140 |
| ctcagggaga | gctacacagg | tggattcgtt | aaagagccag | aaaaggggtt gtgggaaaac | 1200 |
| atagtatacc | tagattttag | agccctatat | ccctcgatta | taattaccca caatgtttct | 1260 |
| cccgatactc | taaatcttga | gggatgcaag | aactatgata | tcgctcctca agtaggccac | 1320 |
| aagttctgca | aggacatccc | tggttttata | ccaagtctct | tgggacattt gttagaggaa | 1380 |
| agacaaaaga | ttaagacaaa | aatgaaggaa | actcaagatc | ctatagaaaa aatactcctt | 1440 |
| gactatagac | aaaaagcgat | aaaactctta | gcaaattctt | tctacggata ttatggctat | 1500 |
| gcaaaagcaa | gatggtactg | taaggagtgt | gctgagagcg | ttactgcctg ggaagaaag | 1560 |
| tacatcgagt | tagtatggaa | ggagctcgaa | gaaaagtttg | gatttaaagt cctctacatt | 1620 |
| gacactgatg | gtctctatgc | aactatccca | ggaggagaaa | gtgaggaaat aaagaaaaag | 1680 |
| gctctagaat | ttgtaaaata | cataaattca | aagctccctg | gactgctaga gcttgaatat | 1740 |
| gaagggtttt | ataagagggg | attcttcgtt | acgaagnnna | ggtatgcagt aatagatgaa | 1800 |
| gaaggaaaag | tcattactcg | tggtttagag | atagttagga | gagattggag tgaaattgca | 1860 |
| aaagaaactc | aagctagagt | tttggagaca | atactaaaac | acggagatgt tgaagaagct | 1920 |
| gtgagaatag | taaagaagt | aatacaaaag | cttgccaatt | atgaaattcc accagagaag | 1980 |
| ctcgcaatat | atgagcagat | aacaagacca | ttacatgagt | ataaggcgat aggtcctcac | 2040 |
| gtagctgttg | caagaaaact | agctgctaaa | ggagttaaaa | taaagccagg aatggtaatt | 2100 |
| ggatacatag | tacttagagg | cgatggtcca | attagcaata | gggcaattct agctgaggaa | 2160 |
| tacgatccca | aaaagcacaa | gtatgacgca | gaatattaca | tggagaacca ggttcttcca | 2220 |
| gcggtactta | ggatattgga | gggatttgga | tacagaaagg | aagacctcag ataccaaaag | 2280 |
| acaagacaag | tcggcctaac | ttcctggctt | aacattaaaa | aatcctag | 2328 |

<210> SEQ ID NO 97
<211> LENGTH: 2325
<212> TYPE: DNA
<213> ORGANISM: Pyrococcus sp.

<400> SEQUENCE: 97

|  |  |  |  |  |
|---|---|---|---|---|
| atgatcctcg | acactgacta | cataaccgag | gatggaaagc | ctgtcataag aattttcaag | 60 |
| aaggaaaacg | gcgagtttaa | gattgagtac | gaccggactt | tgaaccccta cttctacgcc | 120 |
| ctcctgaagg | acgattctgc | cattgaggaa | gtcaagaaga | taaccgccga gaggcacggg | 180 |
| acggttgtaa | cggttaagcg | ggttgaaaag | gttcagaaga | agttcctcgg agaccagtt | 240 |
| gaggtctgga | aactctactt | tactcatccg | caggacgtcc | cagcgataag ggacaagata | 300 |
| cgagagcatc | cagcagttat | tgacatctac | gagtacgaca | taccttcgc caagcgctac | 360 |
| ctcatagaca | agggattagt | gccaatggaa | ggcgacgagg | agctgaaaat gctcgccttc | 420 |
| gacattgaaa | ctctctacca | tgagggcgag | gagttcgccg | aggggccaat ccttatgata | 480 |
| agctacgccg | acgaggaagg | ggccagggtg | ataacttgga | agaacgtgga tctcccctac | 540 |
| gttgacgtcg | tctcgacgga | gagggagatg | ataaagcgct | tcctccgtgt tgtgaaggag | 600 |
| aaagacccgg | acgttctcat | aacctacaac | ggcgacaact | tcgacttcgc ctatctgaaa | 660 |
| aagcgctgtg | aaaagctcgg | aataaacttc | gccctcggaa | gggatggaag cgagccgaag | 720 |
| attcagagga | tgggcgacag | gtttgccgtc | gaagtgaagg | gacggataca cttcgatctc | 780 |
| tatcctgtga | taagcggac | gataaacctg | cccacataca | cgcttgaggc cgtttatgaa | 840 |
| gccgtcttcg | gtcagccgaa | ggagaaggtt | tacgctgagg | aaataaccac agcctgggaa | 900 |

```
accggcgaga accttgagag agtcgcccgc tactcgatgg aagatgcgaa ggtcacatac      960
gagcttggga aggagttcct tccgatggag gcccagcttt ctcgcttaat cggccagtcc     1020
ctctgggacg tctcccgctc cagcactggc aacctcgttg agtggttcct cctcaggaag     1080
gcctatgaga ggaatgagct ggccccgaac aagcccgatg aaaaggagct ggccagaaga     1140
cggcagagct atgaaggagg ctatgtaaaa gagcccgaga gagggttgtg ggagaacata     1200
gtgtacctag attttagatc cctgtacccc tcaatcatca tcacccacaa cgtctcgccg     1260
gatacgctca acagagaagg atgcaaggaa tatgacgttg ccccacaggt cggccaccgc     1320
ttctgcaagg acttcccagg atttatcccg agcctgcttg agacctcct agaggagagg      1380
cagaagataa agaagaagat gaaggccacg attgacccga tcgagaggaa gctcctcgat     1440
tacaggcaga gggccatcaa gatcctggca acagctact acggttacta cggctatgca      1500
agggcgcgct ggtactgcaa ggagtgtgca gagagcgtaa cggcctgggg aagggagtac     1560
ataacgatga ccatcaagga gatagaggaa aagtacggct ttaaggtaat ctacagcgac     1620
accgacggat tttttgccac aatacctgga gccgatgctg aaaccgtcaa aaagaaggct     1680
atggagttcc tcaagtatat caacgccaaa cttccgggcg cgcttgagct cgagtacgag     1740
ggcttctaca acgcggctt cttcgtcacg aagaagaagt atgcggtgat agacgaggaa      1800
ggcaagataa caacgcgcgg acttgagatt gtgaggcgtg actggagcga atagcgaaa      1860
gagacgcagg cgagggttct tgaagctttg ctaaaggacg gtgacgtcga aaggccgtg      1920
aggatagtca agaagttac cgaaaagctg agcaagtacg aggttccgcc ggagaagctg       1980
gtgatccacg agcagataac gagggattta aaggactaca aggcaaccgg tccccacgtt     2040
gccgttgcca agaggttggc cgcgagagga gtcaaaatac gccctggaac ggtgataagc     2100
tacatcgtgc tcaagggctc tgggaggata ggcgacaggg cgataccgtt cgacgagttc     2160
gacccgacga agcacaagta cgacgccgag tactacattg agaaccaggt tctcccagcc     2220
gttgagagaa ttctgagagc cttcggttac cgcaaggaag acctgcgcta ccagaagacg     2280
agacaggttg gtttgagtgc ttggctgaag ccgaagggaa cttga                     2325
```

<210> SEQ ID NO 98
<211> LENGTH: 2325
<212> TYPE: DNA
<213> ORGANISM: Pyrococcus sp.
<220> FEATURE:
<221> NAME/KEY: misc_feature
<222> LOCATION: (1150)..(1152)
<223> OTHER INFORMATION: Ns at positions 1150-1152 may be any
    nucleotides so that the codon at 1150-1152 encodes for Asn, Leu,
    His, Gln, or Ser.

<400> SEQUENCE: 98

```
atgatcctcg acactgacta cataaccgag gatggaaagc ctgtcataag aattttcaag      60
aaggaaaacg gcgagtttaa gattgagtac gaccggactt tgaaccccta cttctacgcc     120
ctcctgaagg acgattctgc cattgaggaa gtcaagaaga taaccgccga gaggcacggg     180
acggttgtaa cggttaagcg ggttgaaaag gttcagaaga agttcctcgg agaccagtt      240
gaggtctgga aactctactt tactcatccg caggacgtcc cagcgataag ggacaagata     300
cgagagcatc cagcagttat tgacatctac gagtacgaca tacccttcgc caagcgctac     360
ctcatagaca agggattagt gccaatggaa ggcgacgagg agctgaaaat gctcgccttc     420
gacattgaaa ctctctacca tgagggcgag gagttcgccg aggggccaat ccttatgata     480
agctacgccg acgaggaagg ggccagggtg ataacttgga agaacgtgga tctcccctac     540
```

```
gttgacgtcg tctcgacgga gagggagatg ataaagcgct tcctccgtgt tgtgaaggag      600
aaagacccgg acgttctcat aacctacaac ggcgacaact tcgacttcgc ctatctgaaa      660
aagcgctgtg aaaagctcgg aataaacttc gccctcggaa gggatggaag cgagccgaag      720
attcagagga tgggcgacag gtttgccgtc gaagtgaagg gacggataca cttcgatctc      780
tatcctgtga taagacggac gataaacctg cccacataca cgcttgaggc cgtttatgaa      840
gccgtcttcg gtcagccgaa ggagaaggtt tacgctgagg aaataaccac agcctgggaa      900
accggcgaga accttgagag agtcgcccgc tactcgatgg aagatgcgaa ggtcacatac      960
gagcttggga aggagttcct tccgatggag gcccagcttt ctcgcttaat cggccagtcc     1020
ctctgggacg tctcccgctc cagcactggc aacctcgttg agtggttcct cctcaggaag     1080
gcctatgaga ggaatgagct ggccccgaac aagcccgatg aaaaggagct ggccagaaga     1140
cggcagagcn nngaaggagg ctatgtaaaa gagcccgaga gagggttgtg ggagaacata     1200
gtgtacctag attttagatc cctgtacccc tcaatcatca tcacccacaa cgtctcgccg     1260
gatacgctca acagagaagg atgcaaggaa tatgacgttg ccccacaggt cggccaccgc     1320
ttctgcaagg acttcccagg atttatcccg agcctgcttg agacctcct agaggagagg     1380 cagaagataa agaagaagat gaaggccacg attgacccga tcgagaggaa gctcctcgat     1440
tacaggcaga gggccatcaa gatcctggca acagctact acggttacta cggctatgca     1500
agggcgcgct ggtactgcaa ggagtgtgca gagagcgtaa cggcctgggg aagggagtac     1560
ataacgatga ccatcaagga gatagaggaa aagtacggct ttaaggtaat ctacagcgac     1620
accgacggat tttttgccac aatacctgga gccgatgctg aaaccgtcaa aaagaaggct     1680
atggagttcc tcaagtatat caacgccaaa cttccgggcg cgcttgagct cgagtacgag     1740
ggcttctaca acgcggctt cttcgtcacg aagaagaagt atgcggtgat agacgaggaa     1800
ggcaagataa caacgcgcgg acttgagatt gtgaggcgtg actggagcga gatagcgaaa     1860
gagacgcagg cgagggttct tgaagctttg ctaaaggacg tgacgtcga aaggccgtg     1920 aggatagtca aagaagttac cgaaaagctg agcaagtacg aggttccgcc ggagaagctg     1980
gtgatccacg agcagataac gagggattta aaggactaca aggcaaccgg tccccacgtt     2040
gccgttgcca agaggttggc cgcgagagga gtcaaaatac gccctggaac ggtgataagc     2100
tacatcgtgc tcaagggctc tgggaggata ggcgacaggg cgataccgtt cgacgagttc     2160 gaccccgacga agcacaagta cgacgccgag tactacattg agaaccaggt tctcccagcc     2220
gttgagagaa ttctgagagc cttcggttac cgcaaggaag acctgcgcta ccagaagacg     2280
agacaggttg gtttgagtgc ttggctgaag ccgaagggaa cttga               2325
```

<210> SEQ ID NO 99
<211> LENGTH: 2325
<212> TYPE: DNA
<213> ORGANISM: Pyrococcus sp.
<220> FEATURE:
<221> NAME/KEY: misc_feature
<222> LOCATION: (1156)..(1158)
<223> OTHER INFORMATION: Ns at position 1156-1158 may be any nucleotides
      so that the codon at 1156-1158 encodes for Ser or Pro.

<400> SEQUENCE: 99

```
atgatcctcg acactgacta cataaccgag gatggaaagc ctgtcataag aattttcaag       60
aaggaaaacg gcgagtttaa gattgagtac gaccggactt ttgaacccta cttctacgcc      120
ctcctgaagg acgattctgc cattgaggaa gtcaagaaga taaccgccga gaggcacggg      180
acggttgtaa cggttaagcg ggttgaaaag gttcagaaga agttcctcgg gagaccagtt      240
```

```
gaggtctgga aactctactt tactcatccg caggacgtcc cagcgataag ggacaagata    300
cgagagcatc cagcagttat tgacatctac gagtacgaca tacccttcgc caagcgctac    360
ctcatagaca agggattagt gccaatggaa ggcgacgagg agctgaaaat gctcgccttc    420
gacattgaaa ctctctacca tgagggcgag gagttcgccg aggggccaat ccttatgata    480
agctacgccg acgaggaagg ggccagggtg ataacttgga agaacgtgga tctcccctac    540
gttgacgtcg tctcgacgga gagggagatg ataaagcgct tcctccgtgt tgtgaaggag    600
aaagacccgg acgttctcat aacctacaac ggcgacaact tcgacttcgc ctatctgaaa    660
aagcgctgtg aaaagctcgg aataaacttc gccctcggaa gggatggaag cgagccgaag    720
attcagagga tgggcgacag gtttgccgtc gaagtgaagg gacggataca cttcgatctc    780
tatcctgtga taagacggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
gagcttggga aggagttcct tccgatggag gcccagcttt ctcgcttaat cggccagtcc   1020
ctctgggacg tctcccgctc cagcactggc aacctcgttg agtggttcct cctcaggaag   1080
gcctatgaga ggaatgagct ggccccgaac aagcccgatg aaaggagct ggccagaaga    1140 cggcagagct atgaannngg ctatgtaaaa gagcccgaga gagggttgtg ggagaacata   1200
gtgtacctag attttagatc cctgtacccc tcaatcatca tcacccacaa cgtctcgccg   1260
gatacgctca acagagaagg atgcaaggaa tatgacgttg ccccacaggt cggccaccgc   1320
ttctgcaagg acttcccagg atttatcccg agcctgcttg gagacctcct agaggagagg   1380
cagaagataa agaagaagat gaaggccacg attgacccga tcgagaggaa gctcctcgat   1440
tacaggcaga gggccatcaa gatcctggca aacagctact acggttacta cggctatgca   1500
agggcgcgct ggtactgcaa ggagtgtgca gagagcgtaa cggcctgggg aagggagtac   1560
ataacgatga ccatcaagga gatagaggaa aagtacggct ttaaggtaat ctacagcgac   1620
accgacggat ttttttgccac aatacctgga gccgatgctg aaaccgtcaa aaagaaggct   1680
atggagttcc tcaagtatat caacgccaaa cttccgggcg cgcttgagct cgagtacgag   1740
ggcttctaca aacgcggctt cttcgtcacg aagaagaagt atgcggtgat agacgaggaa   1800
ggcaagataa caacgcgcgg acttgagatt gtgaggcgtg actggagcga gatagcgaaa   1860
gagacgcagg cgagggttct tgaagctttg ctaaaggacg gtgacgtcga gaaggccgtg   1920
aggatagtca agaagttac cgaaaagctg agcaagtacg aggttccgcc ggagaagctg    1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtttgagtgc ttggctgaag ccgaagggaa cttga                   2325
```

<210> SEQ ID NO 100  
<211> LENGTH: 2325  
<212> TYPE: DNA  
<213> ORGANISM: Pyrococcus sp.  
<220> FEATURE:  
<221> NAME/KEY: misc_feature  
<222> LOCATION: (1159)..(1161)  
<223> OTHER INFORMATION: Ns at position 1159-1161 may be any nucleotides so that the codon at 1159-1161 encodes for Ala or Pro.

<400> SEQUENCE: 100

| | | | | | |
|---|---|---|---|---|---|
| atgatcctcg | acactgacta | cataaccgag | gatggaaagc | ctgtcataag | aattttcaag | 60 |
| aaggaaaacg | gcgagtttaa | gattgagtac | gaccggactt | ttgaacccta | cttctacgcc | 120 |
| ctcctgaagg | acgattctgc | cattgaggaa | gtcaagaaga | taaccgccga | gaggcacggg | 180 |
| acggttgtaa | cggttaagcg | ggttgaaaag | gttcagaaga | agttcctcgg | gagaccagtt | 240 |
| gaggtctgga | aactctactt | tactcatccg | caggacgtcc | cagcgataag | ggacaagata | 300 |
| cgagagcatc | cagcagttat | tgacatctac | gagtacgaca | tacccttcgc | caagcgctac | 360 |
| ctcatagaca | agggattagt | gccaatggaa | ggcgacgagg | agctgaaaat | gctcgccttc | 420 |
| gacattgaaa | ctctctacca | tgagggcgag | gagttcgccg | aggggccaat | ccttatgata | 480 |
| agctacgccg | acgaggaagg | ggccagggtg | ataacttgga | agaacgtgga | tctcccctac | 540 |
| gttgacgtcg | tctcgacgga | gagggagatg | ataaagcgct | tcctccgtgt | tgtgaaggag | 600 |
| aaagacccgg | acgttctcat | aacctacaac | ggcgacaact | tcgacttcgc | ctatctgaaa | 660 |
| aagcgctgtg | aaaagctcgg | aataaacttc | gccctcggaa | gggatggaag | cgagccgaag | 720 |
| attcagagga | tgggcgacag | gtttgccgtc | gaagtgaagg | gacggataca | cttcgatctc | 780 |
| tatcctgtga | taagacggac | gataaacctg | cccacataca | cgcttgaggc | cgtttatgaa | 840 |
| gccgtcttcg | gtcagccgaa | ggagaaggtt | tacgctgagg | aaataaccac | agcctgggaa | 900 |
| accggcgaga | accttgagag | agtcgcccgc | tactcgatgg | aagatgcgaa | ggtcacatac | 960 |
| gagcttggga | aggagttcct | tccgatggag | gcccagcttt | ctcgcttaat | cggccagtcc | 1020 |
| ctctgggacg | tctcccgctc | cagcactggc | aacctcgttg | agtggttcct | cctcaggaag | 1080 |
| gcctatgaga | ggaatgagct | ggccccgaac | aagcccgatg | aaaaggagct | ggccagaaga | 1140 |
| cggcagagct | atgaaggann | ntatgtaaaa | gagcccgaga | gagggttgtg | ggagaacata | 1200 |
| gtgtacctag | attttagatc | cctgtacccc | tcaatcatca | tcacccacaa | cgtctcgccg | 1260 |
| gatacgctca | acagagaagg | atgcaaggaa | tatgacgttg | ccccacaggt | cggccaccgc | 1320 |
| ttctgcaagg | acttcccagg | atttatcccg | agcctgcttg | gagacctcct | agaggagagg | 1380 |
| cagaagataa | agaagaagat | gaaggccacg | attgacccga | tcgagaggaa | gctcctcgat | 1440 |
| tacaggcaga | gggccatcaa | gatcctggca | acagctact | acggttacta | cggctatgca | 1500 |
| agggcgcgct | ggtactgcaa | ggagtgtgca | gagagcgtaa | cggcctgggg | aagggagtac | 1560 |
| ataacgatga | ccatcaagga | gatagaggaa | aagtacggct | ttaaggtaat | ctacagcgac | 1620 |
| accgacggat | tttttgccac | aatacctgga | gccgatgctg | aaaccgtcaa | aagaaggct | 1680 |
| atggagttcc | tcaagtatat | caacgccaaa | cttccgggcg | cgcttgagct | cgagtacgag | 1740 |
| ggcttctaca | acgcggctt | cttcgtcacg | aagaagaagt | atgcggtgat | agacgaggaa | 1800 |
| ggcaagataa | caacgcgcgg | acttgagatt | gtgaggcgtg | actggagcga | gatagcgaaa | 1860 |
| gagacgcagg | cgagggttct | tgaagctttg | ctaaaggacg | gtgacgtcga | gaaggccgtg | 1920 |
| aggatagtca | agaagttac | cgaaaagctg | agcaagtacg | aggttccgcc | ggagaagctg | 1980 |
| gtgatccacg | agcagataac | gagggattta | aaggactaca | aggcaaccgg | tcccccacgtt | 2040 |
| gccgttgcca | agaggttggc | cgcgagagga | gtcaaaatac | gccctggaac | ggtgataagc | 2100 |
| tacatcgtgc | tcaagggctc | tgggaggata | ggcgacaggg | cgataccgtt | cgacgagttc | 2160 |
| gacccgacga | agcacaagta | cgacgccgag | tactacattg | agaaccaggt | tctcccagcc | 2220 |
| gttgagagaa | ttctgagagc | cttcggttac | cgcaaggaag | acctgcgcta | ccagaagacg | 2280 |

| | |
|---|---|
| agacaggttg gtttgagtgc ttggctgaag ccgaagggaa cttga | 2325 |

<210> SEQ ID NO 101
<211> LENGTH: 2325
<212> TYPE: DNA
<213> ORGANISM: Pyrococcus sp.
<220> FEATURE:
<221> NAME/KEY: misc_feature
<222> LOCATION: (1210)..(1212)
<223> OTHER INFORMATION: Ns at positions 1210-1212 may be any
      nucleotides so that the codon at 1210-1212 encodes for Glu.

<400> SEQUENCE: 101

| | |
|---|---|
| atgatcctcg acactgacta cataaccgag gatggaaagc ctgtcataag aattttcaag | 60 |
| aaggaaaacg gcgagtttaa gattgagtac gaccggactt ttgaacccta cttctacgcc | 120 |
| ctcctgaagg acgattctgc cattgaggaa gtcaagaaga taaccgccga gaggcacggg | 180 |
| acggttgtaa cggttaagcg ggttgaaaag gttcagaaga agttcctcgg gagaccagtt | 240 |
| gaggtctgga aactctactt tactcatccg caggacgtcc cagcgataag ggacaagata | 300 |
| cgagagcatc cagcagttat tgacatctac gagtacgaca taccttcgc caagcgctac | 360 |
| ctcatagaca agggattagt gccaatggaa ggcgacgagg agctgaaaat gctcgccttc | 420 |
| gacattgaaa ctctctacca tgagggcgag gagttcgccg aggggccaat ccttatgata | 480 |
| agctacgccg acgaggaagg ggccagggtg ataacttgga gaacgtgga tctcccctac | 540 |
| gttgacgtcg tctcgacgga gagggagatg ataaagcgct ccctccgtgt tgtgaaggag | 600 |
| aaagacccgg acgttctcat aacctacaac ggcgacaact tcgacttcgc ctatctgaaa | 660 |
| aagcgctgtg aaaagctcgg aataaacttc gccctcggaa gggatggaag cgagccgaag | 720 |
| attcaggaga tgggcgacag gtttgccgtc gaagtgaagg gacggataca cttcgatctc | 780 |
| tatcctgtga taagacggac gataaacctg cccacataca cgcttgaggc cgtttatgaa | 840 |
| gccgtcttcg gtcagccgaa ggagaaggtt tacgctgagg aaataaccac agcctgggaa | 900 |
| accggcgaga accttgagag agtcgcccgc tactcgatgg aagatgcgaa ggtcacatac | 960 |
| gagcttggga aggagttcct tccgatggag gcccagcttt ctcgcttaat cggccagtcc | 1020 |
| ctctgggacg tctcccgctc cagcactggc aacctcgttg agtggttcct cctcaggaag | 1080 |
| gcctatgaga ggaatgagct ggcccccgaac aagcccgatg aaaaggagct ggccagaaga | 1140 |
| cggcagagct atgaaggagg ctatgtaaaa gagcccgaga gagggttgtg ggagaacata | 1200 |
| gtgtaccctan nntttagatc cctgtacccc tcaatcatca tcaccacaa cgtctcgccg | 1260 |
| gatacgctca acagagaagg atgcaaggaa tatgacgttg ccccacaggt cggccaccgc | 1320 |
| ttctgcaagg acttcccagg atttatcccg agcctgcttg agacctcct agaggagagg | 1380 |
| cagaagataa agaagaagat gaaggccacg attgacccga tcgagaggaa gctcctcgat | 1440 |
| tacaggcaga gggccatcaa gatcctggca aacagctact acggttacta cggctatgca | 1500 |
| agggcgcgct ggtactgcaa ggagtgtgca gagagcgtaa cggcctgggg aagggagtac | 1560 |
| ataacgatga ccatcaagga gatagaggaa aagtacggct ttaaggtaat ctacagcgac | 1620 |
| accgacggat ttttgccac aatacctgga gccgatgctg aaaccgtcaa aaagaaggct | 1680 |
| atggagttcc tcaagtatat caacgccaaa cttccgggcg cgcttgagct cgagtacgag | 1740 |
| ggcttctaca acgcggctt cttcgtcacg aagaagaagt atgcggtgat agacgaggaa | 1800 |
| ggcaagataa caacgcgcgg acttgagatt gtgaggcgtg actggagcga gatagcgaaa | 1860 |
| gagacgcagg cgagggttct tgaagctttg ctaaggacg gtgacgtcga aaggccgtg | 1920 |
| aggatagtca agaagttac cgaaaagctg agcaagtacg aggttccgcc ggagaagctg | 1980 |

```
gtgatccacg agcagataac gagggattta aaggactaca aggcaaccgg tccccacgtt    2040
gccgttgcca agaggttggc cgcgagagga gtcaaaatac gccctggaac ggtgataagc    2100
tacatcgtgc tcaagggctc tgggaggata ggcgacaggg cgataccgtt cgacgagttc    2160
gacccgacga agcacaagta cgacgccgag tactacattg agaaccaggt tctcccagcc    2220
gttgagagaa ttctgagagc cttcggttac cgcaaggaag acctgcgcta ccagaagacg    2280
agacaggttg gtttgagtgc ttggctgaag ccgaagggaa cttga                    2325
```

<210> SEQ ID NO 102
<211> LENGTH: 2325
<212> TYPE: DNA
<213> ORGANISM: Pyrococcus sp.
<220> FEATURE:
<221> NAME/KEY: misc_feature
<222> LOCATION: (1621)..(1623)
<223> OTHER INFORMATION: Ns at positions 1621-1623 may be any
      nucleotides so that the codon at 1621-1623 encodes for Pro.

<400> SEQUENCE: 102

```
atgatcctcg acactgacta cataaccgag gatggaaagc ctgtcataag aattttcaag      60
aaggaaaacg gcgagtttaa gattgagtac gaccggactt ttgaacccta cttctacgcc     120
ctcctgaagg acgattctgc cattgaggaa gtcaagaaga taaccgccga gaggcacggg     180
acggttgtaa cggttaagcg ggttgaaaag gttcagaaga agttcctcgg agaccagtt      240 gaggtctgga aactctactt tactcatccg caggacgtcc cagcgataag ggacaagata     300
cgagagcatc cagcagttat tgacatctac gagtacgaca taccctccgc caagcgctac    360
ctcatagaca agggattagt gccaatgaaa ggcgacgagg agctgaaaat gctcgccttc     420
gacattgaaa ctctctacca tgagggcgag gagttcgccg agggggccaat ccttatgata     480 agctacgccg acgaggaagg ggccagggtg ataacttgga agaacgtgga tctcccctac    540
gttgacgtcg tctcgacgga gagggagatg ataaagcgct cctccgtgt tgtgaaggag     600 aaagacccgg acgttctcat aacctacaac ggcgacaact tcgacttcgc ctatctgaaa     660
aagcgctgtg aaaagctcgg aataaacttc gccctcggaa gggatggaag cgagccgaag    720
attcagagga tgggcgacag gttttgccgtc gaagtgaagg gacggataca cttcgatctc     780
tatcctgtga taagacggac gataaaacctg cccacataca cgcttgaggc cgtttatgaa     840
gccgtcttcg gtcagccgaa ggagaaggtt tacgctgagg aaataaccac agcctgggaa     900
accggcgaga accttgagag agtcgcccgc tactcgatgg aagatgcgaa ggtcacatac     960
gagcttggga aggagttcct tccgatggag gcccagcttt ctcgcttaat cggccagtcc    1020
ctctgggacg tctcccgctc cagcactggc aacctcgttg agtggttcct cctcaggaag   1080
gcctatgaga ggaatgagct ggccccgaac aagcccgatg aaaaggagct ggccagaaga    1140
cggcagagct atgaaggagg ctatgtaaaa gagcccgaga gagggttgtg ggagaacata   1200
gtgtacctag attttagatc cctgtacccc tcaatcatca tcacccacaa cgtctcgccg    1260
gatacgctca acagagaagg atgcaaggaa tatgacgttg ccccacaggt cggccaccgc    1320
ttctgcaagg acttcccagg atttatcccg agcctgcttg agacctcct agaggagagg    1380 cagaagataa agaagaagat gaaggccacg attgacccga tcgagaggaa gctcctcgat     1440
tacaggcaga gggccatcaa gatcctggca aacagctact acggttacta cggctatgca   1500
agggcgcgct ggtactgcaa ggagtgtgca gagagcgtaa cggcctgggg aagggagtac    1560
ataacgatga ccatcaagga gatagaggaa aagtacggct ttaaggtaat ctacagcgac    1620
```

```
nnngacggat tttttgccac aatacctgga gccgatgctg aaaccgtcaa aagaaggct   1680 atggagttcc tcaagtatat caacgccaaa cttccgggcg cgcttgagct cgagtacgag   1740
ggcttctaca aacgcggctt cttcgtcacg aagaagaagt atgcggtgat agacgaggaa   1800
ggcaagataa caacgcgcgg acttgagatt gtgaggcgtg actggagcga datagcgaaa   1860
```

*(Note: line 1860 contains "gatagcgaaa" — reading again)*

```
ggcaagataa caacgcgcgg acttgagatt gtgaggcgtg actggagcga gatagcgaaa   1860
gagacgcagg cgagggttct tgaagctttg ctaaggacg gtgacgtcga aaggccgtg    1920 aggatagtca agaagttac cgaaaagctg agcaagtacg aggttccgcc ggagaagctg    1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtttgagtgc ttggctgaag ccgaagggaa cttga                  2325
```

<210> SEQ ID NO 103
<211> LENGTH: 2325
<212> TYPE: DNA
<213> ORGANISM: Pyrococcus sp.
<220> FEATURE:
<221> NAME/KEY: misc_feature
<222> LOCATION: (1624)..(1626)
<223> OTHER INFORMATION: Ns at positions 1624-1626 may be any
      nucleotides so that the codon at 1624-1626 encodes for Gly.

<400> SEQUENCE: 103

```
atgatcctcg acactgacta cataaccgag gatggaaagc ctgtcataag aattttcaag     60
aaggaaaacg gcgagtttaa gattgagtac gaccggactt tgaaccccta cttctacgcc    120
ctcctgaagg acgattctgc cattgaggaa gtcaagaaga taaccgccga gaggcacggg    180
acggttgtaa cggttaagcg ggttgaaaag gttcagaaga agttcctcgg agaccagtt    240 gaggtctgga aactctactt tactcatccg caggacgtcc cagcgataag ggacaagata    300
cgagagcatc cagcagttat tgacatctac gagtacgaca taccctttgc caagcgctac    360
ctcatagaca agggattagt gccaatggaa ggcgacgagg agctgaaaat gctcgccttc    420
gacattgaaa ctctctacca tgagggcgag gagttcgccg aggggccaat ccttatgata    480
agctacgccg acgaggaagg ggccagggtg ataacttgga agaacgtgga tctcccctac    540
gttgacgtcg tctcgacgga gagggagatg ataaagcgct cctccgtgt tgtgaaggag    600 aaagacccgg acgttctcat aacctacaac ggcgacaact tcgacttcgc ctatctgaaa    660
aagcgctgtg aaaagctcgg aataaacttc gccctcggaa gggatggaag cgagccgaag    720
attcagagga tgggcgacag gtttgccgtc gaagtgaagg gacggataca cttcgatctc    780
tatcctgtga taagcggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
gagcttggga aggagttcct tccgatggag gcccagcttt tcgcttaat cggccagtcc   1020 ctctgggacg tctcccgctc cagcactggc aacctcgttg agtggttcct cctcaggaag   1080
gcctatgaga ggaatgagct ggccccgaac aagcccgatg aaaaggagct ggccagaaga   1140
cggcagagct atgaaggagg ctatgtaaaa gagcccgaga gagggttgtg ggagaacata   1200
gtgtacctag atttagatc cctgtacccc tcaatcatca tcacccacaa cgtctcgccg   1260
gatacgctca acagagaagg atgcaaggaa tatgacgttg ccccacaggt cggccaccgc   1320
```

```
ttctgcaagg acttcccagg atttatcccg agcctgcttg agacctcct agaggagagg    1380 cagaagataa agaagaagat gaaggccacg attgacccga tcgagaggaa gctcctcgat    1440
tacaggcaga gggccatcaa gatcctggca aacagctact acggttacta cggctatgca    1500
agggcgcgct ggtactgcaa ggagtgtgca gagagcgtaa cggcctgggg aagggagtac    1560
ataacgatga ccatcaagga gatagaggaa aagtacggct ttaaggtaat ctacagcgac    1620
accnnnggat tttttgccac aatacctgga gccgatgctg aaaccgtcaa aaagaaggct    1680
atggagttcc tcaagtatat caacgccaaa cttccgggcg cgcttgagct cgagtacgag    1740
ggcttctaca aacgcggctt cttcgtcacg aagaagaagt atgcggtgat agacgaggaa    1800
ggcaagataa caacgcgcgg acttgagatt gtgaggcgtg actggagcga gatagcgaaa    1860
gagacgcagg cgagggttct tgaagctttg ctaaggacg tgacgtcga aaggccgtg     1920 aggatagtca aagaagttac cgaaaagctg agcaagtacg aggttccgcc ggagaagctg    1980
gtgatccacg agcagataac gagggattta aaggactaca aggcaaccgg tccccacgtt    2040
gccgttgcca agaggttggc cgcgagagga gtcaaaatac gccctggaac ggtgataagc    2100
tacatcgtgc tcaagggctc tgggaggata ggcgacaggg cgataccgtt cgacgagttc    2160
gacccgacga agcacaagta cgacgccgag tactacattg agaaccaggt tctcccagcc    2220
gttgagagaa ttctgagagc cttcggttac cgcaaggaag acctgcgcta ccagaagacg    2280
agacaggttg gtttgagtgc ttggctgaag ccgaagggaa cttga              2325
```

<210> SEQ ID NO 104
<211> LENGTH: 2325
<212> TYPE: DNA
<213> ORGANISM: Pyrococcus sp.
<220> FEATURE:
<221> NAME/KEY: misc_feature
<222> LOCATION: (1774)..(1776)
<223> OTHER INFORMATION: Ns at positions 1774-1776 may be any
      nucleotides so that the codon at 1774-1776 encodes for Thr.

<400> SEQUENCE: 104

```
atgatcctcg acactgacta cataaccgag gatggaaagc ctgtcataag aatttttcaag    60 aaggaaaacg gcgagtttaa gattgagtac gaccggactt ttgaacccta cttctacgcc    120
ctcctgaagg acgattctgc cattgaggaa gtcaagaaga taaccgccga gaggcacggg    180
acggttgtaa cggttaagcg ggttgaaaag gttcagaaga agttcctcgg gagaccagtt    240
gaggtctgga aactctactt tactcatccg caggacgtcc cagcgataag ggacaagata    300
cgagagcatc cagcagttat tgacatctac gagtacgaca tacccttcgc caagcgctac    360
ctcatagaca agggattagt gccaatggaa ggcgacgagg agctgaaaat gctcgccttc    420
gacattgaaa ctctctacca tgagggcgag gagttcgccg aggggccaat ccttatgata    480
agctacgccg acgaggaagg ggccagggtg ataacttgga agaacgtgga tctcccctac    540
gttgacgtcg tctcgacgga gagggagatg ataaagcgct tcctccgtgt tgtgaaggag    600
aaagacccgg acgttctcat aacctacaac ggcgacaact cgacttcgc ctatctgaaa    660 aagcgctgtg aaaagctcgg aataaacttc gccctcggaa gggatggaag cgagccgaag    720
attcagagga tgggcgacag gtttgccgtc gaagtgaagg acggatacga cttcgatctc    780
tatcctgtga taagacggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
```

```
gagcttggga aggagttcct tccgatggag gcccagcttt ctcgcttaat cggccagtcc   1020
ctctgggacg tctcccgctc cagcactggc aacctcgttg agtggttcct cctcaggaag   1080
gcctatgaga ggaatgagct ggccccgaac aagcccgatg aaaaggagct ggccagaaga   1140
cggcagagct atgaaggagg ctatgtaaaa gagcccgaga gagggttgtg ggagaacata   1200
gtgtacctag attttagatc cctgtacccc tcaatcatca tcacccacaa cgtctcgccg   1260
gatacgctca acagagaagg atgcaaggaa tatgacgttg ccccacaggt cggccaccgc   1320
ttctgcaagg acttcccagg atttatcccg agcctgcttg agacctcct agaggagagg    1380 cagaagataa agaagaagat gaaggccacg attgacccga tcgagaggaa gctcctcgat   1440
tacaggcaga gggccatcaa gatcctggca acagctact acggttacta cggctatgca    1500
agggcgcgct ggtactgcaa ggagtgtgca gagagcgtaa cggcctgggg aagggagtac   1560
ataacgatga ccatcaagga gatagaggaa aagtacggct ttaaggtaat ctacagcgac   1620
accgacggat tttttgccac aatacctgga gccgatgctg aaaccgtcaa aaagaaggct   1680
atggagttcc tcaagtatat caacgccaaa cttccgggcg cgcttgagct cgagtacgag   1740
ggcttctaca aacgcggctt cttcgtcacg aagnnnaagt atgcggtgat agacgaggaa   1800
ggcaagataa caacgcgcgg acttgagatt gtgaggcgtg actggagcga gatagcgaaa   1860
gagacgcagg cgagggttct tgaagctttg ctaaaggacg gtgacgtcga gaaggccgtg   1920
aggatagtca agaagttac cgaaaagctg agcaagtacg aggttccgcc ggagaagctg    1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtttgagtgc ttggctgaag ccgaagggaa cttga                   2325

<210> SEQ ID NO 105
<211> LENGTH: 2325
<212> TYPE: DNA
<213> ORGANISM: Thermococcus litoralis

<400> SEQUENCE: 105
atgatactgg acactgatta cataacaaaa gatggcaagc ctataatccg aattttaag      60 aaagagaacg gggagtttaa aatagaactt gaccctcatt ttcagcccta tatatatgct    120
cttctcaaag atgactccgc tattgaggag ataaaggcaa taagggcga gagacatgga    180 aaaactgtga gagtgctcga tgcagtgaaa gtcaggaaaa aattttggg aagggaagtt     240 gaagtctgga agctcatttt cgagcatccc caagacgttc cagctatgcg gggcaaaata    300
agggaacatc cagctgtggt tgacatttac gaatatgaca taccctttgc caagcgttat    360
ctcatagaca agggcttgat tcccatggag ggagacgagg agcttaagct ccttgccttt    420
gatattgaaa cgtttatca tgagggagat gaatttggaa agggcgagat aataatgatt    480
agttatgccg atgaagaaga ggccagagta atcacatgga aaaatatcga tttgccgtat    540
gtcgatgttg tgtccaatga aagagaaatg ataaagcgtt ttgttcaagt tgttaaagaa    600
aaagaccccg atgtgataat aacttacaat ggggacaatt ttgatttgcc gtatctcata    660
aaacgggcag aaaagctggg agttcggctt gtcttaggaa gggacaaaga acatcccgaa    720
cccaagattc agaggatggg tgatagtttt gctgtggaaa tcaagggtag aatccacttt    780
```

| | | |
|---|---|---|
| gatctttttcc cagttgtgcg aaggacgata aacctcccaa cgtatacgct tgaggcagtt | 840 |
| tatgaagcag ttttaggaaa aaccaaaagc aaattaggag cagaggaaat tgccgctata | 900 |
| tgggaaacag aagaaagcat gaaaaaacta gcccagtact caatggaaga tgctagggca | 960 |
| acgtatgagc tcgggaagga attcttcccc atggaagctg agctggcaaa gctgataggt | 1020 |
| caaagtgtat gggacgtctc gagatcaagc accggcaacc tcgtggagtg gtatctttta | 1080 |
| agggtggcat acgcgaggaa tgaacttgca ccgaacaaac ctgatgagga agagtataaa | 1140 |
| cggcgcttaa gaacaactta cctgggagga tatgtaaaag agccagaaaa aggtttgtgg | 1200 |
| gaaaatatca tttatttgga tttccgcagt ctgtacccttt caataatagt tactcacaac | 1260 |
| gtatccccag atacccttga aaaagagggc tgtaagaatt acgatgttgc tccgatagta | 1320 |
| ggatataggt tctgcaagga cttccgggc tttattccct ccatactcgg ggacttaatt | 1380 |
| gcaatgaggc aagatataaa gaagaaatg aaatccacaa ttgacccgat cgaaaagaaa | 1440 |
| atgctcgatt ataggcaaag ggctattaaa ttgcttgcaa acagctatta cggctatatg | 1500 |
| gggtatccta aggcaagatg gtactcgaag gaatgtgctg aaagcgttac cgcatggggg | 1560 |
| agacactaca tagagatgac gataagagaa atagaggaaa agttcggctt taaggttctt | 1620 |
| tatgcggaca ctgacggctt ttatgccaca ataccccgggg aaaagcctga actcattaaa | 1680 |
| aagaaagcca aggaattcct aaactacata aactccaaac ttccaggtct gcttgagctt | 1740 |
| gagtatgagg gcttttactt gagaggattc tttgttacaa aaaagcgcta tgcagtcata | 1800 |
| gatgaagagg gcaggataac aacagggggc ttggaagtag taaggagaga ttggagtgag | 1860 |
| atagctaagg agactcaggc aaaggtttta gaggctatac ttaaagaggg aagtgttgaa | 1920 |
| aaagctgtag aagttgttag agatgttgta gagaaaatag caaaatacag ggttccactt | 1980 |
| gaaaagcttg ttatccatga gcagattacc agggatttaa aggactacaa agccattggc | 2040 |
| cctcatgtcg cgatagcaaa aagacttgcc gcaagaggga taaaagtgaa accgggcaca | 2100 |
| ataataagct atatcgttct caaagggagc ggaaagataa gcgataggggt aattttactt | 2160 |
| acagaatacg atcctagaaa acacaagtac gatccggact actacataga aaaccaagtt | 2220 |
| ttgccggcag tacttaggat actcgaagcg tttggataca gaaaggagga tttaaggtat | 2280 |
| caaagctcaa acaaaaccgg cttagatgca tggctcaaga ggtag | 2325 |

<210> SEQ ID NO 106
<211> LENGTH: 2325
<212> TYPE: DNA
<213> ORGANISM: Thermococcus litoralis
<220> FEATURE:
<221> NAME/KEY: misc_feature
<222> LOCATION: (1159)..(1161)
<223> OTHER INFORMATION: Ns at positions 1159-1161 may be any
    nucleotides so that the codon at 1159-1161 encodes for Asn, Leu,
    His, Gln, or Ser.

<400> SEQUENCE: 106

| | | |
|---|---|---|
| atgatactgg acactgatta cataacaaaa gatggcaagc ctataatccg aattttttaag | 60 |
| aaagagaacg gggagtttaa aatagaactt gaccctcatt ttcagcccta tatatatgct | 120 |
| cttctcaaag atgactccgc tattgaggag ataaaggcaa taaagggcga gagacatgga | 180 |
| aaaactgtga gagtgctcga tgcagtgaaa gtcaggaaaa aattttttggg aagggaagtt | 240 |
| gaagtctgga agctcatttt cgagcatccc caagacgttc cagctatgcg gggcaaaata | 300 |
| agggaacatc cagctgtggt tgacatttac gaatatgaca tacccctttgc caagcgttat | 360 |
| ctcatagaca agggcttgat tcccatggag ggagacgagg agcttaagct ccttgccttt | 420 |

```
gatattgaaa cgtttatca tgagggagat gaatttggaa agggcgagat aataatgatt      480
agttatgccg atgaagaaga ggccagagta atcacatgga aaaatatcga tttgccgtat      540
gtcgatgttg tgtccaatga aagagaaatg ataaagcgtt ttgttcaagt tgttaaagaa      600
aaagaccccg atgtgataat aacttacaat ggggacaatt ttgatttgcc gtatctcata      660
aaacgggcag aaaagctggg agttcggctt gtcttaggaa gggacaaaga acatcccgaa      720
cccaagattc agaggatggg tgatagtttt gctgtgaaaa tcaagggtag aatccacttt      780
gatcttttcc cagttgtgcg aaggacgata aacctcccaa cgtatacgct tgaggcagtt      840
tatgaagcag tttaggaaa aaccaaaagc aaattaggag cagaggaaat tgccgctata      900
tgggaaacag aagaaagcat gaaaaaacta gcccagtact caatggaaga tgctagggca      960
acgtatgagc tcgggaagga attcttcccc atggaagctg agctggcaaa gctgataggt     1020
caaagtgtat gggacgtctc gagatcaagc accggcaacc tcgtggagtg gtatctttta     1080
agggtggcat acgcgaggaa tgaacttgca ccgaacaaac ctgatgagga agagtataaa     1140
cggcgcttaa gaacaactnn nctggggagga tatgtaaaag agccagaaaa aggtttgtgg     1200
gaaaatatca tttatttgga tttccgcagt ctgtacccctt caataatagt tactcacaac     1260
gtatccccag ataccctcga aaaagagggc tgtaagaatt acgatgttgc tccgatagta     1320 ggatatagt tctgcaagga cttccggggc tttattccct ccatactcgg ggacttaatt      1380
gcaatgaggc aagatataaa gaagaaaatg aaatccacaa ttgacccgat cgaaaagaaa     1440
atgctcgatt ataggcaaag ggctattaaa ttgcttgcaa acagctatta cggctatatg     1500
gggtatccta aggcaagatg gtactcgaag gaatgtgctg aaagcgttac cgcatggggg     1560
agacactaca tagagatgac gataagagaa atagaggaaa agttcggctt taaggttctt     1620
tatgcggaca ctgacggctt ttatgccaca ataccccgggg aaaagcctga actcattaaa     1680
aagaaagcca aggaattcct aaactacata aactccaaac ttccaggtct gcttgagctt     1740
gagtatgagg gcttttactt gagaggattc tttgttacaa aaaagcgcta tgcagtcata     1800
gatgaagagg gcaggataac aacaaggggc ttgaagtag taaggagaga ttggagtgag     1860
atagctaagg agactcaggc aaaggttta gaggctatac ttaaagaggg aagtgttgaa     1920
aaagctgtag aagttgttag agatgttgta gagaaaatag caaaatacag ggttccactt     1980
gaaaagcttg ttatccatga gcagattacc agggatttaa aggactacaa agccattggc     2040
cctcatgtcg cgatagcaaa aagacttgcc gcaagaggga taaaagtgaa accgggcaca     2100
ataataagct atatcgttct caagggagc ggaaagataa gcgatagggt aatttactt     2160 acagaatacg atcctagaaa acacaagtac gatccggact actacataga aaaccaagtt     2220
ttgccggcag tacttaggat actcgaagcg tttggataca gaaaggagga tttaaggtat     2280
caaagctcaa aacaaaccgg cttagatgca tggctcaaga ggtag                     2325
```

<210> SEQ ID NO 107
<211> LENGTH: 2325
<212> TYPE: DNA
<213> ORGANISM: Thermococcus litoralis
<220> FEATURE:
<221> NAME/KEY: misc_feature
<222> LOCATION: (1165)..(1167)
<223> OTHER INFORMATION: Ns at positions 1165-1167 may be any
nucleotides so that the codon at 1165-1167 encodes for Ser or Pro.

<400> SEQUENCE: 107

```
atgatactgg acactgatta cataacaaaa gatggcaagc ctataatccg aattttaag       60 aaagagaacg gggagtttaa aatagaactt gaccctcatt ttcagcccta tatatatgct      120
```

```
cttctcaaag atgactccgc tattgaggag ataaaggcaa taaagggcga gagacatgga    180
aaaactgtga gagtgctcga tgcagtgaaa gtcaggaaaa aattttttggg aagggaagtt   240 gaagtctgga agctcatttt cgagcatccc caagacgttc cagctatgcg ggcaaaata    300 agggaacatc cagctgtggt tgacatttac gaatatgaca taccctttgc caagcgttat   360
ctcatagaca agggcttgat tcccatggag ggagacgagg agcttaagct ccttgccttt   420
gatattgaaa cgttttatca tgagggagat gaatttggaa agggcgagat aataatgatt   480
agttatgccg atgaagaaga ggccagagta atcacatgga aaaatatcga tttgccgtat   540
gtcgatgttg tgtccaatga aagagaaatg ataaagcgtt ttgttcaagt tgttaaagaa   600
aaagaccccg atgtgataat aacttacaat ggggacaatt ttgatttgcc gtatctcata   660
aaacgggcag aaaagctggg agttcggctt gtcttaggaa gggacaaaga acatcccgaa   720
cccaagattc agaggatggg tgatagtttt gctgtggaaa tcaagggtag aatccacttt   780
gatcttttcc cagttgtgcg aaggacgata aacctcccaa cgtatacgct tgaggcagtt   840
tatgaagcag tttttaggaaa aaccaaaagc aaattaggag cagaggaaat tgccgctata   900
tgggaaacag aagaaagcat gaaaaaacta gcccagtact caatggaaga tgctagggca   960
acgtatgagc tcgggaagga attcttcccc atggaagctg agctggcaaa gctgataggt  1020
caaagtgtat gggacgtctc gagatcaagc accggcaacc tcgtggagtg gtatcttta   1080 agggtggcat acgcgaggaa tgaacttgca ccgaacaaac ctgatgagga agagtataaa   1140
cggcgcttaa gaacaactta cctgnnngga tatgtaaaag agccagaaaa aggtttgtgg  1200
gaaaatatca tttatttgga tttccgcagt ctgtacccctt caataatagt tactcacaac  1260
gtatccccag atacccttga aaagagggc tgtaagaatt acgatgttgc tccgatagta   1320
ggatataggt tctgcaagga cttccgggc tttattccct ccatactcgg ggacttaatt   1380
gcaatgaggc aagatataaa gaagaaaatg aaatccacaa ttgacccgat cgaaaagaaa   1440
atgctcgatt ataggcaaag ggctattaaa ttgcttgcaa acagctatta cggctatatg   1500
gggtatccta aggcaagatg gtactcgaag gaatgtgctg aaagcgttac cgcatggggg   1560
agacactaca tagagatgac gataagagaa atagaggaaa agttcggctt taaggttctt   1620
tatgcggaca ctgacggctt ttatgccaca atacccgggg aaaagcctga actcattaaa   1680
aagaaagcca aggaattcct aaactacata aactccaaac ttccaggtct gcttgagctt   1740
gagtatgagg gcttttactt gagaggattc tttgttacaa aaaagcgcta tgcagtcata   1800
gatgaagagg gcaggataac aacaagggc ttggaagtag taaggagaga ttggagtgag   1860
atagctaagg agactcaggc aaaggtttta gaggctatac ttaaagaggg aagtgttgaa   1920
aaagctgtag aagttgttag agatgttgta gagaaaatag caaaatacag ggttccactt   1980
gaaaagcttg ttatccatga gcagattacc agggatttaa aggactacaa agccattggc   2040
cctcatgtcg cgatagcaaa aagacttgcc gcaagaggga taaaagtgaa accgggcaca   2100
ataataagct atatcgttct caagggagc ggaaagataa gcgatagggt aattttactt   2160
acagaatacg atcctagaaa acacaagtac gatccggact actacataga aaaccaagtt   2220
ttgccggcag tacttaggat actcgaagcg tttggataca gaaaggagga tttaaggtat   2280
caaagctcaa aacaaaccgg cttagatgca tggctcaaga ggtag                    2325
```

<210> SEQ ID NO 108
<211> LENGTH: 2325
<212> TYPE: DNA
<213> ORGANISM: Thermococcus litoralis
<220> FEATURE:
<221> NAME/KEY: misc_feature
<222> LOCATION: (1168)..(1170)
<223> OTHER INFORMATION: Ns at positions 1168-1170 may be any
      nucleotides so that the codon at 1168-1170 encodes for Ala, or
      Pro.

<400> SEQUENCE: 108

| | | | | | |
|---|---|---|---|---|---|
| atgatactgg | acactgatta | cataacaaaa | gatggcaagc | ctataatccg | aatttttaag | 60 |
| aaagagaacg | gggagtttaa | aatagaactt | gaccctcatt | ttcagcccta | tatatatgct | 120 |
| cttctcaaag | atgactccgc | tattgaggag | ataaaggcaa | taaagggcga | gagacatgga | 180 |
| aaaactgtga | gagtgctcga | tgcagtgaaa | gtcaggaaaa | aattttttggg | aagggaagtt | 240 |
| gaagtctgga | agctcatttt | cgagcatccc | caagacgttc | cagctatgcg | ggcaaaata | 300 |
| agggaacatc | cagctgtggt | tgacatttac | gaatatgaca | tacccttttgc | caagcgttat | 360 |
| ctcatagaca | agggcttgat | tcccatggag | ggagacgagg | agcttaagct | ccttgccttt | 420 |
| gatattgaaa | cgttttatca | tgagggagat | gaatttggaa | agggcgagat | aataatgatt | 480 |
| agttatgccg | atgaagaaga | ggccagagta | atcacatgga | aaaatatcga | tttgccgtat | 540 |
| gtcgatgttg | tgtccaatga | aagagaaatg | ataaagcgtt | ttgttcaagt | tgttaaagaa | 600 |
| aaagaccccg | atgtgataat | aacttacaat | ggggacaatt | ttgatttgcc | gtatctcata | 660 |
| aaacgggcag | aaaagctggg | agttcggctt | gtcttaggaa | gggacaaaga | acatcccgaa | 720 |
| cccaagattc | agaggatggg | tgatagtttt | gctgtggaaa | tcaagggtag | aatccacttt | 780 |
| gatcttttcc | cagttgtgcg | aaggacgata | aacctcccaa | cgtatacgct | tgaggcagtt | 840 |
| tatgaagcag | tttttaggaaa | aaccaaaagc | aaattaggag | cagaggaaat | tgccgctata | 900 |
| tgggaaacag | aagaaagcat | gaaaaaacta | gcccagtact | caatgaagaa | tgctagggca | 960 |
| acgtatgagc | tcgggaagga | attcttcccc | atggaagctg | agctggcaaa | gctgataggt | 1020 |
| caaagtgtat | gggacgtctc | gagatcaagc | accggcaacc | tcgtggagtg | gtatcttta | 1080 |
| agggtggcat | acgcgaggaa | tgaacttgca | ccgaacaaac | ctgatgagga | agagtataaa | 1140 |
| cggcgcttaa | gaacaactta | cctggganng | tatgtaaaag | agccagaaaa | aggtttgtgg | 1200 |
| gaaaatatca | tttatttgga | tttccgcagt | ctgtacccctt | caataatagt | tactcacaac | 1260 |
| gtatccccag | ataccctttga | aaaagagggc | tgtaagaatt | acgatgttgc | tccgatagta | 1320 |
| ggataaggt | tctgcaagga | ctttccgggc | tttattccct | ccatactcgg | ggacttaatt | 1380 |
| gcaatgaggc | aagatataaa | gaagaaaatg | aaatccacaa | ttgacccgat | cgaaaagaaa | 1440 |
| atgctcgatt | ataggcaaag | ggctattaaa | ttgcttgcaa | acagctatta | cggctatatg | 1500 |
| gggtatccta | aggcaagatg | gtactcgaag | gaatgtgctg | aaagcgttac | cgcatggggg | 1560 |
| agacactaca | tagagatgac | gataagagaa | atagaggaaa | agttcggctt | taaggttctt | 1620 |
| tatgcggaca | ctgacggctt | ttatgccaca | atacccgggg | aaaagcctga | actcattaaa | 1680 |
| aagaaagcca | aggaattcct | aaactacata | aactccaaac | ttccaggtct | gcttgagctt | 1740 |
| gagtatgagg | gcttttactt | gagaggattc | tttgttacaa | aaaagcgcta | tgcagtcata | 1800 |
| gatgaagagg | gcaggataac | aacaagggc | ttggaagtag | taaggagaga | ttggagtgag | 1860 |
| atagctaagg | agactcaggc | aaaggtttta | gaggctatac | ttaaagaggg | aagtgttgaa | 1920 |
| aaagctgtag | aagttgttag | agatgttgta | gagaaaatag | caaaatacag | ggttccactt | 1980 |
| gaaaagcttg | ttatccatga | gcagattacc | agggatttaa | aggactacaa | agccattggc | 2040 |
| cctcatgtcg | cgatagcaaa | aagacttgcc | gcaagaggga | taaaagtgaa | accgggcaca | 2100 |
| ataataagct | atatcgttct | caagggagc | ggaaagataa | gcgatagggt | aattttactt | 2160 |

| | |
|---|---|
| acagaatacg atcctagaaa acacaagtac gatccggact actacataga aaaccaagtt | 2220 |
| ttgccggcag tacttaggat actcgaagcg tttggataca gaaggagga tttaaggtat | 2280 |
| caaagctcaa acaaaccgg cttagatgca tggctcaaga ggtag | 2325 |

<210> SEQ ID NO 109
<211> LENGTH: 2325
<212> TYPE: DNA
<213> ORGANISM: Thermococcus litoralis
<220> FEATURE:
<221> NAME/KEY: misc_feature
<222> LOCATION: (1219)..(1221)
<223> OTHER INFORMATION: Ns at positions 1219-1221 may be any
      nucleotides so that the codon at 1219-1221 encodes for Glu.

<400> SEQUENCE: 109

| | |
|---|---|
| atgatactgg acactgatta cataacaaaa gatggcaagc ctataatccg aattttaag | 60 |
| aaagagaacg gggagtttaa aatagaactt gaccctcatt ttcagcccta tatatatgct | 120 |
| cttctcaaag atgactccgc tattgaggag ataaaggcaa taaagggcga gagacatgga | 180 |
| aaaactgtga gagtgctcga tgcagtgaaa gtcaggaaaa aattttttggg aagggaagtt | 240 |
| gaagtctgga agctcatttt cgagcatccc caagacgttc cagctatgcg gggcaaaata | 300 |
| agggaacatc cagctgtggt tgacatttac gaatatgaca tacccttgc caagcgttat | 360 |
| ctcatagaca agggcttgat tcccatggag ggagacgagg agcttaagct ccttgccttt | 420 |
| gatattgaaa cgttttatca tgagggagat gaatttggaa agggcgagat aataatgatt | 480 |
| agttatgccg atgaagaaga ggccagagta atcacatgga aaaatatcga tttgccgtat | 540 |
| gtcgatgttg tgtccaatga agagaaatg ataaagcgtt ttgttcaagt tgttaaagaa | 600 |
| aaagaccccg atgtgataat aacttacaat ggggacaatt ttgatttgcc gtatctcata | 660 |
| aaacgggcag aaaagctggg agttcggctt gtcttaggaa gggacaaaga acatcccgaa | 720 |
| cccaagattc agaggatggg tgatagtttt gctgtggaaa tcaagggtag aatccacttt | 780 |
| gatcttttcc cagttgtgcg aaggacgata aacctcccaa cgtatacgct tgaggcagtt | 840 |
| tatgaagcag ttttaggaaa aaccaaaagc aaattaggag cagaggaaat tgccgctata | 900 |
| tgggaaacag aagaaagcat gaaaaaacta gcccagtact caatggaaga tgctagggca | 960 |
| acgtatgagc tcgggaagga attcttcccc atggaagctg agctggcaaa gctgataggt | 1020 |
| caaagtgtat gggacgtctc gagatcaagc accggcaacc tcgtggagtg gtatctttta | 1080 |
| agggtggcat acgcgaggaa tgaacttgca ccgaacaaac ctgatgagga agagtataaa | 1140 |
| cggcgcttaa gaacaactta cctgggagga tatgtaaaag agccagaaaa aggtttgtgg | 1200 |
| gaaaatatca tttatttgnn nttccgcagt ctgtacccct caataatagt tactcacaac | 1260 |
| gtatccccag ataccctga aaaagagggc tgtaagaatt acgatgttgc tccgatagta | 1320 |
| ggatataggt tctgcaagga ctttccgggc tttattccct ccatactcgg ggacttaatt | 1380 |
| gcaatgaggc aagatataaa gaagaaaatg aaatccacaa ttgacccgat cgaaaagaaa | 1440 |
| atgctcgatt ataggcaaag ggctattaaa ttgcttgcaa acagctatta cggctatatg | 1500 |
| gggtatccta aggcaagatg gtactcgaag gaatgtgctg aaagcgttac cgcatggggg | 1560 |
| agacactaca tagagatgac gataagagaa atagaggaaa agttcggctt taaggttctt | 1620 |
| tatgcggaca ctgacggctt ttatgccaca ataccgggg aaaagcctga actcattaaa | 1680 |
| aagaaagcca aggaattcct aaactacata aactccaaac ttccaggtct gcttgagctt | 1740 |
| gagtatgagg gcttttactt gagaggattc tttgttacaa aaaagcgcta tgcagtcata | 1800 |

```
gatgaagagg gcaggataac aacaaggggc ttggaagtag taaggagaga ttggagtgag    1860
atagctaagg agactcaggc aaaggtttta gaggctatac ttaaagaggg aagtgttgaa    1920
aaagctgtag aagttgttag agatgttgta gagaaaatag caaaatacag ggttccactt    1980
gaaaagcttg ttatccatga gcagattacc agggatttaa aggactacaa agccattggc    2040
cctcatgtcg cgatagcaaa aagacttgcc gcaagaggga taaaagtgaa accgggcaca    2100
ataataagct atatcgttct caagggagc ggaaagataa gcgataggt aattttactt    2160 acagaatacg atcctagaaa acacaagtac gatccggact actacataga aaaccaagtt    2220
ttgccggcag tacttaggat actcgaagcg tttggataca gaaaggagga tttaaggtat    2280
caaagctcaa acaaaccgg cttagatgca tggctcaaga ggtag                     2325
```

<210> SEQ ID NO 110
<211> LENGTH: 2325
<212> TYPE: DNA
<213> ORGANISM: Thermococcus litoralis
<220> FEATURE:
<221> NAME/KEY: misc_feature
<222> LOCATION: (1630)..(1632)
<223> OTHER INFORMATION: Ns at positions 1630-1632 may be any
      nucleotides so that the codon at 1630-1632 encodes for Pro.

<400> SEQUENCE: 110

```
atgatactgg acactgatta cataacaaaa gatggcaagc ctataatccg aattttaag      60 aaagagaacg gggagtttaa aatagaactt gaccctcatt ttcagcccta tatatatgct    120
cttctcaaag atgactccgc tattgaggag ataaaggcaa taaagggcga gagacatgga    180
aaaactgtga gagtgctcga tgcagtgaaa gtcaggaaaa aattttttggg aagggaagtt    240 gaagtctgga agctcatttt cgagcatccc caagacgttc cagctatgcg gggcaaaata    300
agggaacatc cagctgtggt tgacatttac gaatatgaca tacccttttgc caagcgttat    360 ctcatagaca agggcttgat tcccatggag ggagacgagg agcttaagct ccttgccttt    420
gatattgaaa cgttttatca tgagggagat gaatttggaa agggcgagat aataatgatt    480
agttatgccg atgaagaaga ggccagagta atcacatgga aaaatatcga tttgccgtat    540
gtcgatgttg tgtccaatga aagagaaatg ataaagcgtt tgttcaagt tgttaaagaa    600 aaagaccccg atgtgataat aacttacaat ggggacaatt ttgatttgcc gtatctcata    660
aaacgggcag aaaagctggg agttcggctt gtcttaggaa gggacaaaga acatcccgaa    720
cccaagattc agaggatggg tgatagtttt gctgtggaaa tcaagggtag aatccacttt    780
gatcttttcc cagttgtgcg aaggacgata aacctcccaa cgtatacgct tgaggcagtt    840
tatgaagcag ttttaggaaa aaccaaaagc aaattaggag cagaggaaat tgccgctata    900
tgggaaacag aagaaagcat gaaaaaacta gcccagtact caatggaaga tgctagggca    960
acgtatgagc tcgggaagga attcttcccc atggaagctg agctggcaaa gctgatagt    1020 caaagtgtat gggacgtctc gagatcaagc accggcaacc tcgtggagtg gtatctttta    1080
agggtggcat acgcgaggaa tgaacttgca ccgaacaaac ctgatgagga agagtataaa    1140
cggcgcttaa gaacaactta cctggggagga tatgtaaaag agccagaaaa aggtttgtgg    1200
gaaaatatca tttatttgga tttccgcagt ctgtaccctt caataatagt tactcacaac    1260
gtatccccag atacccttga aaagagggc tgtaagaatt acgatgttgc tccgatagta    1320
ggatataggt tctgcaagga cttccgggc tttattccct ccatactcgg ggacttaatt    1380
gcaatgaggc aagatataaa gaagaaaatg aaatccacaa ttgacccgat cgaaaagaaa    1440
atgctcgatt ataggcaaag ggctattaaa ttgcttgcaa acagctatta cggctatatg    1500
```

```
gggtatccta aggcaagatg gtactcgaag gaatgtgctg aaagcgttac cgcatggggg      1560
agacactaca tagagatgac gataagagaa atagaggaaa agttcggctt taaggttctt      1620
tatgcggacn nngacggctt ttatgccaca atacccgggg aaaagcctga actcattaaa      1680
aagaaagcca aggaattcct aaactacata aactccaaac ttccaggtct gcttgagctt      1740
gagtatgagg ctttttactt gagaggattc tttgttacaa aaaagcgcta tgcagtcata      1800
gatgaagagg gcaggataac aacaaggggc ttggaagtag taaggagaga ttggagtgag      1860
atagctaagg agactcaggc aaaggtttta gaggctatac ttaaagaggg aagtgttgaa      1920
aaagctgtag aagttgttag agatgttgta gagaaaatag caaaatacag ggttccactt      1980
gaaaagcttg ttatccatga gcagattacc agggatttaa aggactacaa agccattggc      2040
cctcatgtcg cgatagcaaa aagacttgcc gcaagaggga taaaagtgaa accgggcaca      2100
ataataagct atatcgttct caagggagc ggaaagataa gcgatagggt aattttactt       2160
acagaatacg atcctagaaa acacaagtac gatccggact actacataga aaaccaagtt      2220
ttgccggcag tacttaggat actcgaagcg tttggataca gaaggagga tttaaggtat       2280 caaagctcaa aacaaaccgg cttagatgca tggctcaaga ggtag                      2325
```

<210> SEQ ID NO 111
<211> LENGTH: 2325
<212> TYPE: DNA
<213> ORGANISM: Thermococcus litoralis
<220> FEATURE:
<221> NAME/KEY: misc_feature
<222> LOCATION: (1633)..(1635)
<223> OTHER INFORMATION: Ns at positions 1633-1635 may be any
      nucleotides so that the codon at 1633-1635 encodes for Gly.

<400> SEQUENCE: 111

```
atgatactgg acactgatta cataacaaaa gatggcaagc ctataatccg aattttaag        60 aaagagaacg gggagtttaa aatagaactt gaccctcatt ttcagcccta tatatatgct      120
cttctcaaag atgactccgc tattgaggag ataaaggcaa taaagggcga gagacatgga      180
aaaactgtga gagtgctcga tgcagtgaaa gtcaggaaaa aatttttggg aagggaagtt      240
gaagtctgga agctcatttt cgagcatccc caagacgttc cagctatgcg gggcaaaata      300
agggaacatc cagctgtggt tgacatttac gaatatgaca tacccttgc caagcgttat       360 ctcatagaca agggcttgat tcccatggag ggagacgagg agcttaagct ccttgccttt      420
gatattgaaa cgttttatca tgagggagat gaatttggaa agggcgagat aataatgatt      480
agttatgccg atgaagaaga ggccagagta atcacatgga aaaatatcga tttgccgtat      540
gtcgatgttg tgtccaatga aagagaaatg ataaagcgtt tgttcaagt tgttaaagaa       600 aaagaccccg atgtgataat aacttacaat ggggacaatt ttgatttgcc gtatctcata      660
aaacgggcag aaaagctggg agttcggctt gtcttaggaa gggacaaaga acatcccgaa      720
cccaagattc agaggatggg tgatagtttt gctgtggaaa tcaagggtag aatccacttt      780
gatcttttcc cagttgtgcg aaggacgata aacctcccaa cgtatacgct tgaggcagtt      840
tatgaagcag tttaggaaa aaccaaaagc aaattaggag cagaggaaat tgccgctata      900
tgggaaacag aagaaagcat gaaaaaacta gcccagtact caatgaaaga tgctagggca      960
acgtatgagc tcgggaagga attcttcccc atggaagctg agctggcaaa gctgataggt      1020
caaagtgtat gggacgtctc gagatcaagc accggcaacc tcgtggagtg gtatcttta     1080 agggtggcat acgcgaggaa tgaacttgca ccgaacaaac ctgatgagga agagtataaa      1140
```

```
cggcgcttaa gaacaactta cctgggagga tatgtaaaag agccagaaaa aggtttgtgg    1200
gaaaatatca tttatttgga tttccgcagt ctgtacccct caataatagt tactcacaac    1260
gtatccccag ataccttgaa aaagagggc tgtaagaatt acgatgttgc tccgatagta    1320
ggatataggt tctgcaagga ctttccgggc tttattccct ccatactcgg ggacttaatt    1380
gcaatgaggc aagatataaa gaagaaaatg aaatccacaa ttgacccgat cgaaaagaaa    1440
atgctcgatt ataggcaaag ggctattaaa ttgcttgcaa acagctatta cggctatatg    1500
gggtatccta aggcaagatg gtactcgaag gaatgtgctg aaagcgttac cgcatggggg    1560
agacactaca tagagatgac gataagagaa atagaggaaa agttcggctt taaggttctt    1620
tatgcggaca ctnnnggctt ttatgccaca atacccgggg aaaagcctga actcattaaa    1680
aagaaagcca aggaattcct aaactacata aactccaaac ttccaggtct gcttgagctt    1740
gagtatgagg ctttttactt gagaggattc tttgttacaa aaagcgcta tgcagtcata    1800 gatgaagagg gcaggataac aacagggggc ttggaagtag taaggagaga ttggagtgag    1860
atagctaagg agactcaggc aaaggtttta gaggctatac ttaaagaggg aagtgttgaa    1920
aaagctgtag aagttgttag agatgttgta gagaaaatag caaaatacag ggttccactt    1980
gaaaagcttg ttatccatga gcagattacc agggatttaa aggactacaa agccattggc    2040
cctcatgtcg cgatagcaaa aagacttgcc gcaagaggga taaagtgaa accgggcaca    2100 ataataagct atatcgttct caagggagc ggaaagataa gcgatagggt aatttactt    2160 acagaatacg atcctagaaa acacaagtac gatccggact actacataga aaaccaagtt    2220
ttgccggcag tacttaggat actcgaagcg tttggataca gaaaggagga tttaaggtat    2280
caaagctcaa acaaaccgg cttagatgca tggctcaaga ggtag                    2325
```

<210> SEQ ID NO 112
<211> LENGTH: 2325
<212> TYPE: DNA
<213> ORGANISM: Thermococcus litoralis
<220> FEATURE:
<221> NAME/KEY: misc_feature
<222> LOCATION: (1783)..(1785)
<223> OTHER INFORMATION: Ns at positions 1783-1785 may be any
      nucleotides so that the codon at 1783-1785 encodes for Thr.

<400> SEQUENCE: 112

```
atgatactgg acactgatta cataacaaaa gatggcaagc ctataatccg aattttaag     60 aaagagaacg gggagtttaa atagaacctt gaccctcatt ttcagcccta tatatatgct    120
cttctcaaag atgactccgc tattgaggag ataaaggcaa taagggcga gagacatgga    180 aaaactgtga gagtgctcga tgcagtgaaa gtcaggaaaa aattttttggg aagggaagtt    240 gaagtctgga agctcatttt cgagcatccc caagacgttc cagctatgcg gggcaaaata    300
agggaacatc cagctgtggt tgacatttac gaatatgaca tacccttgc caagcgttat    360 ctcatagaca agggcttgat tcccatggag ggagacgagg agcttaagct ccttgccttt    420
gatattgaaa cgtttttatca tgagggagat gaatttggaa agggcgagat aataatgatt    480
agttatgccg atgaagaaga ggccagagta atcacatgga aaaatatcga tttgccgtat    540
gtcgatgttg tgtccaatga aagagaaatg ataaagcgtt tgttcaagt tgttaaagaa    600 aaagaccccg atgtgataat aacttacaat ggggacaatt ttgatttgcc gtatctcata    660
aaacgggcag aaaagctggg agttcggctt gtcttaggaa gggacaaaga acatcccgaa    720
cccaagattc agaggatggg tgatagtttt gctgtggaaa tcaagggtag aatccacttt    780 gatctttcc cagttgtgcg aaggacgata aacctcccaa cgtatacgct tgaggcagtt    840
```

```
tatgaagcag tttaggaaa aaccaaaagc aaattaggag cagaggaaat tgccgctata      900
tgggaaacag aagaaagcat gaaaaaacta gcccagtact caatggaaga tgctagggca     960
acgtatgagc tcgggaagga attcttcccc atggaagctg agctggcaaa gctgataggt    1020
caaagtgtat gggacgtctc gagatcaagc accggcaacc tcgtggagtg gtatcttta    1080 agggtggcat acgcgaggaa tgaacttgca ccgaacaaac ctgatgagga agagtataaa   1140
cggcgcttaa gaacaactta cctgggagga tatgtaaaag agccagaaaa aggtttgtgg   1200
gaaaatatca tttatttgga tttccgcagt ctgtacccctt caataatagt tactcacaac  1260
gtatccccag ataccttga aaaagagggc tgtaagaatt acgatgttgc tccgatagta    1320
ggatataggt tctgcaagga ctttccgggc tttattccct ccatactcgg ggacttaatt   1380
gcaatgaggc aagatataaa gaagaaaatg aaatccacaa ttgacccgat cgaaaagaaa   1440
atgctcgatt ataggcaaag ggctattaaa ttgcttgcaa acagctatta cggctatatg   1500
gggtatccta aggcaagatg gtactcgaag gaatgtgctg aaagcgttac cgcatggggg   1560
agacactaca tagagatgac gataagagaa atagaggaaa agttcggctt taaggttctt   1620
tatgcggaca ctgacggctt ttatgccaca ataccggggg aaaagcctga actcattaaa   1680
aagaaagcca aggaattcct aaactacata aactccaaac ttccaggtct gcttgagctt   1740
gagtatgagg cttttactt gagaggattc tttgttacaa aannncgcta tgcagtcata    1800
gatgaagagg gcaggataac aacaaggggc ttggaagtag taaggagaga ttggagtgag  1860
atagctaagg agactcaggc aaaggtttta gaggctatac ttaaagaggg aagtgttgaa   1920
aaagctgtag aagttgttag agatgttgta gagaaaatag caaaatacag ggttccactt   1980
gaaaagcttg ttatccatga gcagattacc agggatttaa aggactacaa agccattggc   2040
cctcatgtcg cgatagcaaa aagacttgcc gcaagaggga taaaagtgaa accgggcaca   2100
ataataagct atatcgttct caaagggagc ggaaagataa gcgataggt aattttactt   2160 acagaatacg atcctagaaa acacaagtac gatccggact actacataga aaaccaagtt   2220
ttgccggcag tacttaggat actcgaagcg tttggataca gaaaggagga tttaaggtat   2280
caaagctcaa acaaaccgg cttagatgca tggctcaaga ggtag                    2325
```

<210> SEQ ID NO 113
<211> LENGTH: 775
<212> TYPE: PRT
<213> ORGANISM: Pyrococcus sp.

<400> SEQUENCE: 113

```
Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110
```

```
Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
                180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
                420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540
```

-continued

| | | | | | | | | | | | | | | | |
|---|---|---|---|---|---|---|---|---|---|---|---|---|---|---|---|
|Leu|Tyr|Ala|Thr|Ile|Pro|Gly|Ala|Lys|Pro|Glu|Glu|Ile|Lys|Lys| |
|545| | | |550| | | |555| | | |560| | | |

| | | | | | | | | | | | |
|---|---|---|---|---|---|---|---|---|---|---|---|
|Ala|Leu|Glu|Phe|Val|Asp|Tyr|Ile|Asn|Ala|Lys|Leu Pro Gly Leu Leu|
| | | | |565| | | |570| | |575|

Glu Leu Glu Tyr Glu Gly Phe Tyr Val Arg Gly Phe Val Thr Lys
    580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
    675                 680                 685

Ala Arg Gly Val Lys Val Arg Pro Gly Met Val Ile Gly Tyr Ile Val
690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
    755                 760                 765

Trp Leu Asn Ile Lys Lys Lys
770                 775

<210> SEQ ID NO 114
<211> LENGTH: 2328
<212> TYPE: DNA
<213> ORGANISM: Pyrococcus sp.
<220> FEATURE:
<221> NAME/KEY: misc_feature
<222> LOCATION: (1153)..(1155)
<223> OTHER INFORMATION: Ns at positions 1153-1155 may be any
      nucleotides so that the codon at 1153-1155 encodes for Asn, Leu,
      His, Gln, or Ser.

<400> SEQUENCE: 114

```
atgatacttg acgctgacta catcaccgag gatgggaagc cgattataag gattttcaag      60
aaagaaaacg gcgagtttaa ggttgagtac gacagaaact ttagacctta catttacgct     120
ctcctcaaag atgactcgca gattgatgag gttaggaaga taaccgccga gaggcatggg     180
aagatagtga gaattataga tgccgaaaag gtaaggaaga agttcctggg gaggccgatt     240
gaggtatgga ggctgtactt tgaacaccct caggacgttc ccgcaataag ggataagata     300
agagagcatt ccgcagttat tgacatcttt gagtacgaca ttccgttcgc gaagaggtac     360
ctaatagaca aaggcctaat tccaatggaa ggcgatgaag agctcaagtt gctcgcattt     420
gacatagaaa ccctctatca cgaaggggag gagttcgcga agggccccat tataatgata     480
agctatgctg atgaggaaga agccaaagtc ataacgtgga aaaagatcga tctcccgtac     540
gtcgaggtag tttccagcga gagggagatg ataaagcggt tcctcaaggt gataagggag     600
```

-continued

```
aaagatcccg atgttataat tacctacaac ggcgattctt tcgaccttcc ctatctagtt    660
aagagggccg aaaagctcgg gataaagcta cccctgggaa gggacggtag tgagccaaag    720
atgcagaggc ttggggatat gacagcggtg gagataaagg gaaggataca ctttgacctc    780
taccacgtga ttaggagaac gataaacctc ccaacataca ccctcgaggc agtttatgag    840
gcaatcttcg gaaagccaaa ggagaaagtt tacgctcacg agatagctga ggcctgggag    900
actggaaagg gactggagag agttgcaaag tattcaatgg aggatgcaaa ggtaacgtac    960
gagctcggta gggagttctt cccaatggag gcccagcttt caaggttagt cggccagccc   1020
ctgtgggatg tttctaggtc ttcaactggc aacttggtgg agtggtacct cctcaggaag   1080
gcctacgaga ggaatgaatt ggctccaaac aagccggatg agagggagta cgagagaagg   1140
ctaagggaga gcnnngctgg gggatacgtt aaggagccgg agaaagggct ctgggagggg   1200 ttagttccc tagatttcag gagcctgtac ccctcgataa taatcaccca taacgtctca   1260
ccggatacgc tgaacaggga agggtgtagg gaatacgatg tcgccccaga ggttgggcac   1320
aagttctgca aggacttccc ggggtttatc cccagcctgc tcaagaggtt attggatgaa   1380
aggcaagaaa taaaaggaa gatgaaagct tctaaagacc caatcgagaa gaagatgctt   1440
gattacaggc aacgggcaat caaaatcctg gcaaacagct attatgggta ttatgggtac   1500
gcaaaagccc gttggtactg taaggagtgc gcagagagcg ttacggcctg ggggagggaa   1560
tatatagagt tcgtaaggaa ggaactggag gaaaagttcg ggttcaaagt cttatacata   1620
gacacagatg gactctacgc cacaattcct ggggcaaaac ccgaggagat aaagaagaaa   1680
gccctagagt tcgtagatta tataaacgcc aagctcccag ggctgttgga gcttgagtac   1740
gagggcttct acgtgagagg gttcttcgtg acgaagaaga agtatgcgtt gatagatgag   1800
gaagggaaga taatcactag ggggcttgaa atagtcagga gggactggag cgaaatagcc   1860
aaagaaaccc aagcaaaagt cctagaggct atcctaaagc atggcaacgt tgaggaggca   1920
gtaaagatag ttaaggaggt aactgaaaag ctgagcaagt acgaaatacc tccagaaaag   1980
ctagttattt acgagcagat cacgaggccc cttcacgagt acaaggctat aggtccgcac   2040
gttgccgtgg caaaaaggtt agccgctaga ggagtaaagg tgaggcctgg catggtgata   2100
gggtacatag tgctgagggg agacgggcca ataagcaaga gggctatcct tgcagaggag   2160
ttcgatctca ggaagcataa gtatgacgct gagtattaca tagaaaatca ggttttacct   2220
gccgttctta gaatattaga ggcctttggg tacaggaaag aagacctcag gtggcagaag   2280
actaaacaga caggtcttac ggcatggctt aacatcaaga agaagtaa             2328
```

<210> SEQ ID NO 115
<211> LENGTH: 2328
<212> TYPE: DNA
<213> ORGANISM: Pyrococcus sp.
<220> FEATURE:
<221> NAME/KEY: misc_feature
<222> LOCATION: (1159)..(1161)
<223> OTHER INFORMATION: Ns at positions 1159-1161 may be any
      nucleotides so that the codon at 1159-1161 encodes for Ser or Pro.

<400> SEQUENCE: 115

```
atgatacttg acgctgacta catcaccgag gatgggaagc cgattataag gattttcaag     60
aaagaaaacg gcgagtttaa ggttgagtac gacagaaact ttagaccctta catttacgct    120 ctcctcaaag atgactcgca gattgatgag gttaggaaga taaccgccga gaggcatggg    180
aagatagtga gaattataga tgccgaaaag gtaaggaaga agttcctggg gaggccgatt    240
gaggtatgga ggctgtactt tgaacaccct caggacgttc ccgcaataag ggataagata    300
```

```
agagagcatt ccgcagttat tgacatcttt gagtacgaca ttccgttcgc gaagaggtac    360
ctaatagaca aaggcctaat tccaatggaa ggcgatgaag agctcaagtt gctcgcattt    420
gacatagaaa ccctctatca cgaaggggag gagttcgcga aggggcccat tataatgata    480
agctatgctg atgaggaaga agccaaagtc ataacgtgga aaaagatcga tctcccgtac    540
gtcgaggtag tttccagcga gagggagatg ataaagcggt tcctcaaggt gataagggag    600
aaagatcccg atgttataat tacctacaac ggcgattctt cgaccttcc ctatctagtt     660 aagagggccg aaaagctcgg gataaagcta cccctgggaa gggacggtag tgagccaaag    720
atgcagaggc ttggggatat gacagcggtg gagataaagg gaaggataca ctttgacctc    780
taccacgtga ttaggagaac gataaacctc ccaacataca ccctcgaggc agtttatgag    840
gcaatcttcg gaaagccaaa ggagaaagtt tacgctcacg atagctgag gcctgggag     900 actggaaagg gactggagag agttgcaaag tattcaatgg aggatgcaaa ggtaacgtac    960
gagctcggta gggagttctt cccaatggag gcccagcttt caaggttagt cggccagccc   1020
ctgtgggatg tttctaggtc ttcaactggc aacttggtgg agtggtacct cctcaggaag   1080
gcctacgaga ggaatgaatt ggctccaaac aagccggatg agagggagta cgagagaagg   1140
ctaagggaga gctacgctnn nggatacgtt aaggagccgg agaaagggct ctgggagggg   1200
ttagtttccc tagatttcag gagcctgtac ccctcgataa taatcaccca taacgtctca   1260
ccggatacgc tgaacaggga agggtgtagg gaatacgatg tcgccccaga ggttgggcac   1320
aagttctgca aggacttccc ggggtttatc cccagcctgc tcaagaggtt attggatgaa   1380
aggcaagaaa taaaaggaa gatgaaagct tctaaagacc caatcgagaa gaagatgctt    1440
gattacaggc aacgggcaat caaaatcctg gcaaacagct attatgggta ttatgggtac   1500
gcaaaagccc gttggtactg taaggagtgc gcagagagcg ttacggcctg ggggagggaa   1560
tatatagagt tcgtaaggaa ggaactggag gaaaagttcg ggttcaaagt cttatacata   1620
gacacagatg gactctacgc cacaattcct ggggcaaaac ccgaggagat aaagaagaaa   1680
gccctagagt tcgtagatta tataaacgcc aagctcccag gctgttgga gcttgagtac    1740 gagggcttct acgtgagagg gttcttcgtg acgaagaaga agtatgcgtt gatagatgag   1800
gaagggaaga taatcactag ggggcttgaa atagtcagga gggactggag cgaaatagcc   1860
aaagaaaccc aagcaaaagt cctagaggct atcctaaagc atggcaacgt tgaggaggca   1920
gtaaagatag ttaaggaggt aactgaaaag ctgagcaagt acgaaatacc tccagaaaag   1980
ctagttattt acgagcagat cacgaggccc cttcacgagt acaaggctat aggtccgcac   2040
gttgccgtgg caaaaaggtt agccgctaga ggagtaaagg tgaggcctgg catggtgata   2100
gggtacatag tgctgagggg agacgggcca ataagcaaga gggctatcct tgcagaggag   2160
ttcgatctca ggaagcataa gtatgacgct gagtattaca tagaaaatca ggttttacct   2220
gccgttctta gaatattaga ggcctttggg tacaggaaag aagacctcag gtggcagaag   2280
actaaacaga caggtcttac ggcatggctt aacatcaaga agaagtaa                2328
```

<210> SEQ ID NO 116
<211> LENGTH: 2328
<212> TYPE: DNA
<213> ORGANISM: Pyrococcus sp.
<220> FEATURE:
<221> NAME/KEY: misc_feature
<222> LOCATION: (1162)..(1164)
<223> OTHER INFORMATION: Ns at positions 1162-1164 may be any
      nucleotides so that the codon at 1162-1164 encodes for Ala or Pro.

```
<400> SEQUENCE: 116
atgatacttg acgctgacta catcaccgag gatgggaagc cgattataag gattttcaag      60
aaagaaaacg gcgagtttaa ggttgagtac gacagaaact ttagacctta catttacgct     120
ctcctcaaag atgactcgca gattgatgag gttaggaaga taaccgccga gaggcatggg     180
aagatagtga gaattataga tgccgaaaag gtaaggaaga agttcctggg gaggccgatt     240
gaggtatgga ggctgtactt tgaacaccct caggacgttc ccgcaataag ggataagata     300
agagagcatt ccgcagttat tgacatcttt gagtacgaca ttccgttcgc gaagaggtac     360
ctaatagaca aaggcctaat tccaatggaa ggcgatgaag agctcaagtt gctcgcattt     420
gacatagaaa ccctctatca cgaaggggag gagttcgcga aggggcccat tataatgata     480
agctatgctg atgaggaaga agccaaagtc ataacgtgga aaaagatcga tctcccgtac     540
gtcgaggtag tttccagcga gagggagatg ataaagcggt tcctcaaggt gataagggag     600
aaagatcccg atgttataat tacctacaac ggcgattctt tcgaccttcc ctatctagtt     660
aagagggccg aaaagctcgg gataaagcta cccctgggaa gggacggtag tgagccaaag     720
atgcagaggc ttggggatat gacagcggtg gagataaagg gaaggataca ctttgacctc     780
taccacgtga ttaggagaac gataaacctc ccaacataca ccctcgaggc agtttatgag     840
gcaatcttcg gaaagccaaa ggagaaagtt tacgctcacg agatagctga ggcctgggag     900
actgaaaagg gactggagag agttgcaaag tattcaatgg aggatgcaaa ggtaacgtac     960
gagctcggta gggagttctt cccaatggag gcccagcttt caaggttagt cggccagccc    1020
ctgtgggatg tttctaggtc ttcaactggc aacttggtgg agtggtacct cctcaggaag    1080
gcctacgaga ggaatgaatt ggctccaaac aagccggatg agagggagta cgagagaagg    1140
ctaagggaga gctacgctgg gnnntacgtt aaggagccgg agaaagggct ctgggagggg    1200
ttagtttccc tagatttcag gagcctgtac ccctcgataa taatcaccca taacgtctca    1260
ccggatacgc tgaacaggga agggtgtagg gaatacgatg tcgccccaga ggttgggcac    1320
aagttctgca aggacttccc ggggtttatc cccagcctgc tcaagaggtt attggatgaa    1380
aggcaagaaa taaaaggaa gatgaaagct tctaaagacc caatcgagaa gaagatgctt    1440
gattacaggc aacgggcaat caaaatcctg gcaaacagct attatgggta ttatgggtac    1500
gcaaaagccc gttggtactg taaggagtgc gcagagagcg ttacggcctg ggggagggaa    1560
tatatagagt tcgtaaggaa ggaactggag gaaaagttcg ggttcaaagt cttatacata    1620
gacacagatg gactctacgc cacaattcct ggggcaaaac ccgaggagat aaagaagaaa    1680
gccctagagt tcgtagatta tataaacgcc aagctcccag ggctgttgga gcttgagtac    1740
gagggcttct acgtgagagg gttcttcgtg acgaagaaga agtatgcgtt gatagatgag    1800
gaagggaaga taatcactag ggggcttgaa atagtcagga gggactggag cgaaatagcc    1860
aaagaaaccc aagcaaaagt cctagaggct atcctaaagc atggcaacgt tgaggaggca    1920
gtaaagatag ttaaggaggt aactgaaaag ctgagcaagt acgaaatacc tccagaaaag    1980
ctagttattt acgagcagat cacgaggccc cttcacgagt acaaggctat aggtccgcac    2040
gttgccgtgg caaaaaggtt agccgctaga ggagtaaagg tgaggcctgg catggtgata    2100
gggtacatag tgctgagggg agacgggcca ataagcaaga gggctatcct tgcagaggag    2160
ttcgatctca ggaagcataa gtatgacgct gagtattaca tagaaaatca ggttttacct    2220
gccgttctta gaatattaga ggcctttggg tacaggaaag aagacctcag gtggcagaag    2280
actaaacaga caggtcttac ggcatggctt aacatcaaga agaagtaa               2328
```

<210> SEQ ID NO 117
<211> LENGTH: 2328
<212> TYPE: DNA
<213> ORGANISM: Pyrococcus sp.
<220> FEATURE:
<221> NAME/KEY: misc_feature
<222> LOCATION: (1213)..(1215)
<223> OTHER INFORMATION: Ns at positions 1213-1215 may be any
      nucleotides so that the codon at 1213-1215 encodes for Glu.

<400> SEQUENCE: 117

```
atgatacttg acgctgacta catcaccgag gatgggaagc cgattataag gattttcaag     60
aaagaaaacg gcgagtttaa ggttgagtac gacagaaact ttagaccttta catttacgct    120
ctcctcaaag atgactcgca gattgatgag gttaggaaga taaccgccga gaggcatggg    180
aagatagtga gaattataga tgccgaaaag gtaaggaaga agttcctggg gaggccgatt    240
gaggtatgga ggctgtactt tgaacaccct caggacgttc ccgcaataag ggataagata    300
agagagcatt ccgcagttat tgacatcttt gagtacgaca ttccgttcgc gaagaggtac    360
ctaatagaca aaggcctaat tccaatggaa ggcgatgaag agctcaagtt gctcgcattt    420
gacatagaaa ccctctatca cgaaggggag gagttcgcga aggggcccat tataatgata    480
agctatgctg atgaggaaga agccaaagtc ataacgtgga aaaagatcga tctcccgtac    540
gtcgaggtag tttccagcga gagggagatg ataaagcggt tcctcaaggt gataagggag    600
aaagatcccg atgttataat tacctacaac ggcgattctt tcgaccttcc ctatctagtt    660
aagagggccg aaaagctcgg gataaagcta cccctgggaa gggacggtag tgagccaaag    720
atgcagaggc ttggggatat gacagcggtg gagataaagg gaaggataca ctttgacctc    780
taccacgtga ttaggagaac gataaacctc caacataca ccctcgaggc agtttatgag     840
gcaatcttcg gaaagccaaa ggagaaagtt tacgctcacg agatagctga ggcctgggag    900
actggaaagg gactggagag agttgcaaag tattcaatgg aggatgcaaa ggtaacgtac    960
gagctcggta gggagttctt cccaatggag gcccagcttt caaggttagt cggccagccc   1020
ctgtgggatt tttctaggtc ttcaactggc aacttggtgg agtggtacct cctcaggaag   1080
gcctacgaga ggaatgaatt ggctccaaac aagccggatg agagggagta cgagagaagg   1140
ctaagggaga gctacgctgg gggatacgtt aaggagccgg agaaagggct ctgggagggg   1200
ttagtttccc tannnttcag gagcctgtac ccctcgataa taatcaccca taacgtctca   1260
ccggatacgc tgaacaggga agggtgtagg gaatacgatg tcgccccaga ggttgggcac   1320
aagttctgca aggacttccc gggtgtttatc cccagcctgc tcaagaggtt attggatgaa   1380
aggcaagaaa taaaaaggaa gatgaaagct tctaaagacc caatcgagaa gaagatgctt   1440
gattacaggc aacgggcaat caaaatcctg gcaaacagct attatgggta ttatgggtac   1500
gcaaaagccc gttggtactg taaggagtgc gcagagagcg ttacggcctg ggggagggaa   1560
tatatagagt tcgtaaggaa ggaactggag gaaaagttcg ggttcaaagt cttatacata   1620
gacacagatg gactctacgc cacaattcct ggggcaaaac ccgaggagat aaagaagaaa   1680
gccctagagt tcgtagatta tataaacgcc aagctcccag gctgttggga gcttgagtac   1740
gagggcttct acgtgagagg gttcttcgtg acgaagaaga gtatgcgtt gatagatgag    1800
gaagggaaga taatcactag ggggcttgaa atagtcagga gggactggag cgaaatagcc    1860
aaagaaccc aagcaaaagt cctagaggct atcctaaagc atggcaacgt tgaggaggca    1920
gtaaagatag ttaaggaggt aactgaaaag ctgagcaagt acgaaatacc tccagaaaag    1980
ctagttattt acgagcagat cacgaggccc cttcacgagt acaaggctat aggtccgcac   2040
```

```
gttgccgtgg caaaaaggtt agccgctaga ggagtaaagg tgaggcctgg catggtgata   2100
gggtacatag tgctgagggg agacgggcca ataagcaaga gggctatcct tgcagaggag   2160
ttcgatctca ggaagcataa gtatgacgct gagtattaca tagaaaatca ggttttacct   2220
gccgttctta gaatattaga ggcctttggg tacaggaaag aagacctcag gtggcagaag   2280
actaaacaga caggtcttac ggcatggctt aacatcaaga agaagtaa              2328
```

<210> SEQ ID NO 118
<211> LENGTH: 2328
<212> TYPE: DNA
<213> ORGANISM: Pyrococcus sp.
<220> FEATURE:
<221> NAME/KEY: misc_feature
<222> LOCATION: (1624)..(1626)
<223> OTHER INFORMATION: Ns at positions 1624-1626 may be any
       nucleotides so that the codon at 1624-1626 encodes for Pro.

<400> SEQUENCE: 118

```
atgatacttg acgctgacta catcaccgag gatgggaagc cgattataag gattttcaag     60
aaagaaaacg gcgagtttaa ggttgagtac gacagaaact ttagacctta catttacgct    120
ctcctcaaag atgactcgca gattgatgag gttaggaaga taaccgccga gaggcatggg    180
aagatagtga gaattataga tgccgaaaag gtaaggaaga agttcctggg gaggccgatt    240
gaggtatgga ggctgtactt tgaacaccct caggacgttc cgcaataag ggataagata     300 agagagcatt ccgcagttat tgacatcttt gagtacgaca ttccgttcgc gaagaggtac    360
ctaatagaca aaggcctaat tccaatggaa ggcgatgaag agctcaagtt gctcgcattt    420
gacatagaaa ccctctatca cgaagggag gagttcgcga aggggcccat tataatgata    480
agctatgctg atgaggaaga agccaaagtc ataacgtgga aaaagatcga tctcccgtac   540
gtcgaggtag tttccagcga gagggagatg ataaagcggt tcctcaaggt gataagggag    600
aaagatcccg atgttataat tacctacaac ggcgattctt tcgaccttcc ctatctagtt    660
aagagggccg aaaagctcgg ataaagcta cccctgggaa gggacggtag tgagccaaag     720
atgcagaggc ttggggatat gacagcgtg gagataaagg gaaggataca ctttgacctc    780
taccacgtga ttaggagaac gataaacctc ccaacataca ccctcgaggc agtttatgag    840
gcaatcttcg gaaagccaaa ggagaaagtt tacgctcacg atagctgaa ggcctgggag    900 actggaaagg gactggagag agttgcaaag tattcaatgg aggatgcaaa ggtaacgtac    960
gagctcggta gggagttctt cccaatggag gcccagcttt caaggttagt cggccagccc   1020
ctgtgggatg tttctaggtc ttcaactggc aacttggtgg agtggtacct cctcaggaag   1080
gcctacgaga ggaatgaatt ggctccaaac aagccggatg agagggagta cgagagaagg   1140
ctaagggaga gctacgctgg gggatacgtt aaggagccgg agaagggct ctgggagggg     1200 ttagtttccc tagatttcag gagcctgtac ccctcgataa taatcaccca taacgtctca   1260
ccggatacgc tgaacaggga agggtgtagg gaatacgatg tcgccccaga ggttgggcac   1320
aagttctgca aggacttccc ggggtttatc cccagcctgc tcaagaggtt attggatgaa   1380
aggcaagaaa taaaaggaa gatgaaagct tctaaagacc caatcgagaa gaagatgctt   1440
gattacaggc aacgggcaat caaaatcctg gcaaacagct attatgggta ttatgggtac   1500
gcaaaagccc gttggtactg taaggagtgc gcagagagcg ttacggcctg ggggagggaa   1560
tatatagagt tcgtaaggaa ggaactggag gaaaagttcg ggttcaaagt cttatacata   1620
gacnnngatg gactctacgc cacaattcct ggggcaaaac ccgaggagat aaagaagaaa   1680
```

```
gccctagagt tcgtagatta tataaacgcc aagctcccag ggctgttgga gcttgagtac    1740
gagggcttct acgtgagagg gttcttcgtg acgaagaaga agtatgcgtt gatagatgag    1800
gaagggaaga taatcactag ggggcttgaa atagtcagga gggactggag cgaaatagcc    1860
aaagaaaccc aagcaaaagt cctagaggct atcctaaagc atggcaacgt tgaggaggca    1920
gtaaagatag ttaaggaggt aactgaaaag ctgagcaagt acgaaatacc tccagaaaag    1980
ctagttattt acgagcagat cacgaggccc cttcacgagt acaaggctat aggtccgcac    2040
gttgccgtgg caaaaaggtt agccgctaga ggagtaaagg tgaggcctgg catggtgata    2100
gggtacatag tgctgagggg agacgggcca ataagcaaga gggctatcct tgcagaggag    2160
ttcgatctca ggaagcataa gtatgacgct gagtattaca tagaaaatca ggttttacct    2220
gccgttctta gaatattaga ggcctttggg tacaggaaaa aagacctcag gtggcagaag    2280
actaaacaga caggtcttac ggcatggctt aacatcaaga agaagtaa                 2328
```

```
<210> SEQ ID NO 119
<211> LENGTH: 2328
<212> TYPE: DNA
<213> ORGANISM: Pyrococcus sp.
<220> FEATURE:
<221> NAME/KEY: misc_feature
<222> LOCATION: (1627)..(1629)
<223> OTHER INFORMATION: Ns at positions 1627-1629 may be any
      nucleotides so that the codon at 1627-1629 encodes for Gly.

<400> SEQUENCE: 119
```

```
atgatacttg acgctgacta catcaccgag gatgggaagc cgattataag gattttcaag      60
aaagaaaacg gcgagtttaa ggttgagtac gacagaaact ttagacctta catttacgct     120
ctcctcaaag atgactcgca gattgatgag gttaggaaga taaccgccga gaggcatggg     180
aagatagtga gaattataga tgccgaaaag gtaaggaaga agttcctggg gaggccgatt     240
gaggtatgga ggctgtactt tgaacaccct caggacgttc ccgcaataag ggataagata     300
agagagcatt ccgcagttat tgacatcttt gagtacgaca ttccgttcgc gaagaggtac     360
ctaatagaca aaggcctaat tccaatggaa ggcgatgaag agctcaagtt gctcgcattt     420
gacatagaaa ccctctatca cgaaggggag gagttcgcga aggggcccat tataatgata     480
agctatgctg atgaggaaga agccaaagtc ataacgtgga aaaagatcga tctcccgtac     540
gtcgaggtag tttccagcga gagggagatg ataaagcggt tcctcaaggt gataagggag     600
aaagatcccg atgttataat tacctacaac ggcgattctt tcgaccttcc ctatctagtt     660
aagagggccg aaaagctcgg gataaagcta ccctgggaa gggacggtag tgagccaaag     720
atgcagaggc ttggggatat gacagcggtg gagataaagg gaaggataca ctttgacctc     780
taccacgtga ttaggagaac gataaacctc ccaacataca ccctcgaggc agtttatgag     840
gcaatcttcg gaaagccaaa ggagaaagtt tacgctcacg agatagctga ggcctgggag     900
actggaaagg gactggagag agttgcaaag tattcaatgg aggatgcaaa ggtaacgtac     960
gagctcggta gggagttctt cccaatggag gcccagcttt caaggttagt cggccagccc    1020
ctgtgggatg tttctaggtc ttcaactggc aacttggtgg agtggtacct cctcaggaag    1080
gcctacgaga ggaatgaatt ggctccaaac aagccggatg agggagta cgagagaagg     1140 ctaagggaga gctacgctgg gggatacgtt aaggagccgg agaaagggct ctgggagggg    1200 ttagttttccc tagatttcag gagcctgtac ccctcgataa taatcaccca taacgtctca    1260
ccggatacgc tgaacaggga agggtgtagg gaatacgatg tcgccccaga ggttgggcac    1320
aagttctgca aggacttccc ggggtttatc cccagcctgc tcaagaggtt attggatgaa    1380
```

```
aggcaagaaa taaaaaggaa gatgaaagct tctaaagacc caatcgagaa gaagatgctt      1440
gattacaggc aacgggcaat caaaatcctg gcaaacagct attatgggta ttatgggtac      1500
gcaaaagccc gttggtactg taaggagtgc gcagagagcg ttacggcctg ggggagggaa      1560
tatatagagt tcgtaaggaa ggaactggag gaaaagttcg ggttcaaagt cttatacata      1620
gacacannng gactctacgc cacaattcct ggggcaaaac ccgaggagat aaagaagaaa      1680
gccctagagt tcgtagatta tataaacgcc aagctcccag ggctgttgga gcttgagtac      1740
gagggcttct acgtgagagg gttcttcgtg acgaagaaga agtatgcgtt gatagatgag      1800
gaagggaaga taatcactag ggggcttgaa atagtcagga gggactggag cgaaatagcc      1860
aaagaaaccc aagcaaaagt cctagaggct atcctaaagc atggcaacgt tgaggaggca      1920
gtaaagatag ttaaggaggt aactgaaaag ctgagcaagt acgaaatacc tccagaaaag      1980
ctagttattt acgagcagat cacgaggccc cttcacgagt acaaggctat aggtccgcac      2040
gttgccgtgg caaaaaggtt agccgctaga ggagtaaagg tgaggcctgg catggtgata      2100
gggtacatag tgctgagggg agacgggcca ataagcaaga gggctatcct tgcagaggag      2160
ttcgatctca ggaagcataa gtatgacgct gagtattaca tagaaaatca ggttttacct      2220
gccgttctta gaatattaga ggcctttggg tacaggaaag aagacctcag gtggcagaag      2280
actaaacaga caggtcttac ggcatggctt aacatcaaga gaagtaa                   2328
```

<210> SEQ ID NO 120
<211> LENGTH: 2328
<212> TYPE: DNA
<213> ORGANISM: Pyrococcus sp.
<220> FEATURE:
<221> NAME/KEY: misc_feature
<222> LOCATION: (1777)..(1779)
<223> OTHER INFORMATION: Ns at positions 1777-1779 may be any
       nucleotides so that the codon at 1777-1779 encodes for Thr.

<400> SEQUENCE: 120

```
atgatacttg acgctgacta catcaccgag gatgggaagc cgattataag gattttcaag        60
aaagaaaacg gcgagtttaa ggttgagtac gacagaaact ttagaccctta catttacgct      120 ctcctcaaag atgactcgca gattgatgag gttaggaaga taaccgccga gaggcatggg      180
aagatagtga gaattataga tgccgaaaag gtaaggaaga agttcctggg gaggccgatt      240
gaggtatgga ggctgtactt tgaacaccct caggacgttc ccgcaataag ggataagata      300
agagagcatt ccgcagttat tgacatcttt gagtacgaca ttccgttcgc gaagaggtac      360
ctaatagaca aaggcctaat tccaatggaa ggcgatgaag agctcaagtt gctcgcattt      420
gacatagaaa ccctctatca cgaaggggag gagttcgcga aggggcccat tataatgata      480
agctatgctg atgaggaaga agccaaagtc ataacgtgga aaaagatcga tctcccgtac      540
gtcgaggtag tttccagcga gagggagatg ataaagcggt tcctcaaggt gataagggag      600
aaagatcccg atgttataat tacctacaac ggcgattctt tcgaccttcc ctatctagtt      660
aagagggccg aaaagctcgg gataaagcta cccctgggaa gggacggtag tgagccaaag      720
atgcagaggc ttggggatat gacagcggtg gagataaagg gaaggataca ctttgacctc      780
taccacgtga ttaggagaac gataaaccct ccaacataca ccctcgaggc agtttatgag      840
gcaatcttcg gaaagccaaa ggagaaagtt tacgctcacg agatagctga ggcctgggag      900
actggaaagg gactggagag agttgcaaag tattcaatgg aggatgcaaa ggtaacgtac      960
gagctcggta gggagttctt cccaatggag gcccagcttt caaggttagt cggccagccc     1020
```

```
ctgtgggatg tttctaggtc ttcaactggc aacttggtgg agtggtacct cctcaggaag    1080
gcctacgaga ggaatgaatt ggctccaaac aagccggatg agagggagta cgagagaagg    1140
ctaagggaga gctacgctgg gggatacgtt aaggagccgg agaaagggct ctgggagggg    1200
ttagtttccc tagatttcag gagcctgtac ccctcgataa taatcaccca taacgtctca    1260
ccggatacgc tgaacaggga agggtgtagg gaatacgatg tcgccccaga ggttgggcac    1320
aagttctgca aggacttccc ggggtttatc cccagcctgc tcaagaggtt attggatgaa    1380
aggcaagaaa taaaaggaa gatgaaagct tctaaagacc caatcgagaa aagatgcttt    1440
gattacaggc aacgggcaat caaaatcctg caaacagct attatgggta ttatgggtac    1500
gcaaaagccc gttggtactg taaggagtgc gcagagagcg ttacggcctg ggggagggaa    1560
tatatagagt tcgtaaggaa ggaactggag gaaaagttcg ggttcaaagt cttatacata    1620
gacacagatg gactctacgc cacaattcct ggggcaaaac ccgaggagat aaagaagaaa    1680
gccctagagt tcgtagatta tataaacgcc aagctcccag gctgttgga gcttgagtac    1740 gagggcttct acgtgagagg gttcttcgtg acgaagnnna agtatgcgtt gatagatgag    1800
gaagggaaga taatcactag ggggcttgaa atagtcagga gggactggag cgaaatagcc    1860
aaagaaaccc aagcaaaagt cctagaggct atcctaaagc atggcaacgt tgaggaggca    1920
gtaaagatag ttaaggaggt aactgaaaag ctgagcaagt acgaaatacc tccagaaaag    1980
ctagttattt acgagcagat cacgaggccc cttcacgagt acaaggctat aggtccgcac    2040
gttgccgtgg caaaaaggtt agccgctaga ggagtaaagg tgaggcctgg catggtgata    2100
gggtacatag tgctgagggg agacgggcca ataagcaaga gggctatcct tgcagaggag    2160
ttcgatctca ggaagcataa gtatgacgct gagtattaca tagaaaatca ggttttacct    2220
gccgttctta gaatattaga ggcctttggg tacaggaaag aagacctcag gtggcagaag    2280
actaaacaga caggtcttac ggcatggctt aacatcaaga agaagtaa                2328
```

<210> SEQ ID NO 121
<211> LENGTH: 2322
<212> TYPE: DNA
<213> ORGANISM: Thermococcus gorgonarius
<220> FEATURE:
<221> NAME/KEY: misc_feature
<222> LOCATION: (1150)..(1152)
<223> OTHER INFORMATION: Ns at positions 1150-1152 may be any
      nucleotides so that the codon at 1150-1152 encodes for Asn, Leu,
      His, Gln, or Ser.

<400> SEQUENCE: 121

```
atgatcctcg atacagacta cataactgag gatggaaagc ccgtcatcag gatcttcaag      60
aaggagaacg gcgagttcac catagactac gacagaaact tgagccata catctacgcg     120 ctcttgaagg acgactctcc gattgaggac gtcaagaaga taactgccga gaggcacggc     180
actaccgtta gggttgtcag ggccgagaaa gtgaagaaga agttcctagg caggccgata     240
gaggtctgga agctctactt cactcacccc caggacgttc ccgcaatcag ggacaagata     300
aaggagcatc ctgccgttgt ggacatctac gagtacgaca tccccttcgc gaagcgctac     360
ctcatagaca aaggcttaat cccgatggag ggcgacgagg aacttaagat gctcgccttc     420
gacatcgaga cgctctatca cgagggcgag gagttcgccg aagggcctat cctgatgata     480
agctacgccg acgaggaagg ggcgcgcgtt attacctgga gaatatcga ccttccctat     540 gtcgacgtca tttccaccga gaaggagatg ataaagcgct tcctcaaggt cgtcaaggaa     600
aaggatcccg acgtcctcat aatctacaac ggcgacaact tcgacttcgc ctacctcaag     660
```

```
aagcgctccg agaagctcgg agtcaagttc atcctcggaa gggaagggag cgaaccgaaa      720
atccagcgca tgggcgatcg ctttgcggtg gaggtcaagg gaaggattca cttcgacctc      780
taccccgtca ttaggagaac gattaacctc cccacttaca cccttgaggc agtatatgaa      840
gccatctttg gacagccgaa ggagaaggtc tacgctgagg agatagcgca ggcctgggaa      900
acgggcgagg gattagaaag ggtggcccgc tactcgatgg aggacgcgaa ggtaacctat      960
gaactcggaa aagagttctt ccctatggaa gcccagctct cgcgcctcgt aggccagagc     1020
ctctgggatg tatctcgctc gagtaccgga aacctcgtcg agtggttttt gctgaggaag     1080
gcctacgaga ggaatgaact tgcaccaaac aagccggacg agagggagct ggcaagaaga     1140
agggagagcn nngcgggtgg atacgtcaag gagcccgaaa ggggactgtg ggagaacatc     1200
gtgtatctgg acttccgctc cctgtatcct tcgataataa tcacccataa cgtctcccct     1260
gatacactca acagggaggg ttgtgaggag tacgacgtgg ctcctcaggt aggccataag     1320
ttctgcaagg acttccccgg cttcatccca agcctcctcg gagacctctt ggaggagaga     1380
cagaaggtaa agaagaagat gaaggccact atagacccaa tcgagaagaa actcctcgat     1440
tacaggcaac gagcaatcaa aatccttgct aatagcttct acggttacta cggctataca     1500
aaggcccgct ggtactacaa ggagtgcgcc gagagcgtta ccggttgggg cagggagtac     1560
atcgagacca cgataaggga aatagaggag aaatttggct ttaaagtcct ctacgcggac     1620
acagatggat ttttcgcaac aatacctgga gcggacgccg aaaccgtcaa aaagaaggca     1680
aaggagttcc tggactacat caacgccaaa ctgcccggcc tgctcgaact cgaatacgag     1740
ggcttctaca gcgcggctt cttcgtgacg aagaagaagt acgcggttat agacgaggag     1800
gacaagataa cgacgcgcgg gcttgaaata gttaggcgtg actggagcga gatagcgaag     1860
gagacgcagg cgagggttct tgaggcgata ctaaagcacg gtgacgttga agaagcggta     1920
aggattgtca aagaggttac ggagaagctg agcaagtacg aggttccacc ggagaagctg     1980
gtcatctacg agcagataac ccgcgacctg aaggactaca aggccaccgg gccgcatgtg     2040
gctgttgcaa aacgcctcgc cgcaaggggg ataaaaatcc ggcccggaac ggtcataagc     2100
tacatcgtgc tcaaaggctc ggggaaggatt ggggacaggg ctataccctt tgacgaattt     2160
gacccggcaa agcacaagta cgatgcagaa tactacatcg agaaccaggt tcttccagct     2220
gtggagagga ttctgagggc ctttggttac cgtaaagaag attttaaggta tcagaaaacg     2280 cggcaggttg gcttgggggc gtggctaaaa cctaagacat ga                        2322
```

<210> SEQ ID NO 122
<211> LENGTH: 2322
<212> TYPE: DNA
<213> ORGANISM: Thermococcus gorgonarius
<220> FEATURE:
<221> NAME/KEY: misc_feature
<222> LOCATION: (1156)..(1158)
<223> OTHER INFORMATION: Ns at positions 1156-1158 may be any
      nucleotides so that codon at 1156-1158 encodes for Ser or Pro.

<400> SEQUENCE: 122

```
atgatcctcg atacagacta cataactgag gatggaaagc ccgtcatcag gatcttcaag       60
aaggagaacg gcgagttcac catagactac gacagaaact ttgagccata catctacgcg      120
ctcttgaagg acgactctcc gattgaggac gtcaagaaga taactgccga gaggcacggc      180
actaccgtta gggttgtcag ggccgagaaa gtgaagaaga agttcctagg caggccgata      240
gaggtctgga agctctactt cactcacccc caggacgttc ccgcaatcag ggacaagata      300
aaggagcatc ctgccgttgt ggacatctac gagtacgaca tccccttcgc gaagcgctac      360
```

```
ctcatagaca aaggcttaat cccgatggag ggcgacgagg aacttaagat gctcgccttc      420
gacatcgaga cgctctatca cgagggcgag gagttcgccg aagggcctat cctgatgata      480
agctacgccg acgaggaagg ggcgcgcgtt attacctgga agaatatcga ccttccctat      540
gtcgacgtcg tttccaccga aaggagatg ataaagcgct tcctcaaggt cgtcaaggaa       600
aaggatcccg acgtcctcat aatctacaac ggcgacaact tcgacttcgc ctacctcaag      660
aagcgctccg agaagctcgg agtcaagttc atcctcggaa gggaagggag cgaaccgaaa      720
atccagcgca tgggcgatcg ctttgcggtg gaggtcaagg gaaggattca cttcgacctc      780
taccccgtca ttaggagaac gattaacctc cccacttaca cccttgaggc agtatatgaa      840
gccatctttg gacagccgaa ggagaaggtc tacgctgagg atagcgcca ggcctgggaa       900 acgggcgagg gattagaaag ggtggcccgc tactcgatgg aggacgcgaa ggtaacctat      960
gaactcggaa aagagttctt ccctatggaa gcccagctct cgcgcctcgt aggccagagc     1020
ctctgggatg tatctcgctc gagtaccgga aacctcgtcg agtggttttt gctgaggaag     1080
gcctacgaga ggaatgaact tgcaccaaac aagccggacg agagggagct ggcaagaaga     1140
agggagagct acgcgnnngg atacgtcaag gagcccgaaa ggggactgtg ggagaacatc     1200
gtgtatctgg acttccgctc cctgtatcct tcgataataa tcacccataa cgtctcccct     1260
gatacactca acagggaggg ttgtgaggag tacgacgtgg ctcctcaggt aggccataag     1320
ttctgcaagg acttccccgg cttcatccca agcctcctcg agacctcttc ggaggagaga     1380
cagaaggtaa agaagaagat gaaggccact atagacccaa tcgagaagaa actcctcgat     1440
tacaggcaac gagcaatcaa aatccttgct aatagcttct acggttacta cggctataca     1500
aaggcccgct ggtactacaa ggagtgcgcc gagagcgtta ccggttgggg cagggagtac     1560
atcgagacca cgataaggga aatagaggag aaatttggct ttaaagtcct ctacgcggac     1620
acagatggat ttttcgcaac aatacctgga gcggacgccg aaaccgtcaa aaagaaggca     1680
aaggagttcc tggactacat caacgccaaa ctgcccggcc tgctcgaact cgaatacgag     1740
ggcttctaca gcgcggctt cttcgtgacg aagaagaagt acgcggttat agacgaggag     1800
gacaagataa cgacgcgcgg gcttgaaata gttaggcgtg actggagcga gatagcgaag     1860
gagacgcagg cgagggttct tgaggcgata ctaaagcacg gtgacgttga agaagcggta     1920
aggattgtca aagaggttac ggagaagctg agcaagtacg aggttccacc ggagaagctg     1980
gtcatctacg agcagataac ccgcgacctg aaggactaca aggccaccgg gccgcatgtg     2040
gctgttgcaa aacgcctcgc cgcaaggggg ataaaaatcc ggcccggaac ggtcataagc     2100
tacatcgtgc tcaaaggctc gggaaggatt ggggacaggg ctatacccct tgacgaattt     2160
gacccggcaa agcacaagta cgatgcagaa tactacatcg agaaccaggt tcttccagct     2220
gtggagagga ttctgagggc cttgggttac cgtaaagaag atttaaggta tcagaaaacg     2280
cggcaggttg gcttgggggc gtggctaaaa cctaagacat ga                        2322
```

<210> SEQ ID NO 123
<211> LENGTH: 2322
<212> TYPE: DNA
<213> ORGANISM: Thermococcus gorgonarius
<220> FEATURE:
<221> NAME/KEY: misc_feature
<222> LOCATION: (1159)..(1161)
<223> OTHER INFORMATION: Ns at positions 1159-1161 may be any
      nucleotides so that the codon at 1159-1161 encodes for Ala or Pro.

<400> SEQUENCE: 123

```
atgatcctcg atacagacta cataactgag gatggaaagc ccgtcatcag gatcttcaag    60
aaggagaacg gcgagttcac catagactac gacagaaact tgagccata  catctacgcg   120
ctcttgaagg acgactctcc gattgaggac gtcaagaaga taactgccga gaggcacggc   180
actaccgtta gggttgtcag ggccgagaaa gtgaagaaga agttcctagg caggccgata   240
gaggtctgga agctctactt cactcacccc caggacgttc ccgcaatcag ggacaagata   300
aaggagcatc ctgccgttgt ggacatctac gagtacgaca tccccttcgc gaagcgctac   360
ctcatagaca aaggcttaat cccgatggag ggcgacgagg aacttaagat gctcgccttc   420
gacatcgaga cgctctatca cgagggcgag gagttcgccg aagggcctat cctgatgata   480
agctacgccg acgaggaagg ggcgcgcgtt attacctgga agaatatcga ccttccctat   540
gtcgacgtcc tttccaccga gaaggagatg ataaagcgct tcctcaaggt cgtcaaggaa   600
aaggatcccg acgtcctcat aatctacaac ggcgacaact tcgacttcgc ctacctcaag   660
aagcgctccg agaagctcgg agtcaagttc atcctcggaa gggaagggag cgaaccgaaa   720
atccagcgca tgggcgatcg cttttgcggtg gaggtcaagg gaaggattca cttcgacctc   780
taccccgtca ttaggagaac gattaacctc cccacttaca cccttgaggc agtatatgaa   840
gccatctttg gacagccgaa ggagaaggtc tacgctgagg agatagcgca ggcctgggaa   900
acgggcgagg gattagaaag ggtggcccgc tactcgatgg aggacgcgaa ggtaacctat   960
gaactcggaa aagagttctt ccctatggaa gcccagctct cgcgcctcgt aggccagagc  1020
ctctgggatg tatctcgctc gagtaccgga aacctcgtcg agtggttttt gctgaggaag  1080
gcctacgaga ggaatgaact tgcaccaaac aagccggacg agagggagct ggcaagaaga  1140
agggagagct acgcgggtnn ntacgtcaag gagcccgaaa gggactgtg  ggagaacatc  1200
gtgtatctgg acttccgctc cctgtatcct tcgataataa tcacccataa cgtctcccct  1260
gatacactca cagggaggg  ttgtgaggag tacgacgtgg ctcctcaggt aggccataag  1320
ttctgcaagg acttccccgg cttcatccca agcctcctcg gagacctctt ggaggagaga  1380
cagaaggtaa agaagaagat gaaggccact atagacccaa tcgagaagaa actcctcgat  1440
tacaggcaac gagcaatcaa aatccttgct aatagcttct acggttacta cggctataca  1500
aaggcccgct ggtactacaa ggagtgcgcc gagagcgtta ccggttgggg cagggagtac  1560
atcgagacca cgataaggga aatagaggag aaatttggct ttaaagtcct ctacgcggac  1620
acagatggat ttttcgcaac aatacctgga gcggacgccg aaaccgtcaa aaagaaggca  1680
aaggagttcc tggactacat caacgccaaa ctgcccggcc tgctcgaact cgaatacgag  1740
ggcttctaca gcgcggctt  cttcgtgacg aagaagaagt acgcggttat agacgaggag  1800
gacaagataa cgacgcgcgg gcttgaaata gttaggcgtg actggagcga gatagcgaag  1860
gagacgcagg cgagggttct tgaggcgata ctaaagcacg gtgacgttga agaagcggta  1920
aggattgtca agaggttac  ggagaagctg agcaagtacg aggttccacc ggagaagctg  1980
gtcatctacg agcagataac ccgcgacctg aaggactaca aggccaccgg gccgcatgtg  2040
gctgttgcaa acgcctcgc  cgcaaggggg ataaaaatcc ggcccggaac ggtcataagc  2100
tacatcgtgc tcaaaggctc gggaaggatt ggggacaggg ctataccctt tgacgaattt  2160
gacccggcaa agcacaagta cgatgcgaaa tactacatcg agaaccaggt tcttccagct  2220
gtggagagga ttctgagggc cttttggttac cgtaaagaag atttaaggta tcagaaaacg  2280
cggcaggttg gcttgggggc gtggctaaaa cctaagacat ga                      2322
```

<210> SEQ ID NO 124

-continued

```
<211> LENGTH: 2322
<212> TYPE: DNA
<213> ORGANISM: Thermococcus gorgonarius
<220> FEATURE:
<221> NAME/KEY: misc_feature
<222> LOCATION: (1210)..(1212)
<223> OTHER INFORMATION: Ns at positions 1210-1212 may be any
      nucleotides so that the codon at 1210-1212 encodes for Glu.

<400> SEQUENCE: 124
atgatcctcg atacagacta cataactgag gatggaaagc ccgtcatcag gatcttcaag      60
aaggagaacg gcgagttcac catagactac gacagaaact ttgagccata catctacgcg     120
ctcttgaagg acgactctcc gattgaggac gtcaagaaga taactgccga gaggcacggc     180
actaccgtta gggttgtcag ggccgagaaa gtgaagaaga agttcctagg caggccgata     240
gaggtctgga agctctactt cactcacccc caggacgttc ccgcaatcag ggacaagata     300
aaggagcatc ctgccgttgt ggacatctac gagtacgaca tcccccttcgc gaagcgctac     360 ctcatagaca aaggcttaat cccgatggag ggcgacgagg aacttaagat gctcgccttc     420
gacatcgaga cgctctatca cgagggcgag gagttcgccg aagggcctat cctgatgata     480
agctacgccg acgaggaagg ggcgcgcgtt attacctgga gaatatcga ccttccctat      540 gtcgacgtcg tttccaccga gaaggagatg ataaagcgct tcctcaaggt cgtcaaggaa     600
aaggatcccg acgtcctcat aatctacaac ggcgacaact tcgacttcgc ctacctcaag     660
aagcgctccg agaagctcgg agtcaagttc atcctcggaa gggaagggag cgaaccgaaa     720
atccagcgca tgggcgatcg ctttgcggtg gaggtcaagg gaaggattca cttcgacctc     780
taccccgtca ttaggagaac gattaacctc cccacttaca cccttgaggc agtatatgaa     840
gccatctttg gacagccgaa ggagaaggtc tacgctgagg agatagcgca ggcctgggaa     900
acgggcgagg gattagaaag ggtggcccgc tactcgatgg aggacgcgaa ggtaacctat     960
gaactcggaa aagagttctt ccctatggaa gcccagctct cgcgcctcgt aggccagagc    1020
ctctgggatg tatctcgctc gagtaccgga aacctcgtcg agtggttttt gctgaggaag    1080
gcctacgaga ggaatgaact tgcaccaaac aagccggacg agagggagct ggcaagaaga    1140
agggagagct acgcgggtgg atacgtcaag gagcccgaaa ggggactgtg ggagaacatc    1200
gtgtatctgn nnttccgctc cctgtatcct tcgataataa tcacccataa cgtctcccct    1260
gatacactca acagggaggg ttgtgaggag tacgacgtgg ctcctcaggt aggccataag    1320
ttctgcaagg acttccccgg cttcatccca agcctcctcg agacctcctt ggaggagaga    1380
cagaaggtaa agaagaagat gaaggccact atagacccaa tcgagaagaa actcctcgat    1440
tacaggcaac gagcaatcaa aatccttgct aatagcttct acggttacta cggctataca    1500
aaggcccgct ggtactacaa ggagtgcgcc gagagcgtta ccggttgggg cagggagtac    1560
atcgagacca cgataaggga aatagaggag aaatttggct ttaaagtcct ctacgcggac    1620
acagatggat ttttcgcaac aatacctgga gcggacgccg aaaccgtcaa aaagaaggca    1680
aaggagttcc tggactacat caacgccaaa ctgcccggcc tgctcgaact cgaatacgag    1740
ggcttctaca gcgcggctt cttcgtgacg aagaagaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga agaagcgta    1920 aggattgtca agagggttac ggagaagctg agcaagtacg aggttccacc ggagaagctg    1980
gtcatctacg agcagataac ccgcgacctg aaggactaca aggccaccgg gccgcatgtg    2040
gctgttgcaa aacgcctcgc cgcaagggggg ataaaaatcc ggcccggaac ggtcataagc    2100
```

```
tacatcgtgc tcaaaggctc gggaaggatt ggggacaggg ctatacccctt tgacgaatttt    2160 gacccggcaa agcacaagta cgatgcagaa tactacatcg agaaccaggt tcttccagct    2220
gtggagagga ttctgagggc ctttggttac cgtaaagaag atttaaggta tcagaaaacg    2280
cggcaggttg gcttgggggc gtggctaaaa cctaagacat ga                      2322

<210> SEQ ID NO 125
<211> LENGTH: 2322
<212> TYPE: DNA
<213> ORGANISM: Thermococcus gorgonarius
<220> FEATURE:
<221> NAME/KEY: misc_feature
<222> LOCATION: (1621)..(1623)
<223> OTHER INFORMATION: Ns at positions 1621-1623 may be any
      nucleotides so that the codon at 1621-1623 encodes for Pro.

<400> SEQUENCE: 125
atgatcctcg atacagacta cataactgag gatggaaagc ccgtcatcag gatcttcaag      60
aaggagaacg gcgagttcac catagactac gacagaaact ttgagccata catctacgcg    120
ctcttgaagg acgactctcc gattgaggac gtcaagaaga taactgccga gaggcacggc    180
actaccgtta ggggttgtcag ggccgagaaa gtgaagaaga agttcctagg caggccgata    240
gaggtctgga agctctactt cactcacccc caggacgttc ccgcaatcag ggacaagata    300
aaggagcatc ctgccgttgt ggacatctac gagtacgaca tcccccttcgc gaagcgctac    360 ctcatagaca aaggcttaat cccgatggag ggcgacgagg aacttaagat gctcgccttc    420
gacatcgaga cgctctatca cgagggcgag gagttcgccg aagggcctat cctgatgata    480
agctacgccg acgaggaagg ggcgcgcgtt attacctgga gaatatcga ccttccctat    540 gtcgacgtcg tttccaccga gaaggagatg ataaagcgct tcctcaaggt cgtcaaggaa    600
aaggatcccg acgtcctcat aatctacaac ggcgacaact tcgacttcgc ctacctcaag    660
aagcgctccg agaagctcgg agtcaagttc atcctcggaa gggaagggag cgaaccgaaa    720
atccagcgca tgggcgatcg cttttcgggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcgaa ggtaacctat    960
gaactcggaa agagttctt cccctatggaa gcccagctct cgcgcctcgt aggccagagc    1020
ctctgggatg tatctcgctc gagtaccgga aacctcgtcg agtggttttt gctgaggaag    1080
gcctacgaga ggaatgaact tgcaccaaac aagccggacg agagggagct ggcaagaaga    1140
agggagagct acgcgggtgg atacgtcaag gagcccgaaa ggggactgtg ggagaacatc    1200
gtgtatctgg acttccgctc cctgtatcct tcgataataa tcacccataa cgtctcccct    1260
gatacactca acaggagggg ttgtgaggag tacgacgtgg ctcctcaggt aggccataag    1320
ttctgcaagg acttccccgg cttcatccca agcctcctcg agacctctt ggaggagaga    1380 cagaaggtaa agaagaagat gaaggccact atagacccaa tcgagaagaa actcctcgat    1440
tacaggcaac gagcaatcaa aatccttgct aatagcttct acggttacta cggctataca    1500
aaggcccgct ggtactacaa ggagtgcgcc gagagcgtta ccggttgggg cagggagtac    1560
atcgagacca cgataaggga aatagaggag aaatttggct ttaaagtcct ctacgcggac    1620
nnngatggat ttttcgcaac aatacctgga gcggacgccg aaaccgtcaa aagaaggca    1680 aaggagttcc tggactacat caacgccaaa ctgcccggcc tgctcgaact cgaatacgag    1740
```

```
ggcttctaca agcgcggctt cttcgtgacg aagaagaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga agaagcggta    1920
aggattgtca aagaggttac ggagaagctg agcaagtacg aggttccacc ggagaagctg    1980
gtcatctacg agcagataac ccgcgacctg aaggactaca aggccaccgg gccgcatgtg    2040
gctgttgcaa acgcctcgc cgcaaggggg ataaaaatcc ggcccggaac ggtcataagc    2100
tacatcgtgc tcaaaggctc gggaaggatt ggggacaggg ctatacccct tgacgaattt    2160
gacccggcaa agcacaagta cgatgcagaa tactacatcg agaaccaggt tcttccagct    2220
gtggagagga ttctgagggc ctttggttac cgtaaagaag atttaaggta tcagaaaacg    2280
cggcaggttg gcttgggggc gtggctaaaa cctaagacat ga                       2322
```

<210> SEQ ID NO 126
<211> LENGTH: 2322
<212> TYPE: DNA
<213> ORGANISM: Thermococcus gorgonarius
<220> FEATURE:
<221> NAME/KEY: misc_feature
<222> LOCATION: (1624)..(1626)
<223> OTHER INFORMATION: Ns at positions 1624-1626 may be any
      nucleotides so that the codon at 1624-1626 encodes for Gly.

<400> SEQUENCE: 126

```
atgatcctcg atacagacta cataactgag gatggaaagc ccgtcatcag gatcttcaag     60
aaggagaacg gcgagttcac catagactac gacagaaact tgagccata catctacgcg    120 ctcttgaagg acgactctcc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggacgttc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gacatcgaga cgctctatca cgagggcgag gagttcgccg aagggcctat cctgatgata    480
agctacgccg acgaggaagg ggcgcgcgtt attacctgga agaatatcga ccttccctat    540
gtcgacgtca tttccaccga gaaggagatg ataaagcgct tcctcaaggt cgtcaaggaa    600
aaggatcccg acgtcctcat aatctacaac ggcgacaact tcgacttcgc ctacctcaag    660
aagcgctccg agaagctcgg agtcaagttc atcctcggaa gggaagggag cgaaccgaaa    720
atccagcgca tgggcgatcg ctttgcggtg gaggtcaagg gaaggattca cttcgacctc    780
tacccggtca ttaggagaac gattaacctc cccacttaca ccttgaggc agtatatgaa    840 gccatcttg acagccgaa ggagaaggtc tacgctgagg agatagcgca ggcctgggaa    900
acgggcgagg gattagaaag ggtggcccgc tactcgatgg aggacgcgaa ggtaacctat    960
gaactcggaa aagagttctt ccctatggaa gcccagctct cgcgcctcgt aggccagagc    1020
ctctgggatg tatctcgctc gagtaccgga aacctcgtcg agtggttttt gctgaggaag    1080
gcctacgaga ggaatgaact tgcaccaaac aagccggacg agagggagct ggcaagaaga    1140
agggagagct acgcgggtgg atacgtcaag gagcccgaaa ggggactgtg ggagaacatc    1200
gtgtatctgg acttccgctc cctgtatcct tcgataataa tcacccataa cgtctccct    1260 gatacactca acaggaggg ttgtgaggag tacgacgtgg ctcctcaggt aggccataag    1320
ttctgcaagg acttccccgg cttcatccca agcctcctcg gagacctctt ggaggagaga    1380
cagaaggtaa agaagaagat gaaggccact atagacccaa tcgagaagaa actcctcgat    1440
```

```
tacaggcaac gagcaatcaa aatccttgct aatagcttct acggttacta cggctataca      1500
aaggcccgct ggtactacaa ggagtgcgcc gagagcgtta ccggttgggg cagggagtac      1560
atcgagacca cgataaggga aatagaggag aaatttggct ttaaagtcct ctacgcggac      1620 acannggat ttttcgcaac aatacctgga gcggacgccg aaaccgtcaa aaagaaggca       1680
aaggagttcc tggactacat caacgccaaa ctgcccggcc tgctcgaact cgaatacgag      1740
ggcttctaca agcgcggctt cttcgtgacg aagaagaagt acgcggttat agacgaggag      1800
gacaagataa cgacgcgcgg gcttgaaata gttaggcgtg actggagcga gatagcgaag      1860
gagacgcagg cgagggttct tgaggcgata ctaaagcacg gtgacgttga agaagcggta      1920
aggattgtca aagaggttac ggagaagctg agcaagtacg aggttccacc ggagaagctg      1980
gtcatctacg agcagataac ccgcgacctg aaggactaca aggccaccgg ccgcatgtg       2040 gctgttgcaa aacgcctcgc cgcaaggggg ataaaaatcc ggcccggaac ggtcataagc      2100
tacatcgtgc tcaaaggctc gggaaggatt ggggacaggg ctatacccct tgacgaattt      2160
gacccggcaa agcacaagta cgatgcagaa tactacatcg agaaccaggt tcttccagct      2220
gtggagagga ttctgagggc cttttggttac cgtaaagaag atttaaggta tcagaaaacg      2280
cggcaggttg gcttgggggc gtggctaaaa cctaagacat ga                         2322
```

<210> SEQ ID NO 127
<211> LENGTH: 2322
<212> TYPE: DNA
<213> ORGANISM: Thermococcus gorgonarius
<220> FEATURE:
<221> NAME/KEY: misc_feature
<222> LOCATION: (1774)..(1776)
<223> OTHER INFORMATION: Ns at positions 1774-1776 may be any
      nucleotides so that the codon at 1774-1776 encodes for Thr.

<400> SEQUENCE: 127

```
atgatcctcg atacagacta cataactgag gatggaaagc ccgtcatcag gatcttcaag       60
aaggagaacg gcgagttcac catagactac gacagaaact ttgagccata catctacgcg      120
ctcttgaagg acgactctcc gattgaggac gtcaagaaga taactgccga gaggcacggc      180
actaccgtta gggttgtcag ggccgagaaa gtgaagaaga agttcctagg caggccgata      240
gaggtctgga agctctactt cactcacccc caggacgttc ccgcaatcag ggacaagata      300
aaggagcatc ctgccgttgt ggacatctac gagtacgaca tcccccttcgc gaagcgctac      360 ctcatagaca aaggcttaat cccgatggag ggcgacgagg aacttaagat gctcgccttc      420
gacatcgaga cgctctatca cgagggcgag gagttcgccg aagggcctat cctgatgata      480
agctacgccg acgaggaagg ggcgcgcgtt attacctgga agaatatcga ccttccctat      540
gtcgacgtcg tttccaccga gaaggagatg ataaagcgct tcctcaaggt cgtcaaggaa      600
aaggatcccg acgtcctcat aatctacaac ggcgacaact cgacttcgc ctacctcaag      660 aagcgctccg agaagctcgg agtcaagttc atcctcggaa gggaagggag cgaaccgaaa      720
atccagcgca tggcgatcg ctttgcggtg gaggtcaagg gaaggattca cttcgacctc      780
taccccgtca ttaggagaac gattaacctc cccacttaca cccttgaggc agtatatgaa      840
gccatctttg gacagccgaa ggagaaggtc tacgctgagg agatagcgca ggcctgggaa      900
acgggcgagg gattagaaag ggtggcccgc tactcgatgg aggacgcgaa ggtaacctat      960
gaactcggaa aagagttctt ccctatggaa gcccagctct cgcgcctcgt aggccagagc     1020
ctctgggatg tatctcgctc gagtaccgga aacctcgtcg agtggttttt gctgaggaag     1080
```

```
gcctacgaga ggaatgaact tgcaccaaac aagccggacg agagggagct ggcaagaaga    1140
agggagagct acgcgggtgg atacgtcaag gagcccgaaa ggggactgtg ggagaacatc    1200
gtgtatctgg acttccgctc cctgtatcct tcgataataa tcacccataa cgtctcccct    1260
gatacactca acagggaggg ttgtgaggag tacgacgtgg ctcctcaggt aggccataag    1320
ttctgcaagg acttccccgg cttcatccca agcctcctcg gagacctctt ggaggagaga    1380
cagaaggtaa agaagaagat gaaggccact atagacccaa tcgagaagaa actcctcgat    1440
tacaggcaac gagcaatcaa aatccttgct aatagcttct acggttacta cggctataca    1500
aaggcccgct ggtactacaa ggagtgcgcc gagagcgtta ccggttgggg cagggagtac    1560
atcgagacca cgataaggga aatagaggag aaatttggct ttaaagtcct ctacgcggac    1620
acagatggat ttttcgcaac aatacctgga gcggacgccg aaaccgtcaa aaagaaggca    1680
aaggagttcc tggactacat caacgccaaa ctgcccggcc tgctcgaact cgaatacgag    1740
ggcttctaca agcgcggctt cttcgtgacg aagnnnaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga agaagcggta    1920
aggattgtca aagaggttac ggagaagctg agcaagtacg aggttccacc ggagaagctg    1980
gtcatctacg agcagataac ccgcgacctg aaggactaca aggccaccgg ccgcatgtg    2040 gctgttgcaa aacgcctcgc cgcaaggggg ataaaaatcc ggcccggaac ggtcataagc    2100
tacatcgtgc tcaaaggctc gggaaggatt ggggacaggg ctatacccctt tgacgaattt    2160 gacccggcaa agcacaagta cgatgcagaa tactacatcg agaaccaggt tcttccagct    2220
gtggagagga ttctgagggc ctttggttac cgtaaagaag atttaaggta tcagaaaacg    2280
cggcaggttg gcttgggggc gtggctaaaa cctaagacat ga                      2322
```

<210> SEQ ID NO 128
<211> LENGTH: 3
<212> TYPE: PRT
<213> ORGANISM: Artificial Sequence
<220> FEATURE:
<223> OTHER INFORMATION: Consensus sequence
<220> FEATURE:
<221> NAME/KEY: DOMAIN
<222> LOCATION: (1)..(3)
<223> OTHER INFORMATION: Consensus sequence

<400> SEQUENCE: 128

Lys Lys Tyr
1

US 7,932,070 B2

HIGH FIDELITY DNA POLYMERASE COMPOSITIONS AND USES THEREFOR

This application is a continuation-in-part of U.S. patent application Ser. No. 10/208,508, filed Jul. 30, 2002, which is a continuation-in-part of U.S. patent application Ser. No. 10/079,241, filed Feb. 20, 2002, which is a continuation-in-part of U.S. patent application Ser. No. 10/035,091, filed Dec. 21, 2001.

FIELD OF THE INVENTION

The present invention is related to the field of high fidelity polynucleotide synthesis.

BACKGROUND OF THE INVENTION

DNA polymerases catalyze the synthesis of DNA and can be found in all cells as well as being encoded in numerous viruses. Although all DNA polymerases possess 5'-3' DNA polymerization activity, DNA polymerases differ from one another in numerous other properties. For example, some enzymatic activities that are possessed by some DNA polymerases, but absent in other DNA polymerases include: double stranded DNA 5'-3' exonuclease activity, single-stranded DNA 3'-5' exonuclease activity, double-stranded 3'-5' DNA exonuclease activity, RNase H activity, reverse transcriptase activity, and the like. Additionally, different DNA polymerases may have different optimal pH and temperature ranges for activity. Furthermore, DNA polymerases may differ in the rate in which they catalyze DNA synthesis.

Purified DNA polymerases have numerous uses in vitro. A detailed description of DNA polymerases, including methods for their isolation, can be found among other places, in DNA *Replication 2nd edition*, by Kornberg and Baker, W.H. Freeman & Company, New York, N.Y. 1991. In vitro uses of DNA polymerases include, for example, the labeling and synthesis of hybridization probes, DNA sequencing, and DNA amplification. A DNA amplification method employing DNA polymerases that has been particularly useful is the polymerase chain reaction (PCR) technique which employs the use of a thermostable DNA polymerase.

The first thermostable DNA polymerase that is widely used for DNA amplification is Taq DNA polymerase isolated from the thermostable, aerobic bacterium *Thermus aquaticus*. Taq DNA polymerase's enzymatic activity at high temperatures allows for primer extension and sequencing of polynucleotide templates with complex secondary structures (i.e., by PCR amplification). However, Taq DNA polymerase has significant error rate when incorporating nucleotides due to the lack of 3'-5' exonuclease activity (i.e., proofreading activity), and therefore may not be suitable if the amplified sequence is to be used in further gene structural/functional studies or cloning.

In the last 10 years, numerous studies have quantified the error rate of thermostable DNA polymerases, and several enzymes have been found to copy DNA more accurately than Taq DNA polymerase (referred to as high fidelity DNA polymerases). U.S. patent describing DNA polymerases include U.S. Pat. Nos. 4,492,130; 4,946,786; 5,210,036; 5,420,029; 5,489,523; 5,506,137; 5,545,552; 5,618,711; 5,624,833; 6,238,905; 6,100,078; 6,077,664; 5,968,799; 5,948,663; 5,885,713; 5,834,285; 5,756,334; 5,747,298; 5,744,312; 5,624,833; 5,602,011; 5,556,772.

High fidelity polymerases alone should definitely increase fidelity rates but usually do not amplify long fragments as efficient as a DNA polymerase lacking a 3'-5' exonuclease activity (e.g., Taq DNA polymerase). Enzyme mixtures that combine a standard polymerase with a small amount of proofreading polymerase may provide a balance between fidelity and yield. A study published in 1994 illustrated that the use of a high level of a DNA polymerase lacking 3'-5' exonuclease activity (an exo⁻ DNA polymerase, Klentaq-1) with a very low level of a thermostable DNA polymerase exhibiting 3'-5' exonuclease activity (an exo⁺ DNA polymerase such as Pfu, Vent, or Deep Vent) generated products with increased base-pair fidelity with a maximum yield of 35 kb DNA from 1 ng of lambda DNA template (Barnes, Proceedings of the National Academy of Sciences, 91:2216-20, 1994). Similarly, U.S. Pat. Nos. 5,436,149 and 6,008,025 disclosed methods for improving DNA amplification fidelity using a DNA polymerase composition comprising a first enzyme substantially lacking 3'-5' exonuclease activity and a second enzyme comprising 3'-5' exonuclease activity. In mixtures such as these, the exo⁺ enzyme acts to correct polymerization errors produced by the exo⁻ DNA polymerase.

The problem inherited in the above composition comprising the mix of two DNA polymerases is that the high polymerization activity resulted from combining the two DNA polymerases may inhibit the efficiency and therefore the yield of the amplification reaction. Therefore, one can not increase fidelity by increasing the proportion of the proofreading DNA polymerase without compromising PCR product yield. It is also known that the amplification fidelity may also be affected by high DNA polymerase concentration (see for example, Mattila et al., 1991, Polynucleotides Research, 19:4967-73).

There is therefore a need in the art for new methods and compositions which improve polymerization fidelity and reduce the side effects resulted from having high polymerization activity in the reaction.

SUMMARY OF THE INVENTION

The present invention provides an enzyme mixture comprising a first enzyme and a second enzyme, where the first enzyme comprises a DNA polymerization activity, and the second enzyme comprises a 3'-5' exonuclease activity and a reduced DNA polymerization activity.

The present invention also provides an enzyme mixture comprising a first enzyme and a second enzyme, where the first enzyme is a wild type Pfu DNA polymerase, the second enzyme is a mutant Pfu DNA polymerase comprising a 3'-5' exonuclease activity and a reduced DNA polymerization activity.

The present invention further provides an enzyme mixture comprising a first enzyme and a second enzyme, where the first enzyme is a Taq DNA polymerase, the second enzyme is a mutant Pfu DNA polymerase comprising a 3'-5' exonuclease activity and a reduced DNA polymerization activity.

The present invention also provides an enzyme mixture comprising a first enzyme and a second enzyme, where the first enzyme comprises a DNA polymerization activity and is a wild-type Pfu DNA polymerase or a wild-type Taq DNA polymerase, and the second enzyme is a mutant Pfu DNA polymerase comprising a 3'-5' exonuclease activity and a reduced DNA polymerization activity.

The present invention provides an enzyme mixture comprising two or more enzymes, where at least a first enzyme in the enzyme mixture comprises a DNA polymerization activity, and at least a second enzyme in the enzyme mixture comprises a 3'-5' exonuclease activity and a reduced DNA polymerization activity.

The present invention further provides a mutant Pfu DNA polymerase with reduced DNA polymerization activity, where the mutant Pfu DNA polymerase comprises one or more mutations at amino acid positions selected from the group consisting of: T542, D543, K593, Y595, Y385, G387, and G388.

The present invention still provides a composition comprising a mutant Pfu DNA polymerase, where the mutant DNA polymerase comprises one or more mutations at amino acid positions selected from the group consisting of: T542, D543, K593, Y595, Y385, G387, and G388.

The present invention provides a mutant Pfu DNA polymerase produced by introducing a mutation in to a polynucleotide encoding a wild type Pfu DNA polymerase to produce a mutant Pfu DNA polymerase comprising one or more mutations at amino acid positions selected from the group consisting of: T542, D543, K593, Y595, Y385, G387, and G388.

The present invention also provides a mutant Pfu DNA polymerase comprising a reduced DNA polymerization activity, where the mutant Pfu DNA polymerase is produced by the steps:
(a) providing a polynucleotide encoding a wild-type Pfu DNA polymerase;
(b) introducing one or more nucleotide mutations into the polynucleotide to produce a mutant polynucleotide encoding the mutant Pfu DNA polymerase; and
(c) expressing the mutant polynucleotide to produce the mutant Pfu DNA polymerase, where the mutant Pfu DNA polymerase comprises one or more mutations at amino acid positions selected from the group consisting of: T542, D543, K593, Y595, Y385, G387, and G388.

The present invention provides a composition comprising a mutant Pfu DNA polymerase produced by expressing a polynucleotide encoding a Pfu DNA polymerase with a reduced DNA polymerization activity, where the mutant Pfu DNA polymerase comprises one or more mutations at amino acid positions selected from the group consisting of: T542, D543, K593, Y595, Y385, G387, and G388.

The present invention also provides a composition comprising a mutant Pfu DNA polymerase comprising a reduced DNA polymerization activity, where the mutant Pfu DNA polymerase is produced by the steps: (a) introducing a mutation into a polynucleotide encoding a wild-type Pfu DNA polymerase to produce a mutant polynucleotide encoding the mutant Pfu DNA polymerase comprising one or more mutations at amino acid positions selected from the group consisting of: T542, D543, K593, Y595, Y385, G387, and G388; (b) expressing the mutant polynucleotide to produce the composition comprising the mutant Pfu DNA polymerase.

The present invention further provides a kit comprising a first enzyme and a second enzyme, where the first enzyme comprises a DNA polymerization activity, the second enzyme comprises a 3'-5' exonuclease activity and a reduced DNA polymerization activity, and packaging material therefore.

The present invention also provides a kit comprising a first enzyme and a second enzyme, and packaging material therefor, where the first enzyme is a wild type Pfu DNA polymerase, the second enzyme is a mutant Pfu DNA polymerase comprising a 3'-5' exonuclease activity and a reduced DNA polymerization activity.

The present invention further provides a kit comprising a first enzyme and a second enzyme, and packaging material therefore, where the first enzyme is a Taq DNA polymerase, and packaging material therefor, the second enzyme is a mutant Pfu DNA polymerase comprising a 3'-5' exonuclease activity and a reduced DNA polymerization activity.

The present invention provides a kit comprising an enzyme mixture which comprises a first enzyme and a second enzyme, where the first enzyme comprises a DNA polymerization activity and is a wild-type Pfu DNA polymerase or a wild-type Taq DNA polymerase, and the second enzyme is a mutant Pfu DNA polymerase comprising a 3'-5' exonuclease activity and a reduced DNA polymerization activity, and packaging means therefor.

The present invention also provides a kit comprising a mutant DNA polymerase which comprises a reduced DNA polymerization activity and packaging material therefor, where the mutant Pfu DNA polymerase comprises one or more mutations at amino acid positions selected from the group consisting of: T542, D543, K593, Y595, Y385, G387, and G388.

In one embodiment, the first enzyme of the present invention is a DNA polymerase or a reverse transcriptase.

Preferably, the DNA polymerase is selected from the group consisting of: Taq DNA polymerase, Tth DNA polymerase, UlTma DNA polymerase, Tli DNA polymerase, Pfu DNA polymerase, KOD DNA polymerase, JDF-3 DNA polymerase, PGB-D DNA polymerase and DP1/DP2 DNA polymerase.

In one embodiment of the present invention, the second enzyme is a mutant DNA polymerase.

Preferably, the mutant DNA polymerase is derived from a DNA polymerase different from the first enzyme.

More preferably, the mutant DNA polymerase is derived from a DNA polymerase selected from the group consisting of: UlTma DNA polymerase, Tli DNA polymerase, Pfu DNA polymerase, KOD DNA polymerase, JDF-3 DNA polymerase, PGB-D DNA polymerase and DP1/DP2 DNA polymerase.

Preferably, the mutant DNA polymerase comprises a mutation in its partitioning domain or the polymerase domain.

More preferably, the mutant Pfu DNA polymerase comprises one or more mutations at amino acid positions selected from the group consisting of: D405, Y410, T542, D543, K593, Y595, Y385, G387, and G388.

More preferably, the mutant Pfu DNA polymerase comprises one or more mutations selected from the group consisting of: D405E, Y410F, T542P, D543G, K593T, Y595S, Y385Q, Y385S, Y385N, Y385L, Y385H, G387S, G387P, and G388P.

In a preferred embodiment of the present invention, the mutant Pfu DNA polymerase comprises a mutation of G387P.

The enzyme mixture, composition, or kit of the present invention may further comprises a PCR enhancing factor and/or an additive.

Preferably, the enzyme mixture, composition, or kit comprising an enzyme mixture comprises a ratio of polymerization activity/exonuclease activity of (2.5-5U)/(0.02-5U).

More preferably, the enzyme mixture, composition, or kit comprising an enzyme mixture comprises a ratio of polymerization activity/exonuclease activity of (2.5U)/(0.04-0.08U).

In the enzyme mixture of the present invention, the first enzyme may be an enzyme of an enzyme blend, where the enzyme mixture is produced by mixing the enzyme blend with the second enzyme.

Preferably, the enzyme blend comprises a wild-type Pfu DNA polymerase and a wild-type Taq DNA polymerase.

Also preferably, the enzyme blend may further comprise a PCR enhancing factor.

The mutant Pfu DNA polymerase of the present invention may comprise one or more mutations selected from the group consisting of: T542P, D543G, K593T, Y595S, Y385Q, Y385S, Y385N, Y385L, Y385H, G387S, G387P, and G388P.

Preferably, the mutant Pfu DNA polymerase comprises one or more mutations selected from the group consisting of: T542P, D543G, K593T, Y595S, Y385Q, Y385S, Y385N, Y385L, Y385H, G387S, G387P, and G388P.

The present invention provides an isolated polynucleotide comprising a nucleotide sequence encoding a mutant enzyme comprises a 3'-5' exonuclease activity and a reduced DNA polymerization activity.

Preferably, the mutant enzyme comprising a 3'-5' exonuclease activity and a reduced DNA polymerization activity which is encoded by the isolated polynucleotide of the present invention is a mutant DNA polymerase or a mutant reverse transcriptase.

More preferably, the isolated polynucleotide encodes a mutant Pfu DNA polymerase.

More preferably, the isolated polynucleotide encodes a mutant Pfu DNA polymerase comprises one or more mutations at amino acid positions selected from the group consisting of: T542, D543, K593, Y595, Y385, G387, and G388.

More preferably, the isolated polynucleotide encodes a mutant Pfu DNA polymerase comprises one or more mutations selected from the group consisting of: Y410F, T542P, D543G, K593T, Y595S, Y385Q, Y385S, Y385N, Y385L, Y385H, G387S, G387P, and G388P.

The present invention provides a pair of isolated polynucleotides, where a first polynucleotide of the pair comprises a polynucleotide sequence encoding a first enzyme comprising a DNA polymerase activity, and a second polynucleotide of the pair comprises a polynucleotide sequence encoding an enzyme comprising a 3'-5' exonuclease activity and a reduced DNA polymerization activity.

The present invention also provides a pair of isolated polynucleotides, where a first polynucleotide of the pair comprises a polynucleotide sequence encoding a wild-type Pfu DNA polymerase or a Taq DNA polymerase, and a second polynucleotide of the pair comprises a polynucleotide sequence encoding an mutant Pfu DNA polymerase comprising a 3'-5' exonuclease activity and a reduced DNA polymerization activity.

Preferably, the second polynucleotide of the pair comprises a polynucleotide sequence encoding a mutant Pfu DNA polymerase which comprises one or more mutations at amino acid positions selected from the group consisting of: D405, Y410, T542, D543, K593, Y595, Y385, G387, and G388.

Also preferably, the second polynucleotide of the pair comprises a polynucleotide sequence encoding a mutant Pfu DNA polymerase which comprises one or more mutations selected from the group consisting of: D405E, Y410F, T542P, D543G, K593T, Y595S, Y385Q, Y385S, Y385N, Y385L, Y385H, G387S, G387P, and G388P.

The present invention provides a method for DNA synthesis comprising: (a) providing an enzyme mixture of the present invention, the enzyme mixture comprising a first enzyme comprising a DNA polymerization activity, and a second enzyme comprising a 3'-5' exonuclease activity and a reduced DNA polymerization activity; and (b) contacting the enzyme mixture with a nucleic acid template, where the enzyme mixture permits DNA synthesis.

Preferably, the nucleic acid template is a DNA or an RNA molecule.

The present invention provides a method for DNA synthesis comprising: (a) providing an enzyme mixture of the present invention, the enzyme mixture comprising a wild type Pfu DNA polymerase as a first enzyme, and a mutant Pfu DNA polymerase as a second enzyme which comprises a 3'-5' exonuclease activity and a reduced DNA polymerization activity; and (b) contacting the enzyme mixture with a nucleic acid template, where the enzyme mixture permits DNA synthesis.

The present invention also provides a method for TA cloning of DNA synthesis product comprising: (a) providing an enzyme mixture of the present invention, the enzyme mixture comprising a Taq DNA polymerase as a first enzyme, and a mutant Pfu DNA polymerase as a second enzyme which comprises a 3'-5' exonuclease activity and a reduced DNA polymerization activity; (b) contacting the enzyme mixture with a nucleic acid template, where the enzyme mixture permits DNA synthesis to generate a synthesized DNA product; and (c) inserting the synthesized DNA product into a TA cloning vector.

BRIEF DESCRIPTION OF DRAWINGS

FIG. 1 is a figure showing PCR proofreading activity assay using Pfu DNA polymerase mutants according to some embodiments of the invention.

FIG. 2 is a figure showing PCR performance of Pfu plus Pfu G387P mutant blends according to some embodiments of the invention.

FIG. 3 is a figure showing PCR performance of Taq plus Pfu G387P mutant blends according to some embodiments of the invention.

FIG. 4 is a figure showing PCR accuracy of PfuTurbo with different amount of PfuG387P according to some embodiments of the invention.

FIG. 5 is a figure showing PCR accuracy of PfuTurbo plus PfuG387P according to some embodiments of the invention.

FIG. 6 is a figure showing the error rate of Taq plus PfuG387P according to some embodiments of the invention.

FIG. 7 is a figure showing the polypeptide and polynucleotide sequences of wild-type DNA polymerases and mutant DNA polymerases according to some embodiments of the invention.

DETAILED DESCRIPTION OF THE INVENTION

The subject invention provides novel composition for high fidelity polynucleotide synthesis, particularly DNA synthesis. The subject compositions comprise an enzyme mixture for DNA synthesis comprising a first enzyme and a second enzyme, where the first enzyme comprises a DNA polymerization activity, and the second enzyme comprises a 3'-5' exonuclease activity and a reduced DNA polymerization activity. In addition to providing high fidelity for DNA synthesis, the compositions of the subject invention prevent side effects of a high polymerization activity, therefore, increase the efficiency of the amplification compared to a mixture in which both DNA polymerases possess wild-type polymerization activities.

DEFINITIONS

As used herein, "synthesis" refers to any in vitro method for making new strand of polynucleotide or elongating existing polynucleotide (i.e., DNA or RNA). Synthesis, according to the invention, include amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

"DNA synthesis", according to the invention, includes, but are not limited to PCR, reverse transcription, the labelling of polynucleotide (i.e., for probes and oligonucleotide primers), polynucleotide sequencing.

As used herein, the term "template dependent manner" is intended to refer to a process that involves the template dependent extension of a primer molecule (e.g., DNA synthesis by DNA polymerase). The term "template dependent manner" refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

As used herein, "polynucleotide polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. "DNA polymerase" catalyzes the polymerization of deoxynucleotides.

As used herein, the "polymerase domain" refers to the one or more domains of a DNA polymerase which is critical for its polymerization activity. The position of the polymerase domain varies, for example, the polymerase domain for Pfu, Tgo, KDO, Tli (Vent) and PGB-D (dee Vent) are located at amino acid positions as described in Table 2B.

As used herein, the "partitioning domain" refers to a domain of a DNA polymerase which plays a critical role in coordinating the balance between synthesis and degradation of the DNA chain. Generally the partitioning domain is characterized by the YXGG motif (Truniger et al., 1996, EMBO J. 15:3430-3441). This region is located within an accessible loop connecting the 3'-5' exonuclease and polymerase domains. The position of the partitioning domain varies. For example, the partitioning domain for Pfu, Tgo, KDO, Tli (Vent) and PGB-D (dee Vent) are located at amino acid positions 384-389, 383-388, 383-388, 386-391, and 384-389 repectively.

According to the invention, another class of DNA polymerase is "reverse transcriptases", also referred to as "RT", is a critical enzyme responsible for the synthesis of cDNA from viral RNA for all retroviruses, including HIV, HTLV-I, HTLV-II, FeLV, FIV, SIV, AMV, MMTV, and MoMuLV. For review, see e.g. Levin, 1997, Cell, 88:5-8; Brosius et al., 1995, Virus Genes 11:163-79. The term "reverse transcriptase (RT) activity" means the ability to synthesize cDNA from RNA template. Methods for measuring RT activity are well known in the art, for example, the Quan-T-RT assay system is commercially available from Amersham (Arlington Heights, Ill.) and is described in Bosworth, et al., Nature 1989, 341:167-168.

As used herein, a mutant DNA polymerase with "reduced polymerization activity" is a DNA polymerase mutant comprising a DNA polymerization activity which is lower than that of the wild-type enzyme, e.g., comprising less than 10% DNA (e.g., less than 8%, 6%, 4%, 2% or less than 1%) polymerization activity of that of the wild-type enzyme.

As used herein, "exonuclease" refers to an enzyme that cleaves bonds, preferably phosphodiester bonds, between nucleotides one at a time from the end of a DNA molecule. An exonuclease can be specific for the 5' or 3' end of a DNA molecule, and is referred to herein as a 5' to 3' exonuclease or a 3' to 5' exonuclease. A useful exonulcease according to the invention is a 3' to 5' exonuclease which degrades DNA by cleaving successive nucleotides from the 3' end of the polynucleotide. During the synthesis or amplification of a polynucleotide template, a DNA polymerase with 3' to 5' exonuclease activity (exo$^+$) has the capacity of removing mispaired base (proofreading activity), therefore is less error-prone than a DNA polymerase without 3' to 5' exonuclease activity (exo$^-$). The exonuclease activity can be defined by methods well known in the art. For example, one unit of exonuclease activity may refer to the amount of enzyme required to cleave 1 μg DNA target in an hour at 37° C. Wild type Tth DNA polymerase and Taq DNA polymerase are "exo$^-$" because they do not have 3' to 5' exonuclease activities, however, wild type Pfu DNA polymerase, *E. coli* DNA polymerase I, T7 DNA polymerase, Tma DNA polymerase, Tli DNA polymerase, KOD DNA polymerase, JDF DNA polymerase, and PGB-D DNA polymerase are "exo$^+$" because they all exhibit 3' to 5' exonuclease activity.

The term "fidelity" as used herein refers to the accuracy of DNA polymerization by template-dependent DNA polymerase. The fidelity of a DNA polymerase is measured by the error rate (the frequency of incorporating an inaccurate nucleotide, i.e., a nucleotide that is not incorporated at a template-dependent manner). The accuracy or fidelity of DNA polymerization is maintained by both the polymerase activity and the 3'-5' exonuclease activity of a DNA polymerase. The term "high fidelity" refers to an error rate of $5 \times 10^{-6}$ per base pair or lower. The fidelity or error rate of a DNA polymerase may be measured using assays known to the art (see for example, Lundburg et al., 1991 Gene, 108:1-6).

As used herein, an "amplified product" refers to the double strand polynucleotide population at the end of a PCR amplification reaction. The amplified product contains the original polynucleotide template and polynucleotide synthesized by DNA polymerase using the polynucleotide template during the PCR reaction.

As used herein, "polynucleotide template" or "target polynucleotide template" refers to a polynucleotide containing an amplified region. The "amplified region," as used herein, is a region of a polynucleotide that is to be either synthesized by reverse transcription or amplified by polymerase chain reaction (PCR). For example, an amplified region of a polynucleotide template resides between two sequences to which two PCR primers are complementary to.

As used herein, the term "primer" refers to a single stranded DNA or RNA molecule that can hybridize to a polynucleotide template and prime enzymatic synthesis of a second polynucleotide strand. A primer useful according to the invention is between 10 to 100 nucleotides in length, preferably 17-50 nucleotides in length and more preferably 17-45 nucleotides in length.

"Complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA polymerase in the present invention is a DNA polymerase which exhibit a reduced DNA polymerization activity.

As used herein, an "enzyme mixture" according to the invention, comprises a first enzyme comprising DNA polymerization activity and a second enzyme comprising a 3'-5' exonuclease activity and a reduced DNA polymerization activity. The ratio of the DNA polymerase activity and the exonuclease activity in the enzyme mixture is about (2.5-5U of DNA polymerization activity)/(0.05-10U of 3'-5' exonuclease activity).

As used herein, the term "enzyme blend" refers to an enzyme composition comprising two or more premixed enzymes. The "enzyme blend" may further comprise other reagents, such as PCR enhancing factor, enzyme storage buffer, or reaction buffer.

Useful DNA Polymerases and Reverse Transcriptases

DNA polymerases and their properties are described in detail in, among other places, *DNA Replication 2nd edition*, Komberg and Baker, W.H. Freeman, New York, N.Y. (1991).

Known conventional DNA polymerases include, for example, *Pyrococcus furiosus* (Pfu) DNA polymerase (Lundberg et al., 1991, *Gene,* 108: 1, provided by Stratagene), *Pyrococcus woesei* (Pwo) DNA polymerase (Hinnisdaels et al., 1996, *Biotechniques,* 20:186-8, provided by Boehringer Mannheim), *Thermus thermophilus* (Tth) DNA polymerase (Myers and Gelfand 1991, *Biochemistry* 30:7661), *Bacillus stearothermophilus* DNA polymerase (Stenesh and McGowan, 1977, *Biochim Biophys Acta* 475:32), *Thermococcus litoralis* (Tli) DNA polymerase (also referred to as Vent DNA polymerase, Cariello et al., 1991, *Polynucleotides Res,* 19: 4193, provided by New England Biolabs), 9°Nm DNA polymerase (discontinued product from New England Biolabs), *Thermotoga maritima* (Tma) DNA polymerase (Diaz and Sabino, 1998 *Braz J Med. Res,* 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, *Appl. Environ. Microbiol.* 63:4504), JDF-3 DNA polymerase (from *thermococcus* sp. JDF-3, Patent application WO 0132887), *Pyrococcus* GB-D (PGB-D) DNA polymerase (also referred as Deep-Vent DNA polymerase, Juncosa-Ginesta et al., 1994, *Biotechniques,* 16:820, provided by New England Biolabs), UlTma DNA polymerase (from *thermophile Thermotoga maritima*; Diaz and Sabino, 1998 Braz J. Med. Res, 31:1239; provided by PE Applied Biosystems), Tgo DNA polymerase (from *thermococcus gorgonarius*, provided by Roche Molecular Biochemicals), *E. coli* DNA polymerase I (Lecomte and Doubleday, 1983, *Polynucleotides Res.* 11:7505), T7 DNA polymerase (Nordstrom et al., 1981, *J Biol. Chem.* 256:3112), and archaeal DP1/DP2 DNA polymerase II (Cann et al., 1998, Proc Natl Acad Sci USA 95:14250-5). The polymerization activity of any of the above enzymes can be defined by means well known in the art. One unit of DNA polymerization activity of conventional DNA polymerase, according to the subject invention, is defined as the amount of enzyme which catalyzes the incorporation of 10 nmoles of total deoxynucleotides (dNTPs) into polymeric form in 30 minutes at optimal temperature (e.g., 72° C. for Pfu DNA polymerase). Assays for DNA polymerase activity and 3'-5' exonuclease activity can be found in *DNA Replication 2nd Ed.*, Komberg and Baker, supra; *Enzymes*, Dixon and Webb, Academic Press, San Diego, Calif. (1979), as well as other publications available to the person of ordinary skill in the art.

When using the subject compositions in reaction mixtures that are exposed to elevated temperatures, e.g., during the PCR technique, use of thermostable DNA polymerases is preferred.

Reverse transcriptases useful according to the invention include, but are not limited to, reverse transcriptases from HIV, HTLV-1, HTLV-II, FeLV, FIV, SIV, AMV, MMTV, MoMuLV and other retroviruses (for reviews, see for example, Levin, 1997, Cell, 88:5-8; Verma, 1977, Biochim Biophys Acta. 473:1-38; Wu et al., 1975, CRC Crit Rev Biochem. 3:289-347).

Useful First Enzyme Comprising DNA Polymerization Activity

Enzymes comprising DNA polymerization activity according to the present invention include enzymes such as DNA polymerases and reverse transcriptases.

The first enzyme used in the subject composition can be any DNA polymerase, with or without a proof reading activity. Preferably, a wild type DNA polymerase is used. However, a mutant DNA polymerase can also be used so long as it provides sufficient DNA polymerization activity required for an amplification reaction.

In a preferred embodiment, the first enzyme comprising DNA polymerization activity is a wild type Pfu DNA polymerase. The enzyme mixture comprising a Pfu DNA polymerase as the first enzyme is also referred to as a Pfu blend herein after.

In preferred embodiments of the invention, a Pfu blend enzyme mixture is used for DNA synthesis reaction, e.g., PCR reaction.

In another preferred embodiment, the first enzyme comprising DNA polymerization activity is a wild type Taq DNA polymerase. The enzyme mixture comprising a Taq DNA polymerase as the first enzyme is also referred to as a Taq blend herein after.

In preferred embodiments of the invention, a Taq blend enzyme mixture is used for DNA synthesis reaction and for subsequent direct cloning, e.g., PCR reaction followed by TA cloning.

In one embodiment, the first enzyme exists in the form of an enzyme blend. This enzyme blend is mixed with a second enzyme comprising a reduced polymerization activity to produce an enzyme mixture of the present invention.

In a preferred embodiment, the enzyme blend is a Herculase® Enhanced or a Herculase® Hotstart DNA polymerase (Stratagene, Cat. No. 600310 or 600260). The enzyme blend can also be selected from commercially available enzyme blend, for example, from the group consisting of: EXL DNA Polymerase (Stratagene, Cat. No. 6003420/2/4), YieldAce DNA Polymerase (Stratagene, Cat. No. 600290/2/4), TaqPlus Precision PCR System (Stratagene, Cat. No. 600210/1/2), TaqPlus Long 100U (Stratagene, Cat. No. 600203/4/5), Advantage 2 PCR Enzyme System (BD Biosciences-Clontech, Cat No. 8430-1), Advantage-GC 2 (BD Biosciences-Clontech, Cat No. 8433-1), Advantage-HF 2 (BD Biosciences-Clontech, Cat No. K1914-y/1), BIO-X-ACT DNA Polymerase (Bioline, Cat. No. BIO-21049/50), TripleMaster PCR System (Brinkmann, Cat. No. 0032-008-216/24/32), FailSafe PCR System (Epicentre, Cat. No. FS99060/100/250/1K), MasterAmp Extra-Long PCR Kit (Epicentre, Cat. No. MHF9220/QU92125/QU92500QU9201K), Synergy DNA Polymerase (GeneCraft, Cat No. GC-005), SynergyN DNA Polymerase (GeneCraft, Cat No. GC-028), Synergy-Plus DNA Polymerase (GeneCraft, Cat No. GC-048), Takara ExTaq DNA Polymerase (Intergen, Cat. No. RR001A/B/C), PCR SuperMix High Fidelity (Invitrogen, Cat. No. 10790020), Elongase Enzyme Mix (Invitrogen, Cat. No. 10481018), Takara ExTaq DNA Polymerase (PanVera, Cat. No. TAK RR001A/B/C), Takara LATaq DNA polymerase (PanVera, Cat. No. TAK RR002M/B/C), Expand High Fidelity PCR System (Roche Molecular Biochemicals, Cat. No. 1 732 641/650/078), Expand Long Template PCR System (Roche Molecular Biochemicals, Cat. No. 1 681 834/842; 1 7659 060), Expand 20 kb PLUS PCR System (Roche Molecular Biochemicals, Cat. No. 1 811 002), GC-RICH PCR System (Roche Molecular Biochemicals, Cat. No. 2 140 306), AccuTaq LA DNA Polymerase (Sigma-Aldrich, Cat. No. D8045), KlenTaq LA DNA Polymerase mix (Sigma- Aldrich, Cat. No. D5062), ProofSprinter DNA Polymerase Mix (Thermo Hybaid, Cat. No. PROOFMIX100/300/600) and ProofExpander PCR Kit (Thermo Hybaid, Cat. No. EXPAND100).

Useful Second Enzyme Comprising 3'-5' Exonuclease Activity

Enzyme comprising 3'-5' exonuclease activity (i.e., proofreading DNA polymerase) according to the invention include, but are not limited to, DNA polymerases, *E. coli* exonuclease I, *E. coli* exonuclease III, *E. coli* recBCD nuclease, mung bean nuclease, and the like (see for example, Kuo, 1994, Ann N Y Acad Sci., 726:223-34).

Any proofreading DNA polymerase could be mutagenized to reduce/eliminate DNA polymerase activity and used in the enzyme reaction of the present invention. Examples can be found in many DNA polymerase families including, but are not limited to such as follows:

Family B DNA Polymerases

Bacteriophage T4 DNA polymerase, φ29 DNA polymerase, T7 DNA polymerase; *E. coli* pol II DNA polymerase; human DNA polymerase δ, human DNA polymerase γ, archaeal DNA polymerase I (Table 1).

Eubacterial Family A DNA Polymerases (with Proofreading Activity)

*E. coli* DNA pol I (Klenow fragment), *Thermotoga maritima* (UlTma fragment)

Family D DNA Polymerases (unrelated to Families A, B, C)

Archaeal DNA polymerase II (DP1/DP2) e.g., as described in Cann et al (1998) PNAS 95:14250-5.

TABLE 1

Accession Information for Cloned Family B Polymerases

```
Vent Thermococcus litoralis
ACCESSION AAA72101
PID g348689
VERSION AAA72101.1 GI:348689
DBSOURCE locus THCVDPE accession M74198.1
THEST THERMOCOCCUS SP. (STRAIN TY)
ACCESSION O33845
PID g3913524
VERSION O33845 GI:3913524
DBSOURCE swissprot: locus DPOL_THEST, accession O33845
Pab Pyrococcus abyssi
ACCESSION P77916
PID g3913529
VERSION P77916 GI:3913529
DBSOURCE swissprot: locus DPOL_PYRAB, accession P77916
PYRHO Pyrococcus horikoshii
ACCESSION O59610
PID g3913526
VERSION O59610 GI:3913526
DBSOURCE swissprot: locus DPOL_PYRHO, accession O059610
PYRSE PYROCOCCUS SP. (STRAIN GE23)
ACCESSION P77932
PID g3913530
VERSION P77932 GI:3913530
DBSOURCE swissprot: locus DPOL_PYRSE, accession P77932
DeepVent Pyrococcus sp.
ACCESSION AAA67131
PID g436495
VERSION AAA67131.1 GI:436495
DBSOURCE locus PSU00707 accession U00707.1
Pfu Pyrococcus furiosus
ACCESSION P80061
PID g399403
VERSION P80061 GI:399403
DBSOURCE swissprot: locus DPOL_PYRFU, accession P80061
JDF-3 Thermococcus sp.
Amino acid sequence of JDF-3 DNA polymerase (Sequence 2 of WO 01/32887):
Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
                20                  25                  30

Glu Phe Glu Pro Tyr Phe Tyr Ala Leu Leu Arg Asp Asp Ser Ala Ile
                35                  40                  45

Glu Glu Ile Lys Lys Ile Thr Ala Glu Arg His Gly Arg Val Val Lys
        50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
                100                 105                 110
```

TABLE 1-continued

Accession Information for Cloned Family B Polymerases

Asp Ile Pro Phe Ala Lys Arg Tyr Leu Ile Asp Lys Gly Leu Ile Pro
            115                 120                 125

Met Glu Gly Glu Glu Leu Lys Leu Met Ser Phe Asp Ile Glu Thr
            130                 135             140

Leu Tyr His Glu Gly Glu Glu Phe Gly Thr Gly Pro Ile Leu Met Ile
145                     150             155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
            210                 215                 220

Lys Leu Gly Val Ser Phe Thr Leu Gly Arg Asp Gly Ser Glu Pro Lys
225                     230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Thr Ala Trp Glu Thr Gly Glu Gly
            290                 295                 300

Leu Glu Arg Val Ala Arg Tyr Ser Met Glu Asp Ala Arg Val Thr Tyr
305                     310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Arg Gly Gly Tyr
            370                 375                 380

Ala Gly Gly Tyr Val Lys Glu Pro Glu Arg Gly Leu Trp Asp Asn Ile
385                     390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asn Leu Leu Glu Glu Arg Gln Lys Ile Lys
            450                 455                 460

Arg Lys Met Lys Ala Thr Leu Asp Pro Leu Glu Lys Asn Leu Leu Asp
465                     470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
            515                 520                 525

TABLE 1-continued

Accession Information for Cloned Family B Polymerases

```
Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
        610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
                660                 665                 670

Tyr Lys Ala Thr Gly Pro His Val Ala Ile Ala Lys Arg Leu Ala Ala
            675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
            755                 760                 765

Leu Lys Pro Lys Gly Lys Lys Lys (SEQ ID NO: 129)
    770                 775
```

Nucleotide sequence of JDF-3 DNA polymerase (Sequence 1 of WO 01/32887)

```
atgatccctg acgttgatta catcaccgag aacggaaagc ccgtcaccag ggtcttcaag    60
aaggagaacg gcgagtccag gattgaatac gaccgcgagt tcgagcccta cttctacgcg   120
ctcctcaggg acgactctgc caccgaagaa atcaaaaaga taaccgcgga gaggcacggc   180
agggtcgtta aggttaagcg cgcggagaag gtgaagaaaa agttccccgg caggtctgtg   240
gaggtctggg tcctctactt cacgcacccg caggacgccc cggcaatccg cgacaaaata   300
aggaagcacc ccgcggccac cgacatctac gagtacgaca tacccttcgc caagcgctac   360
ctcatagaca agggcctaat cccgatggaa ggtgaggaag agcctaaacc catgtccttc   420
gacatcgaga cgctctacca cgagggagaa gagttcggaa ccgggccgat tctgatgata   480
agctacgccg atgaaagcga ggcgcgcgtg ataacctgga agaagatcga ccttccttac   540
gctgaggccg tctccaccga aaggagacg attaagcgct tcttgaggc cgttaaggag   600 aaggacccgg acgtgctgat aacacacaac ggcgacaact tcgacttcgc ccacctgaaa   660
aagcgctgtg agaagcctgg cgcgagctct accctcggga gggacgggag cgagccgaag   720
atacagcgca tggggacag gtttgcggcc gaggtgaagg caggtgtaca ccccgacctt   780
tatccagtca taaggcgcac cataaacctc ccgacccaca cccttgaggc tgtatacgag   840
gcggttttcg gcaagcccaa ggagaaggcc cacgccgagg agatagccac cgcctgggag   900
```

TABLE 1-continued

Accession Information for Cloned Family B Polymerases

```
accggcgagg ggcttgagag ggtcgcgcgc tacccgacgg aggacgcgag ggttacctac      960
gagcccggca gggagctctt cccgatggag gcccagcttt ccaggcccac cggccaaggc     1020
ctccgggacg tttcccgctc cagcaccggc aacctcgtcg agtggttcct cctaaggaag     1080
gcctacgaga ggaacgaact cgctcccaac aagcccgacg agagggagct ggcgaggaga     1140 aggggggggct acgccggtgg ctacgtcaag gagccggagc ggggactgcg ggacaatatc    1200
gtgtatctag actttcgtag tctctaccct tcaatcataa tcaccacaa cgtctcgcca      1260 gatacgctca accgcgaggg gtgtaggagc tacgacgttg cccccgaggt cggtcacaag     1320
ttctgcaagg acttccccgg cttcattccg agcctgctcg gaaacctgct ggaggaaagg     1380
cagaagataa agaggaagat gaaggcaact ctcgacccgc tggagaagaa tctcctcgat     1440
tacaggcaac gcgccatcaa gattctcgcc aacagctact acggctacta cggctatgcc     1500
agggcaagat ggtactgcag gggagtgcgcc gagagcgtta cggcatgggg aagggagtac    1560
atcgaaatgg tcatcagaga gcttgaggaa aagttcggtt ttaaagtcct ccatgcagac    1620
acagacggtc tccatgccac cattcctgga gcggacgctg aaacagtcaa gaaaaaggca    1680
atggagttct taaactatat caatcccaaa ctgcccggcc ttctcgaact cgaatacgag    1740
ggcttctacg tcaggggctt cttcgccacg aagaaaaagt acgcggtcat cgacgaggag    1800
ggcaagataa ccacgcgcgg gcttgagata gtcaggcgcg actggagcga gatagcgaag    1860
gagacgcagg cgagggtttt ggaggcgata ctcaggcacg gtgacgttga agaggccgtc    1920
agaattgtca gggaagtcac cgaaaagctg agcaagtacg aggttccgcc ggagaagctg    1980
gttatccacg agcagataac gcgcgagctc aaggactaca aggccaccgg cccgcacgta    2040
gccatagcga agcgtttggc cgccagaggt gttaaaatcc ggcccggaac tgtgataagc    2100
tacatcgttc tgaagggctc cggaaggata ggcgacaggg cgattcccct cgacgagttc    2160
gacccgacga agcacaagta cgatgcggac tactacatcg agaaccaggt tctgccggca    2220
gttgagagaa tcctcagggc cttcggctac cgcaaggaag acctgcgcta ccagaagacg    2280
aggcaggtcg ggcttggcgc gtggcCgaag ccgaagggga agaagaagtg a             2331
(SEQ ID NO: 130)
```

Unpublished
Baross gi|20977561|pat|US|5602011|12 Sequence 12 from U.S. Pat.
No. 5,602,011.
9degN *THERMOCOCCUS SP. (STRAIN 9ON-7)*.
ACCESSION Q56366
PID g3913540
VERSION Q56366 GI:3913540
DBSOURCE swissprot: locus DPOL_THES9, accession Q56366
KOD *Pyrococcus sp.*
ACCESSION BAA06142
PID g1620911
VERSION BAA06142.1 GI:1620911
DBSOURCE locus PYWKODPOL accession D29671.1
Tgo *Thermococcus gorgonarius*.
ACCESSION 4699806
PID g4699806
VERSION GI:4699806
DBSOURCE pdb: chain 65, release Feb. 23, 1999
THEFM *Thermococcus fumicolans*
ACCESSION P74918
PID g3913528
VERSION P74918 GI:3913528
DBSOURCE swissprot: locus DPOL_THEFM, accession P74918
METTH *Methanobacterium thermoautotrophicum*
ACCESSION O27276
PID g3913522
VERSION O27276 GI:3913522
DBSOURCE swissprot: locus DPOL_METTH, accession O27276

TABLE 1-continued

Accession Information for Cloned Family B Polymerases

```
Metja Methanococcus jannaschii
ACCESSION Q58295
PID g3915679
VERSION Q58295 GI:3915679
DBSOURCE swissprot: locus DPOL_METJA, accession Q58295
POC Pyrodictium occultum
ACCESSION B56277
PID g1363344
VERSION B56277 GI:1363344
DBSOURCE pir: locus B56277
ApeI Aeropyrum pernix
ACCESSION BAA81109
PID g5105797
VERSION BAA81109.1 GI:5105797
DBSOURCE locus AP000063 accession AP000063.1
ARCFU Archaeoglobus fulgidus
ACCESSION O29753
PID g3122019
VERSION O29753 GI:3122019
DBSOURCE swissprot: locus DPOL_ARCFU, accession O29753
Desulfurococcus sp. Tok.
ACCESSION 6435708
PID g64357089
VERSION GT:6435708
DBSOURCE pdb. chain 65, release Jun. 2, 1999
```

Enzymes possessing 3'-5' exonuclease activity for use in the present compositions and methods may be isolated from natural sources or produced through recombinant DNA techniques. Preferably, the enzyme comprising 3'-5' exonuclease activity is a DNA polymerase.

A DNA polymerase comprising 3'-5' exonuclease activity (referred as exo+) is capable of proofreading the incorporated nucleotides produced by its own polymerization activity. Among other applications, exo+ DNA polymerases are particularly suited for cloning of PCR products, characterization of polynucleotide sequences. Useful exo+ DNA polymerases include, but are not limited to, Pwo DNA polymerase; Vent DNA polymerases; Deep Vent DNA polymerase; 9°Nm DNA polymerase; UlTma DNA polymerase; Tli DNA polymerase; Pfu DNA polymerase; JDF-3 DNA polymerase; Tgo DNA polymerase; KOD DNA polymerase; and PGB-D DNA polymerase.

In preferred embodiments of the subject invention, an exo+ DNA polymerase with reduced DNA polymerization activity is used as the second enzyme.

Preparing Exo+ DNA Polymerase With Reduced DNA Polymerization Activity

The cloned wild-type Exo+ DNA polymerase may be modified to generate forms exhibiting reduced polymerization activity by a number of methods. These include the methods described below and other methods known in the art. Any exo+ DNA polymerase can be used to prepare for the exo+ DNA polymerase with reduced DNA polymerization activity in the invention.

A. Genetic Modifications—Mutagenesis

The preferred method of preparing a DNA polymerase with reduced polymerization activity is by genetic modification (e.g., by modifying the DNA sequence of a wild-type DNA polymerase). Within the sequence of an exo+ DNA polymerase, the preferred sequence for genetic modification is the DNA sequence encoding the polymerization domain. Polymerization and exonuclease domains (i.e., their crystal structures) of many DNA polymerases are known in the art (for examples, see Rodriguez et al., 2000, J. Mol. Biol. 299: 447-62; Zhao et al., 1999, Structure Fold Des. 7:1189-99; Baker et al., 1998, Proc Natl Acad Sci USA. 95:3507-12; Kiefer et al., 1997, Structure 5:95-108; Kim et al., 1995, Nature, 376:612-6; Kong et al., 1993, J Biol Chem. 268:1965-75).

General structure features of DNA polymerization domain is known in the art. For example, Blanco et al. (1991, Gene, 100:27-38) discloses that significant amino acid (aa) sequence similarity has been found in the C-terminal portion of 27 DNA-dependent DNA polymerases belonging to the two main superfamilies: (i) *Escherichia coli* DNA polymerase I (PolI)-like prokaryotic DNA polymerases, and (ii) DNA polymerase alpha-like prokaryotic and eukaryotic (viral and cellular) DNA polymerases. The six most conserved C-terminal regions, spanning approximately 340 amino acids, are located in the same linear arrangement and contain highly conserved motifs and critical residues involved in the polymerization function.

According to the three-dimensional model of PolIk (Klenow fragment), these six conserved regions are located in the proposed polymerization domain, forming the metal and dNTP binding sites and the cleft for holding the DNA template. Site-directed mutagenesis studies support these structural predictions.

The 3'-5' exonuclease active site of *E. coli* DNA polymerase I is predicted to be conserved for both prokaryotic and eukaryotic DNA polymerases based on amino acid sequence homology (Bernad et al., 1989, Cell, 59:219-28). Three amino acid regions containing the critical residues in the *E. coli* DNA polymerase I involved in metal binding, single-stranded DNA binding, and catalysis of the exonuclease reaction are located in the amino-terminal half and in the same linear arrangement in several prokaryotic and eukaryotic DNA polymerases. Site-directed mutagenesis at the predicted exonuclease active site of the phi 29 DNA polymerase, a model enzyme for prokaryotic and eukaryotic alpha-like DNA polymerases, specifically inactivated the 3'-5' exonuclease activity of the enzyme. These results reflect a high evolutionary conservation of this catalytic domain.

With the great availability of sequences from DNA polymerases, it has become possible to delineate a few highly conserved regions for various polymerase types (for review, see for example, Johnson, 1993, Annu Rev Biochem. 62:685-

713). Delarue et al. reported an approach for unifying the structure of DNA polymerase (1990, Protein Eng., 3:461-7). The speculative hypothesis should provide a useful model to direct genetic modifications for preparing DNA polymerase with reduced polymerization activity.

Preferably, the genetic modification for preparing exo$^+$ DNA polymerase with reduced polymerization activity does not significantly reduces its 3'-5' exonuclease activity (i.e., the proof reading activity).

Known DNA polymerase mutants that selectively reduce DNA polymerization activity can be found in the art, for example, in Blanco et al., 1995 Methods of Enzymology 262:283-294 ((Bacteriophage φ29); Truniger et al., 1996, EMBO J. 15:3430-3441 (Bacteriophage φ29); Abdus Sattar et al., 1996, Biochemistry 35:16621-9 (Bacteriophage T4); Tuske et al., 2000, J. Biological Chemistry 275:23759-68 (Klenow fragment); Bohlke et al., 2000, Nucleic Acid Research 28:3910-3917 (*Thermococcus aggregans*); Pisani et al., 1998, Biochemistry 37:15005-15012 (*Sulfolobus solfataricus*); Komori et al., 2000, Protein Eng 13:41-7 (*Pyrococcus furiosus*); Shen et al., 2001 J. Biological Chemistry 276:27376-83 (*Pyrococcus horikoshi* Family D).

Site-directed mutagenesis of bacteriophage φ29 DNA polymerase leads to the identification of mutations in the polymerase domain which reduce DNA polymerase activity, while having minimal effects on 3'-5' exonuclease activity (Blanco, L. and Salas, M. 1995, Methods of Enzymology 262:283-294). In one embodiment of the invention, one or more corresponding amino acids in Pfu DNA polymerases are mutated (e.g., by substitutions: D405E, Y410F, T542P, D543G, K593T, Y595S). It is understood that other amino acid side substitutions at these same sites would also selectively reduce DNA polymerase activity.

The φ29 DNA polymerase mutagenesis studies targeted amino acid residues within highly conserved Family B motifs (DXXSLYP (SEQ ID NO.1), KXXXNSXYG (SEQ ID NO.2), TXXGR (SEQ ID NO.3), YXDTDS (SEQ ID NO.4), and KXY (SEQ ID NO.5)), although other regions of the protein presumably can be mutagenized to selectively decrease DNA polymerase activity. One such region is the partitioning domain, characterized by the YXGG motif (SEQ ID NO.6) (Truniger et al., 1996, EMBO J. 15:3430-3441). This region is located within an accessible loop connecting the 3'-5' exonuclease and polymerase domains. The partitioning domain plays a critical role in coordinating the balance between synthesis and degradation of the DNA chain. Mutations within this region disrupt the equilibrium between polymerization and proofreading, and produce phenotypes favoring either polymerization (reduced proofreading) or proofreading (reduced polymerization).

Non-conservative (S,N) substitutions at $Y_{387}$ (equivalent to $Y_{385}$ in Pfu) in the partitioning domain of the archaeal *Thermococcus aggregans* DNA polymerase lead to a significant reduction in DNA polymerase activity and enhanced exonuclease activity, which results in improved enzyme fidelity (used alone in PCR) (Bohlke, K. et al (2000) NAR 28:3910-3917). In contrast, conservative substitutions at $Y_{387}$ (F, W, H) lead to wild-type-like fidelity and enhanced PCR performance, which may be related to improved polymerization. A G389A mutation (equivalent to Pfu G387) in *Thermococcus aggregans* DNA polymerase lead to reduced DNA polymerase activity (10% wt), increased exonuclease activity (236% wt), and loss of product synthesis in PCR (Bohlke, K. et al (2000) NAR 28:3910-3917). Analogous mutations have been investigated in bacteriophage φ29 DNA polymerase (Truniger, V., et al (1996) EMBO J. 15:3430-3441) and in the archaeal *Solfolobus solfataricus* (Sso) DNA polymerase (Pisani, F. M., DeFelice, M., and Rossi, M. (1998) *Biochemistry* 37:15005-15012), where a G→A mutation either decreases (pol/exo=0.6 for Sso) or increases (pol/exo=91 for φ29) DNA polymerase activity relative to exonuclease activity.

In one embodiment of the invention, Pfu DNA polymerase was mutated within the partitioning domain at amino acids 384-389 (SYTGGF) (SEQ ID NO. 7) to obtain a Pfu DNA polymerase with reduced polymerization activity. It is understood that other amino acid side substitutions within the partitioning domain, e.g., at positions Y385, G387, G388, could also selectively reduce DNA polymerase activity while having minimal effects on exonuclease activity.

In another embodiment, two or mutations are combined (e.g., by introducing additional site-directed mutations into a mutant Pfu DNA polymerase) to effectively eliminate DNA polymerase activity, while retaining high levels of proofreading activity.

U.S. Pat. Nos. 5,691,142, 5,614,402 and 5,541,311 disclose methods of deriving 5'-3' nucleases from thermostable DNA polymerases for the detection of target polynucleotide molecules (hereby incorporated by reference). These methods can be applied to the subject invention for preparing DNA polymerase comprising 3'-5' exonuclease activity with a reduced polymerization activity. Other techniques for genetic modification are well known in the art (see for example, Ausubel et. al. *Short Protocols in Molecular Biology* (1995) 3$^{rd}$ Ed. John Wiley & Sons, Inc.).

Modification to the primary structure of a wild type enzyme by deletion, addition, or alteration of the amino acids incorporated into the sequence during translation can be made without destroying the high temperature DNA polymerase activity of the protein. Such substitutions or other alterations result in proteins useful in the methods of the present invention. The availability of DNA encoding these sequences provides the opportunity to modify the codon sequence to generate mutant enzymes having reduced polymerization activity. A few methods for altering DNA sequences are provided below, any other method known in the art may also be used.

There are a number of site-directed mutagenesis methods known in the art which allow one to mutate a particular site or region in a straightforward manner, based on the sequences of the polymerization domain of a DNA polymerase. There are a number of kits available commercially for the performance of site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

Older methods of site-directed mutagenesis known in the art relied upon sub-cloning of the sequence to be mutated into a vector, such as an M13 bacteriophage vector, that allows the isolation of single-stranded DNA template. In these methods one anneals a mutagenic primer (i.e., a primer capable of annealing to the site to be mutated but bearing one or mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease DpnI (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the method is described in detail as follows:

Plasmid template DNA (approximately 0.5 pmole) is added to a PCR cocktail containing: 1× mutagenesis buffer (20 mM Tris HCl, pH 7.5; 8 mM $MgCl_2$; 40 μg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 μM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

Methods of random mutagenesis which will result in a panel of mutants bearing one or more randomly-situated mutations exist in the art. Such a panel of mutants may then be screened for those exhibiting reduced polymerization relative to the wild-type polymerase (e.g., by measuring the incorporation of 10 nmoles of dNTPs into polymeric form in 30 minutes at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer and the inherited fidelity of the PCR enzyme. The use of manganese ion and/or variation of the magnesium or manganese ion concentration may therefore be applied to influence the error rate of the polymerase.

In a preferred embodiment, the second enzyme with reduced polymerization activity is derived from Pfu DNA polymerase.

The DNA coding sequence of a wild-type Pfu DNA polymerase can be found in the art, for example, from Genbank (accession No. U84155). A detailed description of the structure and function of Pfu DNA polymerase can be found, among other places in U.S. Pat. Nos. 5,948,663; 5,866,395; 5,545,552; 5,556,772, all of which thereby incorporated by references. A not-limiting detailed procedure for preparing Pfu DNA polymerase with reduced polymerization activity is provided in Example 1.

A person of average skill in the art having the benefit of this disclosure will recognize that polymerases with reduced polymerization activity derived from other exo+ DNA polymerases including Vent DNA polymerase, JDF-3 DNA polymerase, Tgo DNA polymerase and the like may be suitably used in the subject compositions.

The first or the second enzyme of the subject composition may comprise DNA polymerases that have not yet been isolated. Assays for both DNA polymerization activity and 3'-5' exonuclease activity can be found in the subject description and in *DNA Replication 2nd Ed.*, Kornberg and Baker, supra; *Enzymes*, Dixon and Webb, Supra, as well as other publications available to the person of ordinary skill in the art.

In preferred embodiments of the invention, mutant Pfu DNA polymerase comprises one or more mutations at amino acid positions selected from the group consisting of: D405, Y410, T542, D543, K593; Y595, Y385, G387, and G388.

More preferably, the mutant Pfu DNA polymerase comprises one or more mutations selected from the group consisting of: D405E, Y410F, T542P, D543G, K593T, Y595S, Y385Q, Y385S, Y385N, Y385L, Y385H, G387S, G387P, and G388P.

The invention encompasses compositions and methods in which a mutant of a related archaeal DNA polymerase is with reduced (e.g., deficient in) polymerase activity, while retaining proofreading activity. Such mutations may be within the partitioning domain or the polymerase domain of the DNA polymerases. Table 2 (A and B) and FIG. 7 provides an unlimited example of such mutations in various DNA polymerases. A mutant DNA polymerase of the invention may comprise a single mutation as indicted in Table 2, or a combination of any two or more mutations.

TABLE 2A

Partitioning Domain Mutations in Various DNA Polymerases

| Enzyme | Domain (bp) | Domain sequence | Predicted Mutations for Reducing DNA Polymerase Activity* | Preferred mutation |
|---|---|---|---|---|
| Pfu | 384-389 | S Y T G G F (SEQ ID NO. 7) | Y385, G387, G388 (Y385N, Y385L, Y385H, Y385Q, Y385S; G387S, G387P; G388A, G388P) | G387P |
| Tgo | 383-388 | S Y A G G Y (SEQ ID NO. 10) | Y384, G386, G387 (Y384N, Y384L, Y384H, Y384Q, Y384S; G386S, G386P; G387A, G387P) | G386P |
| KOD | 383-388 | S Y E G G Y (SEQ ID NO. 11) | Y384, G386, G387 (Y384N, Y384L, Y384H, Y384Q, Y384S; G386S, G386P; G387A, G387P) | G386P |
| Vent | 386-391 | T Y L G G Y (SEQ ID NO. 12) | Y387, G389, G390 (Y387N, Y387L, Y387H, Y387Q, Y387S; G389S, G389P; G390A, G390P) | G389P |
| DeepVent | 384-389 | S Y A G G Y (SEQ ID NO. 10) | Y385, G387, G388 (Y385N, Y385L, Y385H, Y385Q, Y385S; G387S, G387P; G388A, G388P) | G387P |

TABLE 2B

Polymerase Domain Mutations in Various DNA Polymerases

| Enzyme | Domain (bp) | Domain sequence | Predicted Mutations for Reducing DNA Polymerase Activity# |
|---|---|---|---|
| | DXXSLYP | | |
| Pfu | 405-411 | DFRALYP (SEQ ID NO. 13) | D405 (D405E) |
| Tgo | 404-410 | DFRSLYP (SEQ ID NO. 14) | D404 (D404E) |
| KOD | 404-410 | DFRSLYP | D404 (D404E) |
| Vent | 407-413 | DFRSLYP | D407 (D404E) |
| Deep Vent | 405-411 | DFRSLYP | D405 (D404E) |
| | YXDTDS | | |
| Pfu | 539-544 | YIDTDG (SEQ ID NO. 15) | T542, D543 (T542P; D543G) |
| Tgo | 538-543 | YADTDG (SEQ ID NO. 16) | T541, D542 (T541P; D542G) |
| KOD | 538-543 | YSDTDG (SEQ ID NO. 17) | T541, D542 (T541P; D542G) |
| Vent | 541-546 | YADTDG | T544, D545 (T544P; D545G) |
| Deep Vent | 539-544 | YIDTDG | T542, D543 (T542P; D543G) |
| | KXY | | |
| Pfu | 593-595 | KRY (SEQ ID NO. 18) | K593 (K593T) |
| Tgo | 592-594 | KKY (SEQ ID NO. 128) | K592 (K592T) |
| KOD | 592-594 | KKY | K592 (K592T) |
| Vent | 595-597 | KRY | K595 (K595T) |
| Deep Vent | 593-595 | KKY | K593 (K593T) | alternative side chain substitutions at key positions are also expected to reduce polymerase activity

B. Methods of Evaluating Mutants for Reduced Polymerization

Random or site-directed mutants generated as known in the art or as described herein and expressed in bacteria may be screened for reduced polymerization by several different assays. Embodiments for the expression of mutant and wild type enzymes is described herein below in section C. In one method, exo+ DNA polymerase proteins expressed in lytic lambda phage plaques generated by infection of host bacteria with expression vectors based on, for example, Lambda ZapII®, are transferred to a membrane support. The immobilized proteins are then assayed for polymerase activity on the membrane by immersing the membranes in a buffer containing a DNA template and the unconventional nucleotides to be monitored for incorporation.

Mutant polymerase libraries may be screened using a variation of the technique used by Sagner et al (Sagner, G., Ruger, R., and Kessler, C. (1991) Gene 97:119-123). For this approach, lambda phage clones are plated at a density of 10-20 plaques per square centimeter. Proteins present in the plaques are transferred to filters and moistened with polymerase screening buffer (50 mM Tris (pH 8.0), 7 mM MgCl2, 3 mM β-ME). The filters are kept between layers of plastic wrap and glass while the host cell proteins are heat-inactivated by incubation at 65° C. for 30 minutes. The heat-treated filters are then transferred to fresh plastic wrap and approximately 35l of polymerase assay cocktail are added for every square centimeter of filter. The assay cocktail consists of 1× cloned Pfu (cPfu) magnesium free buffer (1× buffer is 20 mM Tris-HCl (pH 8.8), 10 mM KCl, 10 mM $(NH4)_2SO_4$, 100 µg/ml bovine serum albumin (BSA), and 0.1% Triton X-100; Pfu Magnesium-free buffer may be obtained from Stratagene (Catalog No. 200534)), 125 ng/ml activated calf thymus or salmon sperm DNA, 1.29 µCi/ml $\alpha$-$^{33}$P ddNTP. The filters are placed between plastic wrap and a glass plate and then incubated at 65° C. for one hour, and then at 70° C. for one hour and fifteen minutes. Filters are then washed three times in 2×SSC for five minutes per wash before rinsing twice in 100% ethanol and vacuum drying. Filters are then exposed to X-ray film (approximately 16 hours), and plaques that incorporate label are identified by aligning the filters with the original plate bearing the phage clones. Plaques identified in this way are re-plated at more dilute concentrations and assayed under similar conditions to allow the isolation of purified plaques.

In assays such as the one described above, the signal generated by the label is a direct measure of the polymerization activity of the polymerase. A plaque comprising a mutant DNA polymerase with reduced DNA polymerization activity compared to that of the wild-type enzyme can be selected.

Incorporation of nucleotides may also be measured in extension reactions by adding, for example, 1 µl of appropriately diluted bacterial extract (i.e., heat-treated and clarified extract of bacterial cells expressing a cloned polymerase or mutated cloned polymerase) to 10 µl of each nucleotide cocktail, followed by incubation at the optimal temperature for 30 minutes (e.g., 73° C. for Pfu DNA polymerase), for example, as described in Hogrefe et al., 2001, Methods in Enzymology, 343:91-116. Extension reactions are quenched on ice, and then 5 µl aliquots are spotted immediately onto DE81 ion-exchange filters (2.3 cm; Whatman #3658323). Unincorporated label is removed by 6 washes with 2×SCC (0.3M NaCl, 30 mM sodium citrate, pH 7.0), followed by a brief wash with 100% ethanol. Incorporated radioactivity is then measured by scintillation counting. Reactions that lack enzyme are also set up along with sample incubations to determine "total cpms" (omit filter wash steps) and "minimum cpms" (wash filters as above). Cpms bound is proportional to the amount of polymerase activity present per volume of bacterial extract.

A Non-limiting method for determining polymerization activity of a DNA polymerase mutant relative to wild type (wt) is provided as follows. Relative percent radioactivity incorporated which indicates the relative polymerization activity of a DNA polymerase mutant can be determined as:

$$\frac{\text{(corrected cpms for mutant DNA polymerase)} \times \text{(ng wt DNA polymerase)}}{\text{(corrected cpms for wt DNA polymerase)} \times \text{(ng mutant DNA polymerase)}}.$$

To more precisely quantify % activity, one should covert cpms incorporated into units of DNA polymerase activity. One unit of polymerase activity is defined as the amount of enzyme that catalyzes the incorporation of 10 nmoles of total dNTP into polymeric form (e.g., binds to DE-81 paper) in 30 minutes at optimal temperature. Units of DNA polymerase activity can be calculated using the following equation:

$$\frac{\text{(corrected sample cpms)}}{\text{total cpms}} \times \frac{\text{(8 nmoles dNTPs)}}{\text{reaction}} \times \frac{\text{(1 unit)}}{\text{(10 nmoles dNTPs incorporated)}}$$

Polymerase specific activity (U/mg) can be extrapolated from the slope of the linear portion of units versus enzyme amount plots. Protein concentrations can be determined relative to a BSA standard (Pierce) in a colorimetric assay (e.g. Pierce's Coomassie Plus Protein Assay). Alternatively, when protein amounts are limiting (or for preparations of limited purity), relative protein concentrations can be verified by SDS-PAGE analysis. Several aliquots of each DNA polymerase preparation, ranging from 1-20 ng of total protein, are subject to SDS-PAGE electrophoresis and the intensity of silver- and/or Sypro orange (Molecular Probes)-stained bands are compared to standards. Finally, % activity can be determined as:

$$\frac{\text{specific polymerase activity}}{\text{(U/mg) of mutant DNA polymerase}}$$
$$\frac{}{\text{specific polymerase activity (U/mg) of wt DNA polymerase}}$$

It is preferred that the polymerases with reduced polymerization activity of the present invention maintain their proofreading activities (i.e., 3'-5' exonuclease activities). The mutant DNA polymerases with reduced DNA polymerization activities, therefore, are also assayed for 3'-5-exonuclease activities.

Suitable exonuclease activity assays include one described in Hogrefe et al (supra, and as described in Example 3).

Another assay employs double-stranded λ DNA, which has been uniformly labeled with $^3$H S-adenosyl methionine (NEN #NET-155) and Sss I methylase (NEB), and then restriction digested with Pal I (Kong et al., 1993, J. Biol. Chem. 268:1965). Using double-stranded labeled DNA templates, one can determine specificity by measuring whether cpms decrease (3'-5' exonuclease) with the addition of dNTPs (10-100 µM). A typical exonuclease reaction cocktail consists of 1× reaction buffer and 20 µg/ml $^3$H-labeled digested double-stranded λ DNA (~$10^6$ cpms/ml), prepared as described (Kong et al., supra). Exonuclease activity can be measured in the appropriate PCR buffer or in a universal assay buffer such as 70 mM Tris HCl (pH 8.8), 2 mM $MgCl_2$, 0.1% Triton-X, and 100 µg/ml BSA.

Percent exonuclease activity can be determined as: (corrected cpms for mutants)/(corrected cpms for wt DNA polymerase). To more precisely quantify % activity, cpms released can be converted into units of exonuclease activity. One unit of exonuclease activity is defined as the amount of enzyme that catalyzes the acid-solubilization of 10 nmoles of total dNMPs in 30 minutes at a defined temperature. To determine units, background (average "minimum cpms" value) is first subtracted from the average sample cpms. Nmoles dNMPs released is calculated using the following equation:

$$\frac{\text{(corrected sample cpms)}}{\text{total cpms}} \times \frac{\text{(ng DNA)}}{\text{reaction}} \times \frac{\text{(1 nmole dNMP)}}{\text{(330 ng dNMP)}}$$

Units of exonuclease activity (in 30 minutes) can then be determined as:

$$\frac{\text{(nmoles dNMPs released per hr)}}{2} \times \frac{\text{(1 unit)}}{\text{(10 nmoles dNMPs released)}}$$

Exonuclease specific activity (U/mg) can be extrapolated from the slope of the linear portion of units versus enzyme amount plots. Finally, % activity can be determined as:

$$\frac{\text{specific exonuclease activity}}{\text{(U/mg) of mutant DNA polymerase}}$$
$$\frac{}{\text{specific exonuclease activity (U/mg) of wt DNA polymerase}}.$$

In addition to the substrate described above, exonuclease activity can be also be quantified using [$^3$H]-*E. coli* genomic DNA (NEN #NET561; 5.8 µCi/µg), a commercially-available substrate. A typical exonuclease reaction cocktail consists of 25 ng/ml $^3$H-labeled *E. coli* genomic DNA and 975 ng/ml cold *E. coli* genomic DNA in 1× reaction buffer. Assays are performed as described above.

Genes for desired mutant DNA polymerases generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

In one embodiment, the Pfu mutant is G387P, which reduces the error rate of wild type Pfu DNA polymerase by 3-fold in a Pfu blend when added at 5-25 ng/50 µl reaction. The Pfu G387P mutant also reduces the error rate of Taq by approximately 5- to 10-fold in a blend when added at 6/60 ng/50 µl reaction. Pfu G387P exhibited 0.4% DNA polymerase activity and 57% exonuclease activity (i.e., relative to wild type Pfu) in a preliminary screen of partially purified (~50% purity) His-tagged proteins, eluted from nickel columns (Table 1). After column chromatography (~95% purity), the His-tagged Pfu G387P mutant was found to be devoid of detectable DNA polymerase activity (<0.01% activity relative to wild type Pfu) (Table 3).

C. Expression of Wild-Type or Mutant Enzymes According to the Invention

Methods known in the art may be applied to express and isolate the mutated forms of DNA polymerase (i.e., the second enzyme) according to the invention. The methods described here can be also applied for the expression of wild-type enzymes useful (e.g., the first enzyme) in the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. BL-21 strains bearing an inducible T7 RNA polymerase gene include WJ56 and ER2566 (Gardner & Jack, 1999, supra). For situations in which codon usage for the particular polymerase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

There are many methods known to those of skill in the art that are suitable for the purification of a modified DNA polymerase of the invention. For example, the method of Lawyer et al. (1993, *PCR Meth. & App.* 2: 275) is well suited for the isolation of DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase. Further, DNA polymerase mutants may be isolated by an ammonium sulfate fractionation, followed by Q Sepharose and DNA cellulose columns, or by adsorption of contaminants on a HiTrap Q column, followed by gradient elution from a HiTrap heparin column.

In one embodiment, the Pfu mutants are expressed and purified as described in U.S. Pat. No. 5,489,523, thereby incorporated by reference in its entirety.

D. Other Methods for Reducing Polymerization Activity

In order to prevent the side effects of having a high DNA polymerization activity in an amplification reaction, the polymerization activity of the composition of the invention may also be reduced by physical and/or chemical modification and/or inhibition.

The polymerization activity of the subject composition may be reduced by chemical and/or physical means. Conditions which preferentially inhibit the polymerization activity of a DNA polymerase is known in the art (for reviews, see Johnson, 1993, supra; Wright, 1996, Acta Biochim Pol. 43:115-24; Elion, 1982, Am J Med., 73:7-13). The level of polymerization activity need only be reduced to that level of activity which does not interfere with amplification reactions (e.g., does not significantly affect the exo$^+$ activity of the composition or the efficiency yield of the amplification reaction).

Concentrations of $Mg^{2+}$ greater than 5 mM inhibit the polymerization activity of the Pfu DNA polymerase. The effect of a given concentration of $Mg^{2+}$ for a given DNA polymerase may be determined by quantitation of the efficiency and specificity of polymerization.

The inhibitory effect of other ions, polyamines, denaturants, such as urea, formamide, dimethylsulfoxide, glycerol and non-ionic detergents (Triton X-100 and Tween-20), polynucleotide binding chemicals such as, actinomycin D, ethidium bromide and psoralens, may be tested by their addition to the standard reaction buffers for polynucleotide amplification (e.g., PCR). Those compounds having a preferential inhibitory effect on the polymerization activity but not significantly affecting the 3'-5' exonuclease activity of a DNA polymerase are then used to create reaction conditions under which 3'-5' nuclease activity is retained while polymerization activity is reduced.

Physical means may be used to preferentially inhibit the polymerization activity of a polymerase. For example, the polymerization activity of thermostable polymerases is destroyed by exposure of the polymerase to extreme heat (typically 96° C. to 100° C.) for extended periods of time (greater than or equal to 20 minutes). While there are minor differences with respect to the specific heat tolerance for each of the enzymes, these are readily determined. The polymerase mixture of the invention or the exo$^+$ DNA polymerase used as the second enzyme with reduced polymerization activity can be treated with heat for various periods of time and the effect of the heat treatment upon the polymerization and 3'-5' nuclease activities is determined. Conditions reducing DNA polymerase activity but not significantly affecting the 3'-5' exonuclease activity may be used to pretreat the polymerase mixture or the exo$^+$ DNA polymerase used as second enzyme with reduced polymerization activity in the present invention.

Enzyme Mixture

The subject enzyme mixture composition comprises a first enzyme comprising DNA polymerization activity and a second enzyme comprising 3'-5' exonuclease activity with reduced DNA polymerase activity.

In one embodiment, the first enzyme is a DNA polymerase with 3'-5' exonuclease activity. The fidelity of the first enzyme for DNA amplification is increased by the use of a second enzyme which also possesses 3'-5' exonuclease activity. A preferred DNA polymerase with 3'-5' exonuclease activity as the first enzyme is a wild type Pfu DNA polymerase.

In another embodiment, the first enzyme is a DNA polymerase without 3'-5' exonuclease activity. The fidelity of an amplification reaction is provided by the second enzyme of the subject invention, which possesses 3'-5' exonuclease activity. A preferred DNA polymerase without 3'-5' exonuclease activity as the first enzyme is a Taq DNA polymerase.

In yet another embodiment, the first enzyme may is a reverse transcriptase with DNA polymerization activity. The fidelity of the reverse transcriptase in cDNA synthesis is increased by the use of a second enzyme which possesses 3'-5' exonuclease activity.

A. Selection of the First and the Second Enzyme Pair

In the subject method for DNA synthesis, any enzyme comprising DNA polymerization activity may be mixed with a second enzyme comprising 3'-5' exonuclease activity and reduced polymerization activity.

When both first and second enzymes in the mixture comprise 3'-5' exonuclease activity, it may be desirable to combine two enzymes with different proofreading activities. By "different proofreading activity", it means that two 3'-5' exonucleases exhibits different proofreading preference for a nucleotide. For example, one 3'-5' exonuclease may proofread a G-T mispair more efficiently than an A-A mispair, another exonuclease having a different proofreading preference may proofread an A-A mispair more efficiently than a G-T mispair. By using a second enzyme with a different proofreading preference from the first enzyme of the subject composition, one can enhance proofreading of the first enzyme by providing proofreading to mispairs which the first enzyme is not capable of recognizing and excising efficiently.

Another factor to consider when selecting the first and the second enzymes of the subject invention is the compatibility of reaction conditions (e.g., pH, buffer composition, temperature requirement, etc.) required by each enzyme.

In a preferred embodiment, the subject composition comprises a wild-type Pfu DNA polymerase as the first enzyme and a mutant Pfu DNA polymerase with reduced DNA polymerization activity as the second enzyme. Preferably, the mixture comprises a ratio of 2.5-5U Pfu DNA polymerase plus an amount of a polymerase reduced mutant corresponding to <0.01U DNA polymerase activity and 0.007U to 0.04U of 3'-5' exonuclease activity (or the amount of exonuclease activity containing within approximately 0.5 to 10U wild type Pfu). More preferably, the mixture comprises a ratio of 2.5-5U Pfu DNA polymerase plus an amount of a polymerase reduced mutant corresponding to <0.01U DNA polymerase activity and 0.02U of 3'-5' exonuclease activity (or the amount of exonuclease activity contained within 2-3U wild type Pfu). In a preferred embodiment, the enzyme mixture composition comprises a wild-type Pfu DNA polymerase with 2.5U DNA polymerization activity and 0.02U 3'-5' exonuclease activity as the first enzyme and a mutant DNA polymerase with reduced DNA polymerization activity (e.g., G387P) with 0.02U 3'-5' exonuclease activity as the second enzyme.

In another preferred embodiment, the subject composition comprises a wild-type Taq DNA polymerase as the first enzyme and a mutant Pfu DNA polymerase with reduced DNA polymerization activity as the second enzyme. Preferably, the enzyme mixture comprises a ratio of 2.5U Taq DNA polymerase plus an amount of a polymerase deficient mutant corresponding to <0.1U DNA polymerase activity and 0.01 to 0.2U of 3'-5' exonuclease activity (or the amount of exonuclease activity contained within 1-20U wild type Pfu). More preferably, the enzyme mixture comprises a ratio of 2.5U Taq DNA polymerase plus an amount of a polymerase deficient mutant corresponding to <0.01U DNA polymerase activity and 0.08U of 3'-5' exonuclease activity (or the amount of exonuclease activity contained within 10-12U wild type Pfu). In a preferred embodiment, the enzyme mixture composition comprises a wild-type Taq DNA polymerase with 2.5U polymerization activity as the first enzyme and a mutant Pfu DNA polymerase with reduced polymerization activity (e.g., G387P) with 0.08U 3'-5' exonuclease activity.

Preferably the mutant Pfu DNA polymerase with reduced DNA polymerization activity comprises one or more mutations at amino acid positions selected from the group consisting of: D405, Y410, T542, D543, K593, Y595, Y385, G387, and G388.

More preferably, the mutant Pfu DNA polymerase comprises one or more mutations selected from the group consisting of: D405E, Y410F, T542P, D543G, K593T, Y595S, Y385Q, Y385S, Y385N, Y385L, Y385H, G387S, G387P, and G388P.

B. The Ratio of Polymerization to Exonuclease Activity in the Enzyme Mixture

In a variety of DNA synthesis and amplification procedures, the compositions of the present invention provide superior synthesis results (e.g., higher fidelity and efficiency), as compared with the synthesis results obtained with a single DNA polymerase or with a mixture comprising two wild type DNA polymerases. When using the subject composition, the ratio of total polymerization activity and total exonuclease activity in the enzyme mixture may be critical for optimal efficiency and fidelity of DNA synthesis.

In the enzyme mixture of the subject invention, when DNA polymerases are used as the first and second enzymes, both enzymes may contribute to the polymerization and/or 3'-5' exonuclease activity. When an enzyme other than a conventional DNA polymerase is used as the first enzyme (e.g., a reverse transcriptase), both enzymes may contribute to DNA polymerization activity, but only the second enzyme contribute to the 3'-5' exonuclease activity. When an enzyme other than a DNA polymerase is used as the second enzyme (e.g., E. coli exonuclease I), both enzymes may contribute to the 3'-5' exonuclease activity, but only the first enzyme contribute to the polymerization activity of the enzyme mixture.

The ratio of the first and the second enzyme in the subject composition may be varied with respect to one another. The ratio of the DNA polymerization activity to 3'-5' exonuclease activity present in the subject composition employed in a given synthesis procedure may be readily optimized by performing a series of simple experiments in which the ratio of the DNA polymerization activity to the exonuclease activity in the reaction mixture are systematically varied with respect to one another and the synthesis results compared.

3'-5' exonuclease activity has been shown to degrade unannealed primers. The degraded primers would not be available in subsequent rounds of DNA amplification and would therefore effect the efficiency of the PCR reaction. In applications requiring very high product yield, it may therefore be desirable to have a low concentration of the exonuclease activity relative to the DNA polymerization activity to decrease this effect and to increase the product yield. However, when fidelity is more important than yield, it may be desirable to have a high concentration of the exonuclease activity relative to the DNA polymerization activity to increase the accuracy of the synthesis or amplification so long as the level of polymerization activity does not significantly inhibit the efficiency of the amplification.

In a preferred embodiment, the ratio of the DNA polymerase activity and the exonuclease activity in the enzyme mixture is about (2.5-5U of DNA polymerization activity)/

(0.02-5U of 3'-5' exonulcease activity), for example, about (2.5U of DNA polymerization activity)/(0.04-0.08U of 3'-5' exonulcease activity).

Applications of the Subject Invention

In one aspect, the invention provides a method for DNA synthesis using the compositions of the subject invention. The subject compositions may be used in various methods of polynucleotide synthesis in essentially the same manner as the DNA polymerase or other synthetic enzyme present in the subject composition. Typically, synthesis of a polynucleotide requires a synthesis primer, a synthesis template, polynucleotide precursors for incorporation into the newly synthesized polynucleotide, (e.g. dATP, dCTP, dGTP, dTTP), and the like. Detailed methods for carrying out polynucleotide synthesis are well known to the person of ordinary skill in the art and can be found, for example, in *Molecular Cloning second edition*, Sambrook et al., Cold Spring Harbor Laboratory Press, Cold Spring Harbor, N.Y. (1989).

A. Application In Amplification Reactions

"Polymerase chain reaction" or "PCR" refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. Patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

For ease of understanding the advantages provided by the present invention, a summary of PCR is provided. The PCR reaction involves a repetitive series of temperature cycles and is typically performed in a volume of 50-100 μl. The reaction mix comprises dNTPs (each of the four deoxynucleotides dATP, dCTP, dGTP, and dTTP), primers, buffers, DNA polymerase, and polynucleotide template. PCR requires two primers that hybridize with the double-stranded target polynucleotide sequence to be amplified. In PCR, this double-stranded target sequence is denatured and one primer is annealed to each strand of the denatured target. The primers anneal to the target polynucleotide at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990, *PCR Protocols: A Guide to Methods and Applications*, Academic Press, Inc., San Diego, Calif., which are incorporated herein by reference.

1. Thermostable Enzymes

For PCR amplifications, the enzymes used in the invention are preferably thermostable. As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

2. PCR Reaction Mixture

In addition to the subject enzyme mixture, one of average skill in the art may also employ other PCR parameters to increase the fidelity of synthesis/amplification reaction. It has been reported PCR fidelity may be affected by factors such as changes in dNTP concentration, pH, units of enzyme used per reaction, and the ratio of $Mg^{2+}$ to dNTPs present in the reaction (Mattila et al., 1991, supra).

$Mg^{2+}$ concentration affects the annealing of the oligonucleotide primers to the template DNA by stabilizing the primer-template interaction, it also stabilizes the replication complex of polymerase with template-primer. It can therefore also increases non-specific annealing and produced undesirable PCR products (gives multiple bands in gel). When non-specific amplification occurs, $Mg^{2+}$ may need to be lowered or EDTA can be added to chelate $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in *DNA Replication $2^{nd}$ edition*, supra). Divalent cation is supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration is between 1 and 200 mM, preferably the concentration is between 5 and 100 mM, although the optimum concentration may vary depending on the polymerase used in the reaction.

Deoxyribonucleotide triphosphates (dNTPs) are added as solutions of the salts of dATP, dCTP, dGTP, dUTP, and dTTP, such as disodium or lithium salts. In the present methods, a final concentration in the range of 1 µM to 2 mM each is suitable, and 100-600 µM is preferable, although the optimal concentration of the nucleotides may vary in the reverse transcription reaction depending on the total dNTP and divalent metal ion concentration, and on the buffer, salts, particular primers, and template. For longer products, i.e., greater than 1500 bp, 500 µM each dNTP may be preferred when using a Tris-HCl buffer.

dNTPs chelate divalent cations, therefore amount of divalent cations used may need to be changed according to the dNTP concentration in the reaction. Excessive amount of dNTPs (e.g., larger than 1.5 mM) can increase the error rate and possibly inhibits DNA polymerases. Lowering the dNTP (e.g., to 10-50 µM) may therefore reduce error rate. PCR reaction for amplifying larger size template may need more dNTPs.

One suitable buffering agent is Tris-HCl, preferably pH 8.3, although the pH may be in the range 8.0-8.8. The Tris-HCl concentration is from 5-250 mM, although 10-100 mM is most preferred. A preferred buffering agent is Bicine-KOH, preferably pH 8.3, although pH may be in the range 7.8-8.7. Bicine acts both as a pH buffer and as a metal buffer.

PCR is a very powerful tool for DNA amplification therefore very little template DNA is needed. However, in some embodiments, to reduce the likelihood of error, a higher DNA concentration may be used, though too many templates may increase the amount of contaminants and reduce efficiency.

Usually, up to 3 µM of primers may be used, but high primer to template ratio can results in non-specific amplification and primer-dimer formation. Therefore it is usually necessary to check primer sequences to avoid primer-dimer formation. In a preferred embodiment, 0.1-0.5 µM of primers are used.

3. Cycling Parameters

Denaturation time may be increased if template GC content is high. Higher annealing temperature may be needed for primers with high GC content or longer primers. Gradient PCR is a useful way of determining the annealing temperature. Extension time should be extended for larger PCR product amplifications. However, extension time may need to be reduced whenever possible to limit damage to enzyme.

The number of cycle can be increased if the number of template DNA is very low, and decreased if high amount of template DNA is used.

4. PCR Enhancing Factors and Additives

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reaction. EDTA less than 0.5 mM may be present in the amplification reaction mix. Detergents such as Tween-20™ and Nonidet™ P-40 are present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 µg/µl) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethlamine N-oxide (TMANO) may also be used. Test PCR reactions may be performed to determine optimum concentration of each additive mentioned above.

Various specific PCR amplification applications are available in the art (for reviews, see for example, Erlich, 1999, *Rev Immunogenet.*, 1:127-34; Prediger 2001, *Methods Mol. Biol.* 160:49-63; Jurecic et al., 2000, *Curr. Opin. Microbiol.* 3:316-21; Triglia, 2000, *Methods Mol. Biol.* 130:79-83; MaClelland et al., 1994, *PCR Methods Appl.* 4:S66-81; Abramson and Myers, 1993, *Current Opinion in Biotechnology* 4:41-47; each of which is incorporated herein by references).

The subject invention can be used in PCR applications include, but are not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be use to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be use as control to verify the quality of PCR; x) Q/C-PCR (Quantitative comparative) which uses an internal control DNA sequence (but of different size) which compete with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis.

It should be understood that this invention is not limited to any particular amplification system. As other systems are developed, those systems may benefit by practice of this invention. A recent survey of amplification systems was published in.

B. Applications in Reverse Transcription

The term "reverse transcriptase" describes a class of polymerase characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation (e.g., PCR amplification by a DNA-dependent DNA polymerase).

Avian myoblastosis virus (AMV) reverse transcriptase was the first widely used RNA-dependent DNA polymerase (Verma, 1977, Biochem. Biophys. Acta 473:1). The enzyme has 5'-3' RNA-directed DNA polymerase activity, 5'-3' DNA-directed DNA polymerase activity, and RNase H activity. RNase H is a processive 5' and 3' ribonuclease specific for the RNA strand of RNA-DNA hybrids (Perbal, 1984, *A Practical Guide to Molecular Cloning*, Wiley & Sons New York). Errors in transcription cannot be corrected by reverse transcriptase because known viral reverse transcriptases lack the 3'-5' exonuclease activity necessary for proofreading (Saunders and Saunders, 1987, *Microbial Genetics Applied to Biotechnology*, Croom Helm, London). The use of the second enzyme in the subject composition provides proofreading for the reverse transcription reaction. A detailed study of the activity of AMV reverse transcriptase and its associated RNase H activity has been presented by Berger et al., 1983, Biochemistry 22:2365-2372.

The reaction mixture for reverse transcription usually includes enzymes, aqueous buffers, salts, oligonucleotide primers, target polynucleotide, and nucleoside triphosphates. Depending upon the context, the mixture can be either a complete or incomplete reverse transcription reaction mixture. The reaction mixture can be modified according to the conditions required by the second enzyme of the subject composition. It is known that cDNAs can be obtained from mRNAs in vitro using a reverse transcriptase (RNA-dependent DNA polymerase). The full length cDNA strands produced in turn may be used as a template for subsequent amplification reaction (e.g., PCR) and the like.

Reverse transcription in combination with PCR (RT-PCT) is utilized to detect the presence of one or many specific RNA molecules which may be present in a sample. The method can be used to detect, for example, RNA from different organisms (such as viruses, bacteria, fungi, plants, and animals), or RNA indicative of an infection, a disease state, or predisposition to a disease. For example, mRNA specific to tumor cells can be detected. The method is also useful for detecting a class of microorganisms or a group of related disease conditions.

Reverse transcription can generally be performed at any temperature within the functional temperature range of the reverse transcriptase. Preferably, the temperature of incubation is any temperature at which the reverse transcriptase is functional and the primer remains hybridized to the RNA molecule. For non-thermostable reverse transcriptases, preferred temperatures are those temperatures that are at or around the optimum temperature for the reverse transcriptase. For most non-thermostable reverse transcriptases this temperature will be between about 25° C. and 45° C.

U.S. Pat. No. 5,994,079 discloses thermostable reverse transcriptases (herein incorporated by reference). $Mn^{2+}$ is preferred as the divalent cation and is typically included as a salt, for example, manganese chloride ($MnCl_2$), manganese acetate ($Mn(OAc)_2$), or manganese sulfate ($MnSO_4$). If $MnCl_2$ is included in a reaction containing 10 mM Tris buffer, for example, the $MnCl_2$ is generally present at a concentration of 0.5-7.0 mM; 0.8-1.4 mM is preferred when 200 µM of each dGTP, dATP, dUTP, and, dCTP are utilized; an 1.2 mM $MnCl_2$ is most preferred.

A thermostable reverse transcriptase may retain at least 5% of its maximum activity at any temperature above 50° C. or has an optimal temperature of at least 50° C. The highest temperature at which a thermostable reverse transcriptase is functional can be quite high. For this reason, preferred temperature ranges for reverse transcription when a thermostable reverse transcriptase is used are most conveniently described in terms of the calculated melting temperature of a hybrid between the RNA molecule of interest and the primer. Such a melting temperature is referred to herein as the RNA/primer melting temperature (R/P Tm). Preferred ranges include a temperature from 20° C. below the melting temperature of a hybrid between the RNA molecule of interest and the primer and 5° C. above the melting temperature of a hybrid between the RNA molecule of interest and the primer. In general, the closer the temperature is to the R/P Tm, the greater the degree of discrimination there will be between specific and non-specific hybrids of the RNA and primer. If the temperature is close to the R/P Tm, however, decreased stability of specific hybrids may cause priming to be less efficient.

R/P Tm can be determined either by calculation or by empirical measurement. For calculating R/P Tm, any established formula for calculating stability of polynucleotide hybrids can be used. A preferred formula for calculating R/P Tm is Tm=81.5+16.6(log M)$^+$0.41(% G$^+$C)−0.72(% formamide), which was derived from studies on the stability of perfectly-matched DNA:DNA hybrids. For RNA:DNA hybrids, incorporating formamide concentration in the formula does not hold because the relationship between formamide concentration and the depression of Tm is not linear. At 80% formamide, RNA:DNA hybrids are more stable than DNA:DNA hybrids, increasing the Tm by about 10 to 30° C. depending on the sequence (Hames & Higgins, Polynucleotide Hybridisation: A Practical Approach (IRL Press Limited, Oxford, England. 1985)). Carrying out the reaction in 80% formamide can therefore also be used to suppress formation of DNA:DNA duplexes, to preferentially select RNA:DNA hybrids, and to estimate the Tm for R/P. Because the empirically derived formulas for the estimation of RNA:DNA hybrid Tm may not be as accurate for short DNA primers, the hybridization temperature is preferably determined by assessing hybrid stability in 0.1-0.4 M monovalent cation at temperatures ranging from 40 to 60° C. R/P Tm can also be determined empirically (Lesnick and Freier, 1995, Biochemistry 34:10807-10815, McGraw et al., 1990, Biotechniques 8:674-678; and Rychlik et al., 1990, Polynucleotides Res. 18:6409-6412).

The fidelity of viral reverse transcriptases, such as AMV-RT and MoMuLV-RT, may be compared to thermoactive reverse transcriptases by a straightforward assay procedure described in U.S. Pat. No. 5,994,079 (supra). Plasmid BS$^+$ (Stratagene) can be used for such an assay.

The plasmid encodes an α-complementing β-galactosidase activity and can be linearized with NdeI. T3 RNA polymerase is used to prepare a cRNA transcript of the α-donor region. After treatment of the cRNA with RNase-free DNase and isolation of the cRNA, the cRNA is used as a template for a reverse transcription/amplification reaction. A reverse transcription primer complementary to the 3' end of the cDNA containing an NdeI sequence at its 5' terminus, and an upstream PCR primer comprising a PstI sequence at the 5' termini provide a 752 bp PCR product. The PCR product and the pBS$^+$ vector are then digested with NdeI and PstI followed by ligation of the PCR product into the vector and transformation into a suitable host. The presence of white colonies indicates that a mutation had occurred during the RT or PCR amplification. The assay provides means for assigning a relative value to the fidelity of the reverse transcriptase activity of various enzymes. Specific mutations can be determined by sequence analysis.

Following reverse transcription of RNA, the RNA can be removed from the RNA/cDNA hybrid by heat denaturation or by a number of other known means such as alkali, heat, or enzyme treatment. Enzyme treatment may consist of, for example, treating the RNA/cDNA hybrid with RNase H. RNase H is specific for RNA strands within an RNA/DNA double-stranded molecule.

The subject composition is suitable for high fidelity transcribing and amplifying RNA from a number of sources. The RNA template may be contained within a polynucleotide preparation from an organism, for example, a viral or bacterial polynucleotide preparation. The preparation may contain cell debris and other components, purified total RNA, or purified mRNA. The RNA template may be a population of heterogeneous RNA molecules in a sample or a specific target RNA molecule.

RNA suitable for use in the present methods may be contained in a biological sample suspected of containing a specific target RNA. The biological sample may be a heterogeneous sample in which RNA is a small portion of the sample, as in for example, a blood sample or a biopsied tissue sample. Thus, the subject composition is useful for clinical detection and diagnosis. The RNA target may be indicative of a specific disease or infectious agent.

RNA may be prepared by any number of methods known in the art; the choice may depend on the source of the sample and availability. Methods for preparing RNA are described in Davis et al., 1986, *Basic Methods in Molecular Biology*, Elsevier, N.Y., Chapter 11; Ausubel et al., 1987, *Current Protocols in Molecular Biology*, Chapter 4, John Wiley and Sons, NY; Kawasaki and Wang, 1989, *PCR Technology*, ed. Erlich, Stockton Press NY; Kawasaki, 1990, *PCR Protocols: A Guide to Methods and Applications*, Innis et al. eds. Academic Press, San Diego; all of which are incorporated herein by references.

C. Detection of Amplified Product

Detection of amplified polynucleotide product can be accomplished by any of a variety of well known techniques. In a preferred embodiment, the amplified product is separated on the basis of molecular weight by gel electrophoresis, and the separated products are then visualized by the use of polynucleotide specific stains which allow one to observe the discrete species of resolved amplified product present in the gel. Although numerous polynucleotide specific stains exist and would be suitable to visualize the electrophoretically separated polynucleotides, ethidium bromide is preferred.

Alternative methods suitable to detect the amplified polynucleotide product include hybridization-based detection means that use a labeled polynucleotide probe capable of hybridizing to the amplified product. Exemplary of such detection means include the Southern blot analysis, ribonuclease protection analysis using in vitro labeled polyribonucleotide probes, and similar methods for detecting polynucleotides having specific nucleotide sequences. See, for example, Ausubel et al., *Current Protocols in Molecular Biology*, John Wiley & Sons, 1987.

Amplified products (e.g., by PCR or RT-PCR) using the subject composition of the invention can be used for subsequent analysis such as sequencing or cloning.

D. Application in Direct Cloning of PCR Amplified Product

While it is understood that the amplified product using subject composition can be cloned by any method known in the art. In one embodiment, the invention provides a composition which allows direct cloning of PCR amplified product.

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation.

A method for directly cloning PCR products eliminates the need for preparing primers having restriction recognition sequences and it would eliminate the need for a restriction step to prepare the PCR product for cloning. Additionally, such method would preferably allow cloning PCR products directly without an intervening purification step.

U.S. Pat. Nos. 5,827,657 and 5,487,993 (hereby incorporated by their entirety) discloses method for direct cloning of PCR products using a DNA polymerase which takes advantage of the single 3'-deoxy-adenosine monophosphate (dAMP) residues attached to the 3' termini of PCR generated nucleic acids. Vectors are prepared with recognition sequences that afford single 3'-terminal deoxy-thymidine monophosphate (dTMP) residues upon reaction with a suitable restriction enzyme. Thus, PCR generated copies of genes can be directly cloned into the vectors without need for preparing primers having suitable restriction sites therein.

Taq DNA polymerase exhibits terminal transferase activity that adds a single dATP to the 3' ends of PCR products in the absence of template. This activity is the basis for the TA cloning method in which PCR products amplified with Taq are directed ligated into vectors containing single 3' dT overhangs. Pfu DNA polymerase, on the other hand, lacks terminal transferase activity, and thus produces blunt-ended PCR products that are efficiently cloned into blunt-ended vectors.

In one embodiment, the subject invention comprises a Taq DNA polymerase as the first enzyme and a mutant Pfu DNA polymerase with reduced polymerization activity as the second enzyme. Taq DNA polymerase in the composition produces amplified DNA product with 3'-dAMP and allows direct cloning of the amplified product, while the mutant Pfu DNA polymerase provides fidelity for the amplification.

Kits

The invention herein also contemplates a kit format which comprises a package unit having one or more containers of the subject composition and in some embodiments including containers of various reagents used for polynucleotide synthesis, including synthesis in PCR. The kit may also contain one or more of the following items: polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

EXAMPLES

The following examples are offered for the purpose of illustrating, not limiting, the subject invention.

Example 1

Constructing Mutants of Pfu DNA Polymerase with Reduced DNA Polymerase Activity

We introduced mutations into Pfu DNA polymerase that were likely to reduce or eliminate DNA polymerase activity, while having minimal effects on proofreading activity. The mutations selected were identified from previous mutagenesis studies carried out using related Family B DNA polymerases. We made the same amino acid side chain substitutions in the polymerization domain at the following residues in Pfu (D405E, Y410F, T542P, D543G, K593T, Y595S) (Table 1).

Mutations were also introduced within the partitioning domain at amino acids 384-389 (SYTGGF) in Pfu DNA polymerase (Table 1).

The DNA template used for mutagenesis contained the Pfu pol gene, cloned into pBluescript (pF72 clone described in U.S. Pat. No. 5,489,523) and expressed with an N-terminal $His_6$ tag for affinity purification. A modified QuikChange (Stratagene) protocol was used to insert the $His_6$ tag at the 5' end of the Pfu pol gene, just after the initiator ATG. The insertion reaction was carried out in two steps. In the first step, a standard QuikChange reaction was carried out in the presence of Tth ligase (10U/RXN) using only the $His_6$ forward primer. After 18 cycles, the reaction was DpnI-digested for one hour at 37° C. and then purified with the StrataPrep® Plasmid Miniprep Kit (Stratagene). The purified material served as the template in the second QuikChange reaction, which employed only the $His_6$ reverse primer. After 18 cycles, the second reaction was DpnI-digested for one hour at 37° C., and then transformed. The $His_6$-Pfu pol construct was confirmed by both PCR amplification and sequencing using the Big Dye sequencing kit.

Point mutations were introduced into the Pfu pol gene using the QuikChange Site-Directed Mutagenesis Kit (Stratagene). Clones were sequenced to verify incorporation of the desired mutations.

TABLE 1

| | Activity of partially-purified His-tagged Pfu mutants (Nickel-resin eluates): | | | | | |
|---|---|---|---|---|---|---|
| | Polymerase activity | | | Exonuclease activity | | Rel. exo/pol |
| Mutation | Cpms @ 50 ng (500 ng) | % wild type @ 50 ng* | | Cpms (50 ng) | % wild type@ | vs. wt (1.0)$ |
| Partitioning | | | | | | |
| S384G | 46920 | 71 | | 1425 | ≧100 | 2.3 |
| S384K | 66545 | 100 | | 554 | 63 | 0.6 |
| Y385N | 1123 | 2 | | 158 | 18 | 10.6 |
| Y385W | 10515 (24519) | 16 | | 36 | 4 | 0.3 |
| Y385L | 2383 | 4 | | 180 | 21 | 5.7 |
| Y385H | 4276 | 6 | | 91 | 10 | 1.6 |
| Y385Q | 386 (5431) | 0.6 | | 252 | 29 | 49.2 |
| Y385S | 1095 (4206) | 2 | | 578 | 66 | 39.8 |
| Y385F | 80685 (21580) | 100 | | 1008 | 100 | 0.9 |
| T386E | 48296 | 73 | | 263 | 30 | 0.4 |
| T386Y | 47318 | 72 | | 1112 | ≧100 | 1.8 |
| T386G | 46289 | 70 | | 1011 | ≧100 | 1.6 |
| G387S | 648 | 1 | | 169 | 19 | 19.7 |
| G387P | 258 (66) | 0.4 | | 500 | 57 | 146.2 |
| G388A | 2560 | 4 | | 73 | .008 | 2.2 |
| G388S | 74551 | 100 | | 670 | 76 | 0.7 |
| G388P | 1222 | 2 | | 202 | 23 | 12.5 |
| F389Y | 43455 (29809) | 66 | | 37 | 4 | .06 |
| F389L | 72647 | 100 | | 1054 | ≧100 | 1.1 |
| F389V | 30641 | 46 | | 614 | 70 | 1.5 |
| F389S | 17998 | 27 | | 1335 | ≧100 | 5.6 |
| F389H | 19623 | 30 | | 543 | 62 | 2.1 |

| | Polymerase activity | | Exo/pol activity | | |
|---|---|---|---|---|---|
| Polymerase | Cpms @ 5 ng | % wild type @ 5 ng# | Cpms exonuclease | Cpms Polymerase | Rel. exo/pol vs. wt (1.0)& |
| DXXSLYP | | | | | |
| D405E | 69 (500 ng) | <0.2 | 321 | 0 | >396 |
| Y410F | 10181 | 27 | 698 | 16189 | 5.3 |

TABLE 1-continued

Activity of partially-purified His-tagged Pfu mutants (Nickel-resin eluates):

| YXDTDS | | | | | |
|---|---|---|---|---|---|
| T542P | 27 | .07 | 1105 | 0 | >1364 |
| D543G | 10 | .03 | 704 | 687 | 127 |
| T542P/D543G | 23 | .06 | 505 | 0 | >623 |
| KXY | | | | | |
| K593T | 155 | .4 | 668 | 0 | >825 |
| Y595S | 6107 | 16 | 1072 | 2684 | 49 |

100% for wt Pfu equals:
*66146 cpms;
38014 cpms;
@877 cpms
exo/pol for wt Pfu equals:
$0.01326;
&0.0081

Example 2

Affinity Purification of His-Tagged Pfu DNA Polymerase Mutants

Bacterial expression of Pfu mutants. Plasmid DNA was purified with the StrataPrep® Plasmid Miniprep Kit (Stratagene), and used to transform XL-10 Gold cells. Ampicillin resistant colonies were grown up in 1-5 liters of LB media containing Turbo Amp™ antibiotic (100 μg/μl) at 37° C. with moderate aeration. The cells were collected by centrifugation and stored at −20° C.

Purification ($His_6$ tag protocol/batch binding method): Cells pellets were resuspended in native binding buffer (20 mM phosphate (pH 7.8), 500 mM NaCl). Egg white lysozyme (100 μg/ml) was added and the cells were incubated for 15 minutes on ice. Cell suspensions were subjected to sonication three times with a Bronson Sonifier 250 at a duty cycle of 80% and an output level of 5 for 45 seconds. The suspensions were left on ice to cool between sonication events. The lysate was cleared by centrifugation at 26,890 g. The cleared lysates were added to 5 mls of ProBond Ni resin (Invitrogen), equilibrated in native binding buffer, and the slurry was incubated for two hours with gentle agitation at 4° C. The resin was settled by low speed centrifugation (800×g). The resin was washed three times with 4 ml of native binding buffer (pH 7.8) by resuspending the resin, rocking the slurry for two minutes, and then separating the resin from the supernatant by gravity centrifugation. The resin was then washed in the same fashion with native wash buffer (20 mM phosphate (pH 6.0), 500 mM NaCl). Protein was eluted with two 5-ml additions of 350 mM Imidazole elution buffer (20 mM phosphate, 500 mM NaCl, 350 mM Imidazole (pH 6.0)) by resuspending the resin, rocking the slurry for five minutes, and then separating the resin from the supernatant by gravity centrifugation. Eluted proteins were spin concentrated using Centricon 30 centrifugal filter devices (Amicon). Protein samples were evaluated for size and purity by SDS-PAGE using Tris-Glycine 4-20% acrylamide gradient gels. Gels were stained with silver stain or Sypro Orange (Molecular Probes).

Alternative expression/purification: Alternatively, Pfu mutants were subcloned into the pCAL-n-EK vector (Affinity™ Protein Expression and Purification System) which contains an upstream, in-frame calmodulin binding peptide (CBP) tag for purifying fusion proteins with calmodulin agarose. Plasmid DNA was purified with the StrataPrep® Plasmid Miniprep Kit (Stratagene), and used to transform BL21 (DE3) CodonPlus® cells. Ampicillin resistant colonies were grown up in 1-5 liters of LB media containing Turbo Amp™ antibiotic (100 μg/μl) at 30° C. with moderate aeration. When cultures reached an absorbance at $OD_{600}$ of 0.6 to 1.0, the cells were induced with 1 mM IPTG and incubated in the same manner for 2 hours to overnight (16 hours). The cells were collected by centrifugation and stored at −20° C.

Cells pellets were resuspended to an approximate concentration of 0.25g/ml in buffers identical or similar to calcium binding buffer (50 mM Tris-HCL (pH 8.0), 150 mM NaCl, 1 mM magnesium acetate and 2 mM CaCl). Egg white lysozyme (100 μg/ml) was added and the cells were incubated for 15 minutes on ice. Cell suspensions were subjected to sonication three times with a Bronson Sonifier 250 at a duty cycle of 80% and an output level of 5 for 45 seconds. The suspensions were left on ice to cool between sonication events. The lysate was cleared by centrifugation at 26,890 g.

The cleared lysates were added to 1 ml of calmodulin agarose (CAM agarose), equilibrated in buffer, and the slurry was incubated with gentle agitation at 4° C. After two hours the reactions were centrifuged at 3000 g for 5 minutes to collect the CAM agarose and recombinant protein. The lysate supernatant was removed and the CAM agarose was washed at least once by resuspending the resin in 50 ml of calcium binding buffer followed by collection of the CAM agarose by centrifugation as described above. The CAM agarose was transferred to a disposable 15 ml column, packed, then washed with at least 200 ml of calcium binding buffer. Recombinant proteins were eluted from the column by using a buffer similar or identical to 50 mM Tris-HCl (pH 8.0), 1M NaCl, 2 mM EGTA.

Protein samples were evaluated for size and purity by SDS-PAGE using Tris-Glycine 4-20% acrylamide gradient gels. Gels were stained with silver stain or Sypro Orange (Molecular Probes).

Example 3

Assaying DNA Polymerase and 3'-5' Exonuclease Activities Of Pfu DNA Polymerase Mutants Pfu mutant preparations were assayed for DNA polymerase and 3'-5' exonuclease activities as follows.

DNA polymerase. DNA polymerase activity was measured by monitoring incorporation of radiolabelled TTP into activated calf thymus DNA. A suitable DNA polymerase reaction cocktail contained: 1×PCR reaction buffer, 200 μM each dATP, dCTP, and dGTP, 195 μM TTP, 5 μM [$^3$H]TTP (NEN #NET-221H, 20.5 Ci/mmole; partially evaporated to remove EtOH), and 250 μg/ml of activated calf thymus DNA (e.g., Pharmacia #27-4575-01). DNA polymerases (wt Pfu or Pfu mutants) were diluted in Pfu storage buffer and 1 μl of each enzyme dilution was added to 10 μl aliquots of polymerase cocktail. Polymerization reactions were conducted in duplicate or triplicate for 30 minutes at 72° C. The extension reactions were quenched on ice, and then 5 μl aliquots were spotted immediately onto DE81 ion-exchange filters (2.3 cm; Whatman #3658323). Unincorporated [$^3$H]TTP was removed by 6 washes with 2×SCC (0.3M NaCl, 30 mM sodium citrate, pH 7.0), followed by a brief wash with 100% ethanol. Incorporated radioactivity was measured by scintillation counting.

Reactions that lack enzyme were set up along with sample incubations to determine "total cpms" (omit filter wash steps) and "minimum cpms" (wash filters as above). Sample cpms were subtracted by minimum cpms to determine "corrected cpms" for each DNA polymerase.

To determine percent (%) activity relative to wild type Pfu, ~50-500 ng of purified Pfu mutants were assayed in a nucleotide incorporation assay, alongside wild type Pfu diluted serially over the linear range of the assay (50-500 pg; 0.003-0.03U).

Exonuclease assays. Exonuclease reactions were performed (in triplicate) by adding 4 μl aliquots of diluted DNA polymerases (0.25-10U wt Pfu; 5-200 ng) to 46 μl of reaction cocktail. Reactions were incubated for 1 hour at 72° C. Reactions lacking DNA polymerase were also set up along with sample incubations to determine "total cpms" (no TCA precipitation) and "minimum cpms" (TCA precipitation, see below).

Exonuclease reactions were stopped by transferring the tubes to ice. Sonicated salmon sperm DNA (150 μl; 2.5 mg/ml stock) and TCA (200 μl; 10% stock) were added to all but the "total cpms" tubes. The precipitation reactions were incubated for ≧15 minutes on ice, and then spun in a microcentrifuge at 14,000 rpm for 10 minutes. 200 μl of the supernatant was removed, being careful not to disturb the pellet, and transferred to scintillation fluid (Bio-Safe II™, Research Products International Corp.). The samples were thoroughly mixed by inversion and then counted in a scintillation counter.

To determine percent (%) exonuclease activity relative to wild type Pfu, equivalent amounts of Pfu and purified Pfu mutants (which fall in the linear range of the assay; ~5-200 ng Pfu) are assayed in an exonuclease assay.

Results: Several Pfu mutants exhibited reductions in DNA polymerase activity compared to wild type Pfu, when tested as partially purified (~50% purity) preparations eluted from nickel resins (Table 1). Pfu mutants showing <10% DNA polymerase activity and at least 10% exonuclease activity include the partitioning domain mutants: Y385QSNLH, G387SP, and G388P and the polymerase domain mutants: D405E, T542P, D543G, and K593T. The initial measurements of % DNA polymerase activity shown in Table 1 was considered as approximate estimates, due to the purity of the protein samples tested and uncertainties as to whether all protein amounts tested were in the linear range of the assay.

Example 4

Purification of Pfu DNA Polymerase Mutants by Conventional Column Chromatography The untagged or affinity-tagged fusions of Pfu K593T and G387P mutants were purified as follows. Cells pellets (12-24 grams) were resuspended in 3 volumes of lysis buffer (buffer A: 50 mM Tris HCl (pH 8.2), 1 mM EDTA, and 10 mM βME). Lysozyme (1 mg/g cells) and PMSF (1 mM) were added and the cells were lysed for 1 hour at 4° C. The cell mixture was sonicated, and the debris removed by centrifugation at 15,000 rpm for 30 minutes (4° C.). Tween 20 and Igepal CA-630 were added to final concentrations of 0.1% and the supernatant was heated at 72° C. for 10 minutes. Heat denatured *E. coli* proteins were then removed by centrifugation at 15,000 rpm for 30 minutes (4° C.).

The supernatant was chromatographed on a Q-Sepharose™ Fast Flow column (~5 ml column), equilibrated in buffer B (buffer A plus 0.1% (v/v) Igepal CA-630, and 0.1% (v/v) Tween 20). Flow-through fractions were collected and then loaded directly onto a P11 Phosphocellulose column (1.6×10 cm), equilibrated in buffer C (same as buffer B, except pH 7.5). The column was washed and then eluted with a 0-0.7M KCl gradient/Buffer C. Fractions containing Pfu DNA polymerase mutants (95 kD by SDS-PAGE) were dialyzed overnight against buffer D (50 mM Tris HCl (pH 7.5), 5 mM βME, 5% (v/v) glycerol, 0.2% (v/v) Igepal CA-630, 0.2% (v/v) Tween 20, and 0.5M NaCl) and then applied to a Hydroxyapatite column (1.0×1.3 cm; ~1 ml), equilibrated in buffer D. The column was washed and Pfu DNA polymerase mutants were eluted with buffer D2 containing 400 mM KPO$_4$, (pH 7.5), 5 mM βME, 5% (v/v) glycerol, 0.2% (v/v) Igepal CA-630, 0.2% (v/v) Tween 20, and 0.5 M NaCl. Purified proteins were spin concentrated using Centricon YM30 devices, and exchanged into Pfu final dialysis buffer (50 mM Tris-HCl (pH 8.2), 0.1 mM EDTA, 1 mM dithiothreitol (DTT), 50% (v/v) glycerol, 0.1% (v/v) Igepal CA-630, and 0.1% (v/v) Tween 20).

Results: His-tagged and untagged Pfu G387P and K593T mutants were purified by ion exchange/hydroxyappetite (IE/HA) chromatography. The purified protein preps were analyzed by SDS-PAGE and determined to be of ≧95% purity. The IE/HA purified mutants were tested in a nucleotide incorporation assay to more precisely quantify percent remaining DNA polymerase activity. As shown in Table 3, the Pfu G387P mutant exhibits no significant DNA polymerase activity (<100 cpms above background) when up to 1.2 μg of protein was assayed. These results indicate that the Pfu G387P mutant exhibits <0.01% of the DNA polymerase activity exhibited by wild type Pfu DNA polymerase. In comparison, the Pfu K593T mutant retains approximately 1-2% of the DNA polymerase activity of wild type Pfu.

TABLE 3

Residual Polymerase Activity in IE/HA Purified Pfu Mutant Preps:

| Pfu DNA Polymerase | Amount. Assayed (ng) | Corrected cpms | Relative (%) Polymerase Activity | Mean Relative Polymerase Activity |
|---|---|---|---|---|
| His$_6$-tagged mutant enzyme preps | | | | |
| Wild type | 25 | 16,661 | 100 | 100 |
| G387P | 240 | 42 | 0.026 | Cpms not significantly (<100 cpms) |
|  | 600 | 0 | — | above background; therefore, assume |
|  | 1200 | 16 | 0.002 | <100/16661 × 25/1200 = <0.01% |
| K593T | 80 | 1228 | 2.3 | 1.8 |
|  | 200 | 1774 | 1.3 | |
| Untagged mutant enzyme prep | | | | |
| Wild type | 2 | 6134 | 100 | 100 |
| G387P | 8.4 | 60 | 0.23 | Cpms not significantly (<100 cpms) |
| Prep J | 42 | 0 | — | above background; therefore, assume |
|  | 420 | 8 | 0.0006 | <100/6134 × 2/420 = <0.008% |

Example 5

Verifying the Presence of Proofreading Activity in Pfu Mutants Under PCR Conditions A qualitative assay was used to verify that His$_6$-tagged Pfu mutants retained 3'-5' exonuclease activity under PCR conditions. In this assay, the 900 bp HαlAT target is amplified with exo⁻ Pfu DNA polymerase (2.5U/50 µl) using a forward primer containing a 3'dG, which produces a dG/dG mismatch upon annealing to the DNA template. The amplicon is amplified from human genomic DNA using the forward primer: 5'-GAG.GAG.AGC.AGG.AAA.GGT.GGA.AG-3' (SEQ ID NO. 8) (100 ng/50 µl rxn) and the reverse primer: 5'-GAG. GTA.CAG.GGT.TGA.GGC.TACT.G-3' (SEQ ID NO. 9) (100 ng/50 µl rxn). Amplification is carried out in the absence or presence of varying amounts of His$_6$-tagged Pfu mutants on a Perkin/Elmer 9600 thermal cycler with the following program: (1 cycle) 95° C. for 2.5 minutes; (30 cycles) 95° C. for 40 seconds, 61° C. for 10 seconds, 72° C. for 2.5 minutes; (1 cycle) 72° C. for 7 minutes. In the absence of proofreading activity, exo⁻ Pfu produces low yields of product, presumably because the enzyme can not efficiently extend a dG/dG mismatch. In the presence of Pfu mutants with proofreading activity, the 3'dG should be excised from the primer, thereby allowing exo⁻ Pfu to amplify the target in high yields. This PCR assay was used to verify that Pfu mutants tested in fidelity assays retained sufficient proofreading activity under PCR conditions to excise mismatched PCR primers. Moreover, the assay allowed us to determine the range of protein concentrations that could be added to PCR reactions without inhibition of amplification.

Results: As shown in FIG. 1, amplifications conducted with exo⁻ Pfu alone produced low yields of product due to poor extension of the dG/dG mismatch. Product yields were significantly higher in the presence of the His$_6$-tagged Pfu G387P and K593T mutants, presumably because these mutants excise the 3'dG from the primer, thereby allowing exo⁻ Pfu to efficiently amplify the target. Additional experiments showed that the polymerase deficient Pfu G387P and K593T mutants were unable to amplify the target in the absence of exo⁻ Pfu (or wild type Pfu).

Example 6

PCR Amplification with Pfu or Taq DNA Polymerase Blends Containing Pfu Mutants

Pfu blends. PCR reactions were conducted under standard conditions in cloned Pfu PCR buffer (10 mM KCl, 10 mM (NH$_4$)$_2$SO$_4$, 20 mM Tris HCl (pH 8.8), 2 mM Mg SO$_4$, 0.1% Triton X-100, and 100 µg/ml BSA) with 2.5-5U PfuTurbo DNA polymerase (2.5U/µl cloned Pfu DNA polymerase plus 1U/µl native or 2U/µl cloned *Pyrococcus furiosus* dUTPase (PEF)) and varying concentrations of polymerase deficient Pfu mutants. For genomic targets 0.3-9 kb in length, PCR reactions contained 2.5U PfuTurbo DNA polymerase, 100 ng of human genomic DNA, 200 µM each dNTP, and 100 ng of each primer. For genomic targets 11.9 kb and 17 kb in length, PCR reactions contained 5U PfuTurbo DNA polymerase, 250 ng of human genomic DNA, 500 µM each dNTP, and 200 ng of each primer.

Taq blends. PCR reactions were conducted under standard conditions in Herculase PCR buffer (50 mM Tricine (pH 9.1), 8 mM (NH$_4$)$_2$SO$_4$, 2.3 mM MgCl$_2$, 0.1% Tween-20, and 75 µg/ml BSA) with 2.5U cloned Taq DNA polymerase, 1U of native or 2U cloned *Pyrococcus furiosus* dUTPase (PEF)), and varying concentrations of polymerase deficient Pfu mutants.

TABLE 4

Cycling Conditions

| Target size (kb) | Target gene | Cycling Parameters |
|---|---|---|
| 0.3 | Aldolase B | (1 cycle) 95° C. 2 min |
|  |  | (30 cycles) 95° C. 40 sec, |
|  |  | 58° C. 30 sec, 72° C. 1 min |
|  |  | (1 cycle) 72° C. 7 min |
| 0.9 | HαlAT | (1 cycle) 95° C. 2 min |
|  |  | (30 cycles) 95° C. 40 sec, |

TABLE 4-continued

Cycling Conditions

| Target size (kb) | Target gene | Cycling Parameters |
|---|---|---|
| 2.3 | Pfu pol (5 ng plasmid DNA) | 58° C. 30 sec, 72° C. 1 min (1 cycle) 72° C. 7 min (1 cycle) 95° C. 2 min (30 cycles) 95° C. 40 sec, 58° C. 30 sec, 72° C. 3 min (1 cycle) 72° C. 7 min |
| 2.6 | HαlAT | (1 cycle) 95° C. 2 min (30 cycles) 95° C. 40 sec, 58° C. 30 sec, 72° C. 3 min (1 cycle) 72° C. 7 min |
| 4 | HαlAT | (1 cycle) 95° C. 2 min (30 cycles) 95° C. 40 sec, 54° C. 30 sec, 72° C. 5 min (1 cycle) 72° C. 7 min |
| 9.3 | HαlAT | (1 cycle) 95° C. 2 min (30 cycles) 95° C. 40 sec, 58° C. 30 sec, 72° C. 18 min (1 cycle) 72° C. 10 min |
| 11.9 | HαlAT | (1 cycle) 95° C. 2 min (30 cycles) 95° C. 40 sec, 58° C. 30 sec, 72° C. 24 min (1 cycle) 72° C. 10 min |
| 17 | β globin | (one cycle) 92° C. 2 min (10 cycles) 92° C. 10 sec, 63° C. 30 sec, 68° C. 30 min (20 cycles) 92° C. 10 sec, 63° C. 30 sec, 68° C. 30 min (plus 10 sec/cycle) (one cycle) 68° C. 10 min |

Results (Pfu blend PCR performance): As shown in FIG. 2, adding 0.5 µl of the His$_6$-tagged Pfu G387P mutant to Pfu (in the presence of PEF/dUTPase), has minimal effects on PCR product yield. Additional experiments have shown that up to 1.5 µl of the His$_6$-tagged Pfu G387P mutant preparation can be added without significantly reducing PCR product yield.

Results (Taq blend PCR performance): As shown in FIG. 3, adding the His$_6$-tagged Pfu G387P mutant to Taq, in the presence of PEF/dUTPase, significantly increases PCR product yields when amplifications are performed in a reaction buffer that supports the activity of both Taq and Pfu DNA polymerases. One such buffer is the Herculase PCR buffer, which was developed specifically for Herculase Enhanced DNA polymerase (3.33U/µl cloned Pfu, 1.67U/µl cloned Taq, 2U/µl cloned *Pyrococcus furiosus* dUTPase). In the example shown in FIG. 3, a 4 kb target could not be amplified in high yield using Taq alone in Taq, Pfu, or Herculase PCR buffer. In the presence of the His$_6$-tagged Pfu G387P mutant (and dUTPase), the 4 kb target could be amplified in cloned Pfu buffer (moderate yield) but not Taq buffer, consistent with the buffer preferences of the Pfu G387P mutant. Other experiments have shown that the Pfu G387P mutant inhibits PCR reactions carried out with Taq in Taq PCR buffer, suggesting that the Pfu G387P mutant binds the 3' ends of PCR products without excising mismatches and dissociating (due to inactivity in Taq buffer), and blocks further product extension. As expected, highest product yields are obtained with Taq plus Pfu G387P blends in the presence of Herculase buffer, since both enzymes are highly active in this particular buffer. The Pfu G387P mutant is thought to enhance the yields of Taq PCR reactions (in buffers where Pfu is active) by excising mispairs that would otherwise stall Taq.

Example 7

Measuring the Fidelity of DNA Polymerase Blends Containing His$_6$-Tagged Pfu DNA Polymerase Mutants The error rates of Pfu and Taq blends containing the His$_6$-tagged Pfu G387P and K593T mutants were tested in the lacI PCR fidelity assay described in Cline, J., Braman, J. C., and Hogrefe, H. H. (96) NAR 24:3546-3551. Briefly, a 1.9 kb fragment encoding the lacIOlacZα target gene was amplified from pPRIAZ plasmid DNA using 2.5U PfuTurbo in cloned Pfu PCR buffer or 2.5U Taq in 2.5 or Herculase PCR buffer. Varying amounts of the Pfu G387P and K593T mutants were added to certain reactions. For comparative purposes, the lacI target was also amplified with Pfx (Thermococcus sp. KOD DNA polymerase; Invitrogen) and Tgo (*Thermococcus gorgonarius* DNA polymerase; Roche) using the manufacturers' recommended PCR buffer. The lacI-containing PCR products were then cloned into lambda GT10 arms, and the percentage of lacI mutants (MF, mutation frequency) was determined in a color screening assay, as described (Lundberg, K. S., Shoemaker, D. D., Adams, M. W. W., Short, J. M., Sorge, J. A., and Mathur, E. J. (1991) Gene 180:1-8). Error rates are expressed as mutation frequency per bp per duplication (MF/bp/d), where bp is the number of detectable sites in the lacI gene sequence (349) and d is the number of effective target doublings. For each enzyme, at least two independent PCR amplifications were performed.

Error rate measurements have shown that Pfu and PfuTurbo DNA polymerases exhibit an average error rate which is ~2-fold lower than that of Vent, Deep Vent, and Pfx (KOD) DNA polymerases, 3 to 6-fold lower than those of DNA polymerase mixtures, and 6- to 12-fold lower than that of Taq DNA polymerase.

Results (Pfu blend): As shown Table 5, adding 0.5-3 µl of the IE/HA-purified His$_6$-tagged Pfu G387P mutant reduced the error rate of PfuTurbo DNA polymerase by 3.2 to 3.5-fold (assay 1) and by 1.8 to 2.8-fold (assay 2) in two independent fidelity assays. As discussed in Example 5, up to 1.5 µl of the IE/HA-purified His$_6$-tagged Pfu G387G mutant can be added to PCR reactions without significantly reducing PCR product yield.

In comparison, adding 0.5 µl of the Pfu K593T mutant reduced the error rate of PfuTurbo DNA polymerase slightly (40%), while the addition of 1.5 µl and 3.0 µl increased error rate by 2.8- and 7.3-fold, respectively. At these amounts, approximately 0.5-1U of additional DNA polymerase activity is added to the PCR reaction (Pfu K593T mutant exhibits 1-2% polymerase activity). The K593T mutation significantly increases the misincorporation or mispair extension rate of Pfu, and when added at high amounts (corresponding to ≥0.5U), the Pfu K593T mutant dramatically increases the error rate of wild type Pfu.

Results (Taq blend): As shown Table 6, adding 0.5 µl and 3.0 µl of the Pfu G387G mutant reduced the error rate of Taq DNA polymerase by 5.1- and 8.3-fold, respectively. Therefore, the error rate of Taq in the presence of the Pfu G387G mutant, can equal the error rate of Pfu alone.

FIG. 6. Fidelity of Pfu Blends Containing IE/HA Purified His$_6$-Pfu Mutants:

| PCR Enzyme | His-Pfu Mutant | Mutant Amount (µl) | Error rate* ($\times 10^{-6}$) Assay 1 | Error rate* ($\times 10^{-6}$) Assay 2 | Mean Relative Accuracy (Pfu) |
|---|---|---|---|---|---|
| Pfu | None | — | 5.55 | 3.60 | 1.0 |
|  | G387P | 0.5 | 1.60 | 2.06 | 2.6 |
|  |  | 1.5 | 1.65 | 1.18 | 3.2 |
|  |  | 2.0 | Nd | 1.30 | 2.8 |
|  |  | 3.0 | 1.75 | Nd | 3.2 |
|  | K593T | 0.5 | 3.9 | Nd | 1.4 |
|  |  | 1.5 | 15.7 | Nd | 0.4 |
|  |  | 3.0 | 40.3 | Nd | 0.1 |
| Tgo | None | — | nd | 6.10 | 0.6 |
| Taq | None | — | 34.7 | 19.0 | 0.2 |

*mean of duplicate measurements

TABLE 6

Fidelity of Taq Blends Containing IE/HA Purified Pfu Mutants:

| PCR Enzyme | His-Pfu Mutant | Mutant Amount (µl) | Error rate* ($\times 10^{-6}$) | Relative Accuracy (Pfu) |
|---|---|---|---|---|
| Taq | None | — | 34.7 | 0.16 |
|  | G387P | 0.5 | 6.8 | 0.82 |
|  |  | 3.0 | 4.2 | 1.32 |
|  | K593T | 0.5 | 37.0 | 0.15 |
| Pfu | None | — | 5.6 | 1.0 |
|  | G387P | 0.5 | 1.60 | 3.47 |
|  |  | 3.0 | 1.75 | 3.17 |
|  | K593T | 0.5 | 3.90 | 1.42 |

*mean of duplicate measurements

Example 8

Determining the TA Cloning Efficiencies of PCR Products Amplified with Taq in the Presence of Pfu Mutants To determine the effects of polymerase deficient Pfu mutants on the terminal transferase activity of Taq, we amplified a series of amplicons with Taq in the absence of the Pfu G387P mutant (in Taq PCR buffer) or in the presence of the Pfu G387P mutant (in Herculase PCR buffer). Similar amplifications were performed using PfuTurbo and Herculase in their recommended PCR buffers. PCR product yields were quantified by analyzing the products on 1% agarose gels, stained with SYBR gold. The same amount of each PCR product was added to 1 µl of the pCR 2.1-TOPO vector (Invitrogen) in a final reaction volume of 6 µl, according the manual for the TOPO TA Cloning Kit (#K4500-01). The reactions were incubated for 5 minutes at room temperature, and then transferred to ice. The reactions were transformed into One-Shot cells (Invitrogen), according to the manufacture's recommendations. Aliquots of each transformation were plated on ampicillin/IPTG/X-gal plates, prepared as described in the Invitrogen TOPO TA Cloning manual. The frequency of clones containing the desired insert (% cloning efficiency) was quantified as the number of (white colonies)/(total number of colonies plated).

Results: As shown in Table 7, PCR products amplified with Taq in the presence of the Pfu G387P mutant are cloned into the TOPO TA cloning vector as efficiently as PCR products amplified with Taq alone. In contrast, PCR products amplified with PfuTurbo DNA polymerase are cloned into the TOPO TA cloning vector much less efficiently, presumably due to the lack of 3' dAs. As discussed in Example 7, PCR products amplified with Taq blends containing the Pfu G387P mutant, should also exhibit fewer errors (5- to 8-fold less) compared to PCR products amplified with Taq alone. Therefore, Taq blends containing the Pfu G387P mutant should be useful to researchers using TA cloning methods, but desiring high-fidelity amplification of inserts. The high TA cloning efficiencies obtained in the presence of the Pfu G387P mutant indicates that 3'dAs added by Taq during PCR are unexpectedly resistant to exonucleolytic degradation. Presumably, Pfu DNA polymerase is not very efficient at excising 3'dA residues from double-stranded PCR products in the presence of nucleotides.

TABLE 7

TopoTA Cloning Efficiencies:

| PCR Product (bp) | PCR enzyme/blend DNA polymerase | $His_6$-Pfu mutant mutant | $His_6$-Pfu mutant amount (µl) | Cloning efficiency (%) |
|---|---|---|---|---|
| 900 | Taq | none | — | 89 |
|  |  | G387P | 0.5 | 80 |
|  |  | G387P | 3.0 | 89 |
|  | Pfu | none | — | 8 |
| 300 | Taq | none | — | 69 |
|  |  | G387P | 0.5 | 73 |
|  |  | G387P | 3.0 | 78 |
|  | Pfu | none | — | 33 |
|  | Herculase | None | — | 46 |
| 2300 | Taq | None | — | 83 |
|  |  | G387P | 0.5 | 88 |
|  |  | G387P | 3.0 | 92 |
|  | Pfu | None | — | 22 |
|  | Herculase | None | — | 85 |

Example 9

Expression and Activity of Untagged Pfu Mutants

The $His_6$-tag was deleted from the $His_6$-tagged Pfu G387P clone and the untagged mutant was expressed and purified as described in Example 4. Four Pfu G387P mutant samples were prepared and their protein concentrations determined by amino acid analysis. Exonuclease activity was measured using $^3$H-*E. coli* genomic DNA as substrate and the specific exonuclease activities of the mutant preparations are compared to that of wild type Pfu in Table 8. The specific exonuclease activities of the Pfu G387P mutant preparations ranged from 1300 to 2200 U/mg, and appeared to be somewhat higher than that of wild type Pfu (350-950U/mg).

TABLE 8

Exonuclease specific activity of Pfu G387P Preparations

| DNA Polymerase | Lot/prep # | Protein concentration (μg/μl) | Exonuclease activity (U/μl) | Exonuclease specific Activity (U/mg) (# assays) | Polymerase activity (U/μl) |
|---|---|---|---|---|---|
| Pfu | 1184447 | ~0.05 | 0.0174 | 348 (1) | 2.5 |
| Pfu | SCS 61 | 2.29 | 2.176 | 950 (1) | 250 |
| Pfu G387P | J | 4.17 | 8.72 | 2090 (5) | 0 |
| Pfu G387P | SCS 1 | 6.8 | 8.86 | 1320 (2) | 0 |
| Pfu G387P | SCS 2 | 3.0 | 5.87 | 1957 (1) | 0 |
| Pfu G387P | SCS 3 | 2.6 | 5.70 | 2192 (1) | 0 |

Example 10

Measuring the Fidelity of DNA Polymerase Blends Containing the Untagged Pfu G387P Mutant The error rates of Pfu and Taq blends containing the untagged Pfu G387P mutant preparations were tested in the lacI PCR fidelity assay as described in Example 7. As shown in FIG. 4, the highest reductions in error rate (~3-fold) were observed when 6 to 10 ng of Pfu G387P prep J was added to 2.5U Pfu (50 μl reaction). Unexpectedly, fidelity appeared to decrease with increasing amounts (>10 ng) of Pfu P387G mutant. The yield of lacI amplicon also decreased with increasing amount of Pfu P387G mutant, suggesting that lower fidelity may in some way be correlated with reduced yield. Using prep J, optimal fidelity (lowest error rate) was achieved by adding 0.0125U to 0.0208U of exonuclease activity (prep J; 2090U/mg), which is the amount of 3'-5' exonuclease activity exhibited by ~1-3U of wild type Pfu.

These assumptions are based upon Pfu exhibiting a specific activity of 348-950U exonuclease/mg and exo/pol ratios of 0.0174U/2.5U-0.02176U/2.5U, see Table 7.

Additional testing with G387P preparations SCS 1-3 showed that 6-24 ng or amounts of protein equivalent to 0.0125U, 0.0209U, or 0.0314U of prep J consistently reduced the error rate of PfuTurbo DNA polymerase by ~3-fold (FIG. 5). There was minimal variation in error rate with lot of PfuTurbo DNA polymerase employed (lots #59, 61, 63).

As shown in FIG. 6, adding 6 ng to 60 ng Pfu G387P prep J reduced the error rate of Taq DNA polymerase by 4.4- to 12.6-fold. Maximum reduction in error rate was achieved by adding 40 ng of prep J, or the equivalent of 0.0836U of exonuclease activity. In this assay, the accuracy of the Taq+40 ng Pfu G387P blend was 50% higher than that of PfuTurbo DNA polymerase.

Example 11

Range of Ratios of Exonuclease and Polymerase Activities to use in Blends

| Enzyme blend | | | | | |
|---|---|---|---|---|---|
| Polymerase proficient enzyme | | Polymerase deficient enzyme | | | |
| | Amount Polymerase | | Range of Amounts Tested that Produce Highest Fidelity and Yield | | |
| Polymerase | (3'-5' Exo) | Pfu Mutant | Ng | Polymerase (U) | 3'-5' Exo (U) |
| Pfu/ | 2.5 | G387P | 5.7-24 | <0.01 | 0.008-0.0314 |
| PfuTurbo | (0.02 U exo) | 4 preps | | | |
| Taq | 2.5 U | G387P | 20-40 | <0.01 | 0.0418-0.0836 |
| | (0 U exo) | prep J | | | |

Other Embodiments

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

The invention claimed is:

1. An enzyme mixture comprising a first enzyme and a second enzyme, wherein said first enzyme comprises 5'-3' polymerization activity of a DNA polymerase or reverse transcriptase, and said second enzyme is a mutant of a wild type DNA polymerase, said wild type DNA polymerase comprising the partitioning domain sequence YXGG (SEQ ID NO:6), the polymerase domain sequence DXXSLYP (SEQ ID NO:1) or DFRALYP (SEQ ID NO:13), the polymerase domain sequence YXDTDS (SEQ ID NO:4), YIDTDG (SEQ ID NO:15), YADTDG (SEQ ID NO:16), or YSDTDG (SEQ ID NO:17), and the polymerase domain sequence KXY, wherein said second enzyme comprises an amino acid substitution at an amino acid position corresponding to G387 of SEQ ID NO:19, and wherein said second enzyme comprises 3'-5' exonuclease activity and reduced 5'-3' DNA polymerization activity as compared to the wild type DNA polymerase.

2. The enzyme mixture of claim 1, wherein said first enzyme is a DNA polymerase or a reverse transcriptase.

3. The enzyme mixture of claim 2, wherein said first enzyme is selected from the group consisting of: Taq DNA polymerase, Tth DNA polymerase, UlTma DNA polymerase, Tli DNA polymerase, Pfu DNA polymerase, KOD DNA polymerase, JDF-3 DNA polymerase, PGB-D DNA polymerase and DP1/DP2 DNA polymerase.

4. The enzyme mixture of claim 1, wherein said first enzyme is a Pfu DNA polymerase.

5. The enzyme mixture of claim 1, further comprising a PCR enhancing factor and/or an additive.

6. The enzyme mixture of claim 1, wherein said enzyme mixture has a ratio of polymerization activity/exonuclease activity of (2.5-5U)/(0.02-5U).

7. The enzyme mixture of claim 6, wherein said enzyme mixture has a ratio of polymerization activity/exonuclease activity of (2.5U)/(0.04-0.08U).

8. An enzyme mixture comprising three or more enzymes, wherein at least one enzyme in said enzyme mixture is a mutant of a wild type DNA polymerase, said wild type DNA polymerase comprising the partitioning domain sequence YXGG (SEQ ID NO:6), the polymerase domain sequence DXXSLYP (SEQ ID NO:1) or DFRALYP (SEQ ID NO:13), the polymerase domain sequence YXDTDS (SEQ ID NO:4), YIDTDG (SEQ ID NO:15), YADTDG (SEQ ID NO:16), or YSDTDG (SEQ ID NO:17), and the polymerase domain sequence KXY, wherein said mutant DNA polymerase comprises 3'-5' exonuclease activity and a reduced DNA polymerization activity as compared to the wild type DNA polymerase, and wherein said mutant DNA polymerase comprises an amino acid substitution at an amino acid position corresponding to G387 of SEQ ID NO:19.

9. The enzyme mixture of claim 8, wherein at least two enzymes in said mixture are mixed as an enzyme blend before being added to said enzyme mixture.

10. The enzyme mixture of claim 9, wherein said enzyme blend comprises a Pfu DNA polymerase and Taq DNA polymerase.

11. The enzyme mixture of claim 10, wherein said enzyme blend further comprises a PCR enhancing factor.

12. A kit comprising a first enzyme, a second enzyme, and packaging material therefor, wherein said first enzyme is a DNA polymerase or reverse transcriptase comprising 5'-3' polymerization activity of a DNA polymerase or reverse transcriptase, said second enzyme is a mutant of a wild type DNA polymerase, said wild type DNA polymerase comprising the partitioning domain sequence YXGG (SEQ ID NO:6), the polymerase domain sequence DXXSLYP (SEQ ID NO:1) or DFRALYP (SEQ ID NO:13), the polymerase domain sequence YXDTDS (SEQ ID NO:4), YIDTDG (SEQ ID NO:15), YADTDG (SEQ ID NO:16), or YSDTDG (SEQ ID NO:17), and the polymerase domain sequence KXY, wherein said second enzyme comprises an amino acid substitution at an amino acid position corresponding to G387 of SEQ ID NO:19 and wherein said second enzyme comprises 3'-5' exonuclease activity and a reduced DNA polymerization activity as compared to the wild type DNA polymerase.

13. The kit of claim 12, wherein said first enzyme is selected from the group consisting of: Taq DNA polymerase, Tth DNA polymerase, UlTma DNA polymerase, Tli DNA polymerase, Pfu DNA polymerase, KOD DNA polymerase, JDF-3 DNA polymerase, PGB-D DNA polymerase and DP1/DP2 DNA polymerase.

14. The kit of claim 12, wherein said first enzyme is a Pfu DNA polymerase.

15. The kit of claim 12 or 14, further comprising one or more components selected from the group consisting of: a deoxynucleotide, a reaction buffer, a PCR enhancing factor and/or an additive, a control DNA template and a control primer.

16. The kit of claim 12, wherein said enzyme mixture has a ratio of polymerization activity/exonuclease activity of (2.5-5U)/(0.02-5U).

17. The kit of claim 16, wherein said enzyme mixture has a ratio of polymerization activity/exonuclease activity of (2.5U)/(0.04-0.08U).

18. The enzyme mixture of claim 1, wherein said first enzyme is Taq DNA polymerase or Pfu DNA polymerase.

19. The kit of claim 12, wherein said first enzyme is Taq DNA polymerase or Pfu DNA polymerase.

20. The enzyme mixture of claim 1 or 4, wherein said second enzyme is a mutant DNA polymerase from the species *Pyrococcus furiosis*.

21. The enzyme mixture of claim 8, wherein said at least one enzyme is a mutant DNA polymerase from the species *Pyrococcus furiosis*.

22. The kit of claim 12 or 14, wherein said second enzyme is a mutant DNA polymerase from the species *Pyrococcus furiosis*.

23. The enzyme mixture of claim 1, wherein said wild type DNA polymerase is a Family B DNA polymerase.

24. The enzyme mixture of claim 1, wherein said wild type DNA polymerase is selected from the group consisting of *Thermococcus litoralis* DNA polymerase (Vent DNA polymerase) having the amino acid sequence of SEQ ID NO:49, *Pyrococcus* GB-D (Deep Vent) DNA polymerase having the amino acid sequence of SEQ ID NO:59, *Thermococcus gorgonarius* DNA polymerase having the amino acid sequence of SEQ ID NO:29, *Pyrococcus furiousus* DNA polymerase having the amino acid sequence of SEQ ID NO:19, and *Pyrococcus kodakaraensis* DNA polymerase having the amino acid sequence of SEQ ID NO:39.

25. The enzyme mixture of claim 24, wherein said second enzyme comprises an amino acid substitution at G387 in the amino acid sequence of SEQ ID NO:19.

26. The enzyme mixture of claim 24, wherein said second enzyme comprises an amino acid substitution at G386 in the amino acid sequence of SEQ ID NO:29.

27. The enzyme mixture of claim 24, wherein said second enzyme comprises an amino acid substitution at G386 in the amino acid sequence of SEQ ID NO:39.

28. The enzyme mixture of claim 24, wherein said second enzyme comprises an amino acid substitution at G389 in the amino acid sequence of SEQ ID NO:49.

29. The enzyme mixture of claim 24, wherein said second enzyme comprises an amino acid substitution at G387 in the amino acid sequence of SEQ ID NO:59.

30. The enzyme mixture of claim 23, wherein said second enzyme comprises the amino acid sequence of SEQ ID NO:19 except for an amino acid substitution at G387.

31. The kit of claim 12, wherein said wild type DNA polymerase is a Family B DNA polymerase.

32. The kit of claim 12, wherein said wild type DNA polymerase is selected from the group consisting of *Thermococcus litoralis* DNA polymerase (Vent DNA polymerase) having the amino acid sequence of SEQ ID NO:49, *Pyrococcus* GB-D (Deep Vent) DNA polymerase having the amino acid sequence of SEQ ID NO:59, *Thermococcus gorgonarius* DNA polymerase having the amino acid sequence of SEQ ID NO:29, *Pyrococcus furiousus* DNA polymerase having the amino acid sequence of SEQ ID NO:19, and *Pyrococcus kodakaraensis* DNA polymerase having the amino acid sequence of SEQ ID NO:39.

33. The kit of claim 32, wherein said second enzyme comprises an amino acid substitution at G387 in the amino acid sequence of SEQ ID NO:19.

34. The kit of claim 32, wherein said second enzyme comprises an amino acid substitution at G386 in the amino acid sequence of SEQ ID NO:29.

35. The kit of claim 32, wherein said second enzyme comprises an amino acid substitution at G386 in the amino acid sequence of SEQ ID NO:39.

36. The kit of claim 32, wherein said second enzyme comprises an amino acid substitution at G389 in the amino acid sequence of SEQ ID NO:49.

37. The kit of claim 32, wherein said second enzyme comprises an amino acid substitution at G387 in the amino acid sequence of SEQ ID NO:59.

38. The kit of claim 32, wherein said second enzyme comprises the amino acid sequence of SEQ ID NO:19 except for an amino acid substitution at G387.

39. The enzyme mixture of claim 25, wherein the amino acid substitution at G387 is a glycine to proline substitution.

40. The enzyme mixture of claim 30, wherein the amino acid substitution at G387 is a glycine to proline substitution.

41. The kit of claim 33, wherein the amino acid substitution at G387 is a glycine to proline substitution.

42. The kit of claim 38, wherein the amino acid substitution at G387 is a glycine to proline substitution.

43. The enzyme mixture of claim 39, wherein the first enzyme is Taq DNA polymerase or Pfu DNA polymerase.

44. The enzyme mixture of claim 40, wherein the first enzyme is Taq DNA polymerase or Pfu DNA polymerase.

45. The kit of claim 41, wherein the first enzyme is Taq DNA polymerase or Pfu DNA polymerase.

46. The kit of claim 42, wherein the first enzyme is Taq DNA polymerase or Pfu DNA polymerase.

47. The enzyme mixture of claim 43, wherein the first enzyme is Taq DNA polymerase.

48. The enzyme mixture of claim 44, wherein the first enzyme is Taq DNA polymerase.

49. The kit of claim 45, wherein the first enzyme is Taq DNA polymerase.

50. The kit of claim 46, wherein the first enzyme is Taq DNA polymerase.

* * * * *

UNITED STATES PATENT AND TRADEMARK OFFICE
CERTIFICATE OF CORRECTION

PATENT NO.        : 7,932,070 B2                                    Page 1 of 1
APPLICATION NO.   : 10/227110
DATED             : April 26, 2011
INVENTOR(S)       : Holly Hogrefe et al.

It is certified that error appears in the above-identified patent and that said Letters Patent is hereby corrected as shown below:

On the cover page, item (56), under "Other Publications", in column 1, line 10, delete "furiosusDNA" and insert -- furiosus DNA --, therefor.

On the cover page, item (56), under "Other Publications", in column 2, line 2, delete "Thennococcus" and insert -- Themococcus --, therefor.

On the cover page, item (56), under "Other Publications", in column 2, line 43, delete "od" and insert -- of --, therefor.

In column 426, line 3, in Claim 20, delete "furiosis." and insert -- furiosus. --, therefor.
In column 426, line 6, in Claim 21, delete "furiosis." and insert -- furiosus. --, therefor.
In column 426, line 9, in Claim 22, delete "furiosis." and insert -- furiosus. --, therefor.
In column 426, line 20, in Claim 24, delete "furiousus" and insert -- furiosus --, therefor.
In column 426, line 52, in Claim 32, delete "furiousus" and insert -- furiosus --, therefor.
In column 427, line 8, in Claim 39, delete "G3 87" and insert -- G387 --, therefor.
In column 427, line 10, in Claim 40, delete "G3 87" and insert -- G387 --, therefor.

Signed and Sealed this
Twenty-fifth Day of October, 2011

David J. Kappos
*Director of the United States Patent and Trademark Office*